United States Patent
Orth et al.

(10) Patent No.: US 12,234,465 B2
(45) Date of Patent: *Feb. 25, 2025

(54) METHODS AND MICROORGANISMS FOR THE FERMENTATION OF METHANE TO MULTI-CARBON COMPOUNDS

(71) Applicant: PRECIGEN, INC., Germantown, MD (US)

(72) Inventors: Jeffrey David Orth, Germantown, MD (US); Louis A. Clark, Germantown, MD (US); Lily Yuin Chao, Germantown, MD (US); Na My Trinh, Germantown, MD (US); Christopher Cheyney Farwell, Germantown, MD (US); Xinhua Zhao, Germantown, MD (US); Matthias Helmut Schmalisch, Germantown, MD (US); Grayson Thomas Wawrzyn, Germantown, MD (US); Xuezhi Li, Germantown, MD (US); Mark Anton Held, Germantown, MD (US); Kevin Lee Dietzel, Germantown, MD (US); James Kealey, Germantown, MD (US)

(73) Assignee: PRECIGEN, INC., Germantown, MD (US)

( * ) Notice: Subject to any disclaimer, the term of this patent is extended or adjusted under 35 U.S.C. 154(b) by 40 days.

This patent is subject to a terminal disclaimer.

(21) Appl. No.: 17/811,776

(22) Filed: Jul. 11, 2022

(65) Prior Publication Data
US 2023/0051667 A1      Feb. 16, 2023

Related U.S. Application Data

(63) Continuation of application No. 16/604,425, filed as application No. PCT/US2018/029688 on Apr. 27, 2018, now Pat. No. 11,421,235.

(Continued)

(51) Int. Cl.
*C12N 1/20*      (2006.01)
*C12N 9/04*      (2006.01)
(Continued)

(52) U.S. Cl.
CPC ........... *C12N 15/52* (2013.01); *C12N 9/0006* (2013.01); *C12N 9/1022* (2013.01);
(Continued)

(58) Field of Classification Search
CPC ...... C12N 9/1022; C12N 9/0006; C12N 9/88; C12N 15/74
See application file for complete search history.

(56) References Cited

U.S. PATENT DOCUMENTS

| | | | |
|---|---|---|---|
| 7,851,188 B2 | 12/2010 | Donaldson et al. | |
| 8,557,562 B2 * | 10/2013 | Bramucci | C12N 15/81 435/254.2 |

(Continued)

FOREIGN PATENT DOCUMENTS

| | | |
|---|---|---|
| WO | 2008/066931 A2 | 6/2008 |
| WO | 2010051527 A2 | 5/2010 |

(Continued)

OTHER PUBLICATIONS

Fransceus. J Ind Microbiol Biotechnol. May 2017;44(4-5):687-695.*

(Continued)

*Primary Examiner* — Yong D Pak
(74) *Attorney, Agent, or Firm* — Barnes & Thornburg LLP; Gene J. Yao

(57) ABSTRACT

Genetically modified microorganisms that have the ability to convert carbon substrates into chemical products such as isobutanol are disclosed. For example, genetically modified methanotrophs that are capable of generating isobutanol at high titers from a methane source are disclosed. Methods of (Continued)

making these genetically modified microorganisms and methods of using them are also disclosed.

18 Claims, 18 Drawing Sheets

Specification includes a Sequence Listing.

Related U.S. Application Data

(60) Provisional application No. 62/512,315, filed on May 30, 2017, provisional application No. 62/491,683, filed on Apr. 28, 2017.

(51) Int. Cl.
| | |
|---|---|
| *C12N 9/10* | (2006.01) |
| *C12N 9/12* | (2006.01) |
| *C12N 9/88* | (2006.01) |
| *C12N 15/52* | (2006.01) |
| *C12N 15/70* | (2006.01) |
| *C12P 7/00* | (2006.01) |
| *C12P 7/16* | (2006.01) |
| *C12P 7/24* | (2006.01) |

(52) U.S. Cl.
CPC ............ *C12N 9/1205* (2013.01); *C12N 9/88* (2013.01); *C12N 15/70* (2013.01); *C12P 7/16* (2013.01); *C12P 7/24* (2013.01); *C12Y 101/01001* (2013.01); *C12Y 101/01086* (2013.01); *C12Y 202/01006* (2013.01); *C12Y 401/01072* (2013.01); *C12Y 402/01009* (2013.01)

(56) References Cited

U.S. PATENT DOCUMENTS

| | | | |
|---|---|---|---|
| 8,758,764 | B2 | 6/2014 | Masignani et al. |
| 9,267,158 | B2 | 2/2016 | Coleman et al. |
| 9,399,783 | B2 | 7/2016 | Coleman et al. |
| 9,745,603 | B2 | 8/2017 | Coleman et al. |
| 10,858,661 | B2 | 12/2020 | Lee et al. |
| 10,876,137 | B2 | 12/2020 | Coleman et al. |
| 11,821,019 | B2 * | 11/2023 | Coleman ........ C12Y 402/01009 |
| 2007/0092957 | A1 | 4/2007 | Donaldson et al. |
| 2007/0292927 | A1 | 12/2007 | Donaldson et al. |
| 2008/0014619 | A1 | 1/2008 | Huang et al. |
| 2011/0014669 | A1 | 1/2011 | Madden et al. |
| 2014/0004526 | A1 | 1/2014 | Dauner et al. |
| 2014/0273128 | A1 | 9/2014 | Coleman et al. |
| 2015/0064759 | A1 | 3/2015 | Perez et al. |
| 2015/0240247 | A1 | 8/2015 | Atsumi et al. |
| 2015/0259389 | A9 | 9/2015 | Berka et al. |
| 2016/0160243 | A1 | 6/2016 | Coleman et al. |

FOREIGN PATENT DOCUMENTS

| | | |
|---|---|---|
| WO | 2014092562 A1 | 6/2014 |
| WO | 2018140928 A1 | 8/2018 |
| WO | 2019075159 A1 | 4/2019 |

OTHER PUBLICATIONS

Sanavia. Computational and Structural Biotechnology Journal, vol. 18, 2020, pp. 1968-1979.*
Chu et al., Journal of Bacteriology, 198:1317-1325 (2016).
International Search Report issued in PCT/US2018/029688.
Written Opinion issued in PCT/US2018/029688.
Kopke et al., Applied and Environmental Microbiology, 77:5467-5475 (2011).
Campbell et al., Cell Calcium, 41 :97-106 (2006).
Cui et al., Journal of Applied Microbiology, 117:690-698 (2014).
Zhang et al., Green Chemistry, 14:3441-3450 (2012).
EC 4.1.1.5—Acetolactate Decarboxylase, IntEz, 2015.
Studer, Biochem. J., 449:581-594 (2013).
KRN57005.1. Gen Bank Database. Nov. 6, 2015.
A0A0B5HLI4_BACLI. UniProtKB/TrEMBL Database. Mar. 16, 2016.
Nguyen et al., Metab Eng (2018), 47:323-333.
Vecherskaya et al., Environmental Microbiology Reports (2009), 1: 442-449.
Felpeto-Santero, Carmen, et al. "Engineering alternative isobutanol production platforms." Amb Express 5.1 (2015): 1-9.
Database NCBI [Online], (Aug. 7, 2015): Synthetic construct IbPSO operon, complete sequence, GeneBank accession No. KP739244.1.

* cited by examiner

SEQUENCE LISTING

```
Sequence total quantity: 100
SEQ ID NO: 1              moltype = DNA   length = 1713
FEATURE                   Location/Qualifiers
source                    1..1713
                          mol_type = other DNA
                          organism = Bacillus subtilis
SEQUENCE: 1
atgaccaagg ccaccaagga acagaaaagc ctggtcaaga accgcggtgc tgaactggtt   60
gtggactgcc tcgtggaaca gggcgtgacc catgtcttcg gcatcccggg cgccaagatc  120
gacgccgtct tcgacgccct gcaggataaa ggtccgaaaa tcatcgtggc acgccatgag  180
cagaacgcag ccttcatggc ccaggccgtc ggtcggctga cgggtaagcc cggcgtggtg  240
ctggtcacct ccggtccggg agcctcgaac ctggccacgg gactgctcac cgccaacacc  300
gaaggcgacc cggtggtcgc cctggccggt aatgtcatcc gggcggatcg cctgaagcgc  360
acccatcagt ccctggataa cgcggccctg ttccagccaa tcaccaaata tagtgtcgaa  420
gtgcaggatg tgaagaacat cccggaagcc gtcaccaatg cgttccgaat cgcgtccgca  480
ggccaagcag gggcagcatt cgtgagcttc cccaggacg tggtcaatga agtgaccaac  540
accaaaaacg tcagagccgt agccccccg aagctgggcc tgcagcagat gacgccatc   600
tccgctgcca tcgcgaagat ccagaccgca aagctgccgg tcgtgctggt cggaatgaag  660
ggcggacgcc cggaggccat caaggccgtg cgtaaactgc tgaagaaggt gcagctaccg  720
ttcgtggaaa cctaccaggc cgccggcacc ctgagtcggg acttggaaga ccagtatttc  780
ggccgtatcg gcctgttccg caaccagccg ggcgacctgc tcctggaaca agccgatgtg  840
gtgctgacca tcggctacga cccgatcgaa tatgaccega agttctggaa catcaatggc  900
gaccgcacga tcatccatct ggacgaaatc atcgccgaca tcgaccatgc ctatcagccg  960
gacctggaac tgatcggcga catcccgagc accatcaacc acatcgaaca cgatgccgtg 1020
aaggtggaat tgccgaacg cgaacagaag atcctgtcgg acctgaagca gtatatgcat 1080
gagggcgaac aggtgcctgc cgactggaag tcggacagag cccatccgct ggaaatcgtg 1140
aaggaactgc gtaacgccgt cgacgaccat gtcaccgtca cctgcgatat cggcagccat 1200
gccatttgga tgagccgcta cttccggagc tatgaaccgc tgaccctgat gatctccaac 1260
ggtatgcaga ccctcggcgt cgccctcccg tgggccatcg gcgcaagtct ggtgaagccg 1320
ggcgaaaaag tggtcagcgt gtccggcgac ggcggcttcc tgttctccgc tatggaactg 1380
gaaaccgcgg tccgcctgaa ggccccgatc gtgcatatcg tgtggaacga cagccactac 1440
gacatggtcg ccttccagca gctgaaaaag tacaaccgca ccagcgccgt ggacttcggc 1500
aatatcgaca tcgtgaagta tgccgaatcc ttcggagcca ccggactgcg cgtgaatcc  1560
ccggaccagc tggcggacgt tctgcgtcag ggcatgaatg ccgaaggtcc cgtgattatc 1620
gatgtgcccg tcgactacag cgacaacatc aacctggcct cggacaaatt gccgaaggag 1680
ttcggcgaac tgatgaaaac aaaagcacta taa                              1713

SEQ ID NO: 2              moltype = AA   length = 570
FEATURE                   Location/Qualifiers
source                    1..570
                          mol_type = protein
                          organism = Bacillus subtilis
SEQUENCE: 2
MTKATKEQKS LVKNRGAELV VDCLVEQGVT HVFGIPGAKI DAVFDALQDK GPEIIVARHE   60
QNAAFMAQAV GRLTGKPGVV LVTSGPGASN LATGLLTANT EGDPVVALAG NVIRADRLKR  120
THQSLDNAAL FQPITKYSVE VQDVKNIPEA VTNAFRIASA GQAGAAFVSF PQDVVNEVTN  180
TKNVRAVAAP KLGPAADDAI SAAIAKIQTA KLPVVLVGMK GGRPEAIKAV RKLLKKVQLP  240
FVETYQAAGT LSRDLEDQYF GRIGLFRNQP GDLLLEQADV VLTIGYDPIE YDPKFWNIG   300
DRTIIHLDEI IADIDHAYQP DLELIGDIPS TINHIEHDAV KVEFAEREQK ILSDLKQYMH  360
EGEQVPADWK SDRAHPLEIV KELRNAVDDH VTVTCDIGSH AIWMSRYFRS YEPLTLMISN  420
GMQTLGVALP WAIGASLVKP GEKVVSVSGD GGFLFSAMEL ETAVRLKAPI VHIVWNDSTY  480
DMVAFQQLKK YNRTSAVDFG NIDIVKYAES FGATGLRVES PDQLADVLRQ GMNAEGPVII  540
DVPVDYSDNI NLASDKLPKE FGELMKTKAL                                   570

SEQ ID NO: 3              moltype = DNA   length = 1476
FEATURE                   Location/Qualifiers
source                    1..1476
                          mol_type = other DNA
                          organism = Escherichia coli
SEQUENCE: 3
atggctaact acttcaacac cctgaacttg cgtcagcagc tggcccagct gggtaagtgc   60
cggttcatgg ccgtgatga gttcgccgat ggcgccagct acctgcaggg caaaaaggtg  120
gtgatcgtgg gctgcggagc ccagggcctg aaccagggcc tgaatatgcg cgatagcggc  180
ctggacatct ccctatgctct gcgcaaggaa gcgatcgcgg aaaagcgggc atcctggcgc  240
aaggccaccg aaaacggttt caaagtgggc acctacgaag aactgatccc gcaggccgat  300
ttggtcataa acctgacccc ggacaagcag cattccgatg tggttcgcac cgtccagccg  360
ctgatgaagg acgggcagc cctgggttac tcccacggct tcaacatcgt ggaagtcggc  420
gaacagatcc gcaaggacat caccgtcgtc atggtcgcac cgaagtgtcc gggcaccgaa  480
gtccgggaag aatataagcg tggattcggc gtaccgaccc tgtcgccgt ccatcccgga   540
aacgacccga agggcgaagg catgccatc gccaaggcct gggctgccgc caccggaggc  600
catcgcgctg cgtgctggga agctcgttc gtcgccgaag tgaagagcga cctgatgggc  660
gaacagacca tcctgtgcgg catgctgcag gccggtagcc tgctgtgttt cgacaagctg  720
gtcgaagaag gcaccgaccc tgcgtatgcc gaaaagctga tccagttcgg ctgggaaacc  780
atcaccgaag cgctgaaaca gggcggtatc accctgatga tggaccgcct gtcgaaccct  840
gccaagttac gtgcctatgc cctgagcgaa cagctgaagg aaatcatggc gctctgttc   900
cagaaacata tggacgatat catcagcggc gagttcagct ccggcatgat ggcggactgg  960
gcgaatgacg acaagaagct gctgacctgg cgggaagaaa ccggcaagac ggccttcgaa 1020
accgcaccgc agtacgaagg caaaatcggc gaacaggagt acttcgacaa aggcgtcctg 1080
```

-continued

```
atgatcgcga tggtcaaggc gggagtcgaa ctggccttcg aaacaatggt cgatagcggc    1140
atcatcgagg aatccgccta ctacgaaagc ctgcatgaac tcccgctgat cgccaatacc    1200
atagcccgca agcggctgta cgaaatgaac gtcgtgatct ccgacactgc cgaatacggc    1260
aattatctct ctcctatgc ctgcgtgccg ctcctgaagc ccttcatggc cgaactgcag     1320
ccaggcgacc tggggaaggc gatccccgaa ggcgctgtcg acaacggcca gctgcgcgat    1380
gtcaacgaag ccattcgctc ccatgccatc gagcaggtcg gcaagaagct gcgtggctat    1440
atgacggaca tgaagcgcat cgccagtagc ggataa                              1476

SEQ ID NO: 4              moltype = AA length = 491
FEATURE                   Location/Qualifiers
source                    1..491
                          mol_type = protein
                          organism = Escherichia coli
SEQUENCE: 4
MANYFNTLNL RQQLAQLGKC RFMGRDEFAD GASYLQGKKV VIVGCGAQGL NQGLNMRDSG     60
LDISYALRKE AIAEKRASWR KATENGFKVG TYEELIPQAD LVINLTPDKQ HSDVVRTVQP    120
LMKDGAALGY SHGFNIVEVG EQIRKDITVV MVAPKCPGTE VREEYKRGFG VPTLIAVHPE    180
NDPKGEGMAI AKAWAAATGG HRAGVLESSF VAEVKSDLMG EQTILCGMLQ AGSLLCFDKL    240
VEEGTDPAYA EKLIQFGWET ITEALKQGGI TLMMDRLSNP AKLRAYALSE QLKEIMAPLF    300
QKHMDDIISG EFSSGMMADW ANDDKKLLTW REETGKTAFE TAPQYEGKIG EQEYFDKGVL    360
MIAMVKAGVE LAFETMVDSG IIEESAYYES LHELPLIANT IARKRLYEMN VVISDTAEYG    420
NYLFSYACVP LLKPFMAELQ PGDLGKAIPE GAVDNGQLRD VNEAIRSHAI EQVGKKLRGY    480
MTDMKRIAVA G                                                        491

SEQ ID NO: 5              moltype = DNA length = 1851
FEATURE                   Location/Qualifiers
source                    1..1851
                          mol_type = other DNA
                          organism = Escherichia coli
SEQUENCE: 5
atgccgaagt atcggtcagc caccactaca catggccgca acatggcagg cgctcgtgcc    60
ctgtggcgtg ctaccggcat gaccgatgcc gacttcggca agccgatcat cgccgtggtc    120
aactctttca cccagttcgt cccagggcac gttcatctgc gcgacctggg caagctggtg    180
gccgaacaga tcgaggccgc aggtggccgtc gcgaaagagt tcaacaccat cgccgtcgac    240
gatgccatcg ctatgggca cggtggcatg ctgtatagcc tgccgtcccg cgaactgatc     300
gccgatagcg tcgaatatat ggtgaacgcc cattgcgccg atgctatggt gtgcatcagc    360
aactgcgaca agatcacacc gggggatgctg atggccagcc tgcggctgaa catcccggtg    420
atcttcgtga gcggtggccc cgatggaagcc ggcaagacca agctgtcgga tcagatcatc    480
aagctggatc tggtcgacgc catgatccaa ggtgccagtc cgaaggtgag cgactcccag    540
tccgatcagg tggaacggag cgcctgcccg acttgcggct catgcagcgg catgttcacc    600
gccaactcca tgaattgcct gacggaagcc ctgggcctgt cccagccggg taacgggagc    660
ctgttggcga cccatgccga ccgcaagcag ctgttcctga atgccggcaa gcgcatcgtg    720
gaactgacca agcgctatta tgaacagaac gacgaatccg ccctgccccg taatatcgct    780
tcaaaagccg ccttcgaaaa cgccatgacc ctggacatcg ctatgggtgg cagcaccaac    840
accgtgctgc acctgctggc tgccgctcag gaagccgaga tcgacttcac catgtccgac    900
atcgacaagc tgagtcggaa ggtgccgcag ctgtgcaagg tggcaccgtc cacccagaag    960
tatcatatgg aagacgtgca tcgcgcaggc ggtgtgatcg gcatcctgag cgaactggat   1020
cgcgctggcc tgctgaatcg cgatgtgaag aacgtcctgg gcctgaccct gccgcagacc   1080
ctggaacagt acgacgttat gctgacccag gatgatgccg tcaagaatat gttccgcgca   1140
ggccctgccg gcattcgcac cacccaagcc ttcagccagg actgccggtg ggataccctg   1200
gatgacgatc gcgccaatgg ctgcatccgt agcctggaac atgcctattc caaggatgcc   1260
ggtctggccg ttctgtatgg caacttcgcg gaaaacggct gcatcgtcaa gaccgctggc   1320
gtggatgatt cgatcctgaa gttcaccgga ccggccaaag tctacgaaag ccaggacgat   1380
gccgtcgaag ccatcctggg aggcaaggtc gtcgccggag atgtcgtggt gatccgctat   1440
gaaggcccga aaggcggtcc gggcatgcag gagatgctgt atccgacctc cttcttaaag   1500
agcatgggct tgggcaaagc cgtgtgcgct catcaccgatg gccgcttcag tggcggcacc   1560
agcggcctgt ccatcggcca tgtctcgccg gaagccgcca gtggcggcag catcggcctc   1620
atcgaagacg gcgatctgat cgccatcgat ccccgaatc gtggcatcca gctgcaggtg    1680
tccgacgccg aactagccgc acggagggaa gcgcaggatg cccgaggcga caaggcctgg   1740
acccgaaga accgtgaacg tcaggtgtcc ttcgcgcttc gcgcctatgc cagcctggcc   1800
accagcgccg ataagggtgc cgtgcgcgac aagagcaaac tagaggata a             1851

SEQ ID NO: 6              moltype = AA length = 616
FEATURE                   Location/Qualifiers
source                    1..616
                          mol_type = protein
                          organism = Escherichia coli
SEQUENCE: 6
MPKYRSATTT HGRNMAGARA LWRATGMTDA DFGKPIIAVV NSFTQFVPGH VHLRDLGKLV     60
AEQIEAAGGV AKEFNTIAVD DGIAMGHGGM LYSLPSRELI ADSVEYMVNA HCADAMVCIS    120
NCDKITPGML MASLRLNIPV IFVSGGPMEA GKTKLSDQII KLDVDAMIQ GADPKVSDSQ     180
SDQVERSACP TCGSCSGMFT ANSMNCLTEA LGLSQPGNGS LLATHADRKQ LFLNAGKRIV    240
ELTKRYYEQN DESALPRNIA SKAAFENAMT LDIAMGGSTN TVHLLAAAQ EAEIDFTMSD     300
IDKLSRKVPQ LCKVAPSTQK YHMEDVHRAG GVIGILGELD RAGLLNRDVK NVLGLTLPQT    360
LEQYDVMLTQ DDAVKNMFRA GPAGIRTTQA FSQDCRWDTL DDDRANGCIR SLEHAYSKDG    420
GLAVLYGNFA ENGCIVKTAG VDDSILKFTG PAKVYESQDD AVEAILGGKV VAGDVVIRY    480
EGPKGGPGMQ EMLYPTSFLK SMGLGKACAL ITDGRFSGGT SGLSIGHVSP EAASGGSIGL    540
IEDGDLIAID IPNRGIQLQV SDAELAARRE AQDARGDKAW TPKNRERQVS FALRAYASLA    600
TSADKGAVRD KSKLGG                                                  616
```

-continued

```
SEQ ID NO: 7              moltype = DNA  length = 1689
FEATURE                   Location/Qualifiers
source                    1..1689
                          mol_type = other DNA
                          organism = Methylococcus capsulatus
SEQUENCE: 7
atgaccgaca agcaccccg tccccattcg tcccaggtcg tcgacggcat ggagcgggcc    60
ccgagccgcg cgatgctgca cgccgtcggc ttcgccgatg cgacttcgc caaaccgcag   120
atcggcatcg cttccacctg ggcgatggtg acgccgtgca acatgcacat caacaagctc   180
gccgaggacg cagcacgcgg cgtcgacggc ggcggcggca aggcagtgat cttcaacacc   240
atcaccattt ccgacggcat ctcgatgggc accgaaggaa tgaaatactc cctcgtgtcg   300
cgggaagtca tcgccgactc gatcgaaacc gtggtggcct gtcagggtta tgacggcgtg   360
gtcgccatcg gcggctgcga caagaacatg cccggctgc tgatcgccct cgccgcctc   420
aaccgtccgg cggtgttcgt ctatggcggc accatcctgc cgggctgcca cgacggcaag   480
aagctggacg tggtgtcgt gttcgaagcg gtcggcgccc gcgccaacca ccgcatcgac   540
gatgccgaac tgcacgccat cgaatccaat gccatcccg gtccgggctc ctgccggtggc   600
atgtataccg cgaacacgat ggcctccgcc atcgaggcat tagggatgag cctgccggcc   660
agttcggccc aggtggccat ttccgcgcgc aaggaactgg attgcgagcg ggccggcgcc   720
caggtcctca agctcctgga cctgggcc aaaccccgcg acatcatgac caagaaggcg   780
ttcgagaacg ccatcacggt ggtgatcgcc ctgggcggct ccaccaacgc cgtgctgcac   840
ctcctggcca tggccaacgc ctgcggcgt gacctgaagc tcgacgattt caccgatc   900
gggcgcaaag tgccgatgct ggcggatctg aaacccagcg gcagatactc gatgccgaa   960
ctggtggaaa tcggcggcat ccagccgctg atgaagacct tgctgacgc gggactcctg  1020
cacggcgact gcatgaccgt aaccggcaag accctggaag aaaacctggc cgacgcgccc  1080
gactacccgg ccggacaaga catgatccgg tcgctgacca ccccatcaa aggacagc  1140
catctggtga tcctcaaggg caacctggcg ccggaaggcg cggtcgccaa gatcaccggc  1200
aaggaaggac tgagcttcac cggcaccgcc cgcgtattcg actgcgagga agcggcgctc  1260
acggccatcc tcgacggcac gatcgtgaaa ggcgacgtaa tcgtcatccg ctatgaaggc  1320
cccaagtcg gccccggcat gcgcgaaatg ctctcgccga cctcggcgt catgggcaag  1380
ggattgggca aggaggtcgc cctcatcacc gacgccgct tttccggcgg caccacggc  1440
ttcgtggtcg gccacatcac gccggaagcc tacaccggcg gcccctggc gatcgtccgg  1500
gacggcgata ccatcaccat cgacgccgaa acccgcgaat gagcctgca cgtcaccgac  1560
gatgaaatcg gccggcgcct ggcgcagtgg actcaaccgg cgccgcgcta ccaagggc  1620
gtgctggcca aatacgccag gttggtgagc ccggcctcgg aaggcgccgt caccgacgac  1680
ggcctctga                                                         1689

SEQ ID NO: 8              moltype = AA  length = 562
FEATURE                   Location/Qualifiers
source                    1..562
                          mol_type = protein
                          organism = Methylococcus capsulatus
SEQUENCE: 8
MTDKHPRPHS SQVVDGMERA PSRAMLHAVG FADADFAKPQ IGIASTWAMV TPCNMHINKL    60
AEDAARGVDG GGGKAVIFNT ITISDGISMG TEGMKYSLVS REVIADSIET VVACQGYDGV   120
VAIGGCDKNM PGCLIALARL NRPAVFVYGG TILPGCHDGK KLDVVSVFEA VGARANHRID   180
DAELHAIESN AIPGPGSCGG MYTANTMASA IEALGMSLPG SSAQVAISRA KELDCERAGA   240
QVLKLLDLGL KPRDIMTKKA FENAITVVIA LGGSTNAVLH LLAMANACGV DLKLDDFTRI   300
GRKVPMLADL KPSGRYSMAE LVEIGGIQPL MKTLLDAGLL HGDCMTVGK TLEENLADAP   360
DYPAGQDMIR SLDNPIKKDS HLVILKGNLA PEGAVAKITG KEGLSFTGTA RVFDCEEAAL   420
TAILDGTIVK GDVIVIRYEG PKGGPGMREM LSPTSAVMGK GLGKEVALIT DGRFSGGTHG   480
FVVGHITPEA YTGGPLAIVR DGDTITIDAE TRELSLHVTD DEIGRRLAQW TQPAPRYTKG   540
VLAKYARLVS PASEGAVTDD GL                                           562

SEQ ID NO: 9              moltype = DNA  length = 1647
FEATURE                   Location/Qualifiers
source                    1..1647
                          mol_type = other DNA
                          organism = Carnobacterium divergens
SEQUENCE: 9
atgtataccg tgggcgacta tctcctggag cggctctcgg aactgggcat caaagagatc    60
ttcggcgtgc cgggcgacta caacctgaag ttcctggatc acatcgtgga gcatccgaac   120
ctgaagtgga tcggcaacgc gaatgaactc aacgcgcgt atgccgccga cggctacgcc   180
cgcacgaagg gcgtctccgc gctggtgacc accttcgagc tcccgccatc                240
aacggcatcg ccggctcgta tgccgagaaa gtcccggtca tccagatcgt gggcagcccc   300
acgatggcgg tgcagaatgc ccataagctg gtgcatcata cctgggcga tggcaaattc   360
gaccacttcg agaacatgca tgagtccgtc accgaagcca tcggcagcct caccaaggag   420
aacgcggtga ccgagatcga tcgcgtgctg cggggcgccg tgctcaaacg cgccggggtg   480
tatctgaacc tcccgatcga cgtggccgaa atggtcgtgg aaaaaccgtc aaaaaccctg   540
ctgcccaagc aggcgagcct gagcgcccgc gaggtcgaac tcgtgcatga gctggagaag   600
gccctgcagc aggcgaagaa cccggtggtc ctggcgggca acgagctggc gtcgttccac   660
ctcgaaacgt acctcgccga cttcatccac aagttcaacc tccccatcac gaccctcccc   720
ttcggcaagg gcgtcttcaa cgaggaagac gagcattatc tgggcgtcta tgcgggctcg   780
ccgaccgaag aaggcctgcg gaagccgtc gatgcgggcg acctggtgt ggcgctggac   840
gcgaagctga cggactccgc cacctccggc ttctcgtacg acttctccga aaaacagctc   900
ttcagcctgc cgtccgacga gtcatcgtc aagagggaac acctgaaggc catccatctg   960
ccggccgtca tgaaggcgct gacgagcatc gactaccagg gctaccaggg cgacatccag  1020
ccgatggccc ggctgaagag catcaaaccc accaaccagg tgctgaccca cgccacttc  1080
tgggaggcca tcgaaggctt cctggaaaag ggcgacaccg ccgtcgcgga gcagggcacg  1140
```

```
agcttcttcg gcctctcgac cgtgccgctg aagagcgaaa tgtcgttcat cggccagccg   1200
ctgtggggct ccatcggcta tacgttcccg gcgatgctgg gcagccagct cgccaacccg   1260
tccagccggc acctcctgtt catcggcgac ggcagcctgc agctgacgat ccaggagctc   1320
ggcatggccc tccgcgaaaa actcaccccg atcgtgttcg tcatcaacaa taacggctat   1380
acggtcgaac gggaaatcca cggcccgaat gaaatctata acgacatccc gatgtgggac   1440
taccagaaac tcccgctcgt cttcggcggc tccgagcagt cggtcatcac ctataaagtg   1500
acgaccgaac tggaactggc gaacgcgctc aaggcgggcc ggctgacaa caaccgcctg   1560
cagtggatcg aagtggtgat ggaccagacc gatgcgccgg agctcctcat gaagctgggc   1620
aagatcttcg cgaagcagaa tagctga                                       1647

SEQ ID NO: 10            moltype = AA   length = 548
FEATURE                  Location/Qualifiers
source                   1..548
                         mol_type = protein
                         organism = Carnobacterium divergens
SEQUENCE: 10
MYTVGDYLLE RLSELGIKEI FGVPGDYNLK FLDHIVEHPN LKWIGNANEL NAAYAADGYA    60
RTKGVSALVT TFGVGELSAI NGIAGSYAEK VPVIQIVGSP TMAVQNAHKL VHHTLGDGKF   120
DHFENMHESV TEAIGSLTKE NAVTEIDRVL RAAVLKRRPV YLNLPIDVAE MVVEKPSGPL   180
LPKQASLSAR EVELVHELEK ALQQAKNPVV LAGNELASFH LETYLADFIH KFNLPITTLP   240
FGKGVFNEED EHYLGVYAGS PTEEGLRKRV DTADLVVALG AKLTDSATSG FSYDFSEKQL   300
FSLASDEVIV KEEHLEGIHL PAVMKALTSI DYQGYQGDIQ PMARLKSIKP TNQVLTQRHF   360
WEAIEGFLEK GDTAVAEQGT SFFGLSTVPL KSEMSFIGQP LWGSIGYTFP AMLGSQLANP   420
SSRHLLFIGD GSLQLTIQEL GMALREKLTP IVFVINNNGY TVEREIHGPN EIYNDIPMWD   480
YQKLPLVFGG SEQSVITYKV TTELELANAL KAARLDNNRL QWIEVVMDQT DAPELLMKLG   540
KIFAKQNS                                                            548

SEQ ID NO: 11            moltype = DNA   length = 1650
FEATURE                  Location/Qualifiers
source                   1..1650
                         mol_type = other DNA
                         organism = Methylococcus capsulatus
SEQUENCE: 11
atgggcacgg ttgagcctgg cgctatcgga caacatctgc tcgcctgcct ttaccaggcg    60
ggcgtcgggc acatcttcgg cgttcccggc gattacgtgc tgggcttcta tgatctgatg   120
gccaaaggtc ccgtccggca tatcgggacc acgcgggagg acaccgccgc cttcgccgcc   180
gacggctatg cccgctgccg gggcatgggc gccctggcgg tgacttacgg ggtcggtgcg   240
ctcaacaccg tcaacgccgt cgccggcgcc tatgcggaat cctcgccggt ggtggtcatc   300
agcggtgcga cggggggtgcg cgagcaaagg gaagacccgt tgatccacca ccgcttcgtg   360
ccgttccggt tccagcgcga gatattcgaa cggatcacct gcgccgccgt ggtgctggac   420
gatccggtga tcgccttccg gcaggtcgag cgtgcgctcg cagccgcccg tcagcactgc   480
aagccggtgt acatcgagat tcccgccgac cgggtgatgg cgccgggata tccgattcca   540
caggaaaccc cggaaacgcc ttccagcgac gattcggccc tggcggaccg gtcgccgag   600
gccgcggagc tcctgggccg tgcggtgtcg ccggtgatcc ttgcaggcgt cgagttgcac   660
cggcgagggc tccaggacgc cctcgtcggc ctcgtcgagc aggcccgcct gccggtggcg   720
gcgaccttga ccggcaagtc ggtgttcgcc gagcgccatc ccgcctatct gggggtgtac   780
gagggtgcga tgagcacgga aaacgcccgc tacatgcgtg agcagtccga cctcctgctg   840
atgctcgggg tcacgctgaa cgatgtcgac acgggcatct acacggcgcg tctcgatccg   900
cagcgcatcg tccgcgcagc ccagaacgag gtcgtgattc gccatcaccg ctatcccgc   960
gtcctgctcg cggacttcgt cacggccctg gcgcggtccg tcaaggcccg gggcgaggcg  1020
tttccgatgc cggcggggcc ggaaccgtgg gactttccg cggaccgg ccgatgacg  1080
atcgcccggc tggtggagcg gctcgaccgc gccctgacct ccgacatgat cgtagtgtgc  1140
gatgtcggcg actgccgtt cgcagccacc gacctgcgcg tgcacgagcg cagcgaattt  1200
ctggcgtccg ccttctatac ctcgatgggg ttcgcggtgc ccgccgccct cggggcccag  1260
atcgcccgtc cggaccaccg ggcgctgatc ctggtcggcg acggtgcctt ccagatgacc  1320
ggaacggagc tgtcgaccca tgccgtctc ggcctggccg ccatcgtggt ggtgctcgac  1380
aatcgcggtt acagcaccga cgcttcatc ctcgacggag ccttcaacga catcgccgac  1440
tggcgcttcc accggctggg cgaggtgttc ggccccctac agggctacga cgcgcccgac  1500
gaagcggcgt tcgaaaacgc gctcagcgaa gcgctggtca accgaaacat gccgagcctc  1560
atcaacgtcc gtctttcccc cggcgatgcc tcgatagcca tgaagcgtct cgccgggcat  1620
ctgcagtgcc gggtcaaggg cgagggctaa                                   1650

SEQ ID NO: 12            moltype = AA   length = 549
FEATURE                  Location/Qualifiers
source                   1..549
                         mol_type = protein
                         organism = Methylococcus capsulatus
SEQUENCE: 12
MGTVEPGAIG QHLLACLYQA GVGHIFGVPG DYVLGFYDLM AKGPVRHIGT TREDTAAFAA    60
DGYARCRGMG ALAVTYGVGA LNTVNAVAGA YAESSPVVVI SGAPGVREQR EDPLIHHRFG   120
PPRFQREIFE RITCAAVVLD DPVIAFRQVE RALAAARQHC KPVYIEIPAD RVMAPGYPIP   180
QETPETPSSD DSALAEAVAE AAELLGRAVS PVILAGVELH RRGLQDALVG LVEQARLPVA   240
ATLTGKSVFA ERHPAYLGVY EGAMSTENAR YMVEQSDLLL MLGVTLNDVD TGIYTARLDP   300
QRIVRAAQNE VVIRHHRYPR VLLADFVTAL ARSVKARGEA FPMPAGPEPW DFPAPDRPMT   360
IARLVERLDR ALTSDMIVVC DVGDCLFAAT DLRVHERSEF LASAFYTSMG FAVPAALGAQ   420
IARPDHRALI LVGDGAFQMT GTELSTHARL GLAPIVVVLD NRGYSTERFI LDGAFNDIAD   480
WRFHRLGEVF GPLQGYDAPD EAAFENALSE ALVNRNMPSL INVRLSPGDA SIAMKRLAGH   540
LQCRVKGEG                                                           549
```

| SEQ ID NO: 13 | moltype = DNA length = 1083 |
| --- | --- |
| FEATURE | Location/Qualifiers |
| source | 1..1083 |
| | mol_type = other DNA |
| | organism = Saccharomyces cerevisiae |

SEQUENCE: 13
```
atgagctatc cgagaagtt cgagggatc gccatccaga gccacgagga ctggaagaac    60
ccgaaaaaga ccaagtatga tccgaagccc ttctacgatc acgacatcga catcaagatc   120
gaggcctgcg gcgtctgcgg cagcgatatc cattgtgcgg ctggccactg gggcaacatg   180
aagatgccgt tggtcgtcgg ccacgaagtc gtgggaacgg tcgtgaagtt aggcccgaaa   240
agcaacagcg gcttgaaggt gggccagcgc gtgggtgtgg gtgcgcaggt cttcagctgt   300
ctggagtgcg accgttgcaa gaacgacaac gaaccgtact gcaccaagtt cgtcaccacc   360
tactcgcagc cctacgagga cggctacgtc tcgcagggcg gttacgccaa ctatgtccga   420
gtccacgaac acttcgtggt gcccatcccg gaaaatatcc cagccatct ggcggctccc   480
ctgctgtgcg gtggcttgac cgtctacagc cccctcgtcc gcaatggctg cggtcccggc   540
aagaaggtgg gtatcgtggg cctcggcggt ataggctcta tgggcacgct gatctcgaaa   600
gcgatgggcg cagaaacgta cgtgatctcg cgttcctcgc gcaagcgcga ggatgcgatg   660
aagatgggtg cggaccacta catcgccacg tggaggagg gtgactgggg tgagaagtac   720
ttcgacacgt tcgacctcat cgtggtgtgc gcgagttccc tgacggacat cgacttcaat   780
atcatgccca aggcgatgaa ggtcggaggg cgcatcgtct ccatctcgat cccggagcag   840
cacgaaatgc tgtcgctgaa gccctacggc ctgaaagccg tctccattag ctactcggcg   900
ctcggtagta tcaaggagct caaccagctg ttgaagttgg tttccgaaaa ggacatcaag   960
atctgggtgg aaacgctccc ggtgggcgaa gccggtgtgc acgaggcctt tgagcggatg  1020
gagaagggg atgtccgtta tcggtttaca ctcgtcggct acgataaaga gttctcggat  1080
taa                                                                1083
```

| SEQ ID NO: 14 | moltype = AA length = 360 |
| --- | --- |
| FEATURE | Location/Qualifiers |
| source | 1..360 |
| | mol_type = protein |
| | organism = Saccharomyces cerevisiae |

SEQUENCE: 14
```
MSYPEKFEGI AIQSHEDWKN PKKTKYDPKP FYDHDIDIKI EACGVCGSDI HCAAGHWGNM    60
KMPLVVGHEI VGKVVKLGPK SNSGLKVGQR VGVGAQVFSC LECDRCKNDN EPYCTKFVTT   120
YSQPYEDGYV SQGGYANYVR VHEHFVVPIP ENIPSHLAAP LLCGGLTVYS PLVRNGCGPG   180
KKVGIVGLGG IGSMGTLISK AMGAETYVIS RSSRKREDAM KMGADHYIAT LEEGDWGEKY   240
FDTFDLIVVC ASSLTDIDFN IMPKAMKVGG RIVSISIPEQ HEMLSLKPYG LKAVSISYSA   300
LGSIKELNQL LKLVSEKDIK IWVETLPVGE AGVHEAFERM EKGDVRYRFT LVGYDKEFSD   360
```

| SEQ ID NO: 15 | moltype = DNA length = 1164 |
| --- | --- |
| FEATURE | Location/Qualifiers |
| source | 1..1164 |
| | mol_type = other DNA |
| | organism = Escherichia coli |

SEQUENCE: 15
```
atgaacaact ttaatctgca caccccaacc cgcattctgt ttggtaaagg cgcaatcgct    60
ggtttacgcg aacaaattcc tcacgatgct cgcgtattga ttacctacgg cggcggcagc   120
gtgaaaaaaa ccggcgttct cgatcaagtt ctggatgccc tgaaaggcat ggacgtgctc   180
gaatttggcg gtattgagcc aaaccccggct tatgaaacgc tgatgaacgc cgtgaaactg   240
gttcgcgaac agaaagtgac tttcctgctg gcggttggcg gcgttctgt actggacggc   300
accaaattta tcgccgcagc ggctaactat ccggaaaata tcgatccgtg gcacattctg   360
caaacgggcg gtaaagagat taaaagcgcc atcccgatgg gctgtgtgct gacgctgcca   420
gcaaccggtt cagaatccaa cgcaggcgcg tgatctccc gtaaaaccac aggcgacaag   480
caggcgttcc attctgccca tgttcagccg gtatttgccg tgctcgatcc ggtttatacc   540
tacaccctgc cgccgcgtca ggtggctaac ggcgtagtgg acgcctttgt acacaccgtg   600
gaacagtatg ttaccaaacc ggttgatgcc aaaattcagg accgtttcgc gaaaggcatt   660
ttgctgacgc taatcgaaga tggtccgaaa gccctgaaag agccagaaaa ctacgatgtg   720
cgcgccaac tcatgtgggc ggcgactcag cgctgaacg tttgattgg cgctggcgta   780
ccgcaggact gggcaacgca tatgctgggc cacgaactga ctgcgatgca cggtctggat   840
cacgcgcaaa cactggctat cgtcctgcct gcactgtgga tgaaaaacg cgataccaag   900
cgcgctaagc tgctgcaata tgctgaacgc gtctggaaca tcactgaagg ttccgatgat   960
gagcgtattg acgccgcgat tgccgcaacc cgcaatttct ttgagcaatt aggcgtgccg  1020
acccacctct ccgactacgg tctggacggc agctccatcc cggctttgct gaaaaaactg  1080
gaagagcacg gcatgaccca actgggcgaa aatcatgaca ttacgttgga tgtcagcgc  1140
cgtatatacg aagccgcccg ctaa                                         1164
```

| SEQ ID NO: 16 | moltype = AA length = 387 |
| --- | --- |
| FEATURE | Location/Qualifiers |
| source | 1..387 |
| | mol_type = protein |
| | organism = Escherichia coli |

SEQUENCE: 16
```
MNNFNLHTPT RILFGKGAIA GLREQIPHDA RVLITYGGGS VKKTGVLDQV LDALKGMDVL    60
EFGGIEPNPA YETLMNAVKL VREQKVTFLL AVGGGSVLDG TKFIAAANY PENIDPWHIL   120
QTGGKEIKSA IPMGCVLTLP ATGSESNAGA VISRKTTGDK QAFHSAHVQP VFAVLDPVYT   180
YTLPPRQVAN GVVDAFVHTV EQYVTKPVDA KIQDRFAEGI LLTLIEDGPK ALKEPENYDV   240
RANVMWAATQ ALNGLIGAGV PQDWATHMLG HELTAMHGLD HAQTLAIVLP ALWNEKRDTK   300
RAKLLQYAER VWNITEGSDD ERIDAAIAAT RNFFEQLGVP THLSDYGLDG SSIPALLKKL   360
EEHGMTQLGE NHDITLDVSR RIYEAAR                                      387
```

```
SEQ ID NO: 17            moltype = DNA  length = 1149
FEATURE                  Location/Qualifiers
source                   1..1149
                         mol_type = other DNA
                         organism = Escherichia coli
SEQUENCE: 17
atggcgaatc ggatgatcct caatgaaacg gcctggttcg gccgcggcgc ggtcggcgcc    60
ctcaccgatg aggtcaagcg gcggggctac cagaaggccc tgatcgtcac ggataaaacc   120
ctggtgcagt gcggcgtcgt cgccaaggtg accgacaaga tggatgcggc cggcctggcc   180
tgggcgatct acgacggcgt ggtgcccaac cccaccatca ccgtggtgaa ggaaggcctg   240
ggcgtgttcc agaactcggg cgcggattat ctcatcgcga tcggcggcgg cagccccag   300
gacacctgca aggccatcgg catcatctcg aacaaccccg agttcgcgga cgtgcgctcc   360
ctggagggcc tgtcgccgac gaacaagccc tccgtcacgc tcctcgccat ccgacgacg   420
gccggcaccg cggccgaggt gaccatcaat tacgtcatca ccgacgagga aaagcggcgc   480
aagttcgtgt gtgtggaccc ccatgacatc ccccaggtcg ccttcatcga cgccgacatg   540
atggatggca tgccccccgc cctcaaggcc gcgacgggcg tggacgcgct gacgcatgcc   600
atcgaaggct acatcacccg gggcgcctgg gccctgacgg atgccctgca tatcaaggcc   660
atcgaaatca tcgccggcgc cctgcgcggg tccgtggccg gcgacaagga tgcgggcgag   720
gagatggcgc tggccagta cgtggccgga tgggcttct ccaatgtggg cctgggcctg   780
gtgcatggca tggcccatcc gctcggcgcc ttctacaaca gccgcatgg cgtcgcgaac   840
gcgatcctcc tgccgcatgt catgcgctac aatgcgatt tcacgggcga gaaataccgc   900
gatatcgccc gggtcatggg cgtgaaggtc gagggcatgt cgctggaaga ggcgcggaac   960
gccgcggtcg aagccgtctt cgccctgaac cgggatgtgg gcatcccgcc gcacctcgcg  1020
gatgtcggc tccgcaagga agacatcccc gcgctggcgc aggccgccct ggacgatgtg  1080
tgcaccggcg gcaaccccg cgaggcgacg ctggaagaca tcgtcgaact ctaccatacc  1140
gcgtggtga                                                         1149

SEQ ID NO: 18            moltype = AA  length = 382
FEATURE                  Location/Qualifiers
source                   1..382
                         mol_type = protein
                         organism = Escherichia coli
SEQUENCE: 18
MANRMILNET AWFGRGAVGA LTDEVKRRGY QKALIVTDKT LVQCGVVAKV TDKMDAAGLA    60
WAIYDGVVPN PTITVVKEGL GVFQNSGADY LIAIGGGSPQ DTCKAIGIIS NNPEFADVRS   120
LEGLSPTNKP SVPILAIPTT AGTAAEVTIN YVITDEEKRR KFVCVDPHDI PQVAFIDADM   180
MDGMPPALKA ATGVDALTHA IEGYITRGAW ALTDALHIKA IEIIAGALRG SVAGDKDAGE   240
EMALGQYVAG MGFSNVGLGL VHGMAHPLGA FYNTPHGVAN AILLPHVMRY NADFTGEKYR   300
DIARVMGVKV EGMSLEEARN AAVEAVFALN RDVGIPPHLR DVGVRKEDIP ALAQAALDDV   360
CTGGNPREAT LEDIVELYHT AW                                           382

SEQ ID NO: 19            moltype = DNA  length = 1254
FEATURE                  Location/Qualifiers
source                   1..1254
                         mol_type = other DNA
                         organism = Escherichia coli
SEQUENCE: 19
atgtactacc tgaagaacac caatttctgg atgttcggcc tgttcttctt cttctatttc    60
ttcatcatgg cgcctactt cccgttcttc ccgatctggc tgcacgatat caatcacatc   120
agcaagtcgg ataccggcat catcttcgcc gccatcagcc tgttcagcct gctgttccag   180
ccgctcttcg gcctcctgag cgacaagctc ggcctgcgga agtacctgct gtggatcatc   240
acgggcatgc tggtgatgtt cgcccccttc ttcatcttca cttcggccc gctcctgcag   300
tacaacatcc tcgtgggcag catcgtgggc ggcatctacc tgggcttctg cttcaatgcg   360
ggcgcccccg ccgtcgaggc cttcatcgag aaagtcgagc ggcgctccaa cttcgagttc   420
ggccgggccc ggatgttcgg ctgcgtcggc tgggcgctgt gcgcgagcat cgtgggcatc   480
atgttcacga tcaacaacca gttcgtgttc tggctgggct ccggctgttg tctcatcctg   540
gccgtcctgc tgttcttcgc caagacggac gccccgagct ccgcgaccgt cgccaacgcg   600
gtcggcgcca atcactccgc gttctcgctg aagctcgcg tggagctgta cgccagccag   660
aagctgtggt tcctgagcct ctacgctgatc ggcgtctcgt gcacgtacga tgtcttcgat   720
cagcagttcg ccaacttctt cacctcgttc ttcgccaccg gcgagcaggg cacgcgcgtc   780
ttcggctatg tgacgacgat gggcgagctg ctgaacgcca gcatcatgtt cttcgccccg   840
ctcatcatca accgcatcgg cggcaaaaac gcgctgctgc tcgccggcac catcatgtcg   900
gtgcggatca tcggctcctc cttcgccacc tcggccctgg aagtcgtcat cctgaagacc  960
ctgcacatgt tcgaagtccc gttcctgctc gtcggctgtt tcaagtacat cacctcccag  1020
ttcgaggtgc gcttcagcgc cacgatctac ctggtgtgct tctgcttctt caagcagctg  1080
gcgatgatct tcatgtccgt gctggcgggc aatatgtatg agtcgatcgg cttccagggc  1140
gcgtatctgg tcctgggcct cgtggccctg gcttcaccc tgatctccgt gttcacgctg  1200
agcggcccgg gcccgctgtc gctgctgcgg cgccaggtga atgaggtcgc ctga         1254

SEQ ID NO: 20            moltype = AA  length = 417
FEATURE                  Location/Qualifiers
source                   1..417
                         mol_type = protein
                         organism = Escherichia coli
SEQUENCE: 20
MYYLKNTNFW MFGLFFFFYF FIMGAYFPFF PIWLHDINHI SKSDTGIIFA AISLFSLLFQ    60
PLFGLLSDKL GLRKYLLWII TGMLVMFAPF FIFIFGPLLQ YNILVGSIVG GIYLGFCFNA   120
GAPAVEAFIE KVSRRSNFEF GRARMFGCVG WALCASIVGI MFTINNQFVF WLGSGCCLIL   180
```

```
AVLLFFAKTD APSSATVANA VGANHSAFSL KLALELFRQP KLWFLSLYVI GVSCTYDVFD    240
QQFANFFTSF FATGEQGTRV FGYVTTMGEL LNASIMFFAP LIINRIGGKN ALLLAGTIMS    300
VRIIGSSFAT SALEVVILKT LHMFEVPFLL VGCFKYITSQ FEVRFSATIY LVCFCFFKQL    360
AMIFMSVLAG NMYESIGFQG AYLVLGLVAL GFTLISVFTL SGPGPLSLLR RQVNEVA       417

SEQ ID NO: 21              moltype = DNA   length = 879
FEATURE                    Location/Qualifiers
source                     1..879
                           mol_type = other DNA
                           organism = Escherichia coli
SEQUENCE: 21
atggccgagg cgcagaacga tccgctcctg ccgggctata gcttcaatgc ccatctggtc    60
gcgggcctga ccccgatcga ggcgaatggc tacctggact tcttcatcga ccgcccgctg   120
ggcatgaagg gctacatcct caatctgacc atcggggcgc agggcgtcgt gaagaatcag   180
ggccgcgagt tcgtgtgccg ccccggcgac atcctcctgt tcccgccggg cgaaatccat   240
cattatggcc gccatccgga agcccgcgag tggtatcatc agtgggtcta tttccggccc   300
cgcgcgtatt ggcatgagtg gctgaactgg ccctcgatct tcgccaacac cggcttcttc   360
cggccggacg aggcccacca gcccattttc tccgacctgt tcggccagat catcaacgcc   420
ggccagggcg aaggccgcta ttcggaactg ctggccatca acctgctcga acagctcctc   480
ctgcggcgga tggaagccat caacgaatcc ctgcatcccc cgatggacaa ccgcgtgcgg   540
gaagcgtgcc agtacatcag cgaccacctg gcggactcga atttcgatat cgcgtccgtg   600
gcccagcatg tctgcctgag cccgagccgg ctgtcccatc tcttccgcca gcagctgggc   660
atctccgtgc tctcgtggcg cgaagaccag cggatctccc aggccaagct gctgctctcc   720
accacccgca tgcccatcgc cacgtcggc gcaacgtcg gcttcgacga ccagctgtat   780
ttctcgcggg tgttcaagaa ggtgtacggg gcctcgccct cggagttccg cgccggctgc   840
gaggagaaag tcaacgacgt ggccgtcaaa ctcagctga                          879

SEQ ID NO: 22              moltype = AA    length = 292
FEATURE                    Location/Qualifiers
source                     1..292
                           mol_type = protein
                           organism = Escherichia coli
SEQUENCE: 22
MAEAQNDPLL PGYSFNAHLV AGLTPIEANG YLDFFIDRPL GMKGYILNLT IRGQGVVKNQ    60
GREFVCRPGD ILLFPPGEIH HYGRHPEARE WYHQWVYFRP RAYWHEWLNW PSIFANTGFF   120
RPDEAHQPHF SDLFGQIINA GQGEGRYSEL LAINLLEQLL LRRMEAINES LHPPMDNRVR   180
EACQYISDHL ADSNFDIASV AQHVCLSPSR LSHLFRQQLG ISVLSWREDQ RISQAKLLLS   240
TTRMPIATVG RNVGFDDQLY FSRVFKKCTG ASPSEFRAGC EEKVNDVAVK LS           292

SEQ ID NO: 23              moltype = AA    length = 389
FEATURE                    Location/Qualifiers
source                     1..389
                           mol_type = protein
                           organism = Clostridium acetobutylicum
SEQUENCE: 23
MLSFDYSIPT KVFFGKGKID VIGEEIKKYG SRVLIVYGGG SIKRNGIYDR ATAILKENNI    60
AFYELSGVEP NPRITTVKKG IEICRENNVD LVLAIGGGSA IDCSKVIAAG VYYDGDTWDM   120
VKDPSKITKV LPIASILTLS ATGSEMDQIA VISNMETNEK LGVGHDDMRP KFSVLDPTYT   180
FTVPKNQTAA GTADIMSHTF ESYFSGVEGA YVQDGIAEAI LRTCIKYGKI AMEKTDDYEA   240
RANLMWASSL AINGLLSLGK DRKWSCHPME HELSAYDIT HGVGLAILTP NWMEYILNDD   300
TLHKFVSYGI NVWGIDKNKD NYEIAREAIK NTREYFNSLG IPSKLREVGI GKDKLELMAK   360
QAVRNSGGTI GSLRPINAED VLEIFKKSY                                     389

SEQ ID NO: 24              moltype = DNA   length = 1170
FEATURE                    Location/Qualifiers
source                     1..1170
                           mol_type = other DNA
                           organism = Clostridium acetobutylicum
SEQUENCE: 24
atgctctcgt tcgactacag catccccacc aaggtcttct tcggcaaagg caagatcgac    60
gtgatcggcg aagagatcaa aaagtacggc tcccgcgtgc tgatcgtcta cggcggcggc   120
tcgatcaaac gcaacggcat ctatgaccgg ccacggcga tcctgaagga aaacaacatc   180
gccttctacg agctgtccgg cgtggagccc aacccgcgga tcaccacggt caagaagggc   240
atcgaaatct gtcgcgaaaa caacgtcgac ctggtgctga tcggcggcgg cggcagcgcg   300
atcgattgct ccaaggtgat cgccgccggc gtctattatg acggcgacac ctgggacatg   360
gtcaaagacc ccagcaagat caccaaagtg ctgccgatcg cctccatcct caccctgagc   420
gcgacgggca gcgaaatgga tcagatcgcc gtgatctcga catggagac gaacgaaaag   480
ctcggcgtgg gccacgacga tatgcggccg aagttctcgg tcctcgatcc gacgtataacc   540
ttcacggtgc cgaagaacca gaccgccgcc ggcacggcgg acatcatgtc gcataccttc   600
gaatcgtatt tcagcggcgt cgaaggcgcg tatgtccagg acggcatcgc ggaagccatc   660
ctccgcacct gcatcaagta tggcaagatc gcgatgaaaa agaccgacga ctacgaggcc   720
cgcgcgaatc tgatgtgggc ctcgtccctg gccatcaatg gcctgctgag cctcggcaag   780
gatcggaaat ggtcgtgcca cccgatggag cacgagctga cgcctatta cgacatcacc   840
cacggcgtgg gcctggccat cctgaccccc aactggatgg aatatatcct gaacgacgac   900
acgctgcata aattcgtgtc gtacggcatc aacgtctggg gcatcgataa gaacaaggac   960
aactacgaga tcgcccgcga agccatcaaa aatacgcggg agtacttcaa cagcctgggc  1020
atcccgtcga agctgcgcga ggtcggcatc ggcaaagata aactggagct gatggccaag  1080
caggcggtgc gcaactcggg cggcacgatc ggcagcctcc gccccatcaa cgcggaggat  1140
gtgctggaga tcttcaagaa gagctattga                                    1170
```

```
SEQ ID NO: 25           moltype = AA   length = 390
FEATURE                 Location/Qualifiers
source                  1..390
                        mol_type = protein
                        organism = Clostridium acetobutylicum
SEQUENCE: 25
MVDFEYSIPT RIFFGKDKIN VLGRELKKYG SKVLIVYGGG SIKRNGIYDK AVSILEKNSI    60
KFYELAGVEP NPRVTTVEKG VKICRENGVE VVLAIGGGSA IDCAKVIAAA CEYDGNPWDI   120
VLDGSKIKRV LPIASILTIA ATGSEMDTWA VINNMDTNEK LIAAHPDMAP KFSILDPTYT   180
YTVPTNQTAA GTADIMSHIF EVYFSNTKTA YLQDRMAEAL LRTCIKYGGI ALEKPDDYEA   240
RANLMWASSL AINGLLTYGK DTNWSVHLME HELSAYYDIT HGVGLAILTP NWMEYILNND   300
TVYKFVEYGV NVWGIDKEKN HYDIAHQAIQ KTRDYFVNVL GLPSRLRDVG IEEEKLDIMA   360
KESVKLTGGT IGNLRPVNAS EVLQIFKKSV                                   390

SEQ ID NO: 26           moltype = DNA  length = 1173
FEATURE                 Location/Qualifiers
source                  1..1173
                        mol_type = other DNA
                        organism = Clostridium acetobutylicum
SEQUENCE: 26
atggtcgatt tcgagtattc gatcccgacg cggatcttct tcggcaagga caaaatcaac    60
gtcctgggcc gcgaactcaa gaaatacggc agcaaagtgc tgatcgtcta cggcggcggc   120
tcgatcaagc ggaacggcat ctacgataag gccgtgtcga tcctggaaaa gaatagcatc   180
aagttctatg aactggcggg cgtcgaaccg aaccccgcg tgaccaccgt cgagaagggc    240
gtcaagatct gccgggaaaa cggcgtggaa gtcgtgctgg cgatcggcgg cggctccggc   300
atcgactgcg ccaaggtgat cgcggcggcc tgcgagtacg acggcaatcc ctggacatc    360
gtcctggacg gctccaagat caagcgcgtc ctcccgatcg ccagcatcct gaccatcgcc   420
gcgacgggct cggaaatgga cacctgggcc gtcatcaaca atatggatac caacgaaaag   480
ctcatcgcgg cccacccgga catggccccg aagttctcga tcctcgatcc cacctacacc   540
tacaccgtcc cgacgaacca gaccgcggcc ggcaccgccg atatcatgtc ccatatcttc   600
gaggtgtatt tctccaacac caagacgcgc tacctccagg accgcatggc ggaggcgctc   660
ctccggacct gcatcaagta cggcggcatc gccctggaga gccggacga ctatgaggcc    720
cgcgccaacc tcatgtgggc gtcctccctg gcgatcaatg gcctgctgac gtacggcaaa   780
gacacgaact ggtccgtgca tctcatggag cacgagctgt cggcctatta tgatatcacc   840
cacggcgtgg gcctcgcgat cctcacgccc aactggatgg aatacatcct caacaatgat   900
acggtgtaca agttcgtcga gtacggcgtc aatgtctggg gcatcgataa ggaaaaaaat   960
cactatgaca tcgcgcatca ggcgatccag aagacgcgcg actacttcgt caacgtgctc  1020
ggcctgccct cccgcctccg cgacgtgggc atcgaagagg aaaagctgga tatcatggcc  1080
aaggagagcg tgaagctgac cggcggcacc atcggcaacc tgcgccccgt gaacgcctcc  1140
gaggtcctcc agatcttcaa aaagtcggtg tga                               1173

SEQ ID NO: 27           moltype = AA   length = 336
FEATURE                 Location/Qualifiers
source                  1..336
                        mol_type = protein
                        organism = Escherichia coli
SEQUENCE: 27
MKAAVVTKDH HVDVTYKTLR SLKHGEALLK MECCGVCHTD LHVKNGDFGD KTGVILGHEG    60
IGVVAEVGPG VTSLKPGDRA SVAWFYEGCG HCEYCNSGNE TLCRSVKNAG YSVDGGMAEE   120
CIVVADYAVK VPDGLDSAAA SSITCAGVTT YKAVKLSKIR PGQWIAIYGL GGLGNLALQY   180
AKNVFNAKVI AIDVNDEQLK LATEMGADLA INSHTEDAAK IVQEKTGGAH AAVVTAVAKA   240
AFNSAVDAVR AGGRVVAVGL PPESMSLDIP RLVLDGIEVV GSLVGTRQDL TEAFQFAAEG   300
KVVPKVALRP LADINTIFTE MEEGKIRGRM VIDFRH                            336

SEQ ID NO: 28           moltype = DNA  length = 1011
FEATURE                 Location/Qualifiers
source                  1..1011
                        mol_type = other DNA
                        organism = Escherichia coli
SEQUENCE: 28
atgaaggccg cggtcgtgac caaggaccat cacgtcgatg tcacgtacaa gacgctgcgc    60
tccctgaagc atggcgaagc gctgctgaag atggagtgct gtggcgtctg ccacacggac   120
ctgcatgtga aaaacggcga cttcggcgac aagaccggca tcatcctcgg ccacgaaggc   180
atcggcgtcg tggccgaggt gggccccggc gtcacgtccc tcaagccggg cgatcggc    240
tcggtggcgt ggttctatga gggctgcggc cactgcgaat attgcaactc gggcaacgaa   300
accctgtgtc ggtcggtgaa aaatgcgggc tactccgtcg acggcggcat ggcggaagaa   360
tgtatcgtgg tggccgacta cgccgtgaag gtccccgatg gcctggacag cgccgccgcc   420
tcgtccatca cctgcgccgg cgtcaccacc tataaggcgg tgaaactgag caaaatccgt   480
ccgggccagt ggatcgccat ctacggcctg ggcggcctgg gcaacctggc cctgcagtac   540
gccaagaatg tcttcaacgc cgaaggtcatc gccatcgatg tcaatgatga acagctgaag   600
ctggccacgg agatgggcgc ggacctggcg atcaacagcc acaccgaaga cgcggccaag   660
atcgtccagg agaagaccgg cggcgcccat gccgccgtgt gaccgccgt ggccaaagcc    720
gccttcaatt ccgcggtcga cgccgtccgg gccggcggcc gtgtcgtcgc cgtcggtctg   780
ccgccggagt cgatgtccct cgacatcccg cgcctggtgc tggatggcat cgaggtggtg   840
ggctccctgg tcggcacccg ccaggacctg accgaagcct tccagttcgc cgccgaaggc   900
aaggtcgtgc ccaaggtcgc cctgcggccc ctcgccgaca tcaacaccat cttcacggag   960
atggaggaag gcaagatccg gggccgcatg gtcatcgatt tccgccactg a            1011
```

```
SEQ ID NO: 29            moltype = AA   length = 339
FEATURE                  Location/Qualifiers
source                   1..339
                         mol_type = protein
                         organism = Escherichia coli
SEQUENCE: 29
MSMIKSYAAK EAGGELEVYE YDPGELRPQD VEVQVDYCGI CHSDLSMIDN EWGFSQYPLV    60
AGHEVIGRVV ALGSAAQDKG LQVGQRVGIG WTARSCGHCD ACISGNQINC EQGAVPTIMN   120
RGGFAEKLRA DWQWVIPLPE NIDIESAGPL LCGGITVFKP LLMHHITATS RVGVIGIGGL   180
GHIAIKLLHA MGCEVTAFSS NPAKEQEVLA MGADKVVNSR DPQALKALAG QFDLIINTVN   240
VSLDWQPYFE ALTYGGNFHT VGAVLTPLSV PAFTLIAGDR SVSGSATGTP YELRKLMRFA   300
ARSKVAPTTE LFPMSKINDA IQHVRDGKAR YRVVLKADF                         339

SEQ ID NO: 30            moltype = DNA   length = 1020
FEATURE                  Location/Qualifiers
source                   1..1020
                         mol_type = other DNA
                         organism = Escherichia coli
SEQUENCE: 30
atgtccatga tcaaaagcta cgccgcgaaa gaggcgggcg gcgagctgga ggtgtatgag    60
tatgacccgg gcgagctgcg gccccaggac gtggaagtgc aggtcgacta ctgcggcatc   120
tgccattcgg acctctcgat gatcgataac gagtggggcg tcagccagta cccctggtg   180
gccggccacg aggtgatcgg ccgcgtggtc gccctgggct cggccgcgca ggataaaggc   240
ctgcaggtcg gccagcgcgt cggcatcggc tggacggccc gcagctgcgg ccattgcgat   300
gcctgcatca gcggcaatca gatcaattgc gaacaggggcg cggtcccgac catcatgaac   360
cggggcggct tcgccgaaaa gctgcgggcc gattggcagt gggtgatccc gctgccggag   420
aacatcgata tcgagtcggc cggccccctg ctgtgcggcg gcatcaccgt cttcaagccg   480
ctcctgatgc atcatatcac ggcgaccagc cgggtcggcg tgatcggcat cggcggcctc   540
ggccacatcg cgatcaaact gctgcacgcg atgggctgcg aggtcaccgc gttctcctcg   600
aacccgcca aggagcagga agtgctggcg atgggcgccg ataaagtcgt gaactcgcgc   660
gaccccagg ccctcaaagc cctggccggc cagttcgatc tcatcatcaa cacggtgaac   720
gtgtcgctgg actggcagcc ctacttcgaa gccctgacct atggcggcaa cttccatacc   780
gtcggcgccg tgctgacccc gctgtccgtc ccggccttca ccctgatcgc cggcgaccgc   840
agcgtgtccg gcagcgccac cggcacgccg tatgagctgc gcaagctgat gcgcttcgcc   900
gcccgcagca aggtcgcccc gaccaccgag ctgttcccca tgtccaagat caatgacgcg   960
atccagcatg tccgggacgg caaggcccgc tatcgcgtcg tcctcaaggc ggacttctga  1020

SEQ ID NO: 31            moltype = AA   length = 382
FEATURE                  Location/Qualifiers
source                   1..382
                         mol_type = protein
                         organism = Escherichia coli
SEQUENCE: 31
MANRMILNET AWFGRGAVGA LTDEVKRRGY QKALIVTDKT LVQCGVVAKV TDKMDAAGLA    60
WAIYDGVVPN PTITVVKEGL GVFQNSGADY LIAIGGGSPQ DTCKAIGIIS NNPEFADVRS   120
LEGLSPTNKP SVPILAIPTT AGTAAEVTIN YVITDEEKRR KFVCVDPHDI PQVAFIDADM   180
MDGMPPALKA ATGVDALTHA IEGYITRGAW ALTDALHIKA IEIIAGALRG SVAGDKDAGE   240
EMALGQYVAG MGFSNVGLGL VHGMAHPLGA FYNTPHGVAN AILLPHVMRY NADFTGEKYR   300
DIARVMGVKV EGMSLEEARN AAVEAVFALN RDVGIPPHLR DVGVRKEDIP ALAQAALDDV   360
CTGGNPREAT LEDIVELYHT AW                                           382

SEQ ID NO: 32            moltype = DNA   length = 1149
FEATURE                  Location/Qualifiers
source                   1..1149
                         mol_type = other DNA
                         organism = Escherichia coli
SEQUENCE: 32
atggcgaatc ggatgatcct caatgaaacg gcctggttcg gccgcggcgc ggtcggcgcc    60
ctcaccgatg aggtcaagcg gcggggctac cagaaggccc tgatcgtcac ggataaaacc   120
ctggtgcagt gcggcgtcgt cgccaaggtg accgacaaga tggatgcggc cggcctggcc   180
tgggcgatct acgacggcgt ggtgcccaac cccaccatca ccgtggtgaa ggaaggcctg   240
ggcgtgttcc agaactcggg cgcggattat ctcatcgcga tcggcggcgg cagccccag   300
gacacctgca aggccatcgg catcatctcg aacaaccccg agttcgcgga cgtgcgctcc   360
ctggagggcc tgtcgccgac gaacaagccc tccgtcccga tcctcgccat cccgacgacg   420
gccggcaccg cggccgaggt gaccatcaat tacgtcatca ccgacgagga aaagcggcgc   480
aagttcgtgt gtgtggaccc ccatgacatc ccccaggtcg cctttatcga cgccgacatg   540
atggatggca tgcccccgc cctcaaggcc gcgacgggcg tggacgcgct gacgcatgcc   600
atcgaaggct acatcacccg gggcgcctgg gcctgacgg atgcccgtgca tcaaggcgc   660
atcgaaatca tcgccggcgc cctgcgcggg tccgtgccgg cgacaaggga tgcggggcgag   720
gagatggcgc tgggccagta cgtggccggc atgggcttct ccaatgtggg cctgggcctg   780
gtgcatggca tggcccatcc gctcggcgcc ttctacaaca cgccgcatgg cgtcgcgaac   840
gcgatcctcc tgccgcatgt catgcgctac aatgcggact tcacgggcga aaataccgc   900
gatatcgccc gggtcatggg cgtgaaggtc gagggcatgt cgctcgaaga ggcgcggaac   960
gccgtggaag cggtcttt cgccctgaac cgggatgtgg gcatcccgcc gcacctgcgc  1020
gatgtcggcg tccgcaagga agacatcccc gcgctggcgc aggccgccct ggacgatgtg  1080
tgcaccggcg gcaaccccgc cgaggcgacg ctggaagaca tcgtcgaact ctaccatacc  1140
gcgtggtga                                                          1149

SEQ ID NO: 33            moltype = AA   length = 339
```

```
FEATURE                 Location/Qualifiers
source                  1..339
                        mol_type = protein
                        organism = Escherichia coli
SEQUENCE: 33
MSMIKSYAAK  EAGGELEVYE  YDPGELRPQD  VEVQVDYCGI  CHSDLSMIDN  EWGFSQYPLV   60
AGHEVIGRVV  ALGSAAQDKG  LQVGQRVGIG  WTARSCGHCD  ACISGNQINC  EQGAVPTIMN  120
RGGFAEKLRA  DWQWVIPLPE  NIDIESAGPL  LCGGITVFKP  LLMHHITATS  RVGVIGIGGL  180
GHIAIKLLHA  MGCEVTAFSS  NPAKEQEVLA  MGADKVVNSR  DPQALKALAG  QPDLIINTVN  240
VSLDWQPYFE  ALTYGGNFHT  VGAVLTPLSV  PAFTLIAGDR  SVSGSATGTP  YELRKLMRFA  300
ARSKVAPTTE  LFPMSKINDA  IQHVRDGKAR  YRVVLKADF                           339

SEQ ID NO: 34           moltype = DNA   length = 1020
FEATURE                 Location/Qualifiers
source                  1..1020
                        mol_type = other DNA
                        organism = Escherichia coli
SEQUENCE: 34
atgtccatga tcaaaagcta tgccgcgaag gaagccggcg gcgagctgga ggtctacgag   60
tacgaccccg gcgaactccg cccgcaggac gtggaggtgc aggtggatta ctgcggcatc  120
tgccacagcg acctgtcgat gatcgacaac gagtgggggct tcagccagta cccgctggtg  180
gccggcatg aagtgatcgg ccgcgtcgtc gcgctgggct ccgcggccca ggataaaggc  240
ctgcaggtcg gccagcgcgt gggcatcggc tggaccgccc ggtcgtgcgg ccactgcgac  300
gcctgcatct cgggcaacca gatcaattgc gagcagggcg ccgtccccac catcatgaac  360
cgcggcggct tcgcggagaa gctccgcgcg gactggcagt gggtgatccc gctgccggaa  420
aatatcgata tcgaatccgc cggccccctg ctgtgcgggg gcatcaccgt cttcaagccg  480
ctcctgatgc atcatatcac cgccacctcc cgcgtcggcg tcatcggcat cggcggcctc  540
ggccacatcg ccatcaaact cctgcatgcg atgggctgtg aagtgaccgc cttcagcagc  600
aaccccgcga agagcagga gtgctcgcg atgggcgcgg acaaggtcgt gaacagccgc  660
gatccccagg ccctgaaagc gctggccggc cagttcgatc tcatcatcaa caccgtcaac  720
gtctcgctcg actggcagcc gtacttcgaa gcgctgacgt acggcggcaa cttccacacc  780
gtgggcgcgg tcctgacgcc cctgtcggtg ccggcgttca ccctgatcgc cggcgatcgg  840
agcgtgtcgg gctccgccac cggcaccccg tatgagctgc ggaagctgat gcggttcgcg  900
gcccgcagca aggtcgcccc gacgaccgag ctgttcccca tgagcaagat caacgacgcc  960
atccagcatg tgcgcgatgg caaagcccgg tatcgcgtgg tcctgaaagc ggatttctga 1020

SEQ ID NO: 35           moltype = AA   length = 387
FEATURE                 Location/Qualifiers
source                  1..387
                        mol_type = protein
                        organism = Escherichia coli
SEQUENCE: 35
MNNFNLHTPT  RILFGKGAIA  GLREQIPHDA  RVLITYGGGS  VKKTGVLDQV  LDALKGMDVL   60
EFGGIEPNPA  YETLMNAVKL  VREQKVTFLL  AVGGGSVLDG  TKFIAAAANY  PENIDPWHIL  120
QTGGKEIKSA  IPMGCVLTLP  ATGSESNAGA  VISRKTTGDK  QAFHSAHVQP  VFAVLDPVYT  180
YTLPPRQVAN  GVVDAFVHTV  EQYVTKPVDA  KIQDRFAEGI  LLTLIEDGPK  ALKEPENYDV  240
RANVMWAATQ  ALNGLIGAGV  PQDWATHMLG  HELTAMHGLD  HAQTLAIVLP  ALWNEKRDTK  300
RAKLLQYAER  VWNITEGSDD  ERIDAAIAAT  RNFFEQLGVP  THLSDYGLDG  SSIPALLKKL  360
EEHGMTQLGE  NHDITLDVSR  RIYEAAR                                        387

SEQ ID NO: 36           moltype = DNA   length = 1164
FEATURE                 Location/Qualifiers
source                  1..1164
                        mol_type = other DNA
                        organism = Escherichia coli
SEQUENCE: 36
atgaacaatt tcaacctcca caccccgacc cgcatcctct tcggcaaggg cgccatcgcc   60
ggcctgcgcg agcagatccc gcacgacgcc cgcgtcctca tcacctatgg cggcggctcc  120
gtcaaaaaga ccggcgtgct cgatcaggtc ctggacgccc tgaagggcat ggacgtgctg  180
gagttcggcg gcatcgagcc gaaccccgcc tacgagacgc tgatgaatgc ggtgaagctg  240
gtgcgcgagc agaaggtcac gttcctgctc gcggtcggcg gcggctcggt gctggacggc  300
accaagttca tcgccgccgc ggcgaattat cccgagaaca tcgatccctg gcacatcctg  360
cagacgggcg gcaaggagat caagtcggcc atcccgatgg gctgcgtcct gaccctcccc  420
gccaccggct cggagagcaa cgccggcgcc gtgatctcgc gcaaaaccac cggcgacaaa  480
caggcgttcc actccgccca tgtgcagccg gtcttcgcgg tgctggaccc cgtctacacg  540
tacacccctcc cgccgcggca ggtcgccaac ggcgtggtcg atgccttcgt gcatacggtg  600
gagcagtacg tcaccaagcc ggtggatgcc aagatccagg accgcttcgc ggagggcatc  660
ctgctgacgc tgatcgagga cggcccgaaa gccctgaagg aaccggaaaa ctacgatgtg  720
cgggcgaacg tcatgtgggc cgcgacccag gccctgaacg gcctgatcgg cgccggcgtg  780
ccccaggatt gggcgacgca catgctgggc cacgaactca ccgcgatgca cggcctcgac  840
cacgcccaga cgctcgccat cgtcctgccg gccctgtgga tgagaagcg ggacaccaag  900
cgggcgaagc tcctgcagta tgccgaacgg gtgtggaaca tcaccgaagg ctcggacgat  960
gaacgcatcg atgccgccat cgcggccacg cggaacttct tcgagcagct gggcgtcccg 1020
acccatctct ccgactcgg cctgatggc tcctccatcc ccgcgctgct gaaaaaactg 1080
gaagaacacg gcatgaccca gctgggcgaa aaccacgaca tcaccctgga tgtctcgcgc 1140
cgcatctacg aagccgcccg gtga                                         1164

SEQ ID NO: 37           moltype = AA   length = 336
FEATURE                 Location/Qualifiers
```

```
source                          1..336
                                mol_type = protein
                                organism = Bacillus stearothermophilus
SEQUENCE: 37
MRAAVVTKDH KVSIEDKKLR ALKPGEALVQ TEYCGVCHTD LHVKNADFGD VTGVTLGHEG     60
IGKVIEVAED VESLKIGDRV SIAWMFESCG RCEYCTTGRE TLCRSVKNAG YTVDGAMAEQ    120
VIVTADYAVK VPEKLDPAAA SSITCAGVTT YKAVKVSNVK PGQWLGVFGI GGLGNLALQY    180
AKNVMGAKIV AFDINDDKLA FAKELGADAI INSKDVDPVA EVMKLTDNKG LDATVVTSVA    240
KTPFNQAVDV VKAGARVVAV GLPVDKMNLD IPRLVLDGIE VVGSLVGTRQ DLREAFEFAA    300
ENKVTPKVQL RKLEEINDIF EEMENGTITG RMVIKF                             336

SEQ ID NO: 38                   moltype = DNA   length = 1011
FEATURE                         Location/Qualifiers
source                          1..1011
                                mol_type = other DNA
                                organism = Bacillus stearothermophilus
SEQUENCE: 38
atgcgggcgg ccgtggtgac caaggaccac aaggtcagca tcgaagataa gaaactgcgg     60
gccctgaaac ccggcgaggc gctggtgcag accgaatatt gtggcgtgtg tcatacggat    120
ctccatgtca aaaacgccga tttcggcgat gtgaccggcg tgacgctcgg ccatgagggc    180
atcggcaagg tgatcgaagt cgccgaagac gtggaaagcc tcaagatcgg cgatcgcgtg    240
tccatcgcct ggatgttcga gtcgtgtggc cgctgcgagt attgcacgac cggccgggaa    300
accctgtgtc ggagcgtcaa gaatgccggc tacaccgtgg acggcgcgat ggccgaacag    360
gtcatcgtga cggccgacta tgcggtcaag gtcccggaaa agctggaccc ggccgcggcg    420
tcgtcgatca cctgcgcggg cgtcaccacc tataaggccg tcaaggtgag caatgtcaaa    480
ccgggccagt ggctgggcgt cttcggcatc ggcggcctgg gcaacctggc cctgcagtac    540
gcgaagaatg tcatgggcgc caaaatcgtg gccttcgata tcaacgatga caagctggcg    600
ttcgccaaag aactcggcgc ggatgcgatc atcaactcga aggacgtgga cccggtggcc    660
gaggtgatga aactgacgga caacaagggc ctggacgcga cggtcgtcac cagcgtcgcg    720
aagacccccct tcaatcaggc ggtcgacgtg gtcaaggcgg gcgcccgcgt ggtggtcgtg    780
ggcctgccgg tcgacaaaat gaacctggat atcccgcgcc tcgtgctgga cggcatcgag    840
gtggtgggca gctggtcgg cacccgccag gacctgcggg aggccttcga gttcgcggcc    900
gagaataaag tgacgcccaa ggtccagctc cggaagctcg aagaaatcaa cgatatcttc    960
gaggagatgg aaaacggcac gatcaccggc cggatggtca tcaagttctg a            1011

SEQ ID NO: 39                   moltype = AA    length = 339
FEATURE                         Location/Qualifiers
source                          1..339
                                mol_type = protein
                                organism = Bacillus stearothermophilus
SEQUENCE: 39
MKAAVVNEFK KALEIKEVER PKLEEGEVLV KIEACGVCHT DLHAAHGDWP IKPKLPLIPG     60
HEGVGIVVEV AKGVKSIKVG DRVGIPWLYS ACGECEYCLT GQETLCPHQL NGGYSVDGGY    120
AEYCKAPADY VAKIPDNLDP VEVAPILCAG VTTYKALKVS GARPGEWVAI YGIGGLGHIA    180
LQYAKAMGLN VVAVDISDEK SKLAKDLGAD IAINGLKEDP VKAIHDQVGG VHAAISVAVN    240
KKAFEQAYQS VKRGGTLVVV GLPNADLPIP IFDTVLNGVS VKGSIVGTRK DMQEALDFAA    300
RGKVRPIVET AELEEINEVF ERMEKGKING RIVLKLKED                          339

SEQ ID NO: 40                   moltype = DNA   length = 1020
FEATURE                         Location/Qualifiers
source                          1..1020
                                mol_type = other DNA
                                organism = Bacillus stearothermophilus
SEQUENCE: 40
atgaaggcgg ccgtcgtgaa cgagttcaag aaggcgctgg aaatcaagga ggtcgagcgg     60
cccaaactcg aagagggcga ggtcctggtg aagatcgagg cctgcggcgt gtgccatacc    120
gacctgcacg ccgccacgg cgactggccg atcaagccga aactgcccct gatcccgggc    180
cacgagggc tgggcatcgt cgtggaagtg gcgaagggcg tgaaaagcat caaagtgggc    240
gatcgcgtcg gcatcccgtg gctgtacagc gcgtgcggcg agtgcgagta ctgcctgacg    300
ggccaggaaa cgctctgccc gcatcagctg aatggcggct attccgtgga cggcggctat    360
gccgagtatt gcaaagcccc ggccgactat gtcgccaaga tcccggacaa tctggacccc    420
gtcgaggtcg cccccatcct gtgcgccggc gtgaccacct ataaggcgct gaaagtctcg    480
ggcgcccggc cgggcgagtg ggtcgcgatc tacggcatcg gcggcctggg ccacatcgcc    540
ctgcagtacg ccaaggcgat gggcctgaac gtggtcgcgg tcgacatctc gacgagaaa    600
tcgaagctgg cgaaagatct cggcgcggac atcgccatca tggcctgaa ggaagacccg    660
gtcaaggcga tccatgacca ggtcggcggc gtccatgccg ccatctccgt cgcggtgaat    720
aagaaagcct tcgagcaggc ctatcagtcc gtcaagcgcg gcggcaccct ggtcgtggtg    780
ggcctcccga atgcggacct gccgatcccc atcttcgata cggtgctcaa cggcgtgtcg    840
gtgaagggca gcatcgtcgg cacccgcaag gacatgcagg aagccctgga tttcgccgcg    900
cggggcaagg tccgcccccat cgtggaaacg gccgagctgg aggaaatcaa cgaagtgttc    960
gagcgcatgg aaaaaggcaa aatcaacggc cgcatcgtcc tgaagctgaa ggaggattga   1020

SEQ ID NO: 41                   moltype = AA    length = 346
FEATURE                         Location/Qualifiers
source                          1..346
                                mol_type = protein
                                organism = Geobacillus thermoglucosidas
SEQUENCE: 41
MKALTYLGPG KKELMEKPKP KIEKETDAIV KMIKTTICGT DLHILSGDVP TVEEGRILGH     60
```

```
EGVGIIEEVG SAVKNFKKGD RVLISCITSC GKCENCKKGL YAHCEDGGWI LGHLIDGTQA    120
EYVRIPHADN SLYPIPEGVD EEALVMLSDI LPTGFEIGVL NGKVQPGQTV AIIGAGPVGM    180
AALLTAQFYS PAEIIMVDLD DNRLEVAKKF GATQVVNSAD GKAVEKIMEL TGGKGVDVAM    240
EAVGIPATFD ICQEIVKPGG YIANIGVHGK SVEFHIEKLW IRNITLTTGL VNTTSTPMLL    300
KTVQSKKLKP EQLITHRFAF SDIMKAYEVF GNAAKEKALK VIISNS                   346

SEQ ID NO: 42           moltype = DNA   length = 1041
FEATURE                 Location/Qualifiers
source                  1..1041
                        mol_type = other DNA
                        organism = Geobacillus thermoglucosidas
SEQUENCE: 42
atgaaagccc tgacctatct gggcccgggc aaaaaagaac tgatggaaaa accgaagccg     60
aagatcgaaa aagagacgga tgccatcgtc aagatgatca aaaccaccat ctgcggcacc    120
gacctccata tcctgtcggg cgacgtgccc accgtggaag agggccgcat cctgggccac    180
gagggcgtcg gcatcatcga ggaagtgggc tccgccgtca agaacttcaa gaaggcgac    240
cgggtgctga tctcgtgcat caccagctgt ggcaagtgcg agaattgcaa gaagggcctg    300
tacgcccact gcgaggacgg cggctggatc ctgggccatc tgatcgacgg caccccaggcc    360
gagtacgtgc gcatccccca tgcggacaac agcctgtacc cgatccccga gggcgtcgac    420
gaggaagccc tggtcatgct gtcggatatc ctgccccaccg gcttcgagat cggcgtgctg    480
aacggcaagg tccagcccgg ccagaccgtg gcgatcatcg gcgccggccc ggtgggcatg    540
gccgcgctgc tgaccgccca gttctacagc ccggccgaga tcatcatggt ggacctggac    600
gataaccgcc tcgaagtggc gaagaagttc ggcgcgaccc aggtcgtcaa cagcgcggat    660
ggcaaggcgt ggagaagat catggaactc accggcggca agggcgtgga cgtggcgatg    720
gaagccgtcg gcatcccggc caccttcgat atctgccagg agatcgtgaa gccgggcggc    780
tacatcgcca acatcggcgt gcatggcaag tccgtggagt tccatatcga aaaactgtgg    840
atccgcaaca tcaccctgac gacgggcctg gtgaacacca cgagcacgcc catgctgctg    900
aagacggtgc agtcgaagaa gctcaagccc gaacagctca tcacccaccg cttcgccttc    960
agcgatatca tgaaagcgta cgaagtcttc ggcaacgccg ccaaggagaa ggcgctgaaa   1020
gtcatcatca gcaattcgtg a                                            1041

SEQ ID NO: 43           moltype = AA   length = 340
FEATURE                 Location/Qualifiers
source                  1..340
                        mol_type = protein
                        organism = Geobacillus thermoglucosidas
SEQUENCE: 43
MKAAVVNEFK QKLEIKEVEK PKLNYGEVLV KIEACGVCHT DLHAAHGDWP VKPKLPLIPG     60
HEGVGIVVEV AEGVKSVKVG DRVGIPWLYS ACGECEYCLS GQETLCPHQL NGGYSADGGY    120
AEYCKAPANY VAKIPEHLDP VEVAPILCAG VTTYKALKVS NAKPGEWVAI YGIGGLGHIA    180
LQYAKAMGLN VIAVDISDEK IELAKQLGAD IAINGLKEDP VEAIQQNVGG AHAAISVAVT    240
KKAFEQAYQS VRRGGCLVVV GLPNEDLPIP IFNTVLNGIT VKGSIVGTRK DMQEALDFAA    300
RGKVRPIVET APLEKINEVF ERMEKGKING RVVLTIGVNR                          340

SEQ ID NO: 44           moltype = DNA   length = 1023
FEATURE                 Location/Qualifiers
source                  1..1023
                        mol_type = other DNA
                        organism = Geobacillus thermoglucosidas
SEQUENCE: 44
atgaaagccg cggtggtcaa tgagttcaag cagaaactcg aaatcaagga agtcgaaaag     60
ccgaagctca actacggcga agtgctggtg aaaatcgagg cctgcggcgt ctgccacacc    120
gacctccatg cggcccacgg cgactggccc gtcaagccga gctgcccct gatcccgggc    180
catgagggcg tgggcatcgt cgtggaagtc gcggagggcg tcaagagcgt caaggtcggc    240
gaccgggtcg gcatcccctg gctgtattcc gcctgcggcg aatgcgaata ctgcctgagc    300
ggccaggaaa ccctgtgccc ccaccagctg aacggcggct atagcgcgga tggcggctat    360
gccgagtact gtaaagcccc cgccaactac gtggcgaaga tcccggaaca tctgaccccc    420
gtggaagtgg cgcccatcct ctgcgcgggc gtgaccacct ataaagccct caaggtgtcc    480
aacgccaaac ccggcgagtg ggtcgcgatc tacggcatcg gcggcctcgg ccatatcgcg    540
ctgcagtacg ccaaggcgat gggcctcaac gtcatcgccg tggatatcag cgacgagaaa    600
atcgaactgg cgaaacagct cggcgcggac atcgcgatca acggcctgaa agaagatccg    660
gtggaagcca tccagcagaa cgtcggcggc gcccacgccg cgatcagcgt cgccgtgacc    720
aagaaggcgt tcgaacaggc ctatcagagc gtccggcggg gcggctgcct ggtcgtggtc    780
ggcctgccca acgaggacct gcccatcccg atcttcaaca ccgtcctgaa tggcatcacc    840
gtcaagggct ccatcgtggg cacgcgcaag gatatgcagg aagcgctgga tttcgcggcc    900
cggggcaagg tgcggccgat cgtcgagacg gccccgctgg agaagatcaa tgaggtcttc    960
gaacgcatgg agaagggcaa gatcaatggc cgcgtcgtgc tcaccatcgg cgtcaaccgc   1020
tga                                                                1023

SEQ ID NO: 45           moltype = AA   length = 340
FEATURE                 Location/Qualifiers
source                  1..340
                        mol_type = protein
                        organism = Lactococcus lactis
SEQUENCE: 45
MKAAVVRHNP DGYADLVEKE LRAIKPNEAL LDMEYCGVCH TDLHVAAGDF GNKAGTVLGH     60
EGIGIVKEIG TDVSSLQVGD RVSVAWFFEG CGHCEYCVSG NETFCREVKS AGYSVDGGMA    120
EEAIVVADYA VKVPDGLDPI EASSITCAGV TTYKAIKVSG VKPGDWQVIF GAGGLGNLAI    180
QYAKNVFGAK VIAVDINQDK LNLAKKIGAD VTINSGDVNP VDEIKKITGG LGAQSAIVCA    240
```

```
VARIAFEQAV ASLKPMGKMV AVAVPNTEMT LSVPTVVFDG VEVAGSLVGT RLDLAEAFQF    300
GAEGKVKPIV ATRKLEEIND IIDEMKAGKI EGRMVIDFTK                          340

SEQ ID NO: 46           moltype = DNA  length = 1023
FEATURE                 Location/Qualifiers
source                  1..1023
                        mol_type = other DNA
                        organism = Lactococcus lactis
SEQUENCE: 46
atgaaggcgg ccgtcgtgcg gcacaacccg gacggctatg ccgatctggt ggagaaggag     60
ctccgcgcga tcaagccgaa cgaggccctc ctggacatgg agtactgcgg cgtgtgccac    120
accgacctgc acgtcgccgc cggcgatttc ggcaacaaag ccggcaccgt cctgggccat    180
gagggcatcg gcatcgtgaa ggaaatcggc accgatgtgt cgtccctcca ggtgggcgac    240
cgggtcagcg tcgcctggtt cttcgaaggc tgcggccact gcgagtactg cgtgtccggc    300
aacgagacgt tctgccggga agtcaagagc gcgggctaca gcgtcgatgg cggcatggcc    360
gaggaagcca tcgtcgtcgc cgactacgcc gtgaaggtcc cggatggcct cgatcccatc    420
gaggccagca gcatcacctg cgcgggcgtg accacctaca aggccatcaa ggtgtccggc    480
gtcaaaccgg gcgattggca ggtgatcttc ggcgccgggg gcctgggcaa cctcgccatc    540
cagtacgcca aaaacgtctt cggcgcgaag gtcatcgcgg tggacatcaa ccaggacaag    600
ctgaacctcg cgaagaagat cggcgccgat gtcaccatca actcgggcga tgtcaacccg    660
gtcgacgaga tcaagaaaat caccggcggc ctgggcgccc agtcggccat cgtgtgcgcg    720
gtcgcccgca tcgcgttcga acaggcggtg gccagcctca aaccgatgga caaaatggtg    780
gcggtggccg tccgaacac cgagatgacc ctgagcgtgc cgaccgtggt cttcgacggc    840
gtcgaggtcg cgggctcgct cgtcggcacc cggctggacc tcgccgaggc cttccagttc    900
ggcgcggagg gcaaagtcaa gccgatcgtc gcgacccgga agctggagga gatcaatgac    960
atcatcgatg agatgaaggc cggcaagatc gaaggccgga tggtcatcga tttcaccaag   1020
tga                                                                 1023

SEQ ID NO: 47           moltype = AA  length = 340
FEATURE                 Location/Qualifiers
source                  1..340
                        mol_type = protein
                        organism = Lactococcus lactis
SEQUENCE: 47
MKAAVVRHNP DGYADLVEKE LRAIKPNEAL LDMEYCGVCH TDLHVAAGDY GNKAGTVLGH     60
EGIGIVKEIG TDVSSLQVGD RVSVAWFFEG CGHCEYCVSG NETFCREVKN AGYSVDGGMA    120
EEAIVVDYA VKVPDGLDPI EASSITCAGV TTYKAIKVSG VKPGDWQVIF GAGGLGNLAI     180
QYAKNVFGAK VIAVDINQDK LNLAKKIGAD VIINSGDVNP VDEIKKITGG LGAQSAIVCA    240
VARIAFEQAV ASLKPMGKMV AVALPNTEMT LSVPTVVFDG VEVAGSLVGT RLDLAEAFQF    300
GAEGKVKPIV ATRKLEEIND IIDEMKAGKI EGRMVIDFTK                          340

SEQ ID NO: 48           moltype = DNA  length = 1023
FEATURE                 Location/Qualifiers
source                  1..1023
                        mol_type = other DNA
                        organism = Lactococcus lactis
SEQUENCE: 48
atgaaggcgg cggtcgtgcg ccataacccg gacggctacg ccgacctggt ggaaaaggag     60
ctgcgggcca tcaagccgaa cgaggcgctc tcgacatgg agtactgcgg cgtctgccat    120
acggacctcc acgtcgccgc cggcgactac ggcaacaagg cgggcacggt gctgggccat    180
gagggcatcg gcatcgtgaa ggaaatcggc accgacgtgt cctccctgca ggtcggcgac    240
cgggtcagcg tcgcctggtt cttcgagggc tgtggccact gcgagtattg tgtcagcggc    300
aatgaaacgt tctgtcgcga agtcaaaaac gccggctact cggtcgatgg cggcatggcg    360
gaagaagcca tcgtggtcgc ggactatgcc gtgaaggtgc cggacggcct ggaccccatc    420
gaagcgtcct cgatcacctg cgcgggcgtc acgacctaca aggcgatcaa agtgtcgggc    480
gtcaagccgg gcgactggca ggtgatcttc ggcgcgggcg gcctcggcaa cctcgccatc    540
cagtacgcca agaacgtctt cggcgccaaa gtgatcgccg tcgacatcaa tcaggacaaa    600
ctgaatctgg cgaaaaagat cggcgccgat gtcatcatca cagcggcga tgtgaacccg    660
gtggacgaga tcaaaaagat caccggcggc ctcggcgccc agagcgcgat cgtgtgcgcc    720
gtggcccgca tcgccttcga acaggcggtc gcgtccctga agccgatggg caagatggtc    780
gccgtcgccc tcccgaacac ggaaatgacg ctgtccgtcc cgaccgtggt cttcgacggc    840
gtggaagtgg ccggctcgct ggtcggcacc cggctggacc tcgccgaggc cttccagttc    900
ggcgcggaag gcaaggtcaa gccgatcgtg gccacgcgca agctcgaaga gatcaatgat    960
atcatcgatg agatgaaggc gggcaagatc gaaggccgca tggtcatcga tttcaccaag   1020
tga                                                                 1023

SEQ ID NO: 49           moltype = AA  length = 401
FEATURE                 Location/Qualifiers
source                  1..401
                        mol_type = protein
                        organism = Oenococcus oeni
SEQUENCE: 49
MRGSHHHHHH GSAERAYDFL MPSVNFFGPG VISKIGERAK MLGMKKPVIV TDKFLENLKN     60
GAVAQTLASL KKSGVDYVVY NGVEPNPKIH NIKEVKTLYE KEDADSIITV GGGSAHDTGK    120
GAGIIMTNGD DITKLAGIET LKNPLPPLIA VNTTAGTGSE LTRHAVITNE ETHLKFVVVS    180
WRNIPLVSFN DPTLMLDIPK GLTAATGMDA FVQAVEPYVS VDHNPITDSQ CIQAIKLIES    240
SLREAVANGH NLQARTKMVE AEMLAGMAFN NANLGYVHAM AHQLGGQYDA PHGVCCALLL    300
PYAEEYNLIA DPERFAELAR IMGENTDGLS TRDAAELSIK AMKQLSEDVG IPHSIKDIGA    360
KPEDFDLMAE NALKDGNAFS NPRKGTKEDI VKIFQEAYDA K                        401
```

```
SEQ ID NO: 50            moltype = DNA  length = 1206
FEATURE                  Location/Qualifiers
source                   1..1206
                         mol_type = other DNA
                         organism = Oenococcus oeni
SEQUENCE: 50
atgcgcggca gccatcatca ccatcaccac ggcagcgccg aacgggccta cgatttcctg    60
atgccctccg tcaacttctt cggcccgggc gtgatctcca agatcggcga acgggcgaaa   120
atgctcggca tgaagaagcc ggtgatcgtc accgataagt tcctggagaa tctgaaaaat   180
ggcgccgtgg cccagaccct ggccagcctc aagaagagcg cgtcgatta cgtcgtgtat    240
aacggcgtgg agcccaaccc caaaatccac aacatcaagg aggtgaaaac cctgtacgaa   300
aaggaagacg ccgacagcat catcaccgtg ggcggcggct cggcccacga tacgggcaag   360
ggcgccggca tcatcatgac gaacggcgat gacatccaca agctgccgg catcgaaacc    420
ctgaagaatc ccctccccc cctgatcgcc gtgaatacca ccgcgggcac cggctcggaa    480
ctcacgcggc acgccgtcat cacgaacgag gaaacccatc tgaagttcgt cgtggtgtcc   540
tggcgcaaca tcccgctggt cagcttcaat gaccccaccc tgatgctgga catccccaag   600
ggcctcaccg cggccacggg catggccgcc ttcgtccagg cgtcgaacc gtacgtgagc    660
gtggatcaca atcccatcac cgactcccag tgtatccagg ccatcaagct gatcgaatcg   720
tcgctgcggg aggccgtggc gaacggccat aacctgcagg cccgcaccaa aatggtggaa   780
gccgaaatgc tcgcgggcat ggcgttcaat aacgccaacc tgggctacgt ccacgcgatg   840
gccatcagc tgggcggcca gtacgccgcc ccgcatgcg tctgctgcga cctgctcctg    900
ccgtatgcgg aggagtacaa cctgatcgcc gacccggaac gcttcgcgga actggccgc    960
atcatgggcg agaacaccga cggcctctcg acccgcgacg cggccgaact gtccatcaag   1020
gcgatgaaac agctgtcgga ggacgtgggc atcccgcact cgatcaagga catcggcgcc   1080
aagccggagg acttcgacct gatggccgaa atgcgctga aggacggcaa tgccttctcc    1140
aacccgcgca aaggcaccaa ggaggatatc gtcaagatct ccaggaggc ctatgacgcc    1200
aaatga                                                              1206

SEQ ID NO: 51            moltype = AA  length = 333
FEATURE                  Location/Qualifiers
source                   1..333
                         mol_type = protein
                         organism = Pectobacterium atrosepticum
SEQUENCE: 51
MLNFTLHTPT KILFGEGQIA ELGKEIPADA RILITYGGGS VKHNGVLDQV YRALEGRNVR    60
EFSGIEPNPT YETLMKAVEV VRAEKIDFLL AVGGGSVVDG TKFIAAAADY QAAQDPWHIL   120
QTGGAEIDRG VALAAVLTLP ATGSESNNGA VITRKSTNDK LAFRSPHTQP LFAVLDPVVT   180
YTLPARQIAN GVVDAFVHTV EQYLTYSVDA KVQDRFAEGL LLTLVEEGPR ALAEPENYKV   240
RANVMWSATM ALNGLIGAGV PQDWSTHMLG HELTALHGLD HAQTLAIVLP AMLAARKSQK   300
RDKLLQYAER VWNLRDGSED QRIDGAIAAT RDF                                333

SEQ ID NO: 52            moltype = DNA  length = 1002
FEATURE                  Location/Qualifiers
source                   1..1002
                         mol_type = other DNA
                         organism = Pectobacterium atrosepticum
SEQUENCE: 52
atgctgaatt tcaccctcca taccccgacg aagatcctgt tcggcgaggg ccagatcgcg    60
gagctgggca aggagatccc ggccgacgcc cgcatcctca tcacctacgg cggcggctcg   120
gtcaaacaca acggcgtgct ggatcaggtg taccgggcgc tggaaggccg gaacgtgcga   180
gagttctccg gcatcgagcc caacccgacc tacgaaacgc tcatgaaggc cgtggaggtg   240
gtccgggcgg aaaagatcga tttcctgctc gccgtgggcg gcggcagcgt cgtcgacggc   300
accaagttca tcgccgcggc ggccgactac caggccgcgc aggacccgtg gcacatcctc   360
cagaccggga gcgccgaaat cgaccgggc gtggccctcg ccgcggtgct gaccctgccg    420
gccacgggca gcgaatccaa taacggcgcc gtcatcaccc gcaaaagcac caatgacaag   480
ctcgcgttcc ggtccccgca tacgcagccc tcttcgccg tcctcgaccc ggtggtcacg    540
tacaccctgc cggcccggca gatcgcgaat ggcgtcgtcg acgccttcgt ccacaccgtc   600
gagcagtacc tgacctactc cgtcgacgcg aaagtccagg atcgcttcgc cgagggcctg   660
ctgctcaccc tggtcgaaga gggccccgg gccctggccg aacccgaaaa ctacaaagtg    720
cgggcgaatg tcatgtggag cgccacgatg gcgctgaacg gcctcatcgg cgccggcgtc   780
ccccaggatt ggtcgaccca catgctgggc acgaactca cggccctgca cggcctgac    840
cacgcgcaga cgctggccat cgtcctgccg gccatgctgg cggcccggaa atcccagaaa   900
cgggataaac tcctgcagta cgccgagcgc gtctggaacc tccgcgacgg ctcggaagat   960
cagcggatcg acggcgccat ccgccgcacg cgcgattct ga                       1002

SEQ ID NO: 53            moltype = AA  length = 351
FEATURE                  Location/Qualifiers
source                   1..351
                         mol_type = protein
                         organism = Psychrobacter cryohalolentis
SEQUENCE: 53
MANTKAYAAT APDSGLAPYA IDRRELRADD VAIEIDYCGV CHSDLHTVEN DWGGSKYPVI    60
PGHEIVGRVT AVGPEVSHFK AGDLVGVGCM VDSCRSCSAC DSGLEQYCIE GSTMTYGSLD   120
RHDGSVTHGG YSERIVVSER FVVRVPEKLD PASAAPILCA GITTYSPLKH FKVGKGHKVG   180
VLGMGGLGHM GVKFAKALGA EVTIFTRSEA KVAEAKKQGA DHVIISTDKE QMKAADSFD    240
FLLDTIPVAH DLNPYLKCLK YDGTHILVGL LTPIEPALQA GLLVTKRRVV AGSLIGGMPE   300
TQEVLDFCAE HDITCDIEML DIRNINEAYV RMKKGDVKYR FVIDMKTLKE G            351
```

-continued

```
SEQ ID NO: 54          moltype = DNA  length = 1056
FEATURE                Location/Qualifiers
source                 1..1056
                       mol_type = other DNA
                       organism = Psychrobacter cryohalolentis
SEQUENCE: 54
atggccaata ccaaggccta cgccgccacg gcgccggatt cgggcctggc ccgtacgcg   60
atcgaccggc gggaactgcg ggccgatgac gtggcgatcg aaatcgacta ctgtggcgtg  120
tgccatagcg atctccatac cgtggaaaac gactggggcg gctcgaagta cccggtgatc  180
cggggccatg agatcgtcgg ccgggtgacg gcggtgggcc ccgaggtcag ccatttcaag  240
gccggcgacc tcgtgggcgt gggctgcatg gtggattcgt gtcgctcgtg cagcgcctgc  300
gacagcggcc tcgaacagta ttgcatcgag gcagcacga tgacctacgg cagcctggac  360
cgccacgatg gctccgtcac ccacggcggc tacagcgaac gcatcgtcgt ctcggaacgg  420
ttcgtcgtgc gggtgcccga aaaactggac ccggcctcgc ccgccccgat cctgtgcgca  480
ggcatcacga cgtacagccc gctgaagcac ttcaaggtgg gcaagggcca taaagtcggc  540
gtcctgggcg tgggcggcct ggccatatg gcgtgaagt cgccaaggc cctgggcgcc   600
gaggtgacga tcttcacccg gtccgaggcg aaagtggccg aagcgaagaa acagggcgcc  660
gaccatgtca tcatctcgac cgataaggag cagatgaagg ccgccgccga cagcttcgat  720
ttcctcctcg acaccatccc ggtggcgcac gacctgaatc cgtatctgaa gtgtctgaaa  780
tacgatggca cccacatcct cgtgggcctg ctgaccccca tcgaaccggc gctgcaggcc  840
ggcctcctgg tcaccaagcg gcgcgtcgtg gcgggcagcc tgatcggcgg catgcccgag  900
acgcaggaag tcctggactt ctgcgccgaa catgacatca cctgtgatat cgagatgctc  960
gacatccgca acatcaacga agcgtacgtc cgcatgaaaa agggcgatgt caagtaccgc 1020
ttcgtgatcg atatgaagac gctgaaggaa ggctga                           1056

SEQ ID NO: 55          moltype = AA  length = 548
FEATURE                Location/Qualifiers
source                 1..548
                       mol_type = protein
                       organism = Methylocaldus szegediense
SEQUENCE: 55
MGTAKADSIG QYLLKRLYEA GVKHIFGVPG DYVLGFYDLM AKSPIQHVGT TREDTAAFAA   60
DGYARCRGLG ALAVTYGVGA LNTVNAVAGA YAESSPVIVI SGAPGVREQK EDPMIHHRFG  120
PFTFQREIFD RITCAAVTLD DPIIAFRQID RVIAAARHSC KPVYIELPRD LVMAEGHPVP  180
TEPPEEPASD EAALSEAVAE TAELMSKSVS PTVLAGVELH RRGLQDALVE LVERARLPVA  240
ATLTGKSVIA ERHPAYLGVY EGAMSSENAR YMVEQSDLLL MLGVTLNDID TGVYTARLDP  300
HRIVRAAQNE VVIRYHRYPR VTLSDFVLSL ARTVKAKHET FPPAPVTTPEA TEFPMPERPM  360
TIARLIERLD RALTPDMIVV SDVGDCLFAA IDLRVYERSE FLSSAFYTTM GPAVPAALGA  420
QIARPDHRAL ILVGDGAFQM TGTELSTHIR FGLAPIVVVF NNCGYSTERY ILDGPFNDIS  480
CWNFDRLGEL FGPLNGYDAP DEESFEKALV EALANHATPS IINVHISRDD SSSAMRRLAE  540
VLKSRVRG                                                          548

SEQ ID NO: 56          moltype = DNA  length = 1647
FEATURE                Location/Qualifiers
source                 1..1647
                       mol_type = other DNA
                       organism = Methylocaldus szegediense
SEQUENCE: 56
atgggcaccg ccaaggcgga tagcatcggc cagtacctcc tgaaacgcct gtacgaggcc   60
ggcgtgaaac atatcttcgg cgtgcccggc gattacgtgc tgggcttcta cgatctgatg  120
gcgaagagcc cgatccagca cgtcggcacg acccgcgagg acaccgcggc cttcgccgca  180
gacggctacg cccgctgtcg cggcctcggc gccctggcgg tcacctatgg cgtcggcgcc  240
ctgaacaccg tgaatgccgt cgcgggcgcc tatgccgaat cgagcccggt gatcgtcatc  300
agcggcgccc cgggcgtgcg cgaacagaag gaagacccga tgatccatca tcggttcggc  360
ccgttcacct tccagcggga aatcttcgac cggatcacct gcgccgcggt cacgctggac  420
gatcccatca tcgccttccg ccagatcgac cgggtgatcg cggccgcccg ccactcgtgc  480
aaacccgtgt atatcgaact gccccgcgac ctggtgatgg ccgaaggcca tccggtcccg  540
acggagcccc cggaagagcc cgcctccgat gaggcggccc tgagcgaagc ggtggccgaa  600
accgcggaac tgatgtccaa gtcggtgagc cccaccgtcc tggcgggcgt cgaactgcac  660
cggcgcggcc tgcaggacgc cctggtggaa ctggtggaac tggtggaac gcgccggcct  720
gccaccctca ccggcaagag cgtgatcgcc gaacgccacc ccgcctatct gggcgtctac  780
gaaggcgcca tgtcctcgga aaacgcccgc tacatggtgg aacagtccga tctcctgctc  840
atgctgggcg tgacgctgaa cgacatcgac accggcgtct ataccgcccg cctcgacccg  900
catcgcatcg tgcgggcggc ccagaacgag gtggtgatcc gctaccatcg ctatccgcgt  960
gtcaccctgt cggacttcgt cctgagcctg gcccgcaccg tgaaagcgaa gcatgaaacc 1020
ttccccgccc cggtcacgac cccgaagccc acggagttcc ccatgccgga gcgcccgatg 1080
acgatcgccc gcctcatcga acgcctggac cgcgccctga ccccgacat gatcgtcgtg 1140
agcgatgtgg gcgattgcct gttcgcggcc atcgatctcc gggtctacga gcggagcgag 1200
ttcctctcgt cggccttcta caccacgatg ggcttcgctg tcccggccgc cctcggcgcg 1260
cagatcgcgc ggccggacca ccgggccctg atcctggtgg gcgatggcgc gttccagatg 1320
acgggcaccg agctcagcac gcacatccgc ttcggcctcg cgcccatcgt ggtcgtgttc 1380
aacaactgtg gctattcgac cgaacggtac atcctggacg gcccgttcaa cgacatctcg 1440
tgctggaact tcgaccggct gggcgaactg ttcggcccgc tgaacggcta tgacgcgccg 1500
gacgaggaga gcttcgagaa ggcgctcgtc gaggccctgg ccaaccatgc cacgccagc 1560
atcatcaacg tccacatcag ccgcgacgac agctccagcg cgatgcggcg gctggccgaa 1620
gtcctgaaga gccgcgtccg gggctga                                    1647

SEQ ID NO: 57          moltype = AA  length = 550
FEATURE                Location/Qualifiers
```

```
source                  1..550
                        mol_type = protein
                        organism = Methylosarcina lacus
SEQUENCE: 57
MNTAKFDTIG QYLLKRLYDA GVKHIFGVPG DYILGFYDLM VNSPVQHIGT TREDTAAFAA    60
DAYARCLGLG AMAVTYGVGA LNTVNAVAGA YAESSPVIVI SGAPGIREQR EDPLIHHRFG   120
PFTFQREIFE RITCATEVLN DPVIAFRQID RAIATARRLC KPVYIEIPRD LVMAEGYPMP   180
DEALEPLESD ETALSEALAE TMELMAKSVS PMIIAGVELH RRGLQSALVN LVERAHLPVV   240
ATLSGKSVMA ERHPAYLGIY EGAMSSENAR YMVEQSDLLL MLGVTLNDID TGIYTAKLDP   300
HHMIRAAQNE VVISSHRYPR VTLSDFLTAL VGLVKTRSEG FSSPPAAYEA SAFPEPKRPI   360
TTARMIGRLN QALSPEMIVV CDVGDCLFAA IDLQVHEQSE FLASCYYATM GFAVPAALGA   420
QIARPDHRLL VLVGDGAFQM TGTELSTHAY LGLNPIVVVF NNSGYGTERG ILEGPFNDIS   480
SWRFDRLGEV FGPLKGYDAA TEEAFEAALI NSLNNRTMPS IINVHLSADD ASSAMKRLAE   540
HLKSRVKGGS                                                         550

SEQ ID NO: 58           moltype = DNA   length = 1653
FEATURE                 Location/Qualifiers
source                  1..1653
                        mol_type = other DNA
                        organism = Methylosarcina lacus
SEQUENCE: 58
atgaacaccg ccaagttcga caccatcggc cagtacctgc tcaagcggct gtacgacgcg    60
ggcgtgaaac acatcttcgg cgtgccgggc gattatatcc tgggcttcta tgacctgatg   120
gtgaacagcc cggtccagca catcggcacc acgcgcgagg acaccgcggc cttcgcggcg   180
gacgcctacg cccgctgcct gggcctcggc gcgatggcgg tcacgtacgg cgtgggcgcc   240
ctgaataccg tgaatgccgt cgccggcgcg tatgccgaaa gctcgccggt gatcgtcatc   300
tccggcgccc ccggcatccg cgagcagcgg gaggacccgc tgatccatca tcggttcggc   360
ccgttcacct tccagcggga gatcttcgag cgcatcacct gcgcgaccga agtgctcaac   420
gacccggtga tcgccttccg ccagatcgat cgcgcgatcg ccaccgcccg gcggctgtgc   480
aagccggtgt acatcgagat cccgcgcgat ctggtgatgg cggaaggcta ccccatgccg   540
gacgaggccc tcgaacccct ggagagcgat gaaaccgccc tgagcgaggc gctggcggaa   600
acgatggaac tgatggcgaa aagcgtctcc ccgatgatca tcgccggcgt cgaactgcat   660
cggcggggcc tgcagagcgc cctcgtcaac ctggtgaacc gcgccatct cccggtggtc   720
gccaccctgt cgggcaaaag cgtcatggcg aacgcgcacc cggcctacct gggcatctac   780
gaaggcgcga tgtcctcgga aaatgcccgg tacatgtcg aacagagcga cctcctcctc   840
atgctgggcg tcaccctcaa cgacatcgat accggcatct atacggcaa gctcgacccg   900
catcatatga tccgggcggc ccagaacgag gtggtgatct cctcgcatcg ctacccgcgc   960
gtcaccctct cggacttcct gacggcgctg gtgggcctgg tcaagacccg gagcgaaggc  1020
ttcagctcgc cgccggccgc ctacgcggcc agcgcctcc cggaaccgaa gcggccgatc  1080
accacgcgcg gatgatcgg ccggctgaac caggcgctgt cgccggaaat gatcgtggtg  1140
tgcgacgtgg cgactgcct cttcgccgcc atcgatctgc aggtgcacga gcagtccgag  1200
ttcctcgcca gctgctacta tgccacgatg ggcttcgccg tgcccgcggc gctcggcgca  1260
cagatcgcgc ggcccgatca ccggctgctc gtgctggtgg gcgacggcgc cttccagatg  1320
acgggcaccg aactgagcac ccatgcctat ctgggcctca cccgatcgt cgtggtgttc  1380
aacaactccg gctacggcac cgaacgcggc atcctggaag cccccttcaa cgacatcagc  1440
agctggcggt cgaccgcct cggcgaagtg ttcgccccgc tgaagggcta tgacgccgcc  1500
accgaggagg ccttcgaagc ggcgctcatc aactccctca acaaccggac gatgccgagc  1560
atcatcaacg tccatctctc cgccgacgac gcctcctccg ccatgaagcg cctcgccgag  1620
cacctgaaga gccgcgtgaa gggcggctcg tga                               1653

SEQ ID NO: 59           moltype = AA   length = 550
FEATURE                 Location/Qualifiers
source                  1..550
                        mol_type = protein
                        organism = Methylomonas denitrificans
SEQUENCE: 59
MSTAKFDTIG QYLLKRLYQA GVKDIFGVPG DYVLGFYDLM IKSQVRHIGT TREDSAAFAA    60
DGYARCVGMG ALAVTYGVGA LNTVNAIAGA YAESSPVVLI SGAPGVSEQK DDPLIHHRFG   120
PFTFQREIFE RISCASVVLN DPVIAFRQID HAIEAARRFC KPVYIELPRD LVMAEGYPMP   180
TETVEKFTSD EAALSEAIAE TMTLLSKAVS PMIVAGVELH RRGLQGALAD FVERTCLPVV   240
ATLTGKSVMS ERHPAYLGIY EGAMSSEAVR DRVEKSDLLL MLGVTLNEID TGIYTAKLNS   300
HSTIRAALNE VVISAHRYPG IALEDFLGAL ASSVSLSSRE VVSSPKPPES IAFPEPDRPI   360
TTARLVERLN SALSNDMIVV CDVGDCLFAA IDLRVHEQSE FLASAFYTTM GFAVPAALGA   420
QIARPDRRAL ILVGDGAFQM TGTELSTHAR LGLNPIVVVF NNGGYSTERC ILEGPFNDIN   480
PWRFDRLGEL FGPLAGYEAA TEAEFEEALL NALDNHGMPS IINVHLAADD SSEAMKRLAE   540
HLQSKIKRDA                                                         550

SEQ ID NO: 60           moltype = DNA   length = 1653
FEATURE                 Location/Qualifiers
source                  1..1653
                        mol_type = other DNA
                        organism = Methylomonas denitrificans
SEQUENCE: 60
atgtcgaccg cgaagttcga caccatcggc cagtatctgc tgaagcggct gtatcaggcc    60
ggcgtcaagg atatcttcgg cgtcccggc gactacgtgc tgggcttcta tgacctgatg   120
atcaagtcgc aggtgcgcca tatcggcacc acgcgggagg acagcgcggc cttcgcggcc   180
gacggctacg cccgctgtgt gggcatgggc gcctggcgg tgacgtacgg cgtcggcgcc   240
ctgaacacgg tgaacgccat cgccggcgcg tacgccgaat cgtccccgt cgtcctcatc   300
agcggcgccc cgggcgtgtc cgagcagaag gacgatccgc tgatccatca tcgcttcggc   360
```

```
cccttcacgt tccagcgcga aatcttcgaa cggatcagct gtgcctccgt cgtcctgaat  420
gacccggtca tcgcgttccg gcagatcgac catgccatcg aggccgcccg gcgcttctgc  480
aagccggtgt atatcgaact gccgcgggac ctcgtgatgg cggagggcta ccccatgccc  540
accgagacgt cgaaaagtt cacctccgat gaggccgcgc tgtccgaagc gatcgcggaa  600
accatgaccc tgctcagcaa ggcggtcagc ccgatgatcg tggcgggcgt ggagctgcat  660
cggcgcggcc tgcagggcgc cctggccgac ttcgtgaaac ggacctgtct gcccgtggtg  720
gccaccctga cgggcaagtc ggtgatgtcg gagcgccatc ccgcctacct gggcatctac  780
gaaggcgcca tgtcctcgga gcggtgcgc gatcgggtgg agaagagcga tctgctcctg  840
atgctgggcg tgaccctcaa cgaaatcgac accggctgca actgaacgcg  900
catagcacga tccgcgccgc gctgaacgag gtcgtgatct ccgcccaccg ctatcccggc  960
atcgcgctgg aagatttcct gggcgccctg gcctcgtcgg tgtccctcag ctcgcgcgag 1020
gtggtcagca gcccgaaacc cccggagtcg atcgccttcc ggaaccggca ccggccgatc 1080
acgacggccc gcctggtcga acggctcaac tccgccctca gcaatgacat gatcgtcgtg 1140
tgtgacgtgg gcgactgcct gttcgacggc atcgacctcc gcgtgcatga gcagagcgag 1200
ttcctggcct ccgccttcta caccacgatg ggcttcgcgg tgcccgcggc cctcggcgcc 1260
cagatcgccc gccccgaccg gcgggcgctg atcctggtcg gcgacggcgc gttccagatg 1320
accggcaccg aactgtccac gcacgcgcgg ctgggcctga cccgatcgt cgtcgtgttc 1380
aataatggcg gctactcgac cgaacgctgc atcctgaagg gcccgttcaa tgatatcaac 1440
ccctggcgct tcgaccgcct gggcgagctg ttccggcccc tggccggcta tgaggccgcc 1500
acggaagccg agttcgagga gcccctgctg aacgcgctgg acaaccacgg catgccgtcc 1560
atcatcaatg tgcatctcgc cgccgacgat agctccgagg cgatgaaacg cctggccgag 1620
cacctgcaga gcaaaatcaa gcgggacgcc tga                               1653

SEQ ID NO: 61         moltype = AA  length = 553
FEATURE               Location/Qualifiers
source                1..553
                      mol_type = protein
                      organism = Methylomonas methanica
SEQUENCE: 61
MNTVKLETMG QYLLNRLYEA GVKHVFGVPG DYVLGFYDLM EKSPIQHIGT TREDTAAFAA  60
DGYARCRGLG ALAVTYGVGA LNTVNAVAGA YAESSPVIVI SGAPGVCEQR DDPLIHHRFG 120
PPFTFQREIFE RITCATAVLN DPVIAFRQID HAIASARHYC KPVYIEIPRD LVSVEGYPMP 180
AIAAAMEPSGS DKSALSEAVA ETMSLLEKSV SPMVIAGIEL HRRGLQNRLL ELIERARLPV 240
TATLTGKSVI AERHPAYLGI YEGAMSSEHA RYMVEQSDLL LMLGVTLNEV DTGIYTAKLD 300
PQHTIRAALN EVVISAHRYP NIALADYLNA LVDAVKPSEA GFSAKPGKPV ARAFPEPDRP 360
ISINRLIERI NQALEPETIV VCDVGDCLFA AIDLEVHEQS EFLASGFYTT MGFAVPAALG 420
AQVARPGHRA LILVGDGAFQ MTGTELSTQA RLGLDSIVIV FNNSGYSTER CILEGPFNDI 480
ARWRFDRLGE VFGPLQGFDA ATEESFESAL IQALNNRSMP SIINVHLASD DTSSAMRRLA 540
EHLKSKVQGE RPA                                                    553

SEQ ID NO: 62         moltype = DNA  length = 1662
FEATURE               Location/Qualifiers
source                1..1662
                      mol_type = other DNA
                      organism = Methylomonas methanica
SEQUENCE: 62
atgaacacgg tcaaactgga aacgatgggc cagtacctgc tgaaccgcct ctatgaggcg  60
ggcgtgaaac atgtcttcgg cgtcccgggc gactatgtcc tgggcttcta cgacctgatg 120
gagaagtccc ccatccagca tatcggcacc acccgcgaag ataccgcggc cttcgccgcc 180
gacggctacg cccgctgccg cggcctgggc gccctggccg tcacgtacgg cgtcggcgcc 240
ctcaacacgg tgaatgcggt ggcggggcgc tacgcggagt cgtcgcccgt gatcgtcatc 300
agcggcgccc cgggcgtctg tgagcagcgc gatgacccgc tgatccacca ccgcttcggc 360
cccttcacct tccagcgcga gatcttcgaa cggatcacct gcgccaccgc ggtgctgaac 420
gacccggtga tcgcgttccg gcagatcgat cacgccatcg cctccgcccg ccattattgc 480
aagccggtct atatcgaaat cccgcgggac ctcgtgtccg tggaaggcta cccgatgcc 540
gccatcgccg cgatggagcc gtcgggctcc gacaagtccg ccctcagcga ggccgtggcc 600
gaaaccatgt cgctgctgga aaagtccgtg tccccgatgg tcatcgccgg catcgagctc 660
caccgccgcg gcctgcagaa ccgcctcctc gaactgatcg aacgcgcccg cctgccgtg  720
acggccaccc tcaccggcaa aagcgtgatc gcggagcggc accccgcgta cctgggcatc 780
tatgagggcg cgatgtccag cgaacacgcc cgctatatgg tcgagcagtc cgacctcctc 840
ctcatgctgg gcgtgaccct gaacgaggtc gacacgggca tctacaccgc gaagctggac 900
ccccagcata ccatccgggc ggcgctgaac gaggtggtga tctcggccca ccgctatccg 960
aatatcgccc tggccgacta tctgaacgcc ctggtgacgg cggtgaagcc gtcggaggcg 1020
ggcttctccg ccaaaccggg caaacccgtc gcgcgggcgt tcccggagcc cgaccgcccg 1080
atctcgatca accgcctgat cgaacgcatc aatcaggcgc tggaaccgga gacgatcgtg 1140
gtgtgcgacg tgggcgactg tctcttcgcc gccatcgatc tggaggtcca cgagcagtcg 1200
gagttcctgg cctcgggctt ctataccacg atgggcttcg ccgtgcccgc cgccctgggc 1260
gccaggtcg cccggcccgg ccaccgcgcc ctgatcctgg tgggcgacgg cgcgttccag 1320
atgaccggca cggaactctc cacccaggcc cggctgggac tcgat cgtgatcgtc 1380
ttcaacaatt cgggctattc cacggagcgg tgcatcctgg agggcccgtt caacgatatc 1440
gcccgctggc gcttcgaccg cctcggcgaa gtcttcggcc cgctgcaggg cttcgacgcg 1500
gcgaccgagg agtccttcga gtcggcgctg atccaggccc tgaacaaccg cagcatgccc 1560
agcatcatca acgtccacct cgcgagcgac gacacgagca gcgcgatgcg gcgcctggcg 1620
gaaacacctga agtcgaaggt gcagggcgaa cgccccgcct ga                   1662

SEQ ID NO: 63         moltype = AA  length = 552
FEATURE               Location/Qualifiers
source                1..552
                      mol_type = protein
```

```
                        organism = Methylohalobius crimeensis
SEQUENCE: 63
MATRNSTTSI GEYLLQRLHE AGAHHIFGVP GDYILKFYEQ ISQGPVRHIG TTREDTAAFA      60
ADGYARCQGI GAMAITYGVG ALNVVNAVAG AYAESSPVVV ISGAPGVWEQ REDPLLHHRF     120
GPYTFQREIF DRITCATTVL DDPITAFRQI DRTIAAAQRE HKPVYIELPR DRVTVAGVPL     180
PAVAEATPQE TSDAATLDEA VAETLALLAQ AKSPVLIAGV EVHRCGLQDA LVDLVVRAGL     240
PVAATLTGKS VVGERHPAYI GVYEGAASSE HTRQMVERAD VLIMLGVTLN DVDTGVYTAN     300
LDPHRLVRAS QGEVNIRYHR YPRVQLQDFI GALARQVSPR REALPSQPFV DSGPAFPVPG     360
QAMTTARLIA RLNCALTPEM IVVSDVGDCL FAAIELRVCE RSEFLASAYY TTMGFAVPAA     420
LGAQVARPDR RALILVGDGA FQMTGTELST HARLNLAPII IVFNNAGYST ERNILEGPFN     480
DIAAWRFDRL GEVFGPLHGY DAKTEDAFET ALARALAETG CPSLINVHLS PDDASPAMRR     540
LTERLSHRVG NQ                                                        552

SEQ ID NO: 64           moltype = DNA  length = 1659
FEATURE                 Location/Qualifiers
source                  1..1659
                        mol_type = other DNA
                        organism = Methylohalobius crimeensis
SEQUENCE: 64
atggccacgc gcaactcgac gacctcgatc ggcgagtatc tcctccagcg cctgcacgag      60
gccggcgccc accacatctt cggcgtcccg ggcgattata tcctgaaatt ctatgaacag     120
atctcgcagg gcccggtccg ccacatcggc accacgcgc aagacaccgc ggcgttcgcg     180
gcggacggct atgcccggtg ccagggcatc ggcgcgatgg ccatcaccta cggcgtgggc     240
gccctcaacg tggtgaatgc cgtcgcgggc gcgtacgccg aaagctcgcc ggtggtcgtg     300
atctcggcg ccccgggcgt gtgggaacag cgcgaggacc cgctgctgca ccaccgcttc     360
ggcccctaca cgttccagcg ggagatcttc gaccggatca cctgtgccac cacggtcctg     420
gacgatccga tcacggcgtt ccgccagatc gatcgcacga tcgccgcggc gcagcgcgaa     480
cataagccgg tctacatcga actgccgcgc gatcgggtca cggtggcgg cgtgccgctc     540
ccggccgtcg cggaggcgac gccccaggaa acgtccgacg ccgccaccct ggacgaggcc     600
gtggccgaaa cgctggccct cctcgcccag gccaagagcc cgtgctgat cgcgggcgtg     660
gaggtccacc gctgcggcct ccaggatgcg ctcgtcgacc tggtcgtccg cgcgggcctg     720
ccggtcgcgg ccaccctgac gggcaaatcc gtcgtgggcg aacgcacccc ggcgtatatc     780
ggcgtctacg agggcgccgc gtcgtccgaa cacacccgcc agatggtgga acgcgcggac     840
gtgctcatca tgctcggcgt gacgctgaac gacgtggaca cgggcgtcta tacggcgaac     900
ctggacccc atcgcctcgt ccgcgcgtcc cagggcgagg tgaacatccg ctaccatcgg     960
tatccgcgcg tccagctgca ggacttcatc ggcgccctcg cccgccaggt cagccccgc    1020
cgcgaggccc tgccgtccca gccccttcgtc gatagcggcc ccgccttccc cgtcccgggc    1080
caggcgatga ccacggcgcg gctcatcgcc cgcctgaact gcgccctcac ccccgaaatg    1140
atcgtggtgt ccgatgtggg cgattgcctg ttccgcgcca tcgaactcg ggtctgcgaa    1200
cggagcgagt tcctggcctc cgcctactat acgacgatgg gcttcgcggt gccggccgcc    1260
ctgggcgccc aggtcgcgcg gccggatcgg cgggccctga tcctggtggg cgacggcgcc    1320
ttccagatga cgggcaccga gctgagcacc cacgcccgcc tgaacctggc gccgatcatc    1380
atcgtcttca acaacgcggg ctacagcacg gagcgcaata tctgaggg cccgttcaat    1440
gacatcgcgg cctggcggtt cgaccgcctc ggcgaagtgt tcggccccct gcatggctac    1500
gacgccaaga cggaagatgc gttcgagacg gcgctcgccc gcgcgcctggc cgagacgggc    1560
tgcccgtcgc tcatcaatgt gcatctgtcc ccggacgacg cctcgccggc catgcgccgc    1620
ctgacggagc ggctgtccca tcgcgtgggc aatcagtga                          1659

SEQ ID NO: 65           moltype = AA  length = 544
FEATURE                 Location/Qualifiers
source                  1..544
                        mol_type = protein
                        organism = Methylobacter marinus
SEQUENCE: 65
MSSNPSIGHY LLTRLYESGV HHIFGVPGDY ILRFYQQLSE SPVQHIGTTR EDTAAFATDA      60
YARCRGLGAM AVTYGVGALN VVNAVAGAHA ESSPIVVISG APGIKERREH PLLHHRFGPF     120
RLQREIFERI TCAVAVLDDP YTAFRQIDRV LAAAREHCKP VYIELPRDRV DTEGYPIPSE     180
SLPAPASDAA SLNEAVEEAL QLLDEAASPV LVAGVELHRR GLQDQLLSLV DKTHLPVAAT     240
LTGKSVLGER HPCYLGIYEG AMGSPLARDR VEQADFLLML GVTLNDVDLG IFTARLDANR     300
IIRASQDEVI IHHHRYPQVL LRDFVSMLNE RMTPRPQTGP AVAAKPAAFD FPVKGQPMKI     360
IRLIARLNRF LTPDMVVVSD VGDCLFSAID LRVHENSEFL ASAYYTSMGF AVPAALGAQI     420
ARPTRRTLVL VGDGAFQMTG TELSTIAHLG LNPIVIVFNN KGYSTERYIL DGPFNDIPAW     480
QFERLGELFG PLTGYAASTE DEFEDCLNQA LAQRSSPSLI NVHLSPDDPS AAMRGLAEHL     540
GKRV                                                                 544

SEQ ID NO: 66           moltype = DNA  length = 1635
FEATURE                 Location/Qualifiers
source                  1..1635
                        mol_type = other DNA
                        organism = Methylobacter marinus
SEQUENCE: 66
atgagcagca acccgtcgat cggccactac ctgctcacgc ggctgtacga atccggcgtg      60
caccacatct tcggcgtccc gggcgactac atcctccgc tctaccagca gctgagcgag     120
agcccgtgc agcatatcgg caccacgcgc gaagaccgcg ccgcgcttcgc gaccgatgcg     180
tatgcccgct gtcggggcct gggcgcgatg gccgtgacct acggcgtcgg cgccctcaat     240
gtggtcaacg ccgtgcgggc gcccatgcc gagtcgagcc catcgtggt catctccggc     300
gccccggca tcaaggaacg ccgggaacac cccctgctgc atcaccgctt cggcccgttc     360
cgcctgcagc gcgagatctt cgaacggatc acctgcgccg tcgcggtgct ggatgaccc     420
tataccgcct tccggcagat cgaccgggtc ctggcggcgg cgcgggagca ctgcaagccc     480
```

```
gtctacatcg agctgccgcg cgatcgcgtg gataccgagg gctatccgat cccgtcggag   540
tccctgccgg cccccgcctc cgacgccgcg agcctcaacg aagccgtgga ggaagccctg   600
cagctcctcg atgaggccgc gtcgccgtg ctggtcgccg gcgtggaact gcaccgccgg    660
ggcctccagg atcagctcct ctcgctggtg gataaaaccc atctgccggt cgccgccacg   720
ctcaccggca agtccgtcct gggcgaacgg cacccgtgtt atctgggcat ctacgagggc   780
gcgatgggct ccccctggc gcgggaccgc gtcgagcagg ccgatttcct gctgatgctg    840
ggcgtcacgc tgaacgatgt ggacctcggc atcttcaccg cccgcctcga cgccaatcgc   900
atcatccggg cctcccagga cgaagtcatc atccaccacc accgctatcc gcaggtcctc   960
ctgcgggact tcgtgtccat gctgaacgaa cggatgaccc cgcgcccca gacgggcccg   1020
gccgtcgccg cgaagccggc cgccttcgat ttcccggtca aaggccagcc gatgaagatc  1080
atccggctga tcgcccggct gaatcggttc ctcaccccgg acatggtcgt ggtcagcgac  1140
gtgggcgatt gcctgttcag cgcgatcgac ctgcgggtgc acgaaaacag cgagttcctc  1200
gcctcggcct actacaccag catgggcttc gcggtcccgg ccgcgctggg cgcccagatc  1260
gcccgcccca cccggcgcac gctggtcctc gtgggcgacg gcgcgttcca gatgaccggc  1320
accgagctct cgaccatcgc gcacctcggc ctgaacccga tcgtgatcga cttcaataac  1380
aagggctact cgaccgaacg ctatatcctg gatggcccgt tcaatgatat cccggcctgg  1440
cagttcgagc gcctgggcga actcttcggc ccgctgaccg gctatgccgc cagcaccgag  1500
gacgagttcg aagattgtct gaaccaggcc ctggcccagc ggtcgagccc ctccctcatc  1560
aacgtccacc tctcccgga cgatccgagc gccgccatgc ggggcctcgc cgaacatctg  1620
ggcaagcgcg tctga                                                   1635

SEQ ID NO: 67          moltype = AA  length = 549
FEATURE                Location/Qualifiers
source                 1..549
                       mol_type = protein
                       organism = Methylobacter luteus
SEQUENCE: 67
MEVHLMSSNP SIGHYLLARL YESGVHHIFG VPGDYILRFY QQLSESPIQH IGTTREDTAA    60
FATDAYARCR GLGAMAVTYG VGALNVVNGV AGAYAESSPV VVISGAPGIK ERHEHPLLHH   120
RFGPFRLQHE IFERITCATA VLDDPYMAFR QIDRVLAAAR EHCKPVYIEL PRDRVDVEGY   180
PMPSESMPAP ASDAESLNEA VEETLQLLGK AASPVLIAGV ELHRRGLQDK LLSLVDKTHL   240
PVAASLTGKS VLGERHPCYL GIYEGAMGSS LARDSVEQSD FLLMLGVTMN DIDLGIFTAK   300
LDANRIIRAT QDEVIIHHHR YPHVLLRDFV TVLNERITPR PGIRPAVAAE PAAFDFPVKD   360
QPMKILRLIE RLNRFLTPDM AVVSDVGDCL FAAIDLRVHE NSEFLASAYY TSMGFAVPAA   420
LGAQIANPTR RTLVLVGDGA FQMTGTELST IARFGLNPIV IVFNNCGYST ERYILDGPFN   480
DIACWQFERL SEVFGPLSGY SARTEDEFEN CLTQAFAQQS SPSLINVHLP PDDPSAAMRG   540
LAEHLGKRV                                                          549

SEQ ID NO: 68          moltype = DNA  length = 1650
FEATURE                Location/Qualifiers
source                 1..1650
                       mol_type = other DNA
                       organism = Methylobacter luteus
SEQUENCE: 68
atggaggtgc atctgatgtc ctccaacccg tccatcggcc attatctgct cgcccgcctg    60
tacgagtccg gcgtgcatca catcttcggc gtccccggcg actacatcct gcgcttctac   120
cagctctca gcgagtcccc gatccagcac atcggcacca cgcgcgagga caccgccgcc   180
ttcgcgaccg acgcctacgc ccgctgccgg ggcctgggcg cgatggccgt gacctacggc   240
gtgggcgccc tgaacgtcgt gaacggcgtg gccggcgcgt acgcggaatc ctcgccggtc   300
gtggtgatct ccggcgcccc gggcatcaag gaacgccatg aacatccgct gctgcatcat   360
cgcttcggcc cgttccgcct gcagcatgaa atcttcgaac gcatcacctg cgcgacggcg   420
gtcctggacg atccctacat ggcgttccgg cagatcgacc gggtgctggc cgccgcccgc   480
gagcactgca gcccgtgta tatcgagctg ccgcgcgacc gggtgatgt cgaaggctat   540
ccgatgccga gcgagagcat gccggcccg gcctccgacg cggaaagcct gaacgaagcg   600
gtcgaagaaa cgctgcagct gctgggcaag gccgcgtcg cgtctgat gcgggcgttg    660
gaactgcacc gccgcggcct ccaggacaaa ctgctctccc tggtcgacaa gacccatctc   720
ccggtggccg cctcgctgac cggcaaatcg gtcctgggcg aacgccaccc gtgctatctg   780
ggcatctatg aaggcgcgat gggctcgtcc ctggcccggg actccgtgga gcagtcggac   840
ttcctcctga tgctgggcgt caccatgaac gacatcgatc tgggcatctt caccgcgaag   900
ctggacgcga accgccatcat ccgcgccacg caggatgagg tcatcatcca ccatcatcgc   960
tatcccacg tcctgctgcg ggacttcgtc accgtcctga tgagcgcat cacgcccgc   1020
ccgggcatcc gcccggccgt cgcggcggag ccggccgcct tcgacttccc ggtcaaggac  1080
cagcccatga aaatcctccg gctgatcgaa cggctcaacc gcttcctgac ccccgacatg  1140
gccgtcgtct ccgatgtcgg cgattgcctc ttcgccgtga tcgacctccg gcgtcacgag  1200
aactcggagt tcctgcgtc ggcgtattat accagcatgg gcttcgccgt gccgcgggcg  1260
ctcggcgccc agatcgcgaa cccgacccgc gcacgctgg tgctggtcgg cgacggcgcc  1320
ttccagatga ccggcaccga actgtccacc atcgcccggt tcggcctgaa cccgatcgtg  1380
atcgtcttca ataactgtgg ctattcgacc gagcggtaca tcctggatgg cccctttcaac  1440
gatatcgcct gctggcagtt cgaacgcctg agcgaggtgt tcggccccgct ctcgggctat  1500
tcggccggga cggaggatga gttcgaaaac tgcctgaccc aggccttcgc ccagcagtcc  1560
tcgccgtccc tcatcaacgt ccacctcccc ccggatgacc cgagcgcggc catgcgcggc  1620
ctcgcggaac acctcggcaa gcgcgtctga                                   1650

SEQ ID NO: 69          moltype = AA  length = 542
FEATURE                Location/Qualifiers
source                 1..542
                       mol_type = protein
                       organism = Lamprocystis purpurea
SEQUENCE: 69
```

```
MGDYLLLRLK EAGVDHCFGV PGDYVLRFYD RLCRSDIRHI GTTREDTAAF AADGYARSRG    60
LGALAVTYGV GALNVVNAVA GANAESSPVV VISGAPGVAE QRDDPQLHHR FGPFRFQREI   120
FERITCACAV LDDPYTALRE IDRTLDAARR YSRPVYIELP RDRVDTPAFP IPHEPEEEAG   180
SDPEALAEAV AETLALVGRA QAPVILAGVE LHRRGLQDLL AGFVLKAHLP VAATLTGKSV   240
VAERQPGYLG VYEGAMGPEG ARRVEEADL LLLLGVTPND IDLGINTARL DPARTVRAGQ    300
EEIWVHRHRY PHVHLRDFLA ALTDAVVPHP GPLPDVPGPV GAPDFPQPGQ PMTMARMMAR   360
LNDFLTPDMQ VVADSGDCLF ASVDLRVHAR SEFLASAYYT TMGFAVPAAL GAQVANPGRR   420
PLVLVGDGAF QMTGTELSTA ARLGLDPIVI IGNNRGYTTE RFILEGPFND IADWRFHRLG   480
ELFGPLRGFS APTEDAFDAA LGAALAFRDG PSVIEVALRP DDCSAALTRL SERLRDVVQQ   540
SA                                                                 542

SEQ ID NO: 70          moltype = DNA  length = 1629
FEATURE                Location/Qualifiers
source                 1..1629
                       mol_type = other DNA
                       organism = Lamprocystis purpurea
SEQUENCE: 70
atgggcgact acctcctgct ccgcctgaag gaagcgggcg tcgaccactg cttcggcgtc     60
cccggcgact acgtcctgcg gttctacgat cggctctgcc ggtcggacat ccggcacatc    120
ggcaccaccc gcgaggacac cgcggccttc gcggccgacg gctacgcccg gtcccgcggc    180
ctgggcgccc tggccgtgac gtatggcgtg ggcgccctca acgtggtcaa cgcggtcgcc    240
ggcgccaacg cggagtcctc cccggtcgtc gtgatctccg gcgccccggg cgtcgcggca    300
cagcgcgacg atcccagct gcaccatcgg ttcggcccgt tccggttcca gcgcgagatc     360
ttcgaacgca tcacctgcgc gtgtgccgtg ctcgacgacc cgtacaccgc cctgcgcgag    420
atcgaccgca cgctcgacgc ggcgcggcgg tacagccggc ccgtgtatat cgaactcccg    480
cgcgacgtgg tcgacacgcc cgccttcccc atccccacg agccggaaga ggaagccggc    540
agcgacccgg aggccctggc cgaggcggtc gccgaaaccc tggcgctcgt cggccgcgcg    600
caggcccccg tcatcctggc cggcgtggag ctgcaccgcc gcggcctgca ggacctcctg    660
gccggcttcg tgctgaaggc ccacctcccg gtggccgcga cgctgacggg caagtcggtg    720
gtcgcggagc gccagccggg ctacctgggc gtgtacgagg gcgcgatggg cccggaaggc    780
gcccgccgcg tcgtggaaga agccgacctg ctgctcctgc tgggcgtgac cccgaacgac    840
atcgacctgg gcatcaacac cgcccggctg gaccccgccc ggaccgtccg ggccggccag    900
gaagaaatct gggtccatcg gcaccgctac ccgcatgtgc acctgcggga tttcctggcc    960
gcgctgacgg atgccgtggt gccccacccc ggccccctgc cggatgtccc cggcccggtc   1020
ggcgcccccg acttcccccca gccgggccag cccatgacga tggcccgcat gatgcccgac   1080
ctgaacgact tcctgacccc cgacatgcag gtggtggccg actccggcga ctgtctgttc   1140
gcgtccgtcg acctgcgcgt ccatgcccgc agcgagttcc tggcctcggc ctattacacg   1200
acgatgggct tcgccgtccc ggccgcgctc ggcgcccagg tcgccaaccc cggccgcgc    1260
ccgctcgtgc tggtgggcga cggcgccttc cagatgaccg gcacggagct gtcgaccgcc   1320
gcccgcctgg gcctcgatcc gatcgtcatc atcggcaata atcgcggcta caccaccgaa   1380
cgcttcatcc tggaaggccc gttcaacgac atcgccgact ggcggttcca tcgcctgggc   1440
gaactgttcg gcccgctgcg gggcttctcg gcccccacgg aagacgcctt cgacgccgcc   1500
ctgggcgccg ccctggcctt ccgggacggc ccctccgtca tcgaggtggc gctcgcccgg   1560
gacgactgct ccgcggcccc gacccggctc tccgaacgcc tgcgcgatgt ggtgcagcag   1620
agcgcctga                                                          1629

SEQ ID NO: 71          moltype = AA   length = 551
FEATURE                Location/Qualifiers
source                 1..551
                       mol_type = protein
                       organism = Andreprevotia chitinilytica
SEQUENCE: 71
MHMRETDMDT MGGYLLQALH REGVRHVFGV PGDYILRWYQ LLSQSNLKHV GTSREDCAAF    60
AADGYARCHG LGALAVTYGV GALNVVNAVA GANAESSPVV VISGAPGVAE QRQNPLLHHR   120
FGPFCFQREI FERMTCYAAA LDDPLLARRQ IDRALELAQL HHKPVYLELP RDLVDAELPP   180
ALSPPTSSAP ISDWDALEEA VAETLSLLAK AKSAAVLAGS ELHRYQLQDE LTQLVERGAL   240
PVAATLTGKS VIAERHPAYM GIYEGAMGGA RTRELIERAD VLLLLLGATLN DVDLGIFTAK   300
LDVQHMVQAT ADGVQIHHHR YTGVPLGDYV RALTAGIERS GRSLPVVEPP LAAIGFPITS   360
QPMTVARLIG RLNDTLPQDM IVVCDTGDCL FASLELRVHA RTAFLASAFY TTMGFAVPAS   420
LGAQLGSGRR PLVLVGDGAF QMTGTELATA AWKGLNPIVI VFNNAGYSTE RFILDGPFND   480
IPSWQFHRLG ELFGPLAGFD VHDEESFDSA WRSALAQTDR PSLLNVHLAP DDPSPAMRRL   540
GEHLGKRVRA G                                                       551

SEQ ID NO: 72          moltype = DNA  length = 1656
FEATURE                Location/Qualifiers
source                 1..1656
                       mol_type = other DNA
                       organism = Andreprevotia chitinilytica
SEQUENCE: 72
atgcacatgc gggagacgga catggatacg atgggcggct acctgctgca ggccctgcat     60
cgcgagggcg tccggcatgt gttcggcgtg ccgggcgact acatcctgcg ctggtatcag    120
ctgctctcgc agagcaacct gaagcacgtc ggcacctcgc gcgaagactg cgccgcgttc    180
gccgccgacg gctacgcgcg gtgccacggc ctgggcgccc tggccgtcac ctacggcgtc    240
ggcgccctga acgtggtgaa cgcggtggcc ggcgcgaacg ccgagtcctc ccccgtggtg    300
gtcatcagcg gcgcccccgg cgtcgcggaa cagcgccaga accgctgct ccaccaccgc     360
ttcggcccgt tctgcttcca gcgcgaaatc ttcgaacgca tgacgtgcta cgcggcggcg    420
ctcgacgatc cctcctggc gcggcgccag atcgaccgcg ccctggagct ggcccagctc     480
catcacaagc cggtctacct cgaactgccg cgggatctcg tggatgcgga actgccgccg    540
gccctctcgc cgcccacctc ctcggcgccc atctcggatt gggacgcgct cgaagaagcg    600
```

```
gtcgcggaaa ccctcagcct cctggcgaag gcgaaaagcg ccgcggtcct cgccggctcg   660
gagctgcacc gctaccagct gcaggacgag ctgacgcagc tcgtggaacg gggcgccctc   720
cccgtggccg ccaccctgac cggcaagtcc gtgatcgccg agcgccaccc ggcctacatg   780
ggcatctacg aaggcgcgat gggcggcgcc cgcacgcggg aactgatcga gcgggcggac   840
gtgctgctgc tgctgggcgc caccctcaat gatgtggatc tgggcatctt caccgccaag   900
ctggatgtcc agcacatggt gcaggcgacc gccgatggcg tccagatcca ccaccaccgc   960
tacaccggcg tcccctcgg cgactatgtg cgggccctga cggcgggcat cgaacgctcg   1020
ggccgctccc tcccggtggt ggaaccccc ctggcggcca tcggcttccc gatcacctcg   1080
cagcccatga ccgtggcccg cctgatcggc cgcctcaatg ataccctgcc gcaggacatg   1140
atcgtcgtct gtgacaccgg cgactgcctc ttcgcctccc tggagctccg cgtccatgcc   1200
cgcaccgcct tcctggcctc ggcgttctac acgacgatgg gcttcgccgt gcccgcctcg   1260
ctgggcgccc agctcggctc gggccggcgc ccctggtgc tggtgggcga tggcgccttc   1320
cagatgacgg gcaccgagct ggccaccgcc gcgtggaagg gcctgaaccc catcgtcatc   1380
gtcttcaaca acgccggctc ctccaccgag cgcttcatcc tggacggccc cttcaacgac   1440
atcccgtcgt ggcagttcca tgcctgggc gaactgttcg gcccgctggc cggcttcgat   1500
gtccacgacg aagagtcgtt cgactccgcc tggcgctcgg ccctcgccca gaccgatcgc   1560
ccgtcgctgc tgaacgtgca tctggccccc gacgacccct cgcccgcgat gcggcggctg   1620
ggcgaacatc tgggcaagcg ggtgcgggcg ggctga                           1656

SEQ ID NO: 73          moltype = AA   length = 548
FEATURE                Location/Qualifiers
source                 1..548
                       mol_type = protein
                       organism = Lactococcus lactis
SEQUENCE: 73
MYTVGDYLLD RLHELGIEEI FGVPGDYNLQ FLDQIISHKD MKWVGNANEL NASYMADGYA    60
RTKKAAAFLT TFGVGELSAV NGLAGSYAEN LPVVEIVGSP TSKVQNEGKF VHHTLADGDF   120
KHFMKMHEPV TAARTLLTAE NATVEIDRVL SALLKERKPV YINLPVDVAA AKAEKPSLPL   180
KKENSTSNTS DQEILNKIQE SLKNAKKPIV ITGHEIISFG LEKTVTQFIS KTKLPITTLN   240
FGKSSVDEAL PSFLGIYNGT LSEPNLKEFV ESADFILMLG VKLTDSSTGA FTHHLNENKM   300
ISLNIDEGKI FNERIQNFDF ESLISSLLDL SEIEYKGKYI DKKQEDFVPS NALLSQDRLW   360
QAVENLTQSN ETIVAEQGTS FFGASSIFLK SKSHFIGQPL WGSIGYTFPA ALGSQIADKE   420
SRHLLFIGDG SLQLTVQELG LAIREKINPI CFIINNDGYT VEREIHGPNQ SYNDIPMWNY   480
SKLPESFGAT EDRVVSKIVR TENEFVSVMK EAQADPNRMY WIELILAKEG APKVLKKMGK   540
LFAEQNKS                                                             548

SEQ ID NO: 74          moltype = DNA   length = 1647
FEATURE                Location/Qualifiers
source                 1..1647
                       mol_type = other DNA
                       organism = Lactococcus lactis
SEQUENCE: 74
atgtacaccg taggagacta cctacttgac agactccatg agctgggcat agaggaaatc    60
ttcggagtcc cgggtgatta caacctgcag ttcctggacc agatcatcag ccacaaggac   120
atgaagtggg tgggcaacgc gaacgaactg aacgcgagct atatggcgga cggttatgcc   180
cgcaccaaga aggcagccgc gttcctcacc actttcggcg tgggcgaact cagcgccgtg   240
aacggcttgg caggcagcta tgcggaaaac ctgccggtg tggaaatcgt tggctccccg   300
acctcgaagg tgcagaacga gggcaagttc gtgcatcata ccctggcgga cggggacttc   360
aagcatttca tgaagatgca cgaacccgtc accgctgccc gcacgctgct gaccgcggaa   420
aacgcgaccg tggagatcga ccgggtcctc tccgccctgc tgaaggaacg gaagcccgtg   480
tacatcaatc tacccgtcga cgtagcagcc gccaaggccg aaaagccctc gctcccgctg   540
aagaaggaga actcgacgag caacacgagt gaccaggaaa tcctgaacaa gatccaggag   600
tcgttaaaga acgcgaagaa gccgatcgtc atcaccggcc atgagatcat cagcttcggc   660
cttgagaaga ccgtgacaca gttcatctcc aagaccaagc tgcccatcac caccctcaac   720
ttcggcaagt ccagcgtgga cgaagccctg ccgagcttcc tgggcatcta caacggcacc   780
ctgtcggaac ccaacctgaa ggagttcgtc gaaagcgcgg acttcatcct gatgctgggc   840
gtgaagctga ccgactcctc gacgggagcc ttcacccatc acctgaacga aaacaagatg   900
atctcctca acatcgatga aggcaagatc ttcaacgagc gcatccaaaa cttcgacttc   960
gaaagcctga tctcctcgct gctggacctg tccgagatcg agtacaaggg caagtacatc  1020
gacaagaagc aggaagactt cgtgccgtcg aacgcgctgc tgtcgcagga ccgcctgtgg  1080
caggcggtcg aaaacctgac gcagtcaaac gaaaccatcg tcgccgaaca gggaacctcg  1140
ttcttcggtg cctcaagtat cttcctgaag tccaagtccc acttcatcgg ccagcccctg  1200
tggggctcga tcggctatac cttcccggca gcgctaggct cccagatcgc ggacaaggaa  1260
tcgcgccacc tgctcttcat cggcgacggc tccctgcagc tgaccgtcca ggagctgggc  1320
ctcgccatcc gggaaaagat caacccgatc tgcttcatca ttaacaacga cggctacacc  1380
gtggagcgcg agattcatgg cccgaaccag agctacaacg acatccccat gtggaactac  1440
tctaagctgc cggaatcgtt tggcgccacg gaggaccggg tggtcagcaa gatcgtccgg  1500
acggagaacg agttcgtctc ggtgatgaag gaagcgcagg cggaccccaa ccggatgtat  1560
tggatcgagc tcatcttggc caaggagggc gctccgaagg tcctgaagaa gatgggcaag  1620
ctcttcgccg aacagaacaa gtcgtaa                                      1647

SEQ ID NO: 75          moltype = AA   length = 570
FEATURE                Location/Qualifiers
source                 1..570
                       mol_type = protein
                       organism = Lactococcus lactis
SEQUENCE: 75
MGSSHHHHHH SSGLVPRGSH MASMYTVGDY LLDRLHELGI EEIFGVPGDY NLQFLDQIIS    60
REDMKWIGNA NELNASYMAD GYARTKKAAA FLTTFGVGEL SAINGLAGSY AENLPVVEIV   120
```

```
GSPTSKVQND  GKFVHHTLAD  GDFKHFMKMH  EPVTAARTLL  TAENATYEID  RVLSQLLKER   180
KPVYINLPVD  VAAAKAEKPA  LSLEKESSTT  NTTEQVILSK  IEESLKNAQK  PVVIAGHEVI   240
SFGLEKTVTQ  FVSETKLPIT  TLNFGKSAVD  ESLPSFLGIY  NGKLSEISLK  NFVESADFIL   300
MLGVKLTDSS  TGAFTHHLDE  NKMISLNIDE  GIIFNKVVED  FDFRAVVSSL  SELKGIEYEG   360
QYIDKQYEEF  IPSSAPLSQD  RLWQAVESLT  QSNETIVAEQ  GTSFFGASTI  FLKSNSRFIG   420
QPLWGSIGYT  FPAALGSQIA  DKESRHLLFI  GDGSLQLTVQ  ELGLSIREKL  NPICFIINND   480
GYTVEREIHG  PTQSYNDIPM  WNYSKLPETF  GATEDRVVSK  IVRTENEFVS  VMKEAQADVN   540
RMYWIELVLE  KEDAPKLLKK  MGKLFAEQNK                                      570

SEQ ID NO: 76           moltype = DNA  length = 1713
FEATURE                 Location/Qualifiers
source                  1..1713
                        mol_type = other DNA
                        organism = Lactococcus lactis
SEQUENCE: 76
atgggctcgt cccatcatca tcaccaccat tccagcggcc tggtcccgcg cggcagccac   60
atggcctcga tgtacaccgt gggcgattac ctgctggacc ggctccacga actgggcatc  120
gaagagatct tcggcgtccc gggcgactat aacctggatca gatcatctcc             180
cgcgaggaca tgaaatggat cggcaatgcg aacgagctga cgcctcctca tatgccgac   240
ggctatgccc gcaccaaaaa agccgccgcc ttcctgacca cgttcggcgt gggcgaactg  300
tcggccatca acggcctggc cggctcctac gccgagaacc tgcccgtggt ggaaatcgtg  360
ggctcgccga cctcgaaggt ccagaacgac ggcaagttcg tgcaccacac gctcggcgac  420
ggcgacttca gcacttcat gaagatgcac gagccggtca ccgccgcccg caccctgctg   480
acggccgaga acgcgaccta tgaaatcgac cgggtgctct cccagctcct gaaggagcgg  540
aagccggtgt acatcaacct ccccgtcgat gtggccgccg ccaaggccga aaacccgcg   600
ctgagcctgg agaaggagtc ctccacgacc aacaccagcg aacaggtgat cctcagcaag  660
atcgaagaat ccctcaagaa cgcccagaaa cccgtggtga tcgcgggcca tgaggtgatc  720
tcgttcggcc tggagaaaac cgtcacccag ttcgtgagcg aaaccaagct ccccatcacc  780
accctcaact tcggcaagtc ggccgtggac gagtccctgc cgtccttcct gggcatctat  840
aatggcaaac tgtcggaaat cagcctgaaa aatttcgtcg aaagcgccga cttcatcctc  900
atgctgggcg tgaagctgac cgactcctcg accggcgcct tcacccacca cctcgatgaa  960
aacaagatga tctccctgaa catcgacgaa ggcatcatct tcaacaaggt ggtcgaagac 1020
ttcgacttcc gggccgtcgt gtcgagcctg tccgaactga aaggcatcga atatgaaggc 1080
cagtacatcg acaagcagta tgaagagttc atccccgtcgt cggcgccgct cagccaggat 1140
cgcctctgga aggccgtgga aagcctgacc cagtccaacg aaacgatcgt cgccgaacag 1200
ggcacctcgt tcttcggcgc cagcacgatc ttcctgaagt ccaactcccg gttcatcggc 1260
cagccgctgt ggggctcgat cggctacacg ttccccggccg cgctgggcag ccagatcgcc 1320
gacaaggaat cccgccacct cctgttcatc ggcgacggct ccctccagct gaccgtgcag 1380
gagctgggcc tgtcgatccg cgaaaagctg aatccgatct gcttcatcat caacaacgac 1440
ggctacacgg tcgaacggga gatccacggc ccgacgcagt cctacaacga catccccatg 1500
tggaactaca gcaaactccc ggaaaccttc ggcgccaccg aagaccgcgt cgtctcgaag 1560
atcgtgcgga ccgaaaacga gttcgtgtcc gtgatgaaag aggcgcaggc ggatgtgaac 1620
cggatgtact ggatcgaact ggtcctggag aagaggacg ccccgaagct cctgaagaag 1680
atgggcaagc tcttcgccga gcagaacaaa tga                                1713

SEQ ID NO: 77           moltype = AA  length = 549
FEATURE                 Location/Qualifiers
source                  1..549
                        mol_type = protein
                        organism = Streptococcus didelphis
SEQUENCE: 77
MYTVGDYLLD  RLKEIGIDHI  FGVPGDYNLQ  FLDQITARDD  LKWVGNANEL  NASYMSDGYA    60
RTKKAAAFVT  TFGVGELSAI  NGLAGSFAEN  VPVIEIVGSP  TTKVQEAGKL  VHHTLGDGNF   120
NHFQEMHKSV  TVAQVKVSAE  HAQTDIDQVL  LSLLKERKPV  YINLPIDVAQ  MPAQKPESAL   180
LVEKVISEQD  KIILQAIEKG  LKTAKQPLIM  VGHEVASFGL  EATINNFIKK  KKYPVTSLSL   240
GKGIVNESPE  TFLGIYSGAL  SPQALKDYVD  QADFILTLGV  KLTDSVTGGF  SQGFDAKQVL   300
SLAANQASLF  GENYQGYHFS  DVIREIENLD  IPSYSGSYIA  KTKVADFEAE  KGQVLSQKRF   360
WQAMESFVQA  GDTIFAEQGT  SYFGASQLNL  KENVAYQGQP  LWGSIGYTFP  AVFGSQLANP   420
DSRHILFVGD  GSLQLTVQDI  GLALREQLNT  IVFVINNDGY  TVERKIHGPE  EVYNDIPWQ    480
YSQLPASFGG  NDSQVLARKV  STEEELVEIL  EKARADVSRM  YWIELMLPKM  DAPEYLEKLG   540
KLFAQQNKA                                                               549

SEQ ID NO: 78           moltype = DNA  length = 1650
FEATURE                 Location/Qualifiers
source                  1..1650
                        mol_type = other DNA
                        organism = Streptococcus didelphis
SEQUENCE: 78
atgtataccg tcggcgatta tctgctggat cggctcaagg aaatcggcat cgaccatatc   60
ttcggcgtcc cgggcgacta caacctccag ttcctggatc agatcaccgc ccgcgacgac  120
ctcaaatggg tgggcaacgc caacgaactc aacgcgagct acatgtccga cggctatgcc  180
cgcaccaaga aggccgccgc cttcgtcacc accttcggcg tgggcgaact gtcggcgatc  240
aacggcctgg ccggctcgtt cgcggaaaac gtccccgtga tcgagatcgt cggctcgccg  300
acgaccaagg tgcaggaagc cggcaaactg gtgcaccata cgctcggcga cggcaacttc  360
aatcacttcc aggagatgca caaatcggtc accgtggccc aggtcaaagt cagcgccgaa  420
catgcccaga ccgacatcga ccaggtgctc ctgtccctgc tgaaggagcg gaagccggtg  480
tatatcaacc tgcccatcga tgtggcccag atgcccgccc agaagccgga atcggccctc  540
ctggtcgaga aggtcatctc cgagcaggac aagatcatcc tgcaggcgat cgagaaaggc  600
ctgaagaccg ccaagcagcc cctcatcatg gtcggccatg aagtcgccag cttcggcctg  660
```

```
gaagccacca tcaacaactt catcaaaaag aagaagtacc ccgtgacctc gctcagcctg    720
ggcaaaggca tcgtcaacga gtcgccggaa accttcctgg gcatctactc cggcgccctg    780
tccccgcagg ccctgaaaga ctacgtcgat caggcggact tcatcctcac cctcggcgtc    840
aagctgaccg actccgtgac gggcggcttc agccagggct cgatgcgaa gcaggtgctg    900
agcctggccg ccaaccaggc gtcgctcttc ggcgaaaact accagggcta tcacttctcg    960
gacgtgatcc gcgaaatcga aaatctggac atccccagct attcgggctc ctatatcgcc   1020
aagaccaagg tcgccgattt cgaagcgag aagggccagg tcctgtccca gaagcgcttc   1080
tggcaggcga tggaatcgtt cgtccaggcc ggcgacacca tcttcgcga gcagggcacc   1140
tcgtacttcg gcgcgagcca gctcaacctg aaagagaacg tggcctacca gggccagccg   1200
ctctggggca gcatcggcta taccttcccg gccgtcttcg gcagccagct cgcgaacccc   1260
gattcgcggc atatcctgtt cgtcggcgac ggcagcctgc agctgaccgt ccaggacatc   1320
ggcctggcgc tgcgcgagca gctgaacacg atcgtgttcg tcatcaacaa cgacggctat   1380
accgtggagc gcaagatcca cggcccgaa gaggtctata tgacatcc gcagtggcag   1440
tacagccagc tccccgcctc cttcagcggc aacgactcgc aggtcctggc ccggaaagtg   1500
agcaccgaag aggagctggt cgaaatcctg gaaaaggcgc gggccgacgt gtcccggatg   1560
tattggatcg agctcatgct ccccaaaatg gacgcgccgg agtatctgga aaagctgggc   1620
aagctgttcg cccagcagaa taaagcctga                                   1650

SEQ ID NO: 79         moltype = AA  length = 548
FEATURE               Location/Qualifiers
source                1..548
                      mol_type = protein
                      organism = Enterococcus caccae
SEQUENCE: 79
MYTVADYLLD RLKELGIDEL FGVPGDYNLQ FLDHITARQD LEWIGNANEL NAAYMADGYA    60
RTKGISAFVT TFGVGELSAI NGLAGSFAEN VPVVEIVGSP TTTVQNDKKL VHHTLGDGNF   120
LHFEKMHEEV TAAIAHLTAE NALTEIDRVL IIAMIEKRPV YINLPIDIAE FKATPPLSPL   180
SRSAEKLTDV EIAILDKVEK ALSQAKNPVV IAGHEILSYH IEHQLDEFIQ KFNLPITTLP   240
LGKRAFNEED PHYLGTYSGS TTEEPLKTRV DTADLVLLLG AKLTDSATSG FSFGFTDQQI   300
ISIGSTEVLF YGETFKAVQL DRFVSALTTL SFSRYEDEIQ PVTRISNQAI KDEKLSQKQF   360
WEMVETFLIP GDTVIGEQGT SFFGLTNVAL KRNMHFIGQP LWGSIGYTFP SALGSQIANK   420
ESRHLLFIGD GSLQLTVQEL GTALREKLTP IVFVINNNGY TVEREIHGAT EQYNDIPMWD   480
YQNLPLVFGG NNQTVATYKV TTAIELDEVM KTARKDTKRL QWIEVVMAQD DAPELLKKLA   540
KIFAKQNS                                                            548

SEQ ID NO: 80         moltype = DNA  length = 1647
FEATURE               Location/Qualifiers
source                1..1647
                      mol_type = other DNA
                      organism = Enterococcus caccae
SEQUENCE: 80
atgtacaccg tcgccgatta cctgctggat cgcctgaagg agctgggcat cgatgagctg     60
ttcggcgtgc cgggcgacta caacctgcag ttcctcgacc acatcaccgc ccgccaggac   120
ctggagtgga tcggcaacgc caacgaactg aacgccgcgt atatggccga cggctacgcc   180
cggaccaagg gcatctcggc gttcgtgacc accttcggcg tgggcgagct gtccgccatc   240
aatggcctcg ccggcagctt cgcggagaac gtcccggtcg tcgagatcgt gggctccccg   300
accaccacgg tccagaacga caagaagctg gtgcatcaca cgctgggcga cggcaatttc   360
ctgcatttcg agaagatgca tgaagaggtc accgccgcca tcgcgcacct caccgccgaa   420
aacgcgctga ccgaaatcga ccgggtgctc atcatcgcca tgatcgagaa gcgcccggtc   480
tatatcaacc tcccgatcga catcgccgag ttcaaagcca cccccgccgct cagcccctg   540
agccggtcgg ccgaaaagct gacggatgtc gaaatcgcca tcctcgacaa ggtggaaaag   600
gcgctgtcgc aggcgaagaa ccccgtcgtg atcgccggcc acgaaatcct cagctaccat   660
atcgaacatc agctggacga gttcatccag aagttcaacc tcccgatcac cacgctgccc   720
ctgggcaaac gcgcgttcaa tgaggaagac ccgcactatc tcggcaccta cagcggctcc   780
accaccgagg agccgctgaa gacccgcgtg gataccgcgg atctggtcct gctgctgggc   840
gcgaagctga cggactcggc cacctcgggc ttctccttcg gcttcaccga ccagcagatc   900
atcagcatcg gctccacgga ggtcctcttc tacggcgaaa ccttcaaagc cgtgcagctc   960
gaccgcttcg tctcggcgct caccaccctg agcttctccc cgtacgaaga tgaaatccag  1020
ccggtgaccc ggatcagcaa ccaggcgatc aaggacgaga agctcgtcga gaagcagttc  1080
tgggagatgg tcgagacgtt cctgatcccg ggcgacaccg tgatcggcga gcagggcacc  1140
tcgttcttcg gcctgaccaa cgtcgccctg aagcggaata tgcacttcat cggccagccg  1200
ctgtggggca gcatcggcta tacgttcccg tcggccctcg gctcgcagat cgccaacaag  1260
gaaagccggc atctgctgtt catcggcgat ggctccctcc agctgaccgt gcaggaactg  1320
ggcaccgccc tgcgcgagaa gctcaccccg atcgtcttcg tcatcaacaa caatggctat  1380
accgtggaac gggagatcca cggcgccacc gagcagtaca acgacatccc catgtgggat  1440
tatcagaacc tgccgctcgt gttcggcggc aacaaccaga ccgtcgccac ctacaaggtc  1500
accaccgcga tcgaactgga tgaggtcatg aaaaccgccc gcaaggacac caagcgcctg  1560
cagtggatcg aagtggtcat ggcgcaggat gacgcgccgg aactgctcaa gaaactcgcc  1620
aaaatcttcg ccaaacagaa cagctga                                      1647

SEQ ID NO: 81         moltype = AA  length = 548
FEATURE               Location/Qualifiers
source                1..548
                      mol_type = protein
                      organism = Enterococcus haemoperoxidus
SEQUENCE: 81
MYTISDYLLD RLKELGIDEV FGVPGDYNLQ FLDHITARED LKWIGNANEL NAAYMADGYA    60
RTKGISAFVT TFGVGELSAV NGLAGSYAEN VPVVEIIGSP TTTVQNNKKL VHHTLGDGDF   120
LRFEKMHEEV TAAIAHLTIE NATSEIDRVL TIAMTEKRPV YINLPIDIAE TKTNKPNKPL   180
```

```
QKMTERLTEA EATILSKVEK ALQQAENPVI IAGHEILSYH IEHQLNEFIQ KFNLPITTLP    240
LGKGAFDEED SHYMGTYSGS PTEEPLKSRV DNADLVLLLG AKLTDSATSG FSFGFTDKQI    300
ISIGATEVLF YGEKHEAIQL DRFVSALSTL SFSRFTGDLL PVKRISKVEF KDEQLTQKRF    360
WKMVETFLLQ GDTVVGEQGT SFFGLTNVPL KKDMHFIGQP LWGSIGYTFP STLGSQIANK    420
DSRHLLFIGD GSLQLTVQEL GTAIREKLTP IVFVINNNGY TVEREIHGAT EQYNDIPMWD    480
YQNLPLVFGG TSQTVATYKA TTEAELAEVM KSARKDTERL QWIEVVMDQE DAPLLLQKLA    540
KIFAKQNS                                                            548

SEQ ID NO: 82           moltype = DNA  length = 1647
FEATURE                 Location/Qualifiers
source                  1..1647
                        mol_type = other DNA
                        organism = Enterococcus haemoperoxidus
SEQUENCE: 82
atgtacacca tcagcgacta cctcctggac cggctgaagg aactcggcat cgacgaagtc     60
ttcggcgtcc cgggcgacta caacctccag ttcctcgatc atatcaccgc ccgcaagac    120
ctgaaatgga tcggcaacgc gaatgaactc aatgccgcct acatggcgga cggctatgcc    180
cgcaccaagg gcatcagcgc cttcgtgacc accttcggcg tcggcgaact gagcgcgtg    240
aacggcctgg ccggctcgta cgccgagaac gtgccggtgg tcgagatcat cggcagcccc    300
accaccaccg tgcagaacaa caagaaactg gtccaccaca cgctgggcga tggcgacttc    360
ctgcgggttc aaaagatgca cgaggaagtc accgccgcga tcgcccatct gaccatcgag    420
aatgccacga gcgaaatcga ccgcgtcctg acgatcgcca tgaccgagaa cgcgccccgg    480
tatatcaacc tgccgatcga tatcgcggaa accaagacga caagccgaa caaaccgctg    540
cagaagatga ccgagcggct cacggaagcc gaagcgacca tcctgtcgaa ggtcgagaag    600
gccctccagc aggcggagaa cccggtcatc atcgccggcc atgagatcct gtcctaccac    660
atcgagcaca gctgaatga gttcatccag aagttcaatc tccccatcac cacgctgccg    720
ctgggcaagg gcgccttcga cgaggaagac tcgcactaca tgggcacgta ttccggctcc    780
cccacggaag agccctgaa gagccgcgtg gataacgccg atctggtcct gctgctcggc    840
gccaagctga ccgattccgc gacctccggc ttctcgttcg gcttcaccga caagcagatc    900
atcagcatcg gcgcgaccga agtcctgttc tacggcagga aacacgagc catccagctc    960
gatcgcttcg tgtccgccct gtccacgctc tccttctccc gcttcaccgg cgatctgctc   1020
ccggtgaaac ggatcagcaa ggtcgagttc aaggacgagc agctcacca gaagcgcttc   1080
tggaagatgg tcgaaacgtt cctgctccag ggcgacaccg tcgtgggcga acagggcacc   1140
agcttcttcg gcctgaccaa tgtgcccctg aagaaggata tgcacttcat cggccagccg   1200
ctctggggca gcatcggcta taccttcccc agcaccctgg gctcgcagat gccaacaag   1260
gactcccgcc acctgctgtt catcggcgat ggctcgctgc agctgaccgt gcaggagctc   1320
ggcacggcca tccgggagaa gctcacgccg atcgtcttcg tcatcaacaa caacggctac   1380
accgtggaac gcgaaatcca cggcgccacc gagcagtaca acgacatccc cgatgtggac   1440
taccagaacc tccccctggt cttcggcggc acgagccaga ccgtcgcgac gtataaagcc   1500
acgaccgaag cggagctggc cgaggtcatg aagtccgcccc ggaaggatac ggagcggctg   1560
cagtggatcg aggtggtgat ggaccaggaa gacgcgcccc tgctgctgca gaagctggcc   1620
aagatcttcg ccaagcagaa ctcgtga                                       1647

SEQ ID NO: 83           moltype = AA  length = 548
FEATURE                 Location/Qualifiers
source                  1..548
                        mol_type = protein
                        organism = Enterococcus moraviensis
SEQUENCE: 83
MYTVADYLLD RLKELGIDEV FGVPGDYNLQ FLDHITARKD LEWIGNANEL NAAYMADGYA     60
RTKGISALVT TFGVGELSAI NGLAGSYAES IPVIEIVGSP TTTVQQNKKL VHHTLGDGDF    120
LRFERIHEEV SAAIAHLSTE NAPSEIDRVL TVAMTEKRPV YINLPIDIAE MKASAPTTPL    180
NHTTDQLTTV ETAILTKVED ALKQSKNPVV IAGHEILSYH IENQLEQFIQ KFNLPITVLP    240
FGKGAFNEED AHYLGTYTGS TTDESMKNRV DHADLVLLLG AKLTDSATSG FSFGFTEKQM    300
ISIGSTEVLF YGEKQETVQL DRFVSALSTL SFSRFTGDMV SVKRLATPKV RDEKLTQKQF    360
WQMVESFLLQ GDTVVGEQGT SFFGLTNVPL KKDMHFIGQP LWGSIGYTFP SALGSQIANK    420
ESRHLLFIGD GSLQLTVQEL GTAIREKLTP IVFVINNNGY TVEREIHGAT EQYNDIPMWD    480
YQKLPFVFGG TDQTVATYKV STEIELDNAM TRARTDVDRL QWIEVVMDQN DAPVLLKKLA    540
KIFAKQNS                                                            548

SEQ ID NO: 84           moltype = DNA  length = 1647
FEATURE                 Location/Qualifiers
source                  1..1647
                        mol_type = other DNA
                        organism = Enterococcus moraviensis
SEQUENCE: 84
atgtacacgg tggcgactac tctgctggac cggctgaaag agctgggcat cgacgaagtg     60
ttcggcgtgc ccggcgacta caacctgcag ttcctcgaca catcacggc ccggaaggac    120
ctcgaatgga tcggcaatgc caacgaactg aacgccgcct acatggccga cggctacgcc    180
cgcaccaagg gcatctccgc gctggtcacc accttcggcg tcggcgaact gtcggccatc    240
aatgccctgg ccggctcgta cgcggaaagc atccgggtga tcgaaatcgt gggctccccg    300
acgacgacgt gcagcagaa caagaagctc gtgcatcata cgctgggcga cggcgatttc    360
ctgcggttcg agcgcatcca cgaggaggtg tcggcggcca tcgcgcacct gtccaccgag    420
aacgcccct ccgagatcga ccgcgtgctg acggtgcgga cgcgaaaa cgcccggtc    480
tatatcaacc tcccgatcga tatcgcggag atgaaagcgt cggccccac cacgccctg    540
aaccacacca cggatcagct gacgaccgtc gagacggcca cctcaccaa ggtcgaggat    600
gcgctgaagc agtccaagaa tcccgtcgtc atcgccggcc acgagatcct gagctaccac    660
atcgaaaatc agctggaaca gttcatccag aagttcaacc tgccgatcac cgtgctcccg    720
ttcggcaagg gcgccttcaa cgaagaggac gcgcattacc tgggcaccta tacgggcagc    780
```

-continued

```
acgaccgacg agtccatgaa gaatcgcgtc gaccatgcgg acctggtcct gctgctcggc   840
gccaagctca ccgactcggc cacctcgggg ttcagcttcg gcttcacgga gaagcagatg   900
atctcgatcg gctcgaccga agtgctgttc tatggcgaga agcaggagac ggtgcagctc   960
gaccgcttcg tgagcgccct gtcgaccctg tccttctccc gcttcaccga cgagatgccg  1020
agcgtgaaac gcctggccac cccgaaggtg cgcgatgaga agctgaccca agacagttc   1080
tggcagatgg tcgagagctt cctgctccag ggcgacaccg tcgtgggcga gcagggcacg  1140
agcttcttcg gcctgacgaa tgtgcccctg aaaaaggaca tgcacttcat cggccagccg  1200
ctgtggggca gcatcggcta tacgttcccc agcgccctgg gcagccagat cgccaacaaa  1260
gagtcccgcc acctgctgtt catcggcgac ggctcgctcc agctgacggt ccaggagctg  1320
ggcaccgcga tccgcgaaaa gctgaccccc atcgtgttcg tcatcaacaa caacggctat  1380
accgtggaac gcgagatcca cggcgcgacc gagcagtaca acgacatccc catgtgggac  1440
taccagaaac tgccgttcgt gttcggcggc accgatcaga cggtgcccac ctataaggtg  1500
tccaccgaaa tcgaactcga taacgcgatg acccgggccc ggacggacgt ggaccgcctc  1560
cagtggatcg aagtcgtgat ggaccagaac gacgccccgg tcctgctgaa gaagctcgcc  1620
aagatcttcg cgaaacagaa ctcctga                                       1647

SEQ ID NO: 85            moltype = AA   length = 548
FEATURE                  Location/Qualifiers
source                   1..548
                         mol_type = protein
                         organism = Carnobacterium maltaromaticum
SEQUENCE: 85
MYTVGNYLLD RLTELGIRDI FGVPGDYNLK FLDHVMTHKE LNWIGNANEL NAAYAADGYA    60
RTKGIAALVT TFGVGELSAA NGTAGSYAEK VPVVQIVGTP TTAVQNSHKL VHHTLGDGRF   120
DHFEKMQTEI NGAIAHLTAD NALAEIDRVL RIAVTERCPV YINLAIDVAE VVAEKPLKPL   180
MEESKKVEEE TALVLNKIEK ALQDSKNPVV LIGNEIASFH LESALADFVK KFNLPVTVLP   240
FGKGGFDEED AHFIGVYTGA PTAESIKERV EKADLILIIG AKLTDSATAG FSYDFEDRQV   300
ISVGSDEVSF YGEIMKPVAF AQFVNGLNSL NYLGYTGEIK QVERVADIEA KASNLTQNNF   360
WKFVEKYLSN GDTLVAEQGT SFFGASLVPL KSKMKFIGQP LWGSIGYTFP AMLGSQIANP   420
ASRHLLFIGD GSLQLTIQEL GMTFREKLTP IVFVINNDGY TVEREIHGPN ELYNDIPMWD   480
YQNLPYVFGG NKGNVATYKV TTEEELVAAM SQARQDTTRL QWIEVVMGKQ DSPDLLVQLG   540
KVFAKQNS                                                            548

SEQ ID NO: 86            moltype = DNA   length = 1647
FEATURE                  Location/Qualifiers
source                   1..1647
                         mol_type = other DNA
                         organism = Carnobacterium maltaromaticum
SEQUENCE: 86
atgtataccg tgggcaacta cctgctggac cgcctcaccg aactgggcat ccgggatatc    60
ttcggcgtcc cgggcgatta taaccctaag ttcctggacc atgtcatgac ccataaggaa   120
ctgaattgga tcgcaacgc caacgagctg aatgcggcct atgccgccga cggctacgcg   180
cggaccaagg gcatcgcggc cctggtcacc accttcggcg tgggcgaact gagcgcggcc   240
aatggcaccg cgggctccta tgccgaaaag gtgcccgtgg tgcagatcgt gggcacgccc   300
acgacggcgg tgcagaactc ccacaaactg gtgcaccata ccctgggcga cggccgcttc   360
gatcacttcg aaaagatgca gaccgagatc aatggcgcca tcgcgcatct gaccgcggac   420
aacgccctgg cggagatcga tcgcgtgctg cggatcgcgg tgaccgaacg gtgcccggtc   480
tatatcaacc tggccatcga tgtcgcggag gtggtggcca aaaaaccgct gaagcccctg   540
atggaggaat cgaagaaagt cgaggaggag acggccctcg tcctcaacaa gatcgaaaag   600
gcgctccagg actccaaaaa cccggtggtc ctgatcggca cgagatcgc cagcttccat   660
ctggaatcga cgctggccga tttcgtcaag aagttcaatc tcccggtcac ggtgctgccc   720
ttcggcaagg gcggcttcga cgaggaggat gcgcacttca tcggcgtcta ccggcgcgcc   780
ccgaccgccg aaagcatcaa ggagcgggtg gaaaaggccg acctcatcct catcatcggc   840
gcgaagctga ccgatagcgc caccgcgggc ttctcctacg acttcgagga ccgccaggtc   900
atcagcgtcg gcagcgacga agtgtccttc tatggcgaga tcatgaaacc cgtggcgttc   960
gcccagttcg tgaacggcct gaactccctg aattacctgg gctacaccgg cgaaatcaag  1020
caggtggagc gggtggcgga catcgaggcg aaggcgtcga atctcaccca gaacaacttc  1080
tggaagttcg tggaaaagta cctgtcgaac ggcgacaccc tggtggccga gcagggcacc  1140
agcttcttcg gcgcctcgct cgtgccgctg aaatcgaaga tgaagttcat cggccagccg  1200
ctgtggggca gcatcggcta tacgttcccc gccatgctgg gcagccagat cgcgaatccc  1260
gcgagccggc atctgctctt catcggcgac ggctccctgc agctgaccat ccaggagctc  1320
ggcatgacct tccgggagaa actgaccccg atcgtgttcg tcatcaacaa cgatggctac  1380
accgtcgagc gggaaatcca cggcccgaac gagctctaca cgatatcccc gatgtgggat  1440
tatcagaacc tcccgtacgt gttcggcggc aacaagggca acgtcgccac ctataaggtc  1500
accaccgagg aagaactggt ggccgccatg tcccaggccc ggcaggacac cacccgctg  1560
cagtggatcg aggtcgtgat gggcaaacag gattcgccgg acctcctggt ccagctgggc  1620
aaggtgttcg ccaagcagaa cagctga                                       1647

SEQ ID NO: 87            moltype = AA   length = 548
FEATURE                  Location/Qualifiers
source                   1..548
                         mol_type = protein
                         organism = Brochothrix thermosphacta
SEQUENCE: 87
MYTIGDYLLD RLNELGVEDI FGVPGDYNLT FLDHITAHPQ LSWVGNANEL NAAYAADGYA    60
RTKGFAALVT TFGVGELSAI NGLAGSFAER VPVIEIVGSP VSTVQTDKKL VHHTLGDGDF   120
LHFEKMHDAV TVSAHLTIQ NATSEIDRVL TTALSLRRPG YINLPIDVAA APAEKAQKKL   180
QLKVTSPIDS TLLEKIQTAF SSAKQPVFIT GHEIQSYHLE DTVAKIAAHT TVPVAALSLG   240
KSSIDETHPQ FVGIYSGALT AEPLKTYVDN ADLVILLGAQ LTDTATSGFS QSFSASKIIA   300
```

```
IHPETTTVFG QDYPSNDFKE LIEALTTIDY RMETSAALKT MPSTKEFIAT DTLLTQNRFW  360
EAIETNFKQN DTIVAEQGTS FFGITNTQFK KDMRLIGQPL WGSIGYTFPA ALGSQLAARS  420
KRHLLFIGDG SLQLTIQELG MALRAKLTPL IFVINNNGYT VEREIHGPNE RYNDIPTWDY  480
AQLPTVFGGT DQNVATYKVT TETELAEALV TAKADTTRLQ WIEVVMDQTD APELLKEMGR  540
IFAKQNTH                                                          548

SEQ ID NO: 88           moltype = DNA   length = 1647
FEATURE                 Location/Qualifiers
source                  1..1647
                        mol_type = other DNA
                        organism = Brochothrix thermosphacta
SEQUENCE: 88
atgtatacga tcggcgacta cctcctcgac cggctgaacg agctgggcgt ggaagacatc   60
ttcggcgtgc cgggcgacta caacctgacg ttcctcgatc atatcaccgc gcatccgcag  120
ctctcctggg tcggcaatgc caacgaactc aacgccgcct acgccgccga tggctatgcg  180
cggacgaaag gcttcgccgc gctggtgacg accttcggcg tcggcgagct gtcggccatc  240
aacggcctcg ccggctcctt cgccgaacgg gtgccggtca tcgagatcgt cggcagcccg  300
gtcagcaccg tgcagaccga caagaagctg gtgcaccaca ccctgggcga cggcgacttc  360
ctgcacttcg agaagatgca tgacgccgtc acggtggcct cggcgcacct cacgatccag  420
aacgccacca gcgaaatcga ccgggtcctg acgaccgccc tctcgctgcg cgcccccggc  480
tatatcaacc tgcccatcga cgtggcggcg gccccgccg aaaaagccca gaaaaagctc  540
cagctgaaag tgaccagccc gatcgacagc acgctgctga aagatcca gacggccttc  600
tcctcggcca gcagcccgt cttcatcacg ggccatgaaa tccagtccta ccacctggag  660
gataccgtgg cgaagatcgc cgcgcacacg accgtgccgg tcgcggccct ctcgctgggc  720
aagagctcca tcgatgaaac ccatcccag ttcgtcggca tctactccgg cgccctgacg  780
gcggaacccc tgaaaaccta cgtcgataac gccgatctgg tgatcctgct cggcgcccag  840
ctgaccgaca cggccacctc gggcttcagc cagtccttct cggccagcaa aatcatcgcc  900
atccaccgg aaacgaccac cgtgttcggc caggattacc cgtcgaacga tttcaaggaa  960
ctgatcgagg ccctcacgac catcgattac cgcatgaaaa cctccgcggc cctgaagacg 1020
atgccgtcca ccaaggagtt catcgccacc gacacgctgc tcacccagaa tcgcttctgg 1080
gaagccatcg aaaccaactt caagcagaac gataccatcg tggcggaaca gggcacgtcg 1140
ttcttcggca tcaccaatac ccagttcaag aaagatatgc gcctgatcgg ccagcccctg 1200
tggggctcga tcggctatac gttccccgcc gccctgggct cgcagctggc cgcccgctcc 1260
aagcggcatc tgctcttcat cggcgatggc tcgctgcagc tgaccatcca ggaactgggc 1320
atggcgctcc gcgccaaact caccccctg atcttcgtca tcaacaacaa cggctacacc 1380
gtggaacgcg agatccacgg cccgaacgaa cggtataatg acatcccgac ctgggactat 1440
gcgcagctgc cgaccgtgtt cggcggcacg gaccagaacg tggccacgta taaggtgacg 1500
accgaaaccg aactggcgga ggcgctcgtc accgccaagt cggacaccac ccgcctgcag 1560
tggatcgagg tggtgatgga ccagacggac gccccggaac tgctgaaaga gatgggccgc 1620
atcttcgcca gcagaacac ccattga                                      1647

SEQ ID NO: 89           moltype = AA   length = 548
FEATURE                 Location/Qualifiers
source                  1..548
                        mol_type = protein
                        organism = Carnobacterium gallinarum
SEQUENCE: 89
MYTVADYLLD RLKELGINDI FGVPGDYNLK FLDHITARDD LKWIGNANEL NAAYMADGYA   60
RTKGMAALVT TFGVGELSAM NGIGGSFAEK VPVIEIVGSP TTAVQNAQKL VHHTLGDGRF  120
NHFEKMHEAI TVGIGSLTKE NAITEIDRIL GLASEKRQPG YLNLPIDVAE MEVEKPNKPL  180
FDTKVMEIKM EQELIKSIEK VLNSVKHPVI IAGNEIASFH LEAKLAEFIE KFNLPVTTLP  240
FGKGVFNEED KHYLGVYTGT PTTEPLKSYV DQADLVLLLG AKLTDSATSG FSQGFTEKQM  300
ISLASDEVIF QGEHLAGIQL PTVLDELLMI NYPGYHGEIQ PMSRLAEVKS SSSLVTQAYF  360
WEAVESYLEE GDTLVAEQGT SFFGASTVPM KKGMSFIGQP LWGSIGYTFP AMLGSQIAKK  420
GSRHLLFIGD GSLQLTVQEL GMTLREKLAP IVFIINNNGY TVEREIHGPE EIYNDIPMWD  480
YQKLPSVFGG TAENVVTYKV QTEAELATAM RKARLDSKRL QWIEVVMNQK DAPDLLVQMG  540
KIFAKQNS                                                          548

SEQ ID NO: 90           moltype = DNA   length = 1647
FEATURE                 Location/Qualifiers
source                  1..1647
                        mol_type = other DNA
                        organism = Carnobacterium gallinarum
SEQUENCE: 90
atgtacacgg tcgccgatta cctgctcgat cggctgaagg aactgggcat caatgacatc   60
ttcggcgtcc cgggcgatta taacctcaag ttcctggacc acatcaccgc ccgcgacgac  120
ctgaaatgga tcggcaacgc gaacgagctg aacgcggcgt atatggccga tggctacgcc  180
cgcaccaaag gcatggccgc gctggtgacg accttcggcg tcggcgaact ctcggccatg  240
aacggcatcg gcggctcgtt cgccgagaaa gtcccccgtca tcgagatcgt cggcagcccg  300
accaccgccg tccagaatgc ccagaaactg gtccatcata ccctgggcga cggccgcttc  360
aaccatttcg agaagatgca tgaggcgatc accgtgggca tcggctcgct gaccaaggag  420
aatgccatca ccgaaatcga tcgcatcctg ggcctggcgt ccgagaagcg gcagcccggc  480
tacctgaacc tgccgatcga tgtggccgaa atggaagtgg agaaaccgaa caagccgctc  540
ttcgatacaa aggtcatgga aatcaaaatg gaacaggaac tcatcaagag cattgagaaa  600
gtgctcaact cggtcaagca tccggtcatc atcgccggca acgagatcgc cagcttccat  660
ctggaggcca agctggccga gttcatcgag aagttcaatc tccccgtcac cacgctgccg  720
ttcggcaagg gcgtcttcaa cgaagaagat aagcattatc tgggcgtgta cacgggcacc  780
cccacgacgg aacccctgaa gtcctacgtc gaccaggcgg atctggtcct cctgctgggc  840
gccaagctga ccgactccgc caccagcggc ttcagccagg gcttcaccga agcagatg   900
```

```
atctcgctgg cctcggacga ggtcatcttc cagggcgagc acctcgccgg catccagctc  960
cccaccgtcc tggatgagct gctgatgatc aactatccgg gctaccacgg cgagatccag 1020
ccgatgtcgc ggctggcgga agtgaagtcg tcctccagcc tcgtcaccca ggcgtacttc 1080
tgggaggccg tcgagtcgta cctggaagaa ggcgatacgc tcgtcgccga cagggcacc  1140
agcttcttcg gcgcctccac cgtccccatg aagaaggcga tgagcttcat cggccagccg 1200
ctgtgggget ccatcggcta cacgttcccg gccatgctcg gctcgcagat cgccaagaag 1260
ggctcgcgcc atctgctgtt catcggcgac ggctcgctcc agctgaccgt ccaggaactg 1320
ggcatgacgc tccgggaaaa gctggcgccg atcgtgttca tcatcaacaa taacggctac 1380
accgtggaac gggaaatcca cggccccgaa gaaatctata acgacatccc gatgtgggac 1440
taccagaagc tcccgtccgt cttcggcggg accgccgaaa acgtggtgac ctataaggtc 1500
cagaccgagg cggagctggc caccgccatg cgcaaggccc gcctggactc gaagcggctg 1560
cagtggatcg aagtggtgat gaaccagaag gacgccccgg acctcctggt gcagatgggc 1620
aagatcttcg ccaagcagaa tagctga                                    1647

SEQ ID NO: 91           moltype = AA  length = 548
FEATURE                 Location/Qualifiers
source                  1..548
                        mol_type = protein
                        organism = Carnobacterium divergens
SEQUENCE: 91
MYTVGDYLLE RLSELGIKEI FGVPGDYNLK FLDHIVEHPN LKWIGNANEL NAAYAADGYA  60
RTKGVSALVT TFGVGELSAI NGIAGSYAEK VPVIQIVGSP TMAVQNAHKL VHHTLGDGKF 120
DHFENMHESV TEAIGSLTKE NAVTEIDRVL RAAVLKRRPV YLNLPIDVAE MVVEKPSGPL 180
LPKQASLSAR EVELVHELEK ALQQAKNPVV LAGNELASFH LETYLADFIH KFNLPITTLP 240
FGKGVFNEED EHYLGVYAGS PTEEGLRKRV DTADLVVALG AKLTDSATSG FSYDFSEKQL 300
FSLASDEVIV KEEHLEGIHL PAVMKALTSI DYQGYQGDIQ PMARLKSIKP TNQVLTQRHF 360
WEAIEGFLEK GDTAVAEQGT SFFGLSTVPL KSEMSFIGQP LWGSIGYTFP AMLGSQLANP 420
SSRHLLFIGD GSLQLTIQEL GMALREKLTP IVFVINNNGY TVEREIHGPN EIYNDIPMWD 480
YQKLPLVFGG SEQSVITYKV TTELELANAL KAARLDNNRL QWIEVVMDQT DAPELLMKLG 540
KIFAKQNS                                                         548

SEQ ID NO: 92           moltype = DNA  length = 1647
FEATURE                 Location/Qualifiers
source                  1..1647
                        mol_type = other DNA
                        organism = Carnobacterium divergens
SEQUENCE: 92
atgtataccg tgggcgacta tctcctggag cggctctcgg aactgggcat caaagagatc  60
ttcggcgtgc cgggcgacta caacctgaag ttcctggate acatcgtgga gcatccgaac 120
ctgaagtgga tcggcaacgc gaatgaactc aacgcggcgt atgccgccga cggctacgcc 180
cgcacgaagg gcgtctccgc gctggtgacc accttcggcg tcggcgagct ctccgccatc 240
aacggcatcg ccggctcgta tgccgagaaa gtcccggtca tccagatcgt gggcagcccc 300
acgatgcgg tgcagaatgc ccataagctg gtgcatcata ccctgggcga tggcaaattc 360
gaccacttcg agaacatgca tgagtccgtc accgaagcca tcggcagcct caccaaggag 420
aacgcggtga ccgagatcga tcgcgtgctg cgggccgccg tgctcaaacg cgcgcccgtg 480
tatctgaacc tcccgatcga cgtggccgaa atggtcgtca aaaaaccgtc gggccccctg 540
ctgccccaagc aggcgagcct gagcgcccgc gaggtcgaac tcgtcgatga gctggagaag 600
gccctgcagc aggcgaagaa cccggtggtc ctgcgcggca acgagctggc gtcgttccac 660
ctcgaaacgt acctcgccga cttcatccac aagttcaacc tccccatcac gaccctcccc 720
ttcggcaagg gcgtcttcaa cgaggaagac gagcattatc tgggcgtcta tgcgggctcg 780
ccgaccgaag aaggcctgcg gaagcgcgtc gatacggcag acctggtggt ggcgctgggc 840
gcgaagctga cggactccgc cacctccggc ttctcgtacg acttctccga aaaacagctc 900
ttcagcctgg cgtccgacga agtcatcgtc aaagaggaac acctcgaagg catccatctg 960
ccggccgtca tgaaggcgct gacgagcatc gactaccagg gctaccaggg cgacatccag 1020
ccgatggccc ggctgaagag catcaaaccc accaaccagg tgctgaccca gcgccacttc 1080
tgggaggcca tcgaaggctt cctggaaaag ggcgacaccg ccgtcgcgga gcagggcacg 1140
agcttcttcg gcctctcgac cgtgccgctg aagagcgaaa tgtcgttcat cggccagccg 1200
ctgtgggget ccatcggcta tacgttcccg gcgatgctgg gcagccagct cgccaacccg 1260
tccagccggc acctcctgtt catcggcgac ggcagcctgc agctgaccat cgaggagctg 1320
ggcatggccc tccgcgaaaa actcaccccg atcgtgttcg tcatcaacaa taacggctat 1380
acggtcgaac gggaaatcca cggcccgaat gaaatctata acgacatccc gatgtgggac 1440
taccagaaac tcccgctcgt cttcggcggg tccgagcagt cggtcatcac ctataaagtg 1500
acgaccgaac tggaactggc gaacgcgctc aaggcggccc ggctggacaa caaccgcctg 1560
cagtggatcg aagtggtgat ggaccagacc gatgcgccgg agctcctcat gaagctgggc 1620
aagatcttcg cgaagcagaa tagctga                                    1647

SEQ ID NO: 93           moltype = AA  length = 174
FEATURE                 Location/Qualifiers
source                  1..174
                        mol_type = protein
                        organism = Helicobacter bizzozeronii
SEQUENCE: 93
MIAEQGTSFF GAISMVLPSG VSFIGQPLWG SIGYTFGALL GTALASPDRR HILLIGDGSF  60
QLVAQELSTM LRENITPIII VINNDGYTVE RCIHGPTRQY NHINMWHYSK LASFFDVHLA 120
REVVSFQVSS VAGLREALCV AQQNSKLALI EACMDKNDAP ILLKKLGALF GAQI       174

SEQ ID NO: 94           moltype = DNA  length = 1104
FEATURE                 Location/Qualifiers
source                  1..1104
```

```
                        mol_type = other DNA
                        organism = Helicobacter bizzozeronii
SEQUENCE: 94
atgcagacga cgatcggcca gtatctcctg gaccggctga agtcctacgg cgtgcagcat    60
ctcttcggcg tgcccggcga ctataacctg gccttcctcg acctgatcga agacgatccg   120
cacatccagt gggtcggcaa ctgcaacgaa ctgaatgcgt cctacgccgc cgacggctac   180
gcgcggctca gagcatgggg cgccctcctg acgaccttcg gcgtcggcga gctgagcgcc   240
atcaacggca tcgccggctc gtacgcggaa tccgtgccgg tcgtgaagat cgtcggcatg   300
ccctcccgcg gcgtggtcca ttcccgcaag ctggtgcacc acaccctggg cgacggcacg   360
ttcctcaagt tctacaacat gtatgccgaa gtgagcgtcg cccagacgat cctcaacaaa   420
cagaacgccc agagcgaaat cgaccgcgtc tgggcgaat gcttcctgca taaaaagccg    480
gtctacatcg gcctccggt ggacgtgacg cacatcccga tcgaaacgta cgcccctcc    540
ccctggtgg ccaagagcga cccgaaatc ctcaacgct tcctgaagga cgcccaggag     600
ctgctgtcga agagcaaatc ccaggtggtc atggcgaatt ccgtcaccag cctgtaccag   660
ttcaaccagg agctgacgcg cttcatcgaa gccgtgaacc tgcccatcgt gtcgctggcg   720
atgggcaagg gcgtcttcga tgaaacgcac ccgaacttca tcggcgtgta acggcatc    780
ctctcggacg cccgggtgag ctcgctgatg aagcacgccg actgcgcgat cctggtgggc   840
gtgaagctga cggactcgct gacggccggc ttccactata tccgcaaca tcacctgtcc   900
atccagatcc acccttcta ctcccagatc ggcgaaaaga cgtacgacga tatcctcatg   960
caggacgtgc tgaaagcgct cgcccagctg aagttccagg cctcgttccc gaaggagacg  1020
caccccaaaa cgccgcacct gaacggcaag ctgacccagg acaagttctt caagatcgac  1080
tcgcgcatcc tgacccccc gtga                                          1104

SEQ ID NO: 95          moltype = AA  length = 273
FEATURE                Location/Qualifiers
source                 1..273
                       mol_type = protein
                       organism = Staphylococcus aureus
SEQUENCE: 95
MKQRIGAYLI DAIHRAGVDK IFGVPGDFNL AFLDDIISNP NVDWVGNTNE LNASYAADGY    60
ARLNGLAALV TTFGVGELSA VNGIAGSYAE RIPVIAITGA PTRAVEQAGK YVHHSLGEGT   120
FDDYRKMFAH ITVAQGYITP ENATTEIPRL INTAIAERRP VHLHLPIDVA ISEIEIPTPF   180
EVTAAKDTDA STYIELLASK LHQSKQPIII TGHEINSFHL HQELEDFVNQ TQIPVAQLSL   240
GKGAFNEENP YYMGIYDGKL PKIKYAIMWT TAI                                273

SEQ ID NO: 96          moltype = DNA  length = 822
FEATURE                Location/Qualifiers
source                 1..822
                       mol_type = other DNA
                       organism = Staphylococcus aureus
SEQUENCE: 96
atgaaacagc gcatcggcgc ctacctgatc gatgccatcc accgcgccgg cgtggacaag    60
atcttcggcg tcccgggcga tttcaacctc gccttcctcg acgatatcat cagcaaccg   120
aacgtggatt gggtcggcaa caccaacgag ctgaacgcct cgtatgcggc cgatggctat   180
gcccgcctca cggcctggc ggccctggtc accaccttcg gcgtgggcga actgtcggcg    240
gtgaatggca tcgcgggcag ctatgccgag cgcatcccgg tgatcgccat caccggcgcc   300
cccaccccgc ccgtcgagca ggccgcaag tatgtgcatc atagcctggg cgaaggcacg    360
ttcgatgact accggaagat gttcgcccat atcaccgtgg cccagggcta catcacgccc   420
gagaatgcga cgaccgaaat ccccgcctc atcaacacgg ccatcgccga cgccgcccc    480
gtgcatctcc acctgccat cgatgtggcg atctcggaga tcgagatccc cacccgttc    540
gaggtgacgg cggcgaaaga cacggacgcc tcgacctata tcgagctgct ggccagcaaa   600
ctgcaccaga gcaagcagcc catcatcatc acgggccatg agatcaactc cttccatctg   660
caccaggaac tggaagattt cgtcaatcag acccagatcc ccgtggcgca gctctcgctg   720
ggcaaaggcg ccttcaacga ggaaaacccg tactatatgg gcatctacga tggcaagctg   780
cccaaaatca gtatgcgat catgtggacc acggcgatct ga                       822

SEQ ID NO: 97          moltype = AA  length = 554
FEATURE                Location/Qualifiers
source                 1..554
                       mol_type = protein
                       organism = Fictibacillus macauensis
SEQUENCE: 97
MNNHYTVGTY LLHRLSELGV RHMFGVPGDY NLTFLDDVID FEGMEWIGNC NELNAAYAAD    60
GYARINGMAA LVTTFGVGEL SAINGIAGSY AEKVPVVKIT GMPTTNVMNQ NLYVHHTLGD   120
GNFQHFGNMF QEVTAAQTML TQENAAQEID RVLLACWHEK RPVHINLPID VYNKPVNPPE   180
HSLLERGISS NATALEQMLT TVIPTIKEAT SPVILADYEV YRYQAQEALM LLAEKTGFPV   240
ATLSMGKGVF NETHPQFIGV YNGDLSSDYV KNMVDHADCI LSIGVKLTDS ITGGFSHEFT   300
EEQVIDISPY SVSKKALKWA PITMLDALGA ITDALEQKPT PATTARLAAY SNESSFTATN   360
TTLTQERFFD QVSHFLQEGD VILAEQGTSF FGAATMPLPK GATFIGQPLW GSIGYTLPAL   420
LGSQLADESR RNLLLIGDGS FQLTAQELST MLRQRIAPII FLINNDGYTV ERAIHGENQV   480
YNDIQMWDYS KLPAVFGAAD ASVTYKVRTE EELEAALHSA QNSSQLVFIE VMMEKNDTPE   540
LLTALSKRFA NQNN                                                    554

SEQ ID NO: 98          moltype = DNA  length = 1665
FEATURE                Location/Qualifiers
source                 1..1665
                       mol_type = other DNA
                       organism = Fictibacillus macauensis
SEQUENCE: 98
```

```
atgaacaacc attataccgt cggcacctat ctgctgcatc gcctgtccga gctgggcgtc    60
cgccatatgt tcggcgtgcc cggcgactat aatctgacgt tcctggacga tgtcatcgac   120
ttcgaaggca tggaatggat cggcaactgt aacgagctca cgccgccta cgcggccgac    180
ggctatgccc gcatcaacgg catggccgcc ctggtgacca ccttcggcgt cggcgagctg   240
tcggccatca acggcatcgc cggctcgtac gccgaaaaag tgccggtcgt caaaatcacg   300
ggcatgccca ccaccaacgt gatgaaccag aatctgtacg tccatcacac gctgggcgac   360
ggcaacttcc agcacttcgg caacatgttc caggaggtca ccgccgcgca gacgatgctg   420
acccaggaaa acgcggcgca ggagatcgat cgcgtgctgc tcgcctgctg gcacgaaaag   480
cgcccggtgc acatcaacct cccgatcgat gtctacaaca agccggtcaa cccccccgag   540
cattcgctcc tggaacgggg catctcgtcg aacgcgaccg cgtcgaaca gatgctgacc    600
accgtgatcc cgacgatcaa ggaggccacc tcgcccgtga tcctggcgga ttatgaggtg   660
tatcgctacc aggcccagga agccctgatg ctgctggcgg aaaagaccgg cttcccggtg   720
gccaccctga gcatgggcaa gggcgtgttc aacgaaaccc atccccagtt catcggccgtg  780
tacaacggcg acctgtcgtc cgactacgtg aagaatatgg tcgaccatgc cgactgtatc   840
ctctccatcg gcgtcaagct gaccgacagc atcacgggcg gcttcagcca tgagttcacc   900
gaggagcagg tcatcgacat ctccccgtat agcgtgagca aaaagcccct caaatgggcg   960
cccatcacga tgctggatgc gctgggcgcc atcacggatg ccctggagca gaagccgacc  1020
ccgccacca ccgcgcggct cgccgcctac tcgaacgaga gctccttcac cgcgacgaac  1080
acgacgctga cccaggagcg cttcttcgac caggtgtccc acttcctcca ggagggcgac  1140
gtgatcctgg cggaacaggg caccagcttc ttcggcgcgg ccacgatgcc gctcccgaag  1200
ggcgccacgt tcatcggcca gccgctgtgg ggcagcatcg gctacaccct gccggccctg  1260
ctgggcagcc agctggccga cgaatcccgc cgcaatctcc tgctcatcgg cgatggctcg  1320
ttccagctca ccgcccagga gctgtcgacg atgctgcgcc agcggatcgc cgcgatcatc  1380
ttcctcatca caacgacgg ctacaccgtg aacgggcga tccacggcga aatcaggtg    1440
tataacgaca tccagatgtg ggactattcg aagctgccgg cggtcttcgg cgcggcgac   1500
gccagcgtca cctacaaggt ccggaccgaa gaggagctgg aggcggccct gcatagcgcc  1560
cagaactcgt cccagctggt cttcatcgaa gtgatgatgg agaagaatga caccccccgaa 1620
ctgctgacgg ccctgagcaa gcgcttcgcg aatcagaaca actga                  1665
```

SEQ ID NO: 99         moltype = AA   length = 572
FEATURE               Location/Qualifiers
source                1..572
                      mol_type = protein
                      organism = Bacillus licheniformis
SEQUENCE: 99

```
MNNVAAKNET LTVRGAELVV DSLIQQGVTH VFGIPGAKID AVFDVLKDKG PELIVCRHEQ    60
NAAFMAAAVG RLTGKPGVCL VTSGPGASNL ATGLVTANTE GDPVVALAGA VKRADRLKKT   120
HQSMDNAALF QPITKYSAEV EDANNIPEAV TNAFRAAASG QAGAAFLSFP QDVTAGPATA   180
KPVKTMPAPK LGAASDEQIS AAIAKIHNAN LPVVLVGMKG GRPEAIEAVR RLLRKVKLPF   240
VETYQAAGTL SHDLEDQYFG RIGLFRNQPG DMLLEKADVV LTVGYDPIEY DPVFWNGKGE   300
RSVIHLDEIQ ADIDHDYQPE IELIGDIAET LNHIEHDSLP VSIDESFAPV LDYLKKALEE   360
QSEPPKETKT DLVHPLQIVR DLRELLSDDI TVTCDIGSHA IWMSRYFRTY RPHGLLISNG   420
MQTLGVALPW AIAATLVNPG QKVVSVSGDG GFLFSAMELE TAVRLKAPIV HIVWNDSTYD   480
MVAFQQEMKY KRTSGVDFGG IDIVKYAESF GAKGLRVNSP DELAEVLKAG LDAEGPVVID   540
IPVDYSDNIH LADQRFPKKF EEHFNKEASK QS                                 572
```

SEQ ID NO: 100        moltype = DNA  length = 1719
FEATURE               Location/Qualifiers
source                1..1719
                      mol_type = other DNA
                      organism = Bacillus licheniformis
SEQUENCE: 100

```
atgaataacg tcgcggccaa gaacgaaacc ctgaccgtcc ggggcgccga actcgtggtg    60
gatagcctga tccagcaggg cgtgacccat gtcttcggca tcccgggcgc caaaatcgac   120
gcggtcttcg acgtgctgaa ggataagggc cccgaactga tcgtctgccg catgagcag   180
aacgcgggcct tcatggccgc ggccgtcggc cgcctgacgg gcaagccggg cgtctgcctg   240
gtcacctccg gccgggcgc ctcgaatctc gcgaccggcc tggtcaccgc gaacacggaa    300
ggcgacccgt tggtcgccct ggcggcgcc gtgaagcggg cggatcggct gaagaagacg    360
caccagtcga tggataacgc cgcccgtttc cagcccatca cgaagtacag cgcggaggtg   420
gaagacgcga acaacatccc ggaggccgtg acgaacgcct tccgcgcgc ggcgtccggc    480
caggccggcg cggccttcct cagcttcccc caggatgtca ccgccggccc ggccaccgcc   540
aagccggtca aaaccatgcc cgccccgaag ctgggcgccg cgagcgatga acagatctcc   600
gccgcgatcg cgaagatcca caacgcgaat ctgccggtgt tcctcgtggg catgaagggc   660
ggccggccgg aagccatcga agccgtgcgc cgcctgttcc gcaaggtcaa gctcccgttc   720
gtggaaacct accaggcggc cggcacgctg tcgcacgatc tggaggatca gtacttcggc   780
cggatcggcc tgttccggaa ccagccgggc gacatgctcc tggaaaaggc cgacgtggtc   840
ctgaccgtgg gctacgaccc gatcgagtac gatccggtgt tctggaatgg caaaggcgaa   900
cgctcggtca tccaccctcga cgaaatccag gccgatatcg atcacgacta ccagcccgag   960
atcgaactca tcggcgacat cgcggaaact ctcaatcaca tcgagcatga ctcgctgccg  1020
gtgtccatcg acgaatcctt cgcgcccgtg ctcgactatc tcaagaaggc gctcgaagaa  1080
cagtcggagc cccgaagga acgaagacc gatctggtcc accccgctcca gatcgtcgcc  1140
gacctgcgcg agctgctctc cgatgacatc accgtcacct gcgacatcgg cagccacgcc  1200
atctggatgt cccgctattt ccgcacctat cgcccgcatg gcctcctgat ctccaacggc  1260
atgcagacgc tgggcgtcgc cctgccggtg gcgatcgccg gcacgctgag gaaccccggca  1320
cagaaggtgg tgtcggtcag cggcgatggc ggcttcctct tctccgcgat ggaactcgaa  1380
accgccgtcc gcctcaaggc gccgatcgtg cacatcgtgt ggaacgactc cacgtacgac  1440
atggtcgcgt tccagcagga aatgaagtac aagcgcacct ccggcgtcga tttcggcggc  1500
atcgacatcg tcaagtatgc ggaatccttc ggcgccaaag gcctccgcgt gaatagcccc  1560
gatgaactgg ccgaggtcct gaaggccggc ctcgacgcgg agggcccggt ggtcatcgac  1620
```

```
atccccgtcg actactcgga taacatccac ctggccgacc agcgcttccc gaagaagttc  1680
gaggagcact tcaacaagga agcgtcgaag cagtcctga                         1719
```

METHODS AND MICROORGANISMS FOR THE FERMENTATION OF METHANE TO MULTI-CARBON COMPOUNDS

CROSS-REFERENCE

This application is a continuation of U.S. application Ser. No. 16/604,425, which is a U.S. national stage filing of International Application No. PCT/US2018/029688, filed Apr. 27, 2018, which in turn claims priority benefit of U.S. Provisional Application Nos. 62/491,683, filed Apr. 28, 2017; and 62/512,315, filed May 30, 2017, Each of these applications is, which are hereby incorporated by reference in its entirety.

SEQUENCE LISTING

The instant application contains a Sequence Listing that has been submitted electronically in XML format and is hereby incorporated by reference in its entirety. The XML copy was created on Jul. 11, 2022, is named 383SeqList.xml and is 179,442 bytes in size.

BACKGROUND OF THE DISCLOSURE

As crude oil becomes very expensive, there has been a push to use alternative methods to produce fuels and fuel additives. Alternative methods, including fermentation, have been pursued in recent years; however, most of these methods require a feedstock that consumes our food supply. For example, sugar (usually in the form of corn) is used to produce ethanol and isobutanol.

A feedstock that is relatively cheap and does not decrease overall food supply is natural gas. The methane ($CH_4$) contained in natural gas has great value as a chemical feedstock for the production of chemicals and food additives. Methane can be obtained from shale gas, oil drilling, municipal solid waste, biomass gasification/conversion, and methanogenic archaea. Wellhead natural gas varies in composition from 40% to 95% methane, wherein the other components include ethane, propane, butane, pentane, and heavier hydrocarbons, along with hydrogen sulfide, carbon dioxide, helium and nitrogen.

One chemical that has recently received a great deal of attention is isobutanol. Isobutanol (also known as 2-methylpropan-1-ol) is an organic compound with the formula $(CH_3)_2CHCH_2OH$. Since isobutanol is a higher-chain alcohol, it has an energy density that is close to gasoline. Currently, ethanol is used to supplement gasoline, and is added up to 10%. However, isobutanol has several advantageous properties that make it an attractive alternative to ethanol as a gasoline additive or biofuel. For example, isobutanol is not as volatile or corrosive as ethanol, and does not readily absorb water. Furthermore, branched-chain alcohols, such as isobutanol, have higher-octane numbers, resulting in less knocking in engines. Thus, isobutanol is fully compatible with gasoline combusting engines as well as in jet engines.

Other uses of isobutanol include, but are not limited to, its use as: a feedstock chemical in the manufacture of isobutyl acetate (which is used in the production of lacquer and similar coatings, and in the food industry as a flavoring agent); a precursor of derivative esters—isobutyl esters such as diisobutyl phthalate (DIM)) (used as plasticizers in plastics, rubbers, and other dispersions); a precursor of p-xylene (a building block for plastic bottles, textiles and clothing); a paint solvent; a varnish remover; an ink ingredient; a paint additive (to reduce viscosity, improve brush flow, and retard formation of oil residues (blush) on painted surfaces); a gasoline additive (to reduce carburetor icing); an automotive polish additive; an automotive paint cleaner additive; a chemical extractant in production of organic compounds; and a mobile phase in thin layer chromatography.

The present inventors have developed a way of using genetically modified microorganisms, such as methanotrophs, bacteria, or yeast, in order to dramatically improve the production of multi-carbon compounds, such as isobutyraldehyde and isobutanol, from cheap carbon compounds, such as methane.

INCORPORATION BY REFERENCE

All publications, patents, and patent applications cited herein are hereby incorporated by reference in their entirety and to the same extent as if each individual publication, patent, or patent application was specifically and individually indicated to be incorporated by reference. In the event of a conflict between a term herein and a term in an incorporated reference, the term herein controls.

SUMMARY

Isobutanol and other alcohols are valuable chemicals that can be used in a variety of ways, such as for fuels and solvents. Disclosed herein are methods and microorganisms that can be used to generate valuable alcohols such as isobutanol.

Aldehydes, such as isobutyraldehyde and isovaleraldehyde, can also be produced by the methods and microorganisms disclosed herein. These aldehydes can be used to generate alcohols and can be converted into different useful polymers.

Disclosed herein are genetically modified microorganisms capable of converting a $C_1$ carbon to a multicarbon product. These microorganisms can comprise a gene encoding an acetolactate synthase (AlsS); a ketol-acid reductoisomerase; a dihydroxy-acid dehydratase (DHAD); and/or a 2-keto acid decarboxylase (KDC). In some cases, the genes encoding for the acetolactate synthase (AlsS); ketol-acid reductoisomerase (KARI); dihydroxy-acid dehydratase (DHAD); and/or 2-keto acid decarboxylase (KDC) is under the control of a rare earth metal switch. In some cases, the rare earth metal switch can be a lanthanum switch.

In one example, disclosed herein is a genetically modified microorganism capable of converting a $C_1$ carbon to a multicarbon product comprising a gene encoding: an acetolactate synthase (AlsS); a ketol-acid reductoisomerase (KARI); a dihydroxy-acid dehydratase (DHAD); and a 2-keto acid decarboxylase (KDC), where the gene encoding the 2-keto acid decarboxylase (KDC) comprises a polynucleotide that is at least 60% identical to SEQ ID NO: 9.

In another example, disclosed herein is a genetically modified microorganism capable of converting a $C_1$ carbon to a multicarbon product comprising a gene encoding for an acetolactate synthase (AlsS); a ketol-acid reductoisomerase (KARI); a dihydroxy-acid dehydratase (DHAD); 2-keto 2-keto acid decarboxylase (KDC); and an alcohol dehydrogenase (ADH), where the gene encoding the alcohol dehydrogenase (ADH) comprises a polynucleotide that is at least 60% identical to SEQ ID NO: 17.

The genetically modified microorganism can produce multicarbon products such as aldehydes. For example, the aldehyde can be isobutyraldehyde. In some cases, the genetically modified microorganism can produce an alcohol as a multicarbon product. The alcohol can be ethanol, methanol, and/or isobutanol. In some cases, isobutanol is produced.

The acetolactate synthase (AlsS) gene used can be a gram positive bacterial AlsS gene. In some cases, the AlsS gene can comprise a polynucleotide that is at least 60% identical SEQ ID NO: 1. In some cases, the AlsS gene can encode for a polypeptide that comprises an amino acid sequence that is at least 90% identical to SEQ ID NO: 2. In some cases, the AlsS gene can comprise a polynucleotide that is at least 60% identical SEQ ID NO: 100. In some cases, the AlsS gene can encode for a polypeptide that comprises an amino acid sequence that is at least 90% identical to SEQ ID NOs: 99.

The ketol-acid reductoisomerase (KARI) gene can be from a gram negative bacterial ketol-acid reductoisomerase gene. In some cases, the gene encoding for a ketol-acid reductoisomerase (KARI) comprises a polynucleotide that is at least 85% identical to SEQ ID NO: 3. In some cases, the ketol-acid reductoisomerase gene can encode for a polypeptide that comprises an amino acid sequence that is at least 90% identical to SEQ ID NO: 4.

The dihydroxy-acid dehydratase (DHAD) gene can be a gram negative bacterial dihydroxy-acid dehydratase (DHAD) gene or a methanotrophic dihydroxy-acid dehydratase (DHAD) gene. In some cases, the gene encoding a dihydroxy-acid dehydratase (DHAD) can comprise a polynucleotide that is at least 82% identical to SEQ ID NO: 5 or can comprise a polynucleotide that is 90% identical to SEQ ID NO: 7. In some cases, the gene encoding for a dihydroxy-acid dehydratase (DHAD) can encode for a polypeptide that comprises an amino acid sequence that is at least 90% identical to SEQ ID NOs: 6 or 8.

The KDC gene used in these microorganisms can comprise a polynucleotide that is at least 60% identical to SEQ ID NO: 9. In some cases, the genetically modified microorganism can further comprise one or more additional genes encoding for a 2-keto acid decarboxylase (KDC), e.g., a second KDC gene. In some cases, the 2-keto acid decarboxylase (KDC) (e.g., the second KDC) can be from a microorganism that is capable of converting a $C_1$ carbon to a multicarbon product. In some cases, the additional gene encoding for a 2-keto acid decarboxylase (KDC) can be a methanotroph KDC gene. In some cases, the additional gene encoding for a 2-keto acid decarboxylase (KDC) can be a *Methylococcus capsulatus* KDC gene. In some cases, the additional gene encoding for a 2-keto acid decarboxylase (KDC) can comprise a polynucleotide that is at least 60% identical to SEQ ID NO: 9. In some cases, the additional gene encoding for a 2-keto acid decarboxylase (KDC) can comprise a polynucleotide that is at least 60% identical to SEQ ID NO: 11. In some cases, the additional gene encoding for a 2-keto acid decarboxylase (KDC) can encode for a polypeptide comprising an amino acid sequence at least 90% identical to the amino acid sequence of any one of SEQ ID NOs: 10, 12, 55, 57, 59, 61, 63, 65, 67, 69, 71, 73, 75, 77, 79, 81, 83, 85, 87, 89, 91, 93, 95, or 97.

Also disclosed herein are microorganisms that can produce an alcohol, such as ethanol, methanol, or isobutanol (or other alcohols such as isopentanol). In these cases, the microorganism can further comprise an alcohol dehydrogenase (ADH) gene. The ADH gene can be from a gram negative or a gram positive bacteria ADH or a yeast. The ADH can be under the control of a rare earth metal switch. In some cases, the rare earth metal switch can be a lanthanum switch. In some cases, the ADH gene can encode for a polynucleotide that comprises at least 60% identical to any one of SEQ ID NOs: 13, 15, or 17. In some cases, the ADH gene encodes for a polypeptide that comprises an amino acid sequence that is at least 90% identical to any one of SEQ ID NOs: 14, 16, or 18. In some cases, the ADH gene comprises a polynucleotide that is substantially similar to any one of SEQ ID NOs: 13, 15, 17, 24, 26, 28, 30, 32, 34, 36, 38, 40, 42, 44, 46, 48, 50, 52, or 54. In some cases, the ADH gene encodes for a polypeptide that comprises an amino acid sequence that is at least 90% identical to the amino acid sequence of any one of SEQ ID NOs: 14, 16, 18, 23, 25, 27, 29, 31, 33, 35, 37, 39, 41, 43, 45, 47, 49, 51, or 53.

In some cases, the ADH gene can be an *E. coli* ADH gene, a *S. cerevisiae* ADH gene, or both. The ADH gene can also be from the genus *Clostridium, Geobacillus*, and/or *Lactococcus*. In some cases, when the ADH gene is an *E. coli* ADH gene, the *E. coli* ADH gene can comprise a polynucleotide that is at least 60% identical to SEQ ID NO: 17. In some cases, when the ADH gene is an *S. cerevisiae* ADH gene, the *S. cerevisiae* ADH gene can comprise a polynucleotide that is at least 60% identical to SEQ ID NO: 13. In some cases, both a *S. cerevisiae* ADH gene and an *E. coli* ADH gene is used, and the *S. cerevisiae* ADH gene can comprise a polynucleotide that is at least 60% identical to SEQ ID NO: 13, whereas the *E. coli* ADH gene can comprise a polynucleotide that is at least 60% identical to SEQ ID NO: 17. Additionally, the genetically modified microorganism can comprise a second ADH gene. The second ADH gene can be from *E. coli, S. cerevisiae*, or both. Additional ADH genes can be used as well (e.g., a third, fourth, or fifth, etc.).

In order to increase the efficiency of aldehyde or alcohol production, the genetically modified microorganism can further comprises a sugar permease gene. The sugar permease gene can be a LacY gene. In some cases, the sugar permease gene is used for gene expression. In some cases, the LacY gene can be under the control of a rare earth metal switch. In some cases, the rare earth metal switch can be a lanthanum switch.

The genetically modified microorganism can use different $C_1$ carbons as a carbon source, such as carbon monoxide (CO), carbon dioxide ($CO_2$), methane ($CH_4$), or any combination thereof. In some cases, the genetically modified microorganism uses $CH_4$ as the $C_1$ carbon source.

In some cases, the genetically modified microorganism can be a methanotroph, for example, from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum*, or *Methyloacidoiphilum*. In particular, methanotrophs that can be used can be from the genera *Methylococcus*, e.g., *Methylococcus capsulatus*.

In some instances, one or more of the acetolactate synthase, ketol-acid reductoisomerase, dihydroxy-acid dehydratase, 2-keto acid decarboxylase (KDC), and alcohol dehydrogenase (ADH) genes can be heterologous to the microorganism. In some cases, one or more of those genes can be endogenous to the microorganism. Further, one or more of the genes can be overexpressed. In some cases, the microorganism can comprise multiple copies of one or more of the genes.

Also disclosed herein is a genetically modified microorganism capable of converting a $C_1$ carbon source to a multicarbon product comprising a sugar permease gene. In some cases, the sugar permease gene can be under the control of rare earth metal switch. In some cases, the rare earth metal switch is a lanthanum switch. The sugar permease genes can be a LacY gene. In some cases, the LacY gene can be a gram negative bacterial LacY gene. In some cases, the LacY gene can comprise a polynucleotide that is at least 80% identical to SEQ ID NO: 19. In some cases, the LacY gene can encode for a polypeptide that comprises an amino acid sequence that is at least 90% identical to SEQ ID NO: 20. In some cases, the genetically modified microorganism can further comprise one or more genes encoding for: (i) acetolactate synthase (AlsS); (ii) ketol-acid reductoisomerase (KARI); (iii) dihydroxy-acid dehydratase (DHAD); (iv) 2-keto acid decarboxylase (KDC); (v) alcohol dehydrogenase (ADH); or (vi) any combination thereof. In some cases, one or more of these additional genes can be under the control of a rare earth metal switch, e.g., a lanthanum switch. One or more of these genes can be heterologous, endogenous, overexpressed, and/or comprise multiple copies (e.g., LacY, AlsS, KARI, DHAD, KDC, and/or ADH).

Further disclosed herein is a vector comprising a polynucleotide that is at least 60% identical to SEQ ID NO: 9. Additionally disclosed is a vector comprising a polynucleotide that is at least 60% identical to SEQ ID NO: 11. Also disclosed is a vector comprising a polynucleotide that is at least 60% identical to SEQ ID NO: 100.

The vector can further comprise an operably linked promoter. The vector can also further comprise one or more genes encoding for: (i) acetolactate synthase (AlsS); (ii) a ketol-acid reductoisomerase (KARI); (iii) a dihydroxy-acid dehydratase (DHAD); (iv) a 2-keto acid decarboxylase (KDC); (v) an alcohol dehydrogenase (ADH); or (vi) any combination thereof. In some cases, the one or more gene encoding for (i) an acetolactate synthase (AlsS); (ii) a ketol-acid reductoisomerase (KARI); (iii) a dihydroxy-acid dehydratase (DHAD); (iv) a 2-keto acid decarboxylase (KDC); (v) an alcohol dehydrogenase (ADH); or (vi) any combination thereof, can be under the control of a rare earth metal switch, e.g., a lanthanum switch. In some cases, the vector can comprise a sugar permease gene. In some instances, the vector can comprise two or more genes encoding for the same enzyme. The two or more genes encoding for the same enzyme can be non-identical genes or in some cases, the two or more gene can be identical genes.

Additionally disclosed herein is a method of making a genetically modified microorganism capable of converting a $C_1$ carbon source to a multicarbon product comprising contacting a microorganism with a polynucleotide encoding for an acetolactate synthase (AlsS); a ketol-acid reductoisomerase (KARI); a dihydroxy-acid dehydratase (DHAD); and/or a 2-keto acid decarboxylase (KDC). In some cases, the 2-keto acid decarboxylase (KDC) can comprise a polynucleotide that is at least 60% identical to SEQ ID NO: 9. In some cases, the microorganism is further contacted with a second polynucleotide encoding for a 2-keto acid decarboxylase (KDC). In some cases, the microorganism is further contacted with a polynucleotide encoding for an alcohol dehydrogenase (ADH). In some cases, the genes can be under the control of a rare earth metal switch, such as a lanthanum switch. One or more of these genes can be heterologous, endogenous, overexpressed, and/or comprise multiple copies (e.g., LacY, AlsS, KARI, DHAD, KDC, and/or ADH). In some cases, the microorganism can be contacted with a sugar permease gene.

In some cases, the microorganism is contacted with a single vector or nucleic acid comprising the acetolactate synthase (AlsS) gene, the ketol-acid reductoisomerase gene, the dihydroxy-acid dehydratase gene, and the 2-keto acid decarboxylase (KDC) gene. In some cases, the microorganism is contacted with the acetolactate synthase (AlsS) gene, the ketol-acid reductoisomerase gene, the dihydroxy-acid dehydratase gene, and the 2-keto acid decarboxylase (KDC) gene using multiple vectors or nucleic acids.

Also described herein is a method of making a genetically modified microorganism capable of converting a $C_1$ carbon source to a multicarbon product comprising contacting a microorganism with a polynucleotide encoding for a sugar permease. The method can further comprise contacting the microorganism with one or more genes encoding for: (i) acetolactate synthase; (ii) ketol-acid reductoisomerase; (iii) dihydroxy-acid dehydratase; (iv) 2-keto acid decarboxylase; (v) alcohol dehydrogenase; or (vi) any combination thereof.

Further disclosed herein is a method of making an aldehyde from a $C_1$ carbon comprising: (a) contacting the $C_1$ carbon with a genetically modified microorganism capable of converting the $C_1$ carbon into a multicarbon product, where the genetically modified microorganism comprises a polynucleotide encoding for an acetolactate synthase (AlsS), a ketol-acid reductoisomerase; a dihydroxy-acid dehydratase; and a 2-keto acid decarboxylase (KDC), where the KDC comprises a polynucleotide that is at least 60% identical to SEQ ID NO: 9; and (b) growing the genetically modified microorganism to produce the aldehyde. In some cases, one or more of the genes can be under the control of a rare earth metal switch, such as a lanthanum switch.

This method can also further comprise (c) isolating the aldehyde. In some cases, the aldehyde can be isobutyraldehyde. The method can result in isobutyraldehyde being produced at a level of at least 1 g/L. The isobutyraldehyde can be isolated and can also be substantially pure.

In some cases, the microorganism can further comprise a second gene encoding for a 2-keto acid decarboxylase (KDC). In some cases, the KDC can comprise a polynucleotide that is at least 60% identical to SEQ ID NOs: 9 or 11. In some cases, the KDC can encode for a polypeptide that comprises an amino acid sequence that is at least 90% identical to any one of SEQ ID NOs: 10, 12, 55, 57, 59, 61, 63, 65, 67, 69, 71, 73, 75, 77, 79, 81, 83, 85, 87, 89, 91, 93, 95, or 97.

In some cases, the microorganism used in the method can further comprise a nucleic acid encoding for an ADH. In this case, the genetically modified microorganism can produce an alcohol, such as isobutanol.

In some cases, one or more of the genes can be under the control of a rare earth metal switch, such as a lanthanum switch.

Also disclosed herein is a method of making an alcohol from a $C_1$ carbon comprising: (a) contacting the $C_1$ carbon with a genetically modified microorganism capable of converting the $C_1$ carbon into a multicarbon product, where the genetically modified microorganism comprises a polynucleotide encoding for an acetolactate synthase (AlsS); a ketol-acid reductoisomerase; a dihydroxy-acid dehydratase; a 2-keto acid decarboxylase (KDC); and an alcohol dehydrogenase (ADH), where the KDC is encoded by a nucleotide sequence at least 60% identical to the nucleic acid sequence of SEQ ID NO: 9; and (b) growing the genetically modified microorganism to produce the alcohol. In some cases, the alcohol can be isobutanol.

The method can further comprise (c) isolating the alcohol. In some cases, the alcohol produced can be used as a gasoline additive, a gasoline substitute, or as jetfuel.

Also disclosed herein is an isolated polynucleotide comprising a nucleic acid sequence at least 84% identical to the nucleic acid sequence of SEQ ID NO: 1. Also disclosed herein is an isolated polynucleotide comprising a nucleic acid sequence at least 60% identical to the nucleic acid sequence of SEQ ID NO: 100. These nucleic acid sequences can encode for a protein that has acetolactate synthase activity.

Also disclosed herein is an isolated polynucleotide comprising a nucleic acid sequence at least 88% identical to the nucleic acid sequence of SEQ ID NO: 3. This nucleic acid sequence can encode for a protein that has ketol-acid reductoisomerase activity.

Further disclosed herein is an isolated polynucleotide comprising a nucleic acid sequence at least 88% identical to the nucleic acid sequence of SEQ ID NO: 5 or an isolated polynucleotide comprising a nucleic acid sequence at least 88% identical to the nucleic acid sequence of SEQ ID NO: 7. These nucleic acid sequences can encode for a protein that has dihydroxy-acid dehydratase activity.

Disclosed herein is an isolated polynucleotide comprising a nucleic acid sequence at least 85% identical to the nucleic acid sequence of SEQ ID NO: 9 or an isolated polynucleotide comprising a nucleic acid sequence at least 85% identical to the nucleic acid sequence of SEQ ID NO: 11. These nucleic acid sequences can encode for a protein that has 2-keto acid decarboxylase activity.

Further disclosed herein is an isolated polynucleotide comprising a nucleic acid sequence at least 85% identical to the nucleic acid sequence of SEQ ID NO: 13; an isolated polynucleotide comprising a nucleic acid sequence at least 85% identical to the nucleic acid sequence of SEQ ID NO: 15; and an isolated polynucleotide comprising a nucleic acid sequence at least 85% identical to the nucleic acid sequence of SEQ ID NO: 17. These nucleic acid sequences can encode for a protein that has alcohol dehydrogenase activity.

Also disclosed herein is an isolated polynucleotide comprising a nucleic acid sequence at least 84% identical to the nucleic acid sequence of SEQ ID NO: 19. This nucleic acid sequence can encode for a protein that has sugar permease activity.

Disclosed herein is an isolated polynucleotide comprising a nucleic acid sequence at least 84% identical to the nucleic acid sequence of SEQ ID NO: 21. This nucleic acid sequence can encode for a protein that has arabinose operon regulatory protein activity.

Disclosed herein is also a genetically modified microorganism capable of converting a $C_1$ carbon source to an aldehyde comprising one or more genes encoding for: (i) acetolactate synthase; (ii) ketol-acid reductoisomerase; (iii) dihydroxy-acid dehydratase; (iv) 2-keto acid decarboxylase; or (v) any combination thereof; where (a) the acetolactate synthase gene comprises a polynucleotide that is at least 60% identical to SEQ ID NO: 1 or 100; (b) the ketol-acid reductoisomerase gene comprises a polynucleotide that is at least 85% identical to SEQ ID NO: 3; (c) the dihydroxy-acid dehydratase gene comprises a polynucleotide that is at least 82% identical to SEQ ID NOs: 5 or 7; and/or (d) the 2-keto acid decarboxylase gene comprises a polynucleotide that is at least 60% identical to SEQ ID NOs: 9 or 11. The genetically modified microorganism can further comprise an ADH gene. The ADH gene can comprise (a) a polynucleotide that is at least 60% identical to SEQ ID NO: 13; (b) the nucleic acid sequence of SEQ ID NO: 15; and/or (c) a polynucleotide that is at least 60% identical to SEQ ID NO: 17.

Also described herein is a vector comprising one or more genes encoding for: (i) acetolactate synthase; (ii) ketol-acid reductoisomerase; (iii) dihydroxy-acid dehydratase; (iv) 2-keto acid decarboxylase; (v) alcohol dehydrogenase; or (vi) any combination thereof; where (i) the acetolactate synthase gene comprises a polynucleotide that is at least 60% identical to SEQ ID NO: 1 or 100; (ii) the ketol-acid reductoisomerase gene comprises a polynucleotide that is at least 85% identical to SEQ ID NO: 3; (iii) the dihydroxy-acid dehydratase gene comprises a polynucleotide that is at least 82% identical to SEQ ID NO: 5 and/or comprises the a polynucleotide sequence that is SEQ ID NO: 7; (iv) the 2-keto acid decarboxylase gene comprises a polynucleotide that is at least 60% identical to SEQ ID NO: 9 and/or comprises a polynucleotide that is SEQ ID NO: 11; and/or (v) the alcohol dehydrogenase gene comprises (a) a polynucleotide that is at least 60% identical to SEQ ID NO: 13; (b) a polynucleotide that is SEQ ID NO: 15; and/or (c) a polynucleotide that is at least 60% identical to SEQ ID NO: 17.

Further disclosed herein is a method of making a genetically modified microorganism capable of converting a $C_1$ carbon source to an aldehyde or an alcohol comprising contacting a microorganism with one or more genes encoding for: (i) an acetolactate synthase; (ii) a ketol-acid reductoisomerase; (iii) a dihydroxy-acid dehydratase; (iv) a 2-keto acid decarboxylase; (v) an alcohol dehydrogenase; or (vi) any combination thereof; where (i) the acetolactate synthase gene comprises a polynucleotide that is at least 60% identical to SEQ ID NO: 1 or 100; (ii) the ketol-acid reductoisomerase gene comprises a polynucleotide that is at least 85% identical SEQ ID NO: 3; (iii) the dihydroxy-acid dehydratase gene comprises a polynucleotide that is at least 82% identical to SEQ ID NO: 5 and/or comprises a polynucleotide that is SEQ ID NO: 7; (iv) the 2-keto acid decarboxylase gene comprises a polynucleotide that is at least 60% identical to SEQ ID NO: 9 and/or comprises a polynucleotide that is SEQ ID NO: 11; and/or (v) the alcohol dehydrogenase gene comprises (a) a polynucleotide that is at least 60% identical to SEQ ID NO: 13; (b) a polynucleotide that is SEQ ID NO: 15; and/or (c) a polynucleotide that is at least 60% identical to SEQ ID NO: 17.

Also disclosed herein is a method of making a useful product comprising: (a) contacting a genetically modified microorganism with a $C_1$ carbon substrate, where the microorganism comprises at least one heterologous gene encoding for: (i) an acetolactate synthase, (ii) a ketol-acid reductoisomerase, (iii) a dihydroxy-acid dehydratase, (iv) a 2-keto acid decarboxylase, (v) an alcohol dehydrogenase, or (vi) any combination thereof; and (b) growing the microorganism to produce the useful product, where the useful product comprises 2-acetolactate; 2,3-butanediol (2,3-BDO), diacetyl; 2,3-dihydroxy-2-methylbutanoic acid; 2,3-dihydroxyisovalerate; amino acids; ketoisovalerate; isobutyraldehyde; methyl methacrylate (MMA); isovaleraldehyde; isovalerate; isopentanol; isoamyl acetate; pentadecanoic acid; isobutene; or p-xylene.

Further disclosed is a genetically modified microorganism capable of converting a $C_1$ carbon to a multicarbon product, where the genetically modified microorganism comprises an acetolactate synthase gene; a ketol-acid reductoisomerase gene; a dihydroxy-acid dehydratase gene; and a 2-keto acid decarboxylase gene, where the acetolactate synthase gene comprises a polynucleotide that is at least 60% identical to SEQ ID NO: 100. In some cases, the genetically modified microorganism can comprise an alcohol dehydrogenase gene. In other cases, the acetolactate synthase gene, the ketol-acid reductoisomerase gene, the dihydroxy-acid dehydratase gene, the 2-keto acid decarboxylase gene, or the alcohol dehydrogenase gene is heterologous to the microorganism.

Further disclosed is a method of making a genetically modified microorganism capable of converting a $C_1$ carbon source to a multicarbon product, the method comprising contacting a microorganism with an acetolactate synthase gene, a ketol-acid reductoisomerase gene, a dihydroxy-acid dehydratase gene, and a 2-keto acid decarboxylase gene, where the acetolactate synthase gene comprises a polynucleotide that is at least 60% identical to SEQ ID NO: 100.

Also disclosed herein is a method of making 2-acetolactate comprising (a) contacting a $C_1$ carbon with a genetically modified microorganism capable of converting the $C_1$ carbon into a multicarbon product, where the genetically modified microorganism comprises an acetolactate synthase gene comprising a polynucleotide that is at least 60% identical to SEQ ID NO: 100; and (b) growing the genetically modified microorganism to produce the 2-acteolactate.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A shows from left to right, a Kanamycin marker, an arabinose induction machinery (LacY and AraC driven by a J23115 promoter) and a BAD promoter (pBAD) driving the isobutanol pathway ((MCA0996=Kdc), Adh6, AlsS, IlvC and IlvD). FIG. 4B shows the vector from FIG. 4A with three differences: the KDC here comes from *Carnobacterium divergens* (Cdi), the IlvD comes from *Methylococcus capsulatus*, and an additional ADH gene has been added (YqhD from *E. coli*). FIG. 4C shows a vector that shares a similar architecture to the vector in FIG. 4A with many of the same genes. However, there are several key differences including: 1) two operons, one with pBAD (inducible by arabinose) and the second using pMxaF (strong endogenous promoter) driving the genes; and 2) the addition of a FucO alcohol dehydrogenase from *E. coli*.

DETAILED DESCRIPTION OF THE DISCLOSURE

Figure 1:
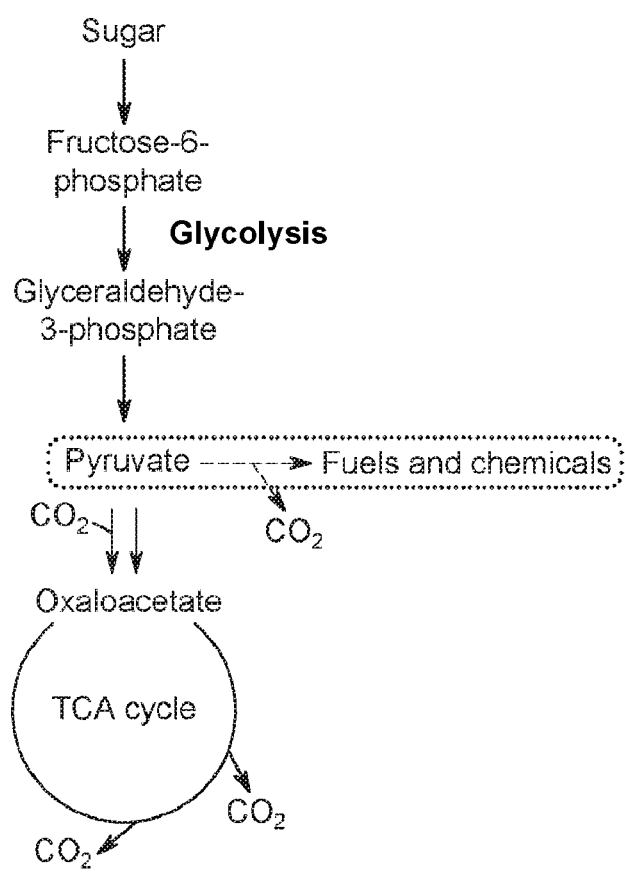
FIG. 1 shows a metabolic pathway from sugar to pyruvate. Pyruvate can then be used to make various products such as fuels and chemicals.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Isobutanol is a high value chemical and fuel that is currently produced from the carbonylation of propylene. Two methods are currently practiced in the industry, including hydroformylation and reppe carbonylation. Hydroformylation is more common and generates a mixture of isobutyraldehydes, which are hydrogenated to the alcohols and then separated. There has been high interest in the biosynthesis of isobutanol. Fermentation typically involves taking a carbon source (usually sugar) and fermenting it using a microorganism that is capable of converting the carbon source into a desired product such as isobutanol.

Costs to produce chemicals, such as isobutanol, by fermentation typically depend on the cost of the carbon source used. Sugars are generally higher cost carbon sources that also result in a decrease of food supply. One carbon source that is currently extremely cost-effective and abundant is natural gas. The primary source of carbon within natural gas is methane. By using cheap carbon sources such as methane, alcohols, such as isobutanol, can be produced economically. However, the challenge lies in engineering fermentation methods and microorganisms to efficiently convert cheap carbon sources, such as methane, into alcohols, such as isobutanol, using a fermentation process.

Only a very few microorganisms are capable of producing isobutanol naturally at very low levels. (Felpeto-Santero, C., et al., "Engineering alternative isobutanol production platforms," *AMB Express*, 5:32 (2015)) At these low titers, the cost of fermentation would be too great to be economically feasible. Thus, genetic engineering is required to produce isobutanol at an economically viable level.

Described herein are genetically modified microorganisms, e.g., methanotrophs, that can convert a carbon substrate, such as methane, into desired products. Some of the genetically modified microorganisms disclosed herein have been designed and altered to efficiently produce alcohols, such as isobutanol, or aldehydes, such as isobutyraldehyde or isovaleraldehyde, multiple folds over what is naturally produced or expected to be produced. Additionally some of the genetically modified microorganisms disclosed herein can be used to convert a carbon substrate (such as methane) into alcohols, such as isobutanol, and subsequently into fuels or other desired products. These genetically modified microorganisms and the novel methods of fermentation and uses thereof are described herein.

Definitions

The term "alcohol" and its grammatical equivalents as used herein can refer to any and all any organic compounds whose molecule contains one or more hydroxyl groups (—OH) attached to a carbon atom. For example, ethanol and isobutanol are alcohols.

The term "aldehyde" and its grammatical equivalents as used herein can refer to any and all organic compounds whose molecule contains a function group with the structure —CHO, which has a carbonyl center (a carbon double-bonded to oxygen) with the carbon atom also bonded to hydrogen and to an R group (which can be any generic alkyl or side chain). For example, isobutyraldehyde and isovaleraldehyde are aldehydes.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

The term "gene" and its grammatical equivalents as used herein can refer to any sequence of DNA or RNA which codes for a molecule that has a function.

The terms "protein", "peptide", "polypeptide", and "amino acid sequence" are used interchangeably herein to refer to polymers of amino acid residues of any length. The polymer can be linear or branched. The polymer can comprise modified amino acids or amino acid analogs, and it can be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

The terms "polynucleotide" and "polynucleic acid" are used interchangeably herein and refer to a polymer of ribonucleic acid (RNA) or deoxyribonucleic acid (DNA). A polynucleotide is made up of four bases: adenine, cytosine, guanine, and thymine/uracil (uracil is used in RNA). A coding sequence from a polynucleotide is indicative of the sequence of the protein encoded by the polynucleotide. The terms include various modifications and analogues.

The terms "nucleotide sequences" and "nucleic acid sequences" are used interchangeably herein and refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double stranded (duplex). Duplex nucleic acids can be homoduplex or heteroduplex.

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "substantially pure" and its grammatical equivalents as used herein can mean that a particular substance does not contain a majority of another substance. For example, "substantially pure isobutanol" can mean at least 90% isobutanol. In some instances, "substantially pure isobutanol" can mean at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, or 99.9999% isobutanol. For example, substantially pure isobutanol can mean at least 70% isobutanol. In some cases, substantially pure isobutanol can mean at least 75% isobutanol. In some cases, substantially pure isobutanol can mean at least 80% isobutanol. In some cases, substantially pure isobutanol can mean at least 85% isobutanol. In some cases, substantially pure isobutanol can mean at least 90% isobutanol. In some cases, substantially pure isobutanol can mean at least 91% isobutanol. In some cases, substantially pure isobutanol can mean at least 92% isobutanol. In some cases, substantially pure isobutanol can mean at least 93% isobutanol. In some cases, substantially pure isobutanol can mean at least 94% isobutanol. In some cases, substantially pure isobutanol can mean at least 95% isobutanol. In some cases, substantially pure isobutanol can mean at least 96% isobutanol. In some cases, substantially pure isobutanol can mean at least 97% isobutanol. In some cases, substantially pure isobutanol can mean at least 98% isobutanol. In some cases, substantially pure isobutanol can mean at least 99% isobutanol.

The terms "heterologous" and "exogenous" and their grammatical equivalents as used herein can mean "from a different species." For example, a "heterologous gene" can mean a gene that is from a different species. In some instances, as "a methanotroph comprising a heterologous gene" can mean that the methanotroph contains a gene that is not from the same methanotroph. The gene can be from a different microorganism such as yeast or from a different species such as a different methanotroph species. In some cases, the terms "heterologous" and "exogenous" and their grammatical equivalents as used herein can refer to polynucleotides and polypeptides.

The term "substantially similar" and its grammatical equivalents in reference to another sequence as used herein can mean at least 50% identical. In some instances, the term substantially similar refers to a sequence that is at least 55% identical. In some instances, the term substantially similar refers to a sequence that is at least 60% identical. In some instances, the term substantially similar refers to a sequence that is at least 65% identical. In some instances, the term substantially similar refers to a sequence that is at least 70% identical. In some instances, the term substantially similar refers to a sequence that is at least 75% identical. In some instances, the term substantially similar refers to a sequence that is at least 80% identical. In other instances, the term substantially similar refers to a sequence that is at least 85% identical. In some instances, the term substantially similar refers to a sequence that is at least 90% identical. In some instances, the term substantially similar refers to a sequence that is at least 91% identical. In some instances, the term substantially similar refers to a sequence that is at least 92% identical. In some instances, the term substantially similar refers to a sequence that is at least 93% identical. In some instances, the term substantially similar refers to a sequence that is at least 94% identical. In some instances, the term substantially similar refers to a sequence that is at least 95% identical. In some instances, the term substantially similar refers to a sequence that is at least 96% identical. In some instances, the term substantially similar refers to a sequence that is at least 97% identical. In some instances, the term substantially similar refers to a sequence that is at least 98% identical. In some instances, the term substantially similar refers to a sequence that is at least 99% identical. In some instances, the term substantially similar refers to a sequence that is 100% identical. In order to determine the percentage of identity between two sequences, the two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. For example, methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations.

Computer programs that can be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences where at least 50% of the total length of one of the two sequences is involved in the alignment.

The terms "acetolactate synthase" or "AlsS" and their grammatical equivalents as used herein can be interchangeably used with acetohydroxy acid synthase; acetolactate pyruvate-lyase; or acetolactate synthease. The terms "acetolactate synthase" or "AlsS" can include enzymes that are capable of converting pyruvate to 2-acetolactate. For example, the terms "acetolactate synthase" or "AlsS" can include an enzyme having an EC 2.2.1.6.

The terms "ketol acid reductoisomerase" or "IlvC" and their grammatical equivalents as used herein can be used interchangeably with acetohydroxy acid isomeroreductase, ketol acid reductoisomerase, alpha-keto-beta-hydroxylacyl reductoisomerase, acetohydroxy acid reductoisomerase, acetolactate reductoisomerase, dihydroxyisovalerate (isomerizing) dehydrogenase, isomeroreductase, and/or reductoisomerase. The terms "ketol acid reductoisomerase" or "IlvC" can include enzymes that are capable of converting 2-acetolactate into 2,3-dihydroxyisovalerate. For example, the terms "ketol acid reductoisomerase" or "IlvC" can include an enzyme having an EC 1.1.1.86.

The terms "dihydroxy-acid dehydratase" or "IlvD" and their grammatical equivalents as used herein can be used interchangeably with acetohydroxyacid dehydratase, alpha, beta-dihydroxyacid dehydratase, 2,3-dihydroxyisovalerate dehydratase, alpha,beta-dihydroxyisovalerate dehydratase, dihydroxy acid dehydrase, DHAD, or 2,3-dihydroxy-acid hydro-lyase. The terms "dihydroxy-acid dehydratase" or "IlvD" can include enzymes that are capable of converting 2,3-dihydroxyisovalerate into ketoisovalerate. For example, the terms "dihydroxy-acid dehydratase" or "IlvD" can include an enzyme having an EC 4.2.1.9.

The terms "2-keto acid decarboxylase" or "KDC" and their grammatical equivalents as used herein can include enzymes that are capable of converting ketoisovalerate into isobutyraldehyde. For example, the terms "2-keto acid decarboxylase" or "KDC" can include an enzyme having an EC 4.1.1.72.

The terms "alcohol dehydrogenase", "ADH" or "Adh" and their grammatical equivalents as used herein can include enzymes that are capable of converting isobutyraldehyde into an alcohol such as isobutanol. For example, in some instances, the terms "alcohol dehydrogenase" or "Adh" can include an enzyme having an EC 1.1.1.1.

I. Genetically Modified Microorganisms and Methods of Making the Same

Isobutanol and/or isobutyraldehyde is produced by some unmodified microorganisms; however, production levels are extremely low. Disclosed herein are genetically modified microorganisms that have dramatically improved isobutanol and/or isobutyraldehyde biosynthesis rates, and in some cases orders of magnitude higher than what could be naturally produced. For example, disclosed herein are microorganisms that do not normally produce isobutanol and/or isobutyraldehyde that can be genetically modified to synthesize isobutanol and/or isobutyraldehyde, including at significantly high levels.

Microorganisms

The microorganisms described herein can use carbon substrates, such as, but not limited to $CH_4$, as carbon source to produce desired products. This however does not mean that these microorganisms use solely $CH_4$ as a carbon source. Some of the microorganisms disclosed herein can be made to utilize additional carbon substrates, including carbon substrates that the microorganism naturally uses in addition to other carbon substrates. For example, the microorganisms can be made to use two or more carbon substrates, such as $CH_4$ and sugar.

The microorganisms disclosed herein can be a prokaryote or eukaryote. In some cases, other microorganisms such as bacteria, yeast, or algae can be used.

Some microorganisms can use a $C_1$ carbon to generate a desired product. For example, some of the microorganisms that can convert $C_1$ carbon substrates into desired products can be a microorganism that is capable of using natural gas as a carbon substrate. In some cases, the microorganism can use the methane contained within the natural gas as a carbon source to make desired products. One type of microorganism that uses $C_1$ carbon substrates to form desired organic compounds are methanotrophs. The methanotrophs that can be particularly useful include methanotrophs from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum, Methylacidiphilum*, or any combinations thereof. Methanotrophs from the genus *Methylococcus* can be particularly useful. When a methanotroph from the genus *Methylococcus* is used, a methanotroph from the species *Methylococcus capsulatus* can be used.

Some microorganisms disclosed throughout are microorganisms that are capable of using $CO_2$ as a carbon substrate. For instance, the microorganisms can be a methanogen. Microorganisms that are capable of using $CO_2$ as a substrate can contain chlorophyll. One type of microorganism that uses $CO_2$ to form desired organic compounds are algae. Another type of microorganism that can use $CO_2$ as a substrate is a cyanobacterium.

Some microorganisms that can convert $C_1$ carbon substrates into desired products can be a microorganism that is capable of using CO as a carbon substrate. Anaerobic microorganisms can typically process CO and therefore can be used herein. One type of microorganism that naturally uses CO to form desired organic compounds are bacterium such as *Clostridium*. These microorganisms can be genetically modified into making substantial amounts of alcohols, such as isobutanol.

Enzymes

In order to genetically engineer certain microorganisms to produce certain useful products such as isobutanol, microorganisms can be transformed with one or more genes that encode for specific enzymes. The genes encoding for these enzymes can be heterologous to the microorganism.

For example, in order to create a microorganism that can produce an alcohol, such as isobutanol, or an aldehyde, such as isobutyraldehyde, one or more genes (e.g., heterologous genes) can be transformed/transfected (i.e., inserted) into the microorganism (transiently or stably). The microorganism can contain an acetolactate synthase (gene name: AlsS), which is an enzyme that coverts two molecules of pyruvate into 2-acetolactate. The microorganism can in some cases comprise an ketol-acid reductoisomerase (gene name: ilvC) which is an enzyme that converts 2-acetolactate into 2,3-dihydroxy-isovalerate using NADPH as a reduced cofactor. The microorganism can also comprise an dihydroxy-acid dehydratase (gene name: ilvD), which is enzyme that converts 2,3-dihydroxy-isovalerate into 2-ketoisovalerate. The microorganism can in some cases comprise an 2-keto acid decarboxylase (gene name: KDC), which is enzyme that converts 2-ketoisovalerate into isobutyraldehyde. In order to produce isobutanol, the microorganism can in some cases comprise an alcohol dehydrogenase (gene name: ADH), which is enzyme that converts isobutyraldehyde into isobutanol.

Described throughout are microorganisms used to make alcohols, such as isobutanol, or an aldehyde, such as isobutyraldehyde, from a $C_1$ carbon (e.g., methane) or other multi-carbon source. In some cases, the microorganism herein can be transformed with a gene encoding for one or more of the following enzymes: (i) acetolactate synthase; (ii) ketol-acid reductoisomerase; (iii) dihydroxy-acid dehydratase; and/or (iv) 2-keto acid decarboxylase. Should the microorganism be directed to making an alcohol, the microorganism can be transformed with (v) an alcohol dehydrogenase. For example, the microorganism can be transformed with a gene encoding for an acetolactate synthase. The microorganism can be transformed with a gene encoding for a ketol-acid reductoisomerase. The microorganism can be transformed with a gene encoding for a dihydroxy-acid dehydratase. The microorganism can be transformed with a gene encoding for a 2-keto acid decarboxylase. The microorganism can be transformed with a gene encoding for an alcohol dehydrogenase. Any one of or more than one of these genes can be heterologous to the microorganism.

In some instances, the microorganism can be transformed with two or more genes selected from (i) acetolactate synthase; (ii) ketol-acid reductoisomerase; (iii) dihydroxy-acid dehydratase; (iv) 2-keto acid decarboxylase; and/or (v) alcohol dehydrogenase. One or more of the genes can be heterologous to the microorganism.

In one instance, the microorganism can be transformed with at least three or more genes selected from (i) acetolactate synthase; (ii) ketol-acid reductoisomerase; (iii) dihydroxy-acid dehydratase; (iv) 2-keto acid decarboxylase; and/or (v) alcohol dehydrogenase. One or more of the genes can be heterologous to the microorganism.

In other instances, the microorganism can be transformed with at least four or more genes selected from (i) acetolactate synthase; (ii) ketol-acid reductoisomerase; (iii) dihydroxy-acid dehydratase; (iv) 2-keto acid decarboxylase; and/or (v) alcohol dehydrogenase. One or more of the genes can be heterologous to the microorganism.

In some cases, the microorganism can be transformed with at least five or more genes encoding for enzymes such as an acetolactate synthase; ketol-acid reductoisomerase; dihydroxy-acid dehydratase; 2-keto acid decarboxylase; and alcohol dehydrogenase. In this case, the output will be an alcohol, such as isobutanol, unless the alcohol dehydrogenase is non-functional. If the alcohol dehydrogenase is non-functional, then the output will be an aldehyde, such as isobutyraldehyde. One or more of the genes can be heterologous to the microorganism.

In some cases, when an acetolactate synthase is used, the acetolactate synthase can be from a bacteria (e.g., a gram positive bacterium), such as from the genus *Bacillus*. For example, an acetolactate synthase can be from the species *Bacillus subtilis*. In some cases, the acetolactate synthase can be from the species *Bacillus licheniformis*.

The acetolactate synthase can comprise an amino acid sequence that is substantially similar to SEQ ID NO: 2 or 99. For example, the acetolactate synthase can comprise an amino acid sequence that is at least 60% identical to SEQ ID NO: 2 or 99. In some cases, the acetolactate synthase can comprise an amino acid sequence that is at least 65% identical to SEQ ID NO: 2 or 99. In some cases, the acetolactate synthase can comprise an amino acid sequence that is at least 70% identical to SEQ ID NO: 2 or 99. In some cases, the acetolactate synthase can comprise an amino acid sequence that is at least 75% identical to SEQ ID NO: 2 or 99. In some cases, the acetolactate synthase can comprise an amino acid sequence that is at least 80% identical to SEQ ID NO: 2 or 99. In some cases, the acetolactate synthase can comprise an amino acid sequence that is at least 85% identical to SEQ ID NO: 2 or 99. In some cases, the acetolactate synthase can comprise an amino acid sequence that is at least 90% identical to SEQ ID NO: 2 or 99. In some cases, the acetolactate synthase can comprise an amino acid sequence that is at least 91% identical to SEQ ID NO: 2 or 99. In some cases, the acetolactate synthase can comprise an amino acid sequence that is at least 92% identical to SEQ ID NO: 2 or 99. In some cases, the acetolactate synthase can comprise an amino acid sequence that is at least 93% identical to SEQ ID NO: 2 or 99. In some cases, the acetolactate synthase can comprise an amino acid sequence that is at least 94% identical to SEQ ID NO: 2 or 99. In some cases, the acetolactate synthase can comprise an amino acid sequence that is at least 95% identical to SEQ ID NO: 2 or 99. In some cases, the acetolactate synthase can comprise an amino acid sequence that is at least 96% identical to SEQ ID NO: 2 or 99. In some cases, the acetolactate synthase can comprise an amino acid sequence that is at least 97% identical to SEQ ID NO: 2 or 99. In some cases, the acetolactate synthase can comprise an amino acid sequence that is at least 98% identical to SEQ ID NO: 2 or 99. In some cases, the acetolactate synthase can comprise an amino acid sequence that is at least 99% identical to SEQ ID NO: 2 or 99. In some cases, the acetolactate synthase can comprise an amino acid sequence that is SEQ ID NO: 2 or 99.

When a ketol-acid reductoisomerase is used, the ketol-acid reductoisomerase can be from a bacteria (e.g., a gram negative bacterium), such as from the genus *Escherichia*. For example, the ketol-acid reductoisomerase can be from the species *Escherichia coli*.

The ketol-acid reductoisomerase can comprise an amino acid sequence that is substantially similar to SEQ ID NO: 4. For example, the ketol-acid reductoisomerase can comprise an amino acid sequence that is at least 60% identical to SEQ ID NO: 4. In some cases, the ketol-acid reductoisomerase can comprise an amino acid sequence that is at least 65% identical to SEQ ID NO: 4. In some cases, the ketol-acid reductoisomerase can comprise an amino acid sequence that is at least 70% identical to SEQ ID NO: 4. In some cases, the ketol-acid reductoisomerase can comprise an amino acid sequence that is at least 75% identical to SEQ ID NO: 4. In some cases, the ketol-acid reductoisomerase can comprise an amino acid sequence that is at least 80% identical to SEQ ID NO: 4. In some cases, the ketol-acid reductoisomerase can comprise an amino acid sequence that is at least 85% identical to SEQ ID NO: 4. In some cases, the ketol-acid reductoisomerase can comprise an amino acid sequence that is at least 90% identical to SEQ ID NO: 4. In some cases, the ketol-acid reductoisomerase can comprise an amino acid sequence that is at least 91% identical to SEQ ID NO: 4. In some cases, the ketol-acid reductoisomerase can comprise an amino acid sequence that is at least 92% identical to SEQ ID NO: 4. In some cases, the ketol-acid reductoisomerase can comprise an amino acid sequence that is at least 93% identical to SEQ ID NO: 4. In some cases, the ketol-acid reductoisomerase can comprise an amino acid sequence that is at least 94% identical to SEQ ID NO: 4. In some cases, the ketol-acid reductoisomerase can comprise an amino acid sequence that is at least 95% identical to SEQ ID NO: 4. In some cases, the ketol-acid reductoisomerase can comprise an amino acid sequence that is at least 96% identical to SEQ ID NO: 4. In some cases, the ketol-acid reductoisomerase can comprise an amino acid sequence that is at least 97% identical to SEQ ID NO: 4. In some cases, the ketol-acid reductoisomerase can comprise an amino acid sequence that is at least 98% identical to SEQ ID NO: 4. In some cases, the ketol-acid reductoisomerase can comprise an amino acid sequence that is at least 99% identical to SEQ ID NO: 4. In some cases, the ketol-acid reductoisomerase can comprise an amino acid sequence that is SEQ ID NO: 4.

When a dihydroxy-acid dehydratase is used, the dihydroxy-acid dehydratase can be from a bacterium (e.g., from a gram negative bacterium or a methanotroph), such as from the genus *Escherichia* and/or *Methylococcus*. More specifically, the dihydroxy-acid dehydratase can be from the species *Escherichia coli* and/or *Methylococcus capsulatus*.

The dihydroxy-acid dehydratase can comprise an amino acid sequence that is substantially similar to SEQ ID NO: 6 or 8. For example, the dihydroxy-acid dehydratase can comprise an amino acid sequence that is at least 60% identical to SEQ ID NO: 6 or 8. In some cases, the dihydroxy-acid dehydratase can comprise an amino acid sequence that is at least 65% identical to SEQ ID NO: 6 or 8. In some cases, the dihydroxy-acid dehydratase can comprise an amino acid sequence that is at least 70% identical to SEQ ID NO: 6 or 8. In some cases, the dihydroxy-acid dehydratase can comprise an amino acid sequence that is at least 75% identical to SEQ ID NO: 6 or 8. In some cases, the dihydroxy-acid dehydratase can comprise an amino acid sequence that is at least 80% identical to SEQ ID NO: 6 or 8. In some cases, the dihydroxy-acid dehydratase can comprise an amino acid sequence that is at least 85% identical to SEQ ID NO: 6 or 8. In some cases, the dihydroxy-acid dehydratase can comprise an amino acid sequence that is at least 90% identical to SEQ ID NO: 6 or 8. In some cases, the dihydroxy-acid dehydratase can comprise an amino acid sequence that is at least 91% identical to SEQ ID NO: 6 or 8. In some cases, the dihydroxy-acid dehydratase can comprise an amino acid sequence that is at least 92% identical to SEQ ID NO: 6 or 8. In some cases, the dihydroxy-acid dehydratase can comprise an amino acid sequence that is at least 93% identical to SEQ ID NO: 6 or 8. In some cases, the dihydroxy-acid dehydratase can comprise an amino acid sequence that is at least 94% identical to SEQ ID NO: 6 or 8. In some cases, the dihydroxy-acid dehydratase can comprise an amino acid sequence that is at least 95% identical to SEQ ID NO: 6 or 8. In some cases, the dihydroxy-acid dehydratase can comprise an amino acid sequence that is at least 96% identical to SEQ ID NO: 6 or 8. In some cases, the dihydroxy-acid dehydratase can comprise an amino acid sequence that is at least 97% identical to SEQ ID NO: 6 or 8. In some cases, the dihydroxy-acid dehydratase can comprise an amino acid sequence that is at least 98% identical to SEQ ID NO: 6 or 8. In some cases, the dihydroxy-acid dehydratase can comprise an amino acid sequence that is at least 99% identical to SEQ ID NO: 6 or 8. In some cases, the dihydroxy-acid dehydratase can comprise an amino acid sequence that is SEQ ID NO: 6 or 8.

When a 2-keto acid decarboxylase (KDC) is used, the (KDC can be from a bacterium (e.g., a gram positive bacterium) such as from the genus *Carnobacterium* and/or a methanotroph such as from the genus *Methylococcus*. More specifically, the KDC can be from the species *Carnobacterium divergens* and/or *Methylococcus capsulatus*.

The KDC can be from other bacterium, such as those listed in Table 4. For example, the KDC can be from the genus *Methylocaldum, Methylosarcina, Methylomonas, Methylohalobius, Methylobacter, Lamprocystis, Andreprevotia, Lactococcus, Streptococcus, Enterococcus, Brochothrix, Carnobacterium, Helicobacter, Staphylococcus,* and/or *Fictibacillus*. For example, KDC from the following species can be particularly useful: *Methylocaldum szegediense, Methylosarcina lacus, Methylomonas denitrificans, Methylomonas methanica, Methylohalobius crimeensis, Methylobacter marinus, Methylobacter luteus, Lamprocystis purpurea, Andreprevotia chitinilytica, Lactococcus lactis, Streptococcus didelphis, Enterococcus caccae, Enterococcus haemoperoxidus, Enterococcus moraviensis, Carnobacterium maltaromaticum, Brochothrix thermosphacta, Carnobacterium gallinarum, Carnobacterium divergens, Helicobacter bizzozeronii, Staphylococcus aureus* subsp. *aureus* CIG290, and/or *Fictibacillus macauensis*.

The 2-keto acid decarboxylase can comprise an amino acid sequence that is substantially similar to any one of SEQ ID NOs: 10, 12, 55, 57, 59, 61, 63, 65, 67, 69, 71, 73, 75, 77, 79, 81, 83, 85, 87, 89, 91, 93, 95, or 97. For example, the 2-keto acid decarboxylase can comprise an amino acid sequence that is at least 60% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 65% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 70% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 75% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 80% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 85% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 90% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 91% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 92% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 93% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 94% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 95% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 96% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 97% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 98% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is at least 99% identical to any one of SEQ ID NOs: 10, 12, 55, 57, 59, 61, 63, 65, 67, 69, 71, 73, 75, 77, 79, 81, 83, 85, 87, 89, 91, 93, 95, or 97. In some cases, the 2-keto acid decarboxylase can comprise an amino acid sequence that is any one of SEQ ID NOs: 10, 12, 55, 57, 59, 61, 63, 65, 67, 69, 71, 73, 75, 77, 79, 81, 83, 85, 87, 89, 91, 93, 95, or 97.

In some cases, two or more KDCs can be used. In some cases, two KDC genes can be used to increase the production of aldehydes, such as isobutyraldehyde, and/or alcohols, such as isobutanol. In other cases, three KDCs can be used to increase the production of isobutyraldehyde and/or isobutanol. In some cases, four, five, or six KDCs can be used to increase the production of isobutyraldehyde and/or isobutanol.

When an alcohol dehydrogenase is used, the alcohol dehydrogenase can be from a yeast such as from the genus *Saccharomyces* or a bacterium (e.g., a gram negative or gram positive bacterium) such as from the genus *Escherichia*. More specifically, the alcohol dehydrogenase can be from the species *Saccharomyces cerevisiae* and/or *Escherichia coli*.

Other ADHs that can be used can be from the genus *Clostridium, Geobacillus, Lactococcus, Oenococcus, Pectobacterium,* and/or *Psychrobacter*. For example, ADHs from the following species can be particularly useful: *Clostridium acetobutylicum, Geobacillus stearothermophilus, Geobacillus thermoglucosidas, Lactococcus lactis, Oenococcus oeni, Pectobacterium atrosepticum,* and/or *Psychrobacter cryohalolentis*.

The alcohol dehydrogenase can comprise an amino acid sequence that is substantially similar to any one of SEQ ID NOs: 14, 16, 18, 23, 25, 27, 29, 31, 33, 35, 37, 39, 41, 43, 45, 47, 49, 51, or 53. For example, the alcohol dehydrogenase can comprise an amino acid sequence that is at least 60% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 65% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 70% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 75% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 80% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 85% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 90% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 91% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 92% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 93% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 94% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 95% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 96% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 97% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 98% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is at least 99% identical to any one of SEQ ID NOs: 14, 16, 18, 23, 25, 27, 29, 31, 33, 35, 37, 39, 41, 43, 45, 47, 49, 51, or 53. In some cases, the alcohol dehydrogenase can comprise an amino acid sequence that is any one of SEQ ID NOs: 14, 16, 18, 23, 25, 27, 29, 31, 33, 35, 37, 39, 41, 43, 45, 47, 49, 51, or 53.

In some cases, two or more ADHs can be used. In some cases, two ADHs can be used to increase the production of alcohols, such as isobutanol. In other cases, three ADHs can be used to increase the production of isobutanol. In some cases, four, five, or six ADHs can be used to increase the production of isobutanol.

Additional enzymes can be placed inside the microorganism in order to make the process more efficient and/or to produce other desired end products.

For example, a sugar permease can be placed within the microorganism in order to increase production of the desired end product, such as an alcohol, e.g., isobutanol, or an aldehyde, e.g., isobutyraldehyde. In some cases, the sugar permease can be from a bacterium (e.g., a gram negative bacterium) such as from the genus *Escherichia*. More specifically, the sugar permease can be from the species *Escherichia coli*.

The sugar permease can comprise an amino acid sequence that is substantially similar to SEQ ID NO: 20. For example, the sugar permease can comprise an amino acid sequence that is at least 60% identical to SEQ ID NO: 20. In some cases, the sugar permease can comprise an amino acid sequence that is at least 65% identical to SEQ ID NO: 20. In some cases, the sugar permease can comprise an amino acid sequence that is at least 70% identical to SEQ ID NO: 20. In some cases, the sugar permease can comprise an amino acid sequence that is at least 75% identical to SEQ ID NO: 20. In some cases, the sugar permease can comprise an amino acid sequence that is at least 80% identical to SEQ ID NO: 20. In some cases, the sugar permease can comprise an amino acid sequence that is at least 85% identical to SEQ ID NO: 20. In some cases, the sugar permease can comprise an amino acid sequence that is at least 90% identical to SEQ ID NO: 20. In some cases, the sugar permease can comprise an amino acid sequence that is at least 91% identical to SEQ ID NO: 20. In some cases, the sugar permease can comprise an amino acid sequence that is at least 92% identical to SEQ ID NO: 20. In some cases, the sugar permease can comprise an amino acid sequence that is at least 93% identical to SEQ ID NO: 20. In some cases, the sugar permease can comprise an amino acid sequence that is at least 94% identical to SEQ ID NO: 20. In some cases, the sugar permease can comprise an amino acid sequence that is at least 95% identical to SEQ ID NO: 20. In some cases, the sugar permease can comprise an amino acid sequence that is at least 96% identical to SEQ ID NO: 20. In some cases, the sugar permease can comprise an amino acid sequence that is at least 97% identical to SEQ ID NO: 20. In some cases, the sugar permease can comprise an amino acid sequence that is at least 98% identical to SEQ ID NO: 20. In some cases, the sugar permease can comprise an amino acid sequence that is at least 99% identical to SEQ ID NO: 20. In some cases, the sugar permease can comprise an amino acid sequence that is SEQ ID NO: 20.

Another peptide that can be placed within the microorganism in order to increase production of the desired end product, such as an alcohol, e.g., isobutanol, or an aldehyde, e.g., isobutyraldehyde, is an arabinose operon regulatory protein (AraC). In some cases, the arabinose operon regulatory protein can be from a bacterium (e.g., a gram negative bacterium) such as from the genus *Escherichia*. More specifically, the arabinose operon regulatory protein can be from the species *Escherichia coli*.

The arabinose operon regulatory protein can comprise an amino acid sequence that is substantially similar to SEQ ID NO: 22. For example, the arabinose operon regulatory protein can comprise an amino acid sequence that is at least 60% identical to SEQ ID NO: 22. In some cases, the arabinose operon regulatory protein can comprise an amino acid sequence that is at least 65% identical to SEQ ID NO: 22. In some cases, the arabinose operon regulatory protein can comprise an amino acid sequence that is at least 70% identical to SEQ ID NO: 22. In some cases, the arabinose operon regulatory protein can comprise an amino acid sequence that is at least 75% identical to SEQ ID NO: 22. In some cases, the arabinose operon regulatory protein can comprise an amino acid sequence that is at least 80% identical to SEQ ID NO: 22. In some cases, the arabinose operon regulatory protein can comprise an amino acid sequence that is at least 85% identical to SEQ ID NO: 22. In some cases, the arabinose operon regulatory protein can comprise an amino acid sequence that is at least 90% identical to SEQ ID NO: 22. In some cases, the arabinose operon regulatory protein can comprise an amino acid sequence that is at least 91% identical to SEQ ID NO: 22. In some cases, the arabinose operon regulatory protein can comprise an amino acid sequence that is at least 92% identical to SEQ ID NO: 22. In some cases, the arabinose operon regulatory protein can comprise an amino acid sequence that is at least 93% identical to SEQ ID NO: 22. In some cases, the arabinose operon regulatory protein can comprise an amino acid sequence that is at least 94% identical to SEQ ID NO: 22. In some cases, the arabinose operon regulatory protein can comprise an amino acid sequence that is at least 95% identical to SEQ ID NO: 22. In some cases, the arabinose operon regulatory protein can comprise an amino acid sequence that is at least 96% identical to SEQ ID NO: 22. In some cases, the arabinose operon regulatory protein can comprise an amino acid sequence that is at least 97% identical to SEQ ID NO: 22. In some cases, the arabinose operon regulatory protein can comprise an amino acid sequence that is at least 98% identical to SEQ ID NO: 22. In some cases, the arabinose operon regulatory protein can comprise an amino acid sequence that is at least 99% identical to SEQ ID NO: 22. In some cases, the arabinose operon regulatory protein can comprise an amino acid sequence that is SEQ ID NO: 22.

The amino acid sequences can also be optimized based on the microorganism in which the enzymes will be expressed. In other words, conservative amino acids substitutions can be made based on whether the respective microorganism typically uses a specific amino acid or how much of that particular amino acid is available for use within the microorganism.

Vectors

Polynucleotide constructs prepared for introduction into a prokaryotic or eukaryotic host can typically, but not always, comprise a replication system (i.e. vector) recognized by the host, including the intended polynucleotide fragment encoding the desired polypeptide, and can, but not necessarily, also include transcription and translational initiation regulatory sequences operably linked to the polypeptide-encoding segment. Expression systems (such as expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides can also be included where appropriate, for example, from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y., 1995).

The manipulation of polynucleotides that encode the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector can be selected to accommodate a polynucleotide encoding a protein of a desired size. Following recombinant modification of a selected vector, a suitable host cell (e.g., the microorganisms described herein) is transfected or transformed with the vector. Each vector contains various functional components, which generally include a cloning site, an origin of replication and at least one selectable marker gene. A vector can additionally possess one or more of the following elements: an enhancer, promoter, and transcription termination and/or other signal sequences. Such sequence elements can be optimized for the selected host species. Such sequence elements can be positioned in the vicinity of the cloning site, such that they are operatively linked to the gene encoding a preselected enzyme.

Vectors, including cloning and expression vectors, can contain nucleic acid sequences that enable the vector to replicate in one or more selected microorganisms. For example, the sequence can be one that enables the vector to replicate independently of the host chromosomal DNA and can include origins of replication or autonomously replicating sequences. Such sequences are known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV40, adenovirus) are useful for cloning vectors.

A cloning or expression vector can contain a selection gene (also referred to as a selectable marker). This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors can be performed in *E. coli*. An *E. coli*-selectable marker, for example, the β-lactamase gene that confers resistance to the antibiotic ampicillin, can be of use. These selectable markers can be obtained from *E. coli* plasmids, such as pBR322 or a pUC plasmid such as pUC18 or pUC19, or pUC119.

Promoters

Vectors can contain a promoter that is recognized by the host microorganism. The promoter can be operably linked to a coding sequence of interest. Such a promoter can be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters. For example, the inducible or repressible promoters that can be used include but are not limited to: (a) sugars such as arabinose and lactose (or non metabolizable analogs, e.g., isopropyl β-D-1-thiogalactopyranoside (IPTG)); (b) metals such as lanthanum, copper, and calcium; (c) temperature; (d) nitrogen-source; (e) oxygen; (f) cell state (growth or stationary); (g) micronutrients such as phosphate, magnesium, and sulfur; (h) CRISPRi; (i) jun; (j) fos; (k) metallothionein and/or (l) heat shock. These promoters can be used in a methanotroph systems. For example, examples of a promoter that can be used within the methanotrophs are a pBAD promoter, a pMxaF promoter, and/or a pTrc promoter.

Constitutively expressed promoters can also be used in the vector systems herein. For example, the promoters that can be used include but are not limited to p.Bba.J23111, p.Bba.J23115, p.Bba.J61111, p.Bba.J61103, p.Bba.J61104, p.Bba.J61105, p.Bba.J61102, p.Bba.J61106, p.Bba.J61107, p.Bba.J61116, p.Bba.J61113, p.Bba.J61101, p.Bba.J61109, p.Bba.J61100, p.Bba.J61114, p.Bba.J61108, p.Bba.J61115, p.Bba.J61110, p.Bba.J61112, uMc.GlgC, uMc_IlvC, uGTW0001, uMc.IlvD, uMCA0996, uMc.IlvK, uMc.pmoB, iIlvE, uMc.IlvC, RL122pM, uMc.MCA, or uMc.GrosES promoters. Other promoters that can be used include but are not limited to pXoxF, pMxaF, pTRC, J12100, J23102, pBAD, J23110, lacO, J23116, J23106, J23105, J23108, J23107, J23115, J23114, J23118, J23104, J23101, J23119, and uMCA3034.

Promoters suitable for use with prokaryotic hosts can include, for example, the a-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter can be employed to provide for high level transcription and expression of the desired product.

One or more promoters of a transcription unit can be an inducible promoter. For example, a green fluorescent protein (GFP) can be expressed from a constitutive promoter while an inducible promoter drives transcription of a gene coding for one or more enzymes as disclosed herein and/or the amplifiable selectable marker.

Some vectors can contain prokaryotic sequences that facilitate the propagation of the vector in bacteria. Thus, the vectors can have other components such as an origin of replication (e.g., a nucleic acid sequence that enables the vector to replicate in one or more selected microorganisms), antibiotic resistance genes for selection in bacteria, and/or an amber stop codon which can permit translation to read through the codon. Additional selectable gene(s) can also be incorporated. Generally, in cloning vectors the origin of replication is one that enables the vector to replicate independently of the host chromosomal DNA, and includes origins of replication or autonomously replicating sequences. Such sequences can include the ColE1 origin of replication in bacteria or other known sequences.

Rare Earth Metal Molecular Switches

In some cases, the gene expression during the fermentation of high value chemicals (such as those described throughout e.g., isobutyraldehyde and isobutanol), requires precise control/timing of gene expression. In these cases, a molecular switch can be used. Switches that are particularly useful can be a rare earth metal switch. For example, a rare earth metal can be used to control gene expression, including but not limited to cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof. Any of the genes disclosed throughout or any combination thereof, can be controlled by a rare earth metal switch.

Lanthanum

In cases where a switch is used, the media can comprise a molecule that induces or represses the switch. For example, when a lanthanum sensitive switch is used to repress the expression of one or more of the genes described herein, the media can comprise lanthanum, which will repress expression of the one or more genes under the control of the switch. In the case of a lanthanum switch any one of the following concentrations can be used to effectively repress expression of the one or more genes that are under the control of a lanthanum switch: 0.1 µM; 0.5 µM; 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 50 µM; 100 µM or more.

In some cases, the lanthanum in the media can be diluted to turn on expression of the one or more lanthanum repressed genes. For example, in some cases, the dilution of lanthanum containing media can be 1:1 (1 part lanthanum containing media to 1 part non-lanthanum containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

In some cases, the microorganism can be grown in media comprising lanthanum. The media can then be diluted to effectively turn on the expression of the lanthanum repressed genes. The microorganism can be then grown to produce desired products, such as the multicarbon products (or others disclosed throughout).

Cerium, Praseodymium and Neodymium

In certain cases, a cerium, praseodymium, and/or neodymium sensitive switch can be used to repress or induce the expression of one or more of the genes described herein. In some cases, the media can comprise cerium, praseodymium, and/or neodymium, which can in some instances repress expression of the one or more genes under the control of the switch. In the case of cerium, praseodymium, and/or neodymium any one of the following concentrations can effectively repress expression of the one or more genes under the control of the cerium, praseodymium, and/or neodymium switch: 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 30 µM; 35 µM; 40 µM; 45 µM; 50 µM; 55 µM; 60 µM; 65 µM; 70 µM; 75 µM; 80 µM; 85 µM; 90 µM; 95 µM; 100 µM; 105 µM; 110 µM; 115 µM; 120 µM; 125 µM; 130 µM; 135 µM; 140 µM; 145 µM; 150 µM; 155 µM; 160 µM; 165 µM; 170 µM; 175 µM; 180 µM; 185 µM; 190 µM; 195 µM; 200 µM or more.

In some cases, the cerium, praseodymium, and/or neodymium in the media can be diluted to turn on expression of the one or more cerium, praseodymium, and/or neodymium repressed genes. For example, in some cases, the dilution of cerium, praseodymium, and/or neodymium containing media can be 1:1 (1 part cerium, praseodymium, and/or neodymium containing media to 1 part non-cerium, praseodymium, and/or neodymium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

In some cases, the microorganism can be grown in media comprising cerium, praseodymium, and/or neodymium. The media can then be diluted to effectively turn on the expression of the cerium, praseodymium, and/or neodymium repressed genes. The microorganism can be then grown to produce desired products, such as the multicarbon products (or others disclosed throughout).

Scandium, Yttrium, Samrium, Europium, Gadolinium, Terbium, Dysprosium, Holmium, Erbium, Thulium, and Yterribium In certain cases, a Scandium, Yttrium, Samrium, Europium, Gadolinium, Terbium, Dysprosium, Holmium, Erbium, Thulium, and/or Yterribium switch can be used to repress or induce the expression of one or more of the genes described herein. In some cases, the media can comprise Scandium, Yttrium, Samrium, Europium, Gadolinium, Terbium, Dysprosium, Holmium, Erbium, Thulium, and/or Yterribium, which will repress or induce expression of the one or more genes under the control of the switch. In the case of Scandium, Yttrium, Samrium, Europium, Gadolinium, Terbium, Dysprosium, Holmium, Erbium, Thulium, and/or Yterribium any one of the following concentrations can effectively repress expression of the one or more genes the switch: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more.

In some cases, the Scandium, Yttrium, Samrium, Europium, Gadolinium, Terbium, Dysprosium, Holmium, Erbium, Thulium, and/or Yterribium in the media can be diluted to reverse the effect of Scandium, Yttrium, Samrium, Europium, Gadolinium, Terbium, Dysprosium, Holmium, Erbium, Thulium, and/or Yterribium. For example, in some cases, the dilution of Scandium, Yttrium, Samrium, Europium, Gadolinium, Terbium, Dysprosium, Holmium, Erbium, Thulium, and/or Yterribium containing media can be 1:1 (1 part Scandium, Yttrium, Samrium, Europium, Gadolinium, Terbium, Dysprosium, Holmium, Erbium, Thulium, and/or Yterribium containing media to 1 part non-Scandium, Yttrium, Samrium, Europium, Gadolinium, Terbium, Dysprosium, Holmium, Erbium, Thulium, and/or Yterribium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

After dilution, the microorganism can be then grown to produce desired products, such as the multicarbon products (or others disclosed throughout).

Other Switches

Arabinose

In some cases, an arabinose switch can be used to induce/repress the expression of one or more of the genes described herein. In these cases, the media can comprise arabinose, which will in some cases, induce the expression of the one or more genes under the control of the switch. In the case of arabinose any one of the following concentrations can effectively induce/repress expression of the one or more genes: 0.1 g/L; 0.5 g/L; 1 g/L; 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; g/L; 20 g/L; 25 g/L; 30 g/L; 35 g/L; 40 g/L; 45 g/L; 50 g/L; 55 g/L; 60 g/L; 65 g/L; 70 g/L; 75 g/L; 80 g/L; 85 g/L; 90 g/L; 95 g/L; 100 g/L or more.

In some cases, any one of the following concentrations of arabinose can effectively induce/repress gene expression of the one or more genes controlled by an arabinose switch: 0.1 mM; 0.2 mM; 0.3 mM; 0.4 mM; 0.5 mM; 0.6 mM; 0.7 mM; 0.8 mM; 0.9 mM; 1 mM; 1.5 mM; 2 mM; 2.5 mM; 3 mM; 3.5 mM; 4 mM; 4.5 mM; 5 mM; 5.5 mM; 6 mM; 6.6 mM; 7 mM; 7.5 mM; 8 mM; 8.5 mM; 9 mM; 9.5 mM; 10 mM; 12.5 mM; 15 mM; 17.5 mM; 20 mM; 25 mM; 50 mM; 100 mM or more.

In some cases, the arabinose in the media can be diluted to turn on/off the expression of the one or more arabinose repressed/induced genes. For example, in some cases, the dilution of arabinose containing media can be 1:1 (1 part arabinose containing media to 1 part non-arabinose containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

isopropyl β-D-1-thiogalactopyranoside

In certain cases, an IPTG sensitive switch can be used to induce or repress the expression of one or more of the genes described herein. In some cases, the media can comprise IPTG, which can in some instances induce expression of the one or more genes under the control of the switch. In the case of IPTG any one of the following concentrations can effectively induce or repress expression of the one or more genes: 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 30 µM; 35 µM; 40 µM; 45 µM; 50 µM; 55 µM; 60 µM; 65 µM; 70 µM; 75 µM; 80 µM; 85 µM; 90 µM; 95 µM; 100 µM; 105 µM; 110 µM; 115 µM; 120 µM; 125 µM; 130 µM; 135 µM; 140 µM; 145 µM; 150 µM; 155 µM; 160 µM; 165 µM; 170 µM; 175 µM; 180 µM; 185 µM; 190 µM; 195 µM; 200 µM or more.

In some cases, the IPTG in the media can be diluted to turn on or off expression of the one or more IPTG induced or repressed genes. For example, in some cases, the dilution of IPTG containing media can be 1:1 (1 part IPTG containing media to 1 part non-IPTG containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000.

In some cases, the microorganism can be grown in media comprising IPTG. IPTG can be added to the media to turn on the expression of IPTG induced genes. The microorganism can be then grown to produce desired products, such as the multicarbon products (or others disclosed throughout). The media can then be diluted to effectively turn off the expression of the IPTG induced genes.

Genes

The vectors described throughout can comprise a nucleic acid sequence of one or more of the following genes: (i) acetolactate synthase; (ii) ketol-acid reductoisomerase; (iii) dihydroxy-acid dehydratase; and/or (iv) 2-keto acid decarboxylase. In the case of alcohol production, the vector can also contain a nucleic acid sequence of an (v) alcohol dehydrogenase. For example, the vector can comprise an acetolactate synthase gene. The vector can comprise a ketol-acid reductoisomerase gene. The vector can comprise a dihydroxy-acid dehydratase gene. The vector can comprise an 2-keto acid decarboxylase gene. The vector can comprise an alcohol dehydrogenase gene. These genes can be heterologous to the microorganism in which the vector is contacted with (and eventually transformed with).

In some instances, the vector can comprise two or more of the following genes: (i) acetolactate synthase; (ii) ketol-acid reductoisomerase; (iii) dihydroxy-acid dehydratase; (iv) 2-keto acid decarboxylase; and/or (v) alcohol dehydrogenase. In one situation, the vector can comprise at least three or more of the genes. In another case, the vector can comprise at least four or more of the genes. In another instance, the vector can comprise all five of the genes. The vector with all five genes in most cases, will be used for alcohol (e.g., isobutanol) producing strains, unless the alcohol dehydrogenase gene is non-functional at the genetic or protein level. One or more of the genes can be heterologous to the microorganism in which the vector is contacted with (and eventually transformed with).

In some cases, when an acetolactate synthase is desired, the acetolactate synthase gene can be from a bacteria (e.g., a gram positive bacterium), such as from the genus *Bacillus*, or the species *Bacillus subtilis*.

The acetolactate synthase gene can comprise a nucleotide sequence that is substantially similar to SEQ ID NO: 1 or 100. For example, the acetolactate synthase gene can comprise a nucleotide sequence that is at least 60% identical to SEQ ID NO: 1 or 100. In some cases, the acetolactate synthase gene can comprise a nucleotide sequence that is at least 65% identical to SEQ ID NO: 1 or 100. In some cases, the acetolactate synthase gene can comprise a nucleotide sequence that is at least 70% identical to SEQ ID NO: 1 or 100. In some cases, the acetolactate synthase gene can comprise a nucleotide sequence that is at least 75% identical to SEQ ID NO: 1 or 100. In some cases, the acetolactate synthase gene can comprise a nucleotide sequence that is at least 80% identical to SEQ ID NO: 1 or 100. In some cases, the acetolactate synthase gene can comprise a nucleotide sequence that is at least 85% identical to SEQ ID NO: 1 or 100. In some cases, the acetolactate synthase gene can comprise a nucleotide sequence that is at least 90% identical to SEQ ID NO: 1 or 100. In some cases, the acetolactate synthase gene can comprise a nucleotide sequence that is at least 91% identical to SEQ ID NO: 1 or 100. In some cases, the acetolactate synthase gene can comprise a nucleotide sequence that is at least 92% identical to SEQ ID NO: 1 or 100. In some cases, the acetolactate synthase gene can comprise a nucleotide sequence that is at least 93% identical to SEQ ID NO: 1 or 100. In some cases, the acetolactate synthase gene can comprise a nucleotide sequence that is at least 94% identical to SEQ ID NO: 1 or 100. In some cases, the acetolactate synthase gene can comprise a nucleotide sequence that is at least 95% identical to SEQ ID NO: 1 or 100. In some cases, the acetolactate synthase gene can comprise a nucleotide sequence that is at least 96% identical to SEQ ID NO: 1 or 100. In some cases, the acetolactate synthase gene can comprise a nucleotide sequence that is at least 97% identical to SEQ ID NO: 1 or 100. In some cases, the acetolactate synthase gene can comprise a nucleotide sequence that is at least 98% identical to SEQ ID NO: 1 or 100. In some cases, the acetolactate synthase gene can comprise a nucleotide sequence that is at least 99% identical to SEQ ID NO: 1 or 100. In some cases, the acetolactate synthase gene can comprise a nucleotide sequence that is SEQ ID NO: 1 or 100.

When a ketol-acid reductoisomerase is desired, the ketol-acid reductoisomerase gene can be from a bacteria (e.g., a gram negative bacterium), such as from the genus *Escherichia*, or from the species *Escherichia coli*.

The ketol-acid reductoisomerase gene can comprise a nucleotide sequence that is substantially similar to SEQ ID NO: 3. For example, the ketol-acid reductoisomerase gene can comprise a nucleotide sequence that is at least 60% identical to SEQ ID NO: 3. In some cases, the ketol-acid reductoisomerase gene can comprise a nucleotide sequence that is at least 65% identical to SEQ ID NO: 3. In some cases, the ketol-acid reductoisomerase gene can comprise a nucleotide sequence that is at least 70% identical to SEQ ID NO: 3. In some cases, the ketol-acid reductoisomerase gene can comprise a nucleotide sequence that is at least 75% identical to SEQ ID NO: 3. In some cases, the ketol-acid reductoisomerase gene can comprise a nucleotide sequence that is at least 80% identical to SEQ ID NO: 3. In some cases, the ketol-acid reductoisomerase gene can comprise a nucleotide sequence that is at least 85% identical to SEQ ID NO: 3. In some cases, the ketol-acid reductoisomerase gene can comprise a nucleotide sequence that is at least 90% identical to SEQ ID NO: 3. In some cases, the ketol-acid reductoisomerase gene can comprise a nucleotide sequence that is at least 91% identical to SEQ ID NO: 3. In some cases, the ketol-acid reductoisomerase gene can comprise a nucleotide sequence that is at least 92% identical to SEQ ID NO: 3. In some cases, the ketol-acid reductoisomerase gene can comprise a nucleotide sequence that is at least 93% identical to SEQ ID NO: 3. In some cases, the ketol-acid reductoisomerase gene can comprise a nucleotide sequence that is at least 94% identical to SEQ ID NO: 3. In some cases, the ketol-acid reductoisomerase gene can comprise a nucleotide sequence that is at least 95% identical to SEQ ID NO: 3. In some cases, the ketol-acid reductoisomerase gene can comprise a nucleotide sequence that is at least 96% identical to SEQ ID NO: 3. In some cases, the ketol-acid reductoisomerase gene can comprise a nucleotide sequence that is at least 97% identical to SEQ ID NO: 3. In some cases, the ketol-acid reductoisomerase gene can comprise a nucleotide sequence that is at least 98% identical to SEQ ID NO: 3. In some cases, the ketol-acid reductoisomerase gene can comprise a nucleotide sequence that is at least 99% identical to SEQ ID NO: 3. In some cases, the ketol-acid reductoisomerase gene can comprise a nucleotide sequence that is SEQ ID NO: 3.

When a dihydroxy-acid dehydratase is desired, the dihydroxy-acid dehydratase gene can be a gene from a bacterium (e.g., a gram negative bacterium) or a methanotroph, such as from the genus *Escherichia* and/or *Methylococcus*, or from the species *Escherichia coli* and/or *Methylococcus capsulatus*.

The dihydroxy-acid dehydratase gene can comprise a nucleotide sequence that is substantially similar to SEQ ID NO: 5 or 7. For example, the dihydroxy-acid dehydratase gene can comprise a nucleotide sequence that is at least 60% identical to SEQ ID NO: 5 or 7. In some cases, the dihydroxy-acid dehydratase gene can comprise a nucleotide sequence that is at least 65% identical to SEQ ID NO: 5 or 7. In some cases, the dihydroxy-acid dehydratase gene can comprise a nucleotide sequence that is at least 70% identical to SEQ ID NO: 5 or 7. In some cases, the dihydroxy-acid dehydratase gene can comprise a nucleotide sequence that is at least 75% identical to SEQ ID NO: 5 or 7. In some cases, the dihydroxy-acid dehydratase gene can comprise a nucleotide sequence that is at least 80% identical to SEQ ID NO: 5 or 7. In some cases, the dihydroxy-acid dehydratase gene can comprise a nucleotide sequence that is at least 85% identical to SEQ ID NO: 5 or 7. In some cases, the dihydroxy-acid dehydratase gene can comprise a nucleotide sequence that is at least 90% identical to SEQ ID NO: 5 or 7. In some cases, the dihydroxy-acid dehydratase gene can comprise a nucleotide sequence that is at least 91% identical to SEQ ID NO: 5 or 7. In some cases, the dihydroxy-acid dehydratase gene can comprise a nucleotide sequence that is at least 92% identical to SEQ ID NO: 5 or 7. In some cases, the dihydroxy-acid dehydratase gene can comprise a nucleotide sequence that is at least 93% identical to SEQ ID NO: 5 or 7. In some cases, the dihydroxy-acid dehydratase gene can comprise a nucleotide sequence that is at least 94% identical to SEQ ID NO: 5 or 7. In some cases, the dihydroxy-acid dehydratase gene can comprise a nucleotide sequence that is at least 95% identical to SEQ ID NO: 5 or 7. In some cases, the dihydroxy-acid dehydratase gene can comprise a nucleotide sequence that is at least 96% identical to SEQ ID NO: 5 or 7. In some cases, the dihydroxy-acid dehydratase gene can comprise a nucleotide sequence that is at least 97% identical to SEQ ID NO: 5 or 7. In some cases, the dihydroxy-acid dehydratase gene can comprise a nucleotide sequence that is at least 98% identical to SEQ ID NO: 5 or 7. In some cases, the dihydroxy-acid dehydratase gene can comprise a nucleotide sequence that is at least 99% identical to SEQ ID NO: 5 or 7. In some cases, the dihydroxy-acid dehydratase gene can comprise a nucleotide sequence that is SEQ ID NO: 5 or 7.

When a 2-keto acid decarboxylase (KDC) gene is desired, the KDC can be a gene from a bacterium (e.g., a gram positive bacterium) or a methanotroph, such as from the genus *Carnobacterium* and/or *Methylococcus*, or from the species *Carnobacterium divergens* and/or *Methylococcus capsulatus*.

The KDC gene can be from other bacterium, such as those listed in Table 4. For example, the KDC gene can be from the genus Methylocaldum, Methylosarcina, *Methylomonas, Methylohalobius, Methylobacter, Lamprocystis, Andreprevotia, Lactococcus, Streptococcus, Enterococcus, Brochothrix, Carnobacterium, Helicobacter, Staphylococcus*, and/or *Fictibacillus*. For example, KDCs from the following species can be particularly useful: *Methylocaldum szegediense, Methylosarcina lacus, Methylomonas denitrificans, Methylomonas methanica, Methylohalobius crimeensis, Methylobacter marinus, Methylobacter luteus, Lamprocystis purpurea, Andreprevotia chitinilytica, Lactococcus lactis, Streptococcus didelphis, Enterococcus caccae, Enterococcus haemoperoxidus, Enterococcus moraviensis, Carnobacterium maltaromaticum, Brochothrix thermosphacta, Carnobacterium gallinarum, Carnobacterium divergens, Helicobacter bizzozeronii, Staphylococcus aureus* subsp. *aureus* CIG290, and/or *Fictibacillus macauensis*.

The 2-keto acid decarboxylase gene can comprise a nucleotide sequence that is substantially similar to any one of SEQ ID NOs: 9, 11, 56, 58, 60, 62, 64, 66, 68, 70, 72, 74, 76, 78, 80, 82, 84, 86, 88, 90, 92, 94, 96, or 98. For example, the 2-keto acid decarboxylase gene can comprise a nucleotide sequence that is at least 60% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 65% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 70% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 75% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 80% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 85% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 90% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 91% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 92% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 93% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 94% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 95% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 96% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 97% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 98% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is at least 99% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the 2-keto acid decarboxylase gene can comprise a nucleotide sequence that is any one of SEQ ID NOs: 9, 11, 56, 58, 60, 62, 64, 66, 68, 70, 72, 74, 76, 78, 80, 82, 84, 86, 88, 90, 92, 94, 96, or 98.

In some cases, two or more KDC genes can be used. In some cases, two KDC genes can be used to increase the production of aldehydes, such as isobutyraldehyde, and/or alcohols, such as isobutanol. In other cases, three KDC genes can be used to increase the production of isobutyraldehyde and/or isobutanol. In some cases, four, five, or six KDC genes can be used to increase the production of isobutyraldehyde and/or isobutanol.

When an alcohol dehydrogenase is desired, the alcohol dehydrogenase gene can be from a bacterium (e.g., a gram negative or gram positive bacterium) or a yeast, such as from the genus *Escherichia* or *Saccharomyces*, or from the species *Escherichia coli* or *Saccharomyces cerevisiae*.

Other ADH genes that can be used can be from the genus *Clostridium*, *Geobacillus*, *Lactococcus*, *Oenococcus*, *Pectobacterium*, and/or *Psychrobacter*. For example, ADH genes from the following species can be particularly useful: *Clostridium acetobutylicum*, *Geobacillus stearothermophilus*, *Geobacillus thermoglucosidas*, *Lactococcus lactis*, *Oenococcus oeni*, *Pectohacterium atrosepticum*, and/or *Psychrobacter cryohalolentis*.

The alcohol dehydrogenase gene can comprise a nucleotide sequence that is substantially similar to any one of SEQ ID NOs: 13, 15, 17, 24, 26, 28, 30, 32, 34, 36, 38, 40, 42, 44, 46, 48, 50, 52, or 54. For example, the alcohol dehydrogenase gene can comprise a nucleotide sequence that is at least 60% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 65% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 70% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 75% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 80% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 85% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 90% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 91% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 92% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 93% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 94% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 95% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 96% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 97% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 98% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is at least 99% identical to any one of SEQ ID NOs: 13, 15, 17, 24, 26, 28, 30, 32, 34, 36, 38, 40, 42, 44, 46, 48, 50, 52, or 54. In some cases, the alcohol dehydrogenase gene can comprise a nucleotide sequence that is any one of SEQ ID NOs: 13, 15, 17, 24, 26, 28, 30, 32, 34, 36, 38, 40, 42, 44, 46, 48, 50, 52, or 54.

In some cases, two or more ADH genes can be used. In some cases, two ADH genes can be used to increase the production of alcohols, such as isobutanol. In other cases, three ADH genes can be used to increase the production of isobutanol. In some cases, four, five, or six ADH genes can be used to increase the production of isobutanol.

Additional genes can be placed inside the microorganism in order to make other desired end products by fermentation.

For example, a sugar permease gene can be place within the microorganism in order to increase production of the desired end product, such as an aldehyde, e.g., isobutyraldehyde, or an alcohol, e.g., isobutanol. In some cases, the sugar permease gene can be from a bacterium (e.g., a gram negative bacterium) such as from the genus *Escherichia*. More specifically, the sugar permease can be from the species *Escherichia coli*.

The sugar permease gene can comprise a nucleotide sequence that is substantially similar to SEQ ID NO: 19. For example, the sugar permease gene can comprise a nucleotide sequence that is at least 60% identical to SEQ ID NO: 19. In some cases, the sugar permease gene can comprise a nucleotide sequence that is at least 65% identical to SEQ ID NO: 19. In some cases, the sugar permease gene can comprise a nucleotide sequence that is at least 70% identical to SEQ ID NO: 19. In some cases, the sugar permease gene can comprise a nucleotide sequence that is at least 75% identical to SEQ ID NO: 19. In some cases, the sugar permease gene can comprise a nucleotide sequence that is at least 80% identical to SEQ ID NO: 19. In some cases, the sugar permease gene can comprise a nucleotide sequence that is at least 85% identical to SEQ ID NO: 19. In some cases, the sugar permease gene can comprise a nucleotide sequence that is at least 90% identical to SEQ ID NO: 19. In some cases, the sugar permease gene can comprise a nucleotide sequence that is at least 91% identical to SEQ ID NO: 19. In some cases, the sugar permease gene can comprise a nucleotide sequence that is at least 92% identical to SEQ ID NO: 19. In some cases, the sugar permease gene can comprise a nucleotide sequence that is at least 93% identical to SEQ ID NO: 19. In some cases, the sugar permease gene can comprise a nucleotide sequence that is at least 94% identical to SEQ ID NO: 19. In some cases, the sugar permease gene can comprise a nucleotide sequence that is at least 95% identical to SEQ ID NO: 19. In some cases, the sugar permease gene can comprise a nucleotide sequence that is at least 96% identical to SEQ ID NO: 19. In some cases, the sugar permease gene can comprise a nucleotide sequence that is at least 97% identical to SEQ ID NO: 19. In some cases, the sugar permease gene can comprise a nucleotide sequence that is at least 98% identical to SEQ ID NO: 19. In some cases, the sugar permease gene can comprise a nucleotide sequence that is at least 99% identical to SEQ ID NO: 19. In some cases, the sugar permease gene can comprise a nucleotide sequence that is SEQ ID NO: 19.

Another enzyme that can be place within the microorganism in order to increase production of the desired end product, such as an aldehyde, e.g., isobutyraldehyde, or an alcohol, e.g., isobutanol, is an arabinose operon regulatory protein (AraC). In some cases, the arabinose operon regulatory protein gene can be from a bacterium (e.g., a gram negative bacterium) such as from the genus *Escherichia*. More specifically, the arabinose operon regulatory protein gene can be from the species *Escherichia coli*.

The arabinose operon regulatory protein gene can comprise a nucleotide sequence that is substantially similar to SEQ ID NO: 21. For example, the arabinose operon regulatory protein gene can comprise a nucleotide sequence that is at least 60% identical to SEQ ID NO: 21. In some cases, the arabinose operon regulatory protein gene can comprise a nucleotide sequence that is at least 65% identical to SEQ ID NO: 21. In some cases, the arabinose operon regulatory protein gene can comprise a nucleotide sequence that is at least 70% identical to SEQ ID NO: 21. In some cases, the arabinose operon regulatory protein gene can comprise a nucleotide sequence that is at least 75% identical to SEQ ID NO: 21. In some cases, the arabinose operon regulatory protein gene can comprise a nucleotide sequence that is at least 80% identical to SEQ ID NO: 21. In some cases, the arabinose operon regulatory protein gene can comprise a nucleotide sequence that is at least 85% identical to SEQ ID NO: 21. In some cases, the arabinose operon regulatory protein gene can comprise a nucleotide sequence that is at least 90% identical to SEQ ID NO: 21. In some cases, the arabinose operon regulatory protein gene can comprise a nucleotide sequence that is at least 91% identical to SEQ ID NO: 21. In some cases, the arabinose operon regulatory protein gene can comprise a nucleotide sequence that is at least 92% identical to SEQ ID NO: 21. In some cases, the arabinose operon regulatory protein gene can comprise a nucleotide sequence that is at least 93% identical to SEQ ID NO: 21. In some cases, the arabinose operon regulatory protein gene can comprise a nucleotide sequence that is at least 94% identical to SEQ ID NO: 21. In some cases, the arabinose operon regulatory protein gene can comprise a nucleotide sequence that is at least 95% identical to SEQ ID NO: 21. In some cases, the arabinose operon regulatory protein gene can comprise a nucleotide sequence that is at least 96% identical to SEQ ID NO: 21. In some cases, the arabinose operon regulatory protein gene can comprise a nucleotide sequence that is at least 97% identical to SEQ ID NO: 21. In some cases, the arabinose operon regulatory protein gene can comprise a nucleotide sequence that is at least 98% identical to SEQ ID NO: 21. In some cases, the arabinose operon regulatory protein gene can comprise a nucleotide sequence that is at least 99% identical to SEQ ID NO: 21. In some cases, the arabinose operon regulatory protein gene can comprise a nucleotide sequence that is SEQ ID NO: 21.

The amino acid sequences can also be optimized based on the microorganism in which the enzymes will be expressed. In other words, conservative amino acids substitutions can be made based on whether the respective microorganism typically uses a specific amino acid or how much of that particular amino acid is available for use within the microorganism.

The nucleotide sequence (or more specifically the codons that are encoded by the nucleotide sequences) can be optimized based on the microorganism in which the nucleotide sequences will be expressed. The nucleotide sequences can be codon optimized based on the amount of tRNA available within each individual microorganism. In other words, conservative codon substitutions can be made based on whether the respective microorganism typically uses a specific codon or how much of a particular tRNA is available within the microorganism.

In some instances, there can be more than one copy of one of the genes described throughout, for example, one or more copy of the following genes: (i) acetolactate synthase; (ii) ketol-acid reductoisomerase; (iii) dihydroxy-acid dehydratase; (iv) 2-keto acid decarboxylase; (v) alcohol dehydrogenase; (vi) sugar permease (LacY); and/or (vii) arabinose operon regulatory protein (AraC). These copies of the genes can come from a single organism, e.g., an *E. coli*, or from multiple organisms, e.g., one copy from an *E. coli* and one copy from *S. cerevisiae*, etc.

Isolated Nucleic Acids

The genes described herein can be in the form of an isolated polynucleic acid. In other words, the genes can be in forms that do not exist in nature, isolated from a chromosome or other endogenous structure. The isolated polynucleic acids can comprise a nucleic acid sequence of one or more of the following genes: (i) acetolactate synthase; (ii) ketol-acid reductoisomerase; (iii) dihydroxy-acid dehydratase; (iv) 2-keto acid decarboxylase; (v) alcohol dehydrogenase; (vi) sugar permease; and/or (vii) arabinose operon regulatory protein. For example, the isolated polynucleic acid can comprise an acetolactate synthase gene. The isolated polynucleic acid can comprise a ketol-acid reductoisomerase gene. The isolated polynucleic acid can comprise a dihydroxy-acid dehydratase gene. The isolated polynucleic acid can comprise a 2-keto acid decarboxylase gene. The isolated polynucleic acid can comprise an alcohol dehydrogenase gene. The isolated polynucleic acid can comprise a sugar permease gene. The isolated polynucleic acid can comprise an arabinose operon regulatory protein gene.

In some cases, the isolated polynucleic acid can encode for an acetolactate synthase. For example, the isolated polynucleic acid can comprise a nucleotide sequence that is substantially similar to SEQ ID NO: 1 or 100. In some cases, the isolated polynucleic acid can comprise a nucleotide sequence that is at least 60% identical to SEQ ID NO: 1 or 100. In some cases, the isolated polynucleic acid can comprise a nucleotide sequence that is at least 65% identical to SEQ ID NO: 1 or 100. In some cases, the isolated polynucleic acid can comprise a nucleotide sequence that is at least 70% identical to SEQ ID NO: 1 or 100. In some cases, the isolated polynucleic acid can comprise a nucleotide sequence that is at least 75% identical to SEQ ID NO: 1 or 100. In some cases, the isolated polynucleic acid can comprise a nucleotide sequence that is at least 80% identical to SEQ ID NO: 1 or 100. In some cases, the isolated polynucleic acid can comprise a nucleotide sequence that is at least 81% identical to SEQ ID NO: 1 or 100. In some cases, the isolated polynucleic acid can comprise a nucleotide sequence that is at least 82% identical to SEQ ID NO: 1 or 100. In some cases, the isolated polynucleic acid can comprise a nucleotide sequence that is at least 83% identical to SEQ ID NO: 1 or 100. In some cases, the isolated polynucleic acid can comprise a nucleotide sequence that is at least 84% identical to SEQ ID NO: 1 or 100. In some cases, the isolated polynucleic acid can comprise a nucleotide sequence that is at least 85% identical to SEQ ID NO: 1 or 100. In some cases, the isolated polynucleic acid can comprise a nucleotide sequence that is at least 86% identical to SEQ ID NO: 1 or 100. In some cases, the isolated polynucleic acid can comprise a nucleotide sequence that is at least 87% identical to SEQ ID NO: 1 or 100. In some cases, the isolated polynucleic acid can comprise a nucleotide sequence that is at least 88% identical to SEQ ID NO: 1 or 100. In some cases, the isolated polynucleic acid can comprise a nucleotide sequence that is at least 89% identical to SEQ ID NO: 1 or 100. In some cases, the isolated polynucleic acid can comprise a nucleotide sequence that is at least 90% identical to SEQ ID NO: 1 or 100. In some cases, the isolated polynucleic acid can comprise a nucleotide sequence that is at least 91% identical to SEQ ID NO: 1 or 100. In some cases, the isolated polynucleic acid can comprise a nucleotide sequence that is at least 92% identical to SEQ ID NO: 1 or 100. In some cases, the isolated polynucleic acid can comprise a nucleotide sequence that is at least 93% identical to SEQ ID NO: 1 or 100. In some cases, the isolated polynucleic acid can comprise a nucleotide sequence that is at least 94% identical to SEQ ID NO: 1 or 100. In some cases, the isolated polynucleic acid can comprise a nucleotide sequence that is at least 95% identical to SEQ ID NO: 1 or 100. In some cases, the isolated polynucleic acid can comprise a nucleotide sequence that is at least 96% identical to SEQ ID NO: 1 or 100. In some cases, the isolated polynucleic acid can comprise a nucleotide sequence that is at least 97% identical to SEQ ID NO: 1 or 100. In some cases, the isolated polynucleic acid can comprise a nucleotide sequence that is at least 98% identical to SEQ ID NO: 1 or 100. In some cases, the isolated polynucleic acid can comprise a nucleotide sequence that is at least 99% identical to SEQ ID NO: 1 or 100. In some cases, the isolated polynucleic acid can comprise a nucleotide sequence that is SEQ ID NO: 1 or 100.

In some cases, the isolated polynucleic acid can encode for a ketol-acid reductoisomerase. For example, the isolated polynucleic acid can comprise a nucleotide sequence that is substantially similar to SEQ ID NO: 3. In some cases, the isolated polynucleic acid can comprise a nucleotide sequence that is at least 60% identical to SEQ ID NO: 3. In some cases, the isolated polynucleic acid can comprise a nucleotide sequence that is at least 65% identical to SEQ ID NO: 3. In some cases, the isolated polynucleic acid can comprise a nucleotide sequence that is at least 70% identical to SEQ ID NO: 3. In some cases, the isolated polynucleic acid can comprise a nucleotide sequence that is at least 75% identical to SEQ ID NO: 3. In some cases, the isolated polynucleic acid can comprise a nucleotide sequence that is at least 80% identical to SEQ ID NO: 3. In some cases, the isolated polynucleic acid can comprise a nucleotide sequence that is at least 81% identical to SEQ ID NO: 3. In some cases, the isolated polynucleic acid can comprise a nucleotide sequence that is at least 82% identical to SEQ ID NO: 3. In some cases, the isolated polynucleic acid can comprise a nucleotide sequence that is at least 83% identical to SEQ ID NO: 3. In some cases, the isolated polynucleic acid can comprise a nucleotide sequence that is at least 84% identical to SEQ ID NO: 3. In some cases, the isolated polynucleic acid can comprise a nucleotide sequence that is at least 85% identical to SEQ ID NO: 3. In some cases, the isolated polynucleic acid can comprise a nucleotide sequence that is at least 86% identical to SEQ ID NO: 3. In some cases, the isolated polynucleic acid can comprise a nucleotide sequence that is at least 87% identical to SEQ ID NO: 3. In some cases, the isolated polynucleic acid can comprise a nucleotide sequence that is at least 88% identical to SEQ ID NO: 3. In some cases, the isolated polynucleic acid can comprise a nucleotide sequence that is at least 89% identical to SEQ ID NO: 3. In some cases, the isolated polynucleic acid can comprise a nucleotide sequence that is at least 90% identical to SEQ ID NO: 3. In some cases, the isolated polynucleic acid can comprise a nucleotide sequence that is at least 91% identical to SEQ ID NO: 3. In some cases, the isolated polynucleic acid can comprise a nucleotide sequence that is at least 92% identical to SEQ ID NO: 3. In some cases, the isolated polynucleic acid can comprise a nucleotide sequence that is at least 93% identical to SEQ ID NO: 3. In some cases, the isolated polynucleic acid can comprise a nucleotide sequence that is at least 94% identical to SEQ ID NO: 3. In some cases, the isolated polynucleic acid can comprise a nucleotide sequence that is at least 95% identical to SEQ ID NO: 3. In some cases, the isolated polynucleic acid can comprise a nucleotide sequence that is at least 96% identical to SEQ ID NO: 3. In some cases, the isolated polynucleic acid can comprise a nucleotide sequence that is at least 97% identical to SEQ ID NO: 3. In some cases, the isolated polynucleic acid can comprise a nucleotide sequence that is at least 98% identical to SEQ ID NO: 3. In some cases, the isolated polynucleic acid can comprise a nucleotide sequence that is at least 99% identical to SEQ ID NO: 3. In some cases, the isolated polynucleic acid can comprise a nucleotide sequence that is SEQ ID NO: 3.

In some cases, the isolated polynucleic acid can comprise a nucleotide sequence that encodes for a dihydroxy-acid dehydratase. In some cases, the isolated polynucleic acid can comprise a nucleotide sequence that is substantially similar to SEQ ID NO: 5 or 7. For example, the isolated polynucleic acid can comprise a nucleotide sequence that is at least 60% identical to SEQ ID NO: 5 or 7. In some cases, the isolated polynucleic acid can comprise a nucleotide sequence that is at least 65% identical to SEQ ID NO: 5 or 7. In some cases, the isolated polynucleic acid can comprise a nucleotide sequence that is at least 70% identical to SEQ ID NO: 5 or 7. In some cases, the isolated polynucleic acid can comprise a nucleotide sequence that is at least 75% identical to SEQ ID NO: 5 or 7. In some cases, the isolated polynucleic acid can comprise a nucleotide sequence that is at least 80% identical to SEQ ID NO: 5 or 7. In some cases, the isolated polynucleic acid can comprise a nucleotide sequence that is at least 81% identical to SEQ ID NO: 5 or 7. In some cases, the isolated polynucleic acid can comprise a nucleotide sequence that is at least 82% identical to SEQ ID NO: 5 or 7. In some cases, the isolated polynucleic acid can comprise a nucleotide sequence that is at least 83% identical to SEQ ID NO: 5 or 7. In some cases, the isolated polynucleic acid can comprise a nucleotide sequence that is at least 84% identical to SEQ ID NO: 5 or 7. In some cases, the isolated polynucleic acid can comprise a nucleotide sequence that is at least 85% identical to SEQ ID NO: 5 or 7. In some cases, the isolated polynucleic acid can comprise a nucleotide sequence that is at least 86% identical to SEQ ID NO: 5 or 7. In some cases, the isolated polynucleic acid can comprise a nucleotide sequence that is at least 87% identical to SEQ ID NO: 5 or 7. In some cases, the isolated polynucleic acid can comprise a nucleotide sequence that is at least 88% identical to SEQ ID NO: 5 or 7. In some cases, the isolated polynucleic acid can comprise a nucleotide sequence that is at least 89% identical to SEQ ID NO: 5 or 7. In some cases, the isolated polynucleic acid can comprise a nucleotide sequence that is at least 90% identical to SEQ ID NO: 5 or 7. In some cases, the isolated polynucleic acid can comprise a nucleotide sequence that is at least 91% identical to SEQ ID NO: 5 or 7. In some cases, the isolated polynucleic acid can comprise a nucleotide sequence that is at least 92% identical to SEQ ID NO: 5 or 7. In some cases, the isolated polynucleic acid can comprise a nucleotide sequence that is at least 93% identical to SEQ ID NO: 5 or 7. In some cases, the isolated polynucleic acid can comprise a nucleotide sequence that is at least 94% identical to SEQ ID NO: 5 or 7. In some cases, the isolated polynucleic acid can comprise a nucleotide sequence that is at least 95% identical to SEQ ID NO: 5 or 7. In some cases, the isolated polynucleic acid can comprise a nucleotide sequence that is at least 96% identical to SEQ ID NO: 5 or 7. In some cases, the isolated polynucleic acid can comprise a nucleotide sequence that is at least 97% identical to SEQ ID NO: 5 or 7. In some cases, the isolated polynucleic acid can comprise a nucleotide sequence that is at least 98% identical to SEQ ID NO: 5 or 7. In some cases, the isolated polynucleic acid can comprise a nucleotide sequence that is at least 99% identical to SEQ ID NO: 5 or 7. In some cases, the isolated polynucleic acid can comprise a nucleotide sequence that is SEQ ID NO: 5 or 7.

In some cases, the isolated polynucleic acid can comprise a nucleotide sequence that encodes for a 2-keto acid decarboxylase. In some cases, the isolated polynucleic acid can comprise a nucleotide sequence that is substantially similar to any one of SEQ ID NOs: 9, 11, 56, 58, 60, 62, 64, 66, 68, 70, 72, 74, 76, 78, 80, 82, 84, 86, 88, 90, 92, 94, 96, or 98. For example, the isolated polynucleic acid can comprise a nucleotide sequence that is at least 60% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 65% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 70% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 75% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 80% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 81% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 82% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 83% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 84% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 85% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 86% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 87% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 88% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 89% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 90% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 91% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 92% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 93% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 94% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 95% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 96% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 97% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 98% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is at least 99% identical to any one of SEQ ID NOs: 9, 11, 56, 58, 60, 62, 64, 66, 68, 70, 72, 74, 76, 78, 80, 82, 84, 86, 88, 90, 92, 94, 96, or 98. In some cases, the isolated polynucleic acid can comprise a nucleotide sequence that is any one of SEQ ID NOs: 9, 11, 56, 58, 60, 62, 64, 66, 68, 70, 72, 74, 76, 78, 80, 82, 84, 86, 88, 90, 92, 94, 96, or 98.

In some cases, the isolated polynucleic acid can comprise a nucleotide sequence that encodes for an alcohol dehydrogenase. In some cases, the isolated polynucleic acid can comprise a nucleotide sequence that is substantially similar to any one of SEQ ID NOs: 13, 15, 17, 24, 26, 28, 30, 32, 34, 36, 38, 40, 42, 44, 46, 48, 50, 52, or 54. For example, the isolated polynucleic acid can comprise a nucleotide sequence that is at least 60% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 65% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 70% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 75% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 80% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 81% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 82% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 83% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 84% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 85% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 86% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 87% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 88% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 89% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 90% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 91% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 92% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 93% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 94% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 95% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 96% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 97% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 98% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is at least 99% identical to any one of SEQ ID NOs: 13, 15, 17, 24, 26, 28, 30, 32, 34, 36, 38, 40, 42, 44, 46, 48, 50, 52, or 54. In some cases, the isolated polynucleic acid can comprise a nucleotide sequence that is any one of SEQ ID NOs: 13, 15, 17, 24, 26, 28, 30, 32, 34, 36, 38, 40, 42, 44, 46, 48, 50, 52, or 54.

In some cases, the isolated polynucleic acid can comprise a nucleotide sequence that encodes for a sugar permease. In some cases, the isolated polynucleic acid can comprise a nucleotide sequence that is substantially similar to SEQ ID NO: 19. For example, the isolated polynucleic acid can comprise a nucleotide sequence that is at least 60% identical to SEQ ID NO: 19. In some cases, the isolated polynucleic acid can comprise a nucleotide sequence that is at least 65% identical to SEQ ID NO: 19. In some cases, the isolated polynucleic acid can comprise a nucleotide sequence that is at least 70% identical to SEQ ID NO: 19. In some cases, the isolated polynucleic acid can comprise a nucleotide sequence that is at least 75% identical to SEQ ID NO: 19. In some cases, the isolated polynucleic acid can comprise a nucleotide sequence that is at least 80% identical to SEQ ID NO: 19. In some cases, the isolated polynucleic acid can comprise a nucleotide sequence that is at least 81% identical to SEQ ID NO: 19. In some cases, the isolated polynucleic acid can comprise a nucleotide sequence that is at least 82% identical to SEQ ID NO: 19. In some cases, the isolated polynucleic acid can comprise a nucleotide sequence that is at least 83% identical to SEQ ID NO: 19. In some cases, the isolated polynucleic acid can comprise a nucleotide sequence that is at least 84% identical to SEQ ID NO: 19. In some cases, the isolated polynucleic acid can comprise a nucleotide sequence that is at least 85% identical to SEQ ID NO: 19. In some cases, the isolated polynucleic acid can comprise a nucleotide sequence that is at least 86% identical to SEQ ID NO: 19. In some cases, the isolated polynucleic acid can comprise a nucleotide sequence that is at least 87% identical to SEQ ID NO: 19. In some cases, the isolated polynucleic acid can comprise a nucleotide sequence that is at least 88% identical to SEQ ID NO: 19. In some cases, the isolated polynucleic acid can comprise a nucleotide sequence that is at least 89% identical to SEQ ID NO: 19. In some cases, the isolated polynucleic acid can comprise a nucleotide sequence that is at least 90% identical to SEQ ID NO: 19. In some cases, the isolated polynucleic acid can comprise a nucleotide sequence that is at least 91% identical to SEQ ID NO: 19. In some cases, the isolated polynucleic acid can comprise a nucleotide sequence that is at least 92% identical to SEQ ID NO: 19. In some cases, the isolated polynucleic acid can comprise a nucleotide sequence that is at least 93% identical to SEQ ID NO: 19. In some cases, the isolated polynucleic acid can comprise a nucleotide sequence that is at least 94% identical to SEQ ID NO: 19. In some cases, the isolated polynucleic acid can comprise a nucleotide sequence that is at least 95% identical to SEQ ID NO: 19. In some cases, the isolated polynucleic acid can comprise a nucleotide sequence that is at least 96% identical to SEQ ID NO: 19. In some cases, the isolated polynucleic acid can comprise a nucleotide sequence that is at least 97% identical to SEQ ID NO: 19. In some cases, the isolated polynucleic acid can comprise a nucleotide sequence that is at least 98% identical to SEQ ID NO: 19. In some cases, the isolated polynucleic acid can comprise a nucleotide sequence that is at least 99% identical to SEQ ID NO: 19. In some cases, the isolated polynucleic acid can comprise a nucleotide sequence that is SEQ ID NO: 19.

In some cases, the isolated polynucleic acid can comprise a nucleotide sequence that encodes for an arabinose operon regulatory protein. In some cases, the isolated polynucleic acid can comprise a nucleotide sequence that is substantially similar to SEQ ID NO: 21. For example, the isolated polynucleic acid can comprise a nucleotide sequence that is at least 60% identical to SEQ ID NO: 21. In some cases, the isolated polynucleic acid can comprise a nucleotide sequence that is at least 65% identical to SEQ ID NO: 21. In some cases, the isolated polynucleic acid can comprise a nucleotide sequence that is at least 70% identical to SEQ ID NO: 21. In some cases, the isolated polynucleic acid can comprise a nucleotide sequence that is at least 75% identical to SEQ ID NO: 21. In some cases, the isolated polynucleic acid can comprise a nucleotide sequence that is at least 80% identical to SEQ ID NO: 21. In some cases, the isolated polynucleic acid can comprise a nucleotide sequence that is at least 81% identical to SEQ ID NO: 21. In some cases, the isolated polynucleic acid can comprise a nucleotide sequence that is at least 82% identical to SEQ ID NO: 21. In some cases, the isolated polynucleic acid can comprise a nucleotide sequence that is at least 83% identical to SEQ ID NO: 21. In some cases, the isolated polynucleic acid can comprise a nucleotide sequence that is at least 84% identical to SEQ ID NO: 21. In some cases, the isolated polynucleic acid can comprise a nucleotide sequence that is at least 85% identical to SEQ ID NO: 21. In some cases, the isolated polynucleic acid can comprise a nucleotide sequence that is at least 86% identical to SEQ ID NO: 21. In some cases, the isolated polynucleic acid can comprise a nucleotide sequence that is at least 87% identical to SEQ ID NO: 21. In some cases, the isolated polynucleic acid can comprise a nucleotide sequence that is at least 88% identical to SEQ ID NO: 21. In some cases, the isolated polynucleic acid can comprise a nucleotide sequence that is at least 89% identical to SEQ ID NO: 21. In some cases, the isolated polynucleic acid can comprise a nucleotide sequence that is at least 90% identical to SEQ ID NO: 21. In some cases, the isolated polynucleic acid can comprise a nucleotide sequence that is at least 91% identical to SEQ ID NO: 21. In some cases, the isolated polynucleic acid can comprise a nucleotide sequence that is at least 92% identical to SEQ ID NO: 21. In some cases, the isolated polynucleic acid can comprise a nucleotide sequence that is at least 93% identical to SEQ ID NO: 21. In some cases, the isolated polynucleic acid can comprise a nucleotide sequence that is at least 94% identical to SEQ ID NO: 21. In some cases, the isolated polynucleic acid can comprise a nucleotide sequence that is at least 95% identical to SEQ ID NO: 21. In some cases, the isolated polynucleic acid can comprise a nucleotide sequence that is at least 96% identical to SEQ ID NO: 21. In some cases, the isolated polynucleic acid can comprise a nucleotide sequence that is at least 97% identical to SEQ ID NO: 21. In some cases, the isolated polynucleic acid can comprise a nucleotide sequence that is at least 98% identical to SEQ ID NO: 21. In some cases, the isolated polynucleic acid can comprise a nucleotide sequence that is at least 99% identical to SEQ ID NO: 21. In some cases, the isolated polynucleic acid can comprise a nucleotide sequence that is SEQ ID NO: 21.

Exemplary Vector Sequences

Vectors that can be integrated into various microorganisms, such as methanotrophs, are disclosed herein (see e.g., FIGS. 4A-4C, 5, and 6). In some cases, minor changes can be made to the vectors without significant changes in the effectiveness of the vectors or the amount of enzymes the vectors are able to produce.

Figure 4B:
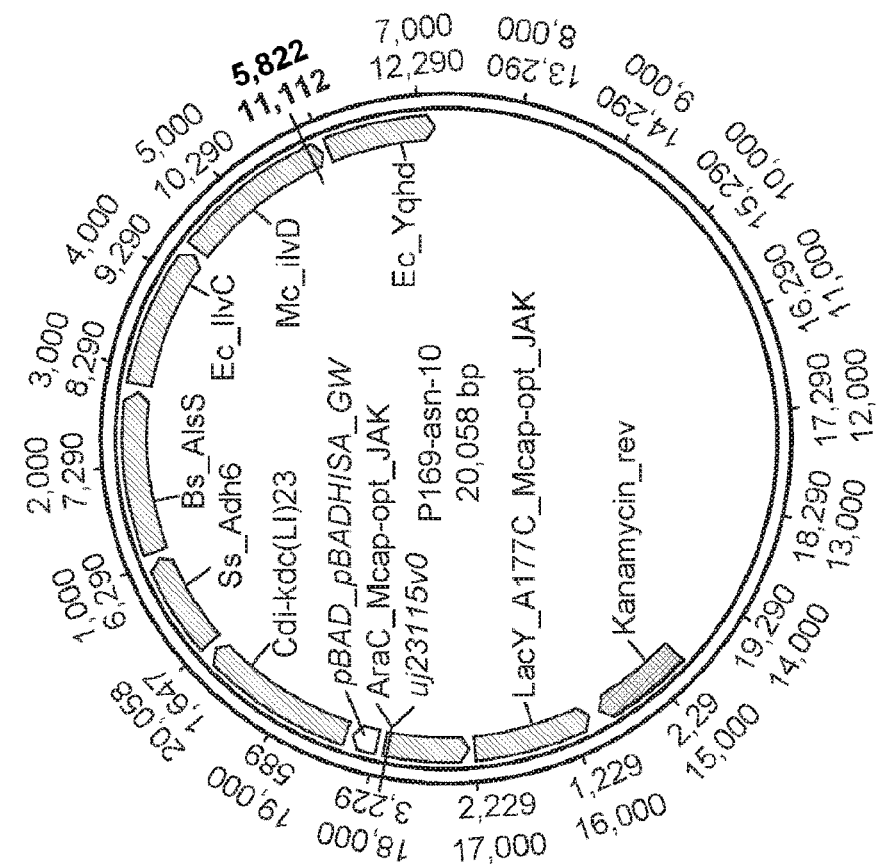
FIGS. 4A-4C show inducible expression vectors useful to express isobutanol pathway enzymes in microorganisms such as methanotrophs.
Figure 4A:
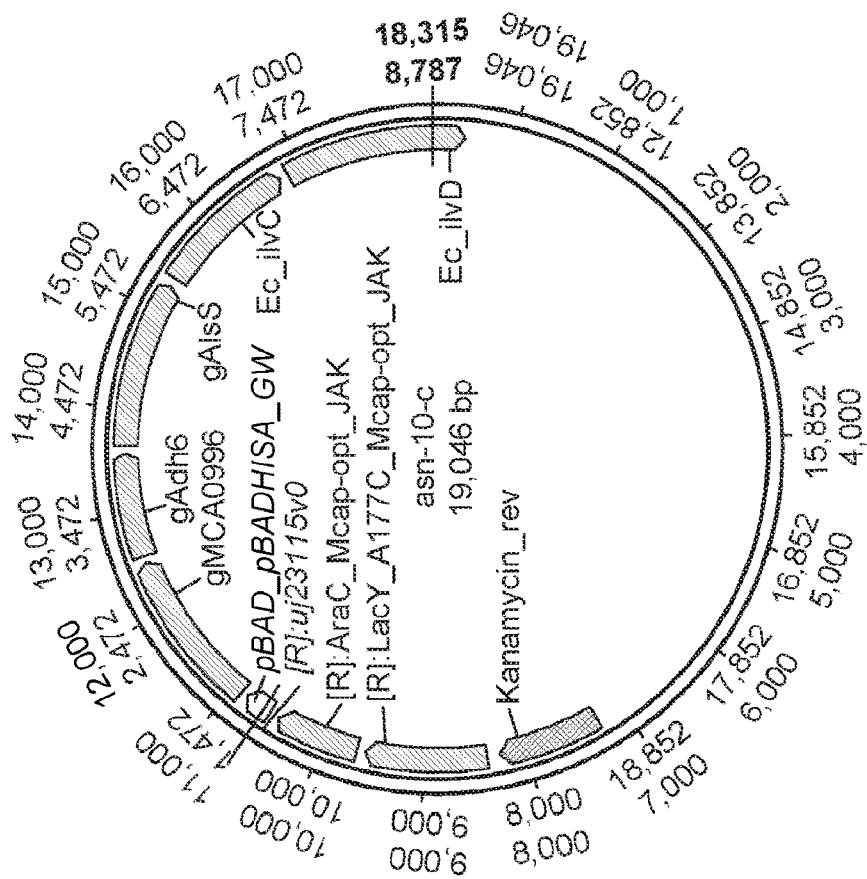

In some cases, the expression plasmid as disclosed in FIG. 4A or 4B, can be contacted with (and inserted into) a microorganism. These expression plasmids comprise a Kanamycin marker, an arabinose induction machinery (LacY and AraC driven by a J23115 promoter) and a BAD promoter (e.g., a pBAD promoter) driving the expression of enzymes useful in the isobutanol pathway ((MCA0996=Kdc), Adh6, AlsS, IlvC and IlvD).

Figure 4C:
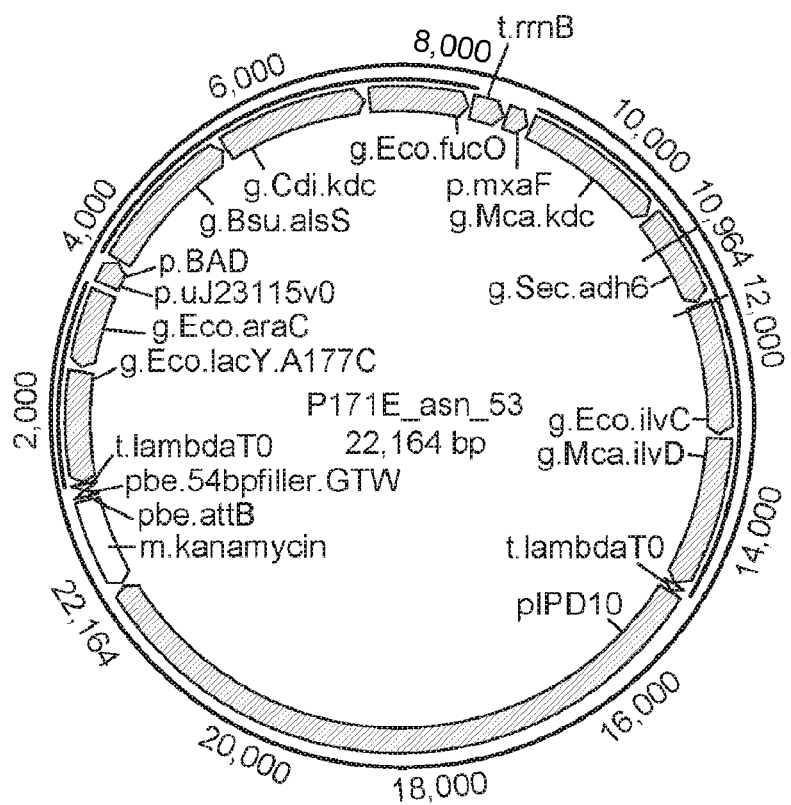
Figure 5:
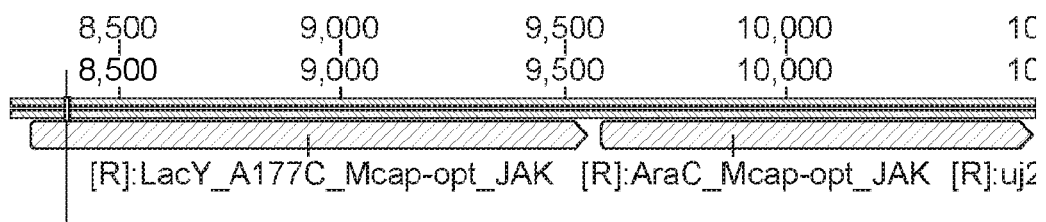
FIG. 5 shows the arabinose induction machinery: LacY and AraC.
Figure 6:
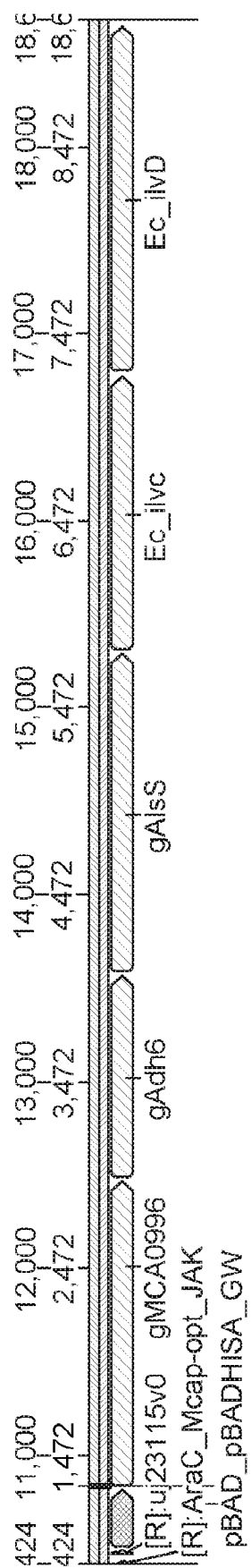
FIG. 6 shows the isobutanol operon expressed from the pBAD promoter. The pBAD promoter uses the pBAD ribosome binding site. In between each of the genes that follow MCA0996, the same RBS GTW0001 is used.

In other cases, the expression plasmid as disclosed in FIG. 4C can be contacted with (and inserted into) a microorganism. This expression plasmid comprises a Kanamycin marker, an arabinose induction machinery (LacY and AraC driven by a J23115 promoter) and two operons with two different promoters (a BAD promoter (pBAD) and a pMxaF promoter) driving the expression of enzymes useful in the isobutanol pathway Kdc, Adh, AlsS, IlvC and IlvD.

II. Method of Making the Genetically Modified Microorganisms

Figure 2:
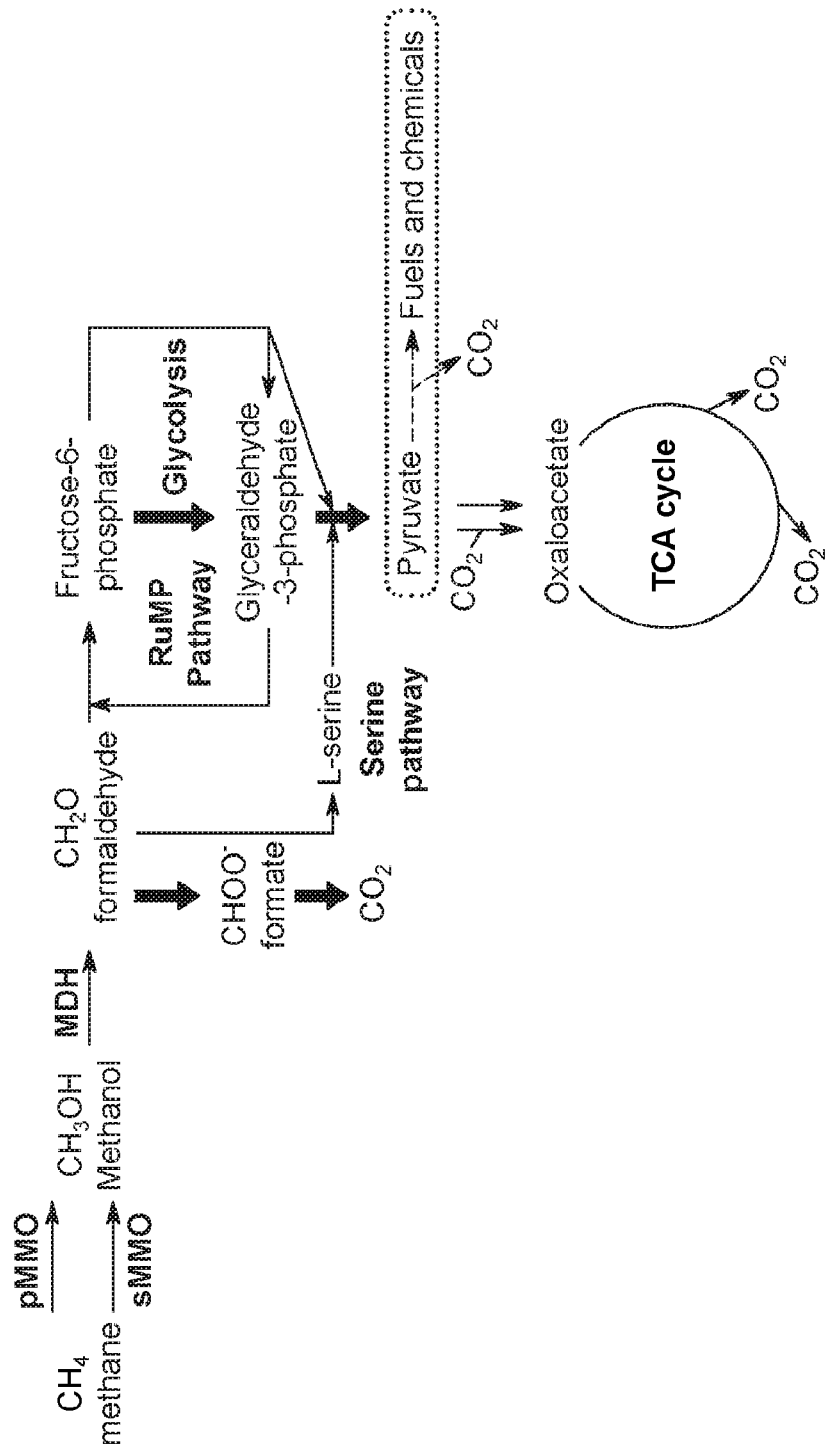
FIG. 2 shows a metabolic pathway from methane ($CH_4$) to pyruvate. Pyruvate can then be used to make various products such as fuels and chemicals.
Figure 3:
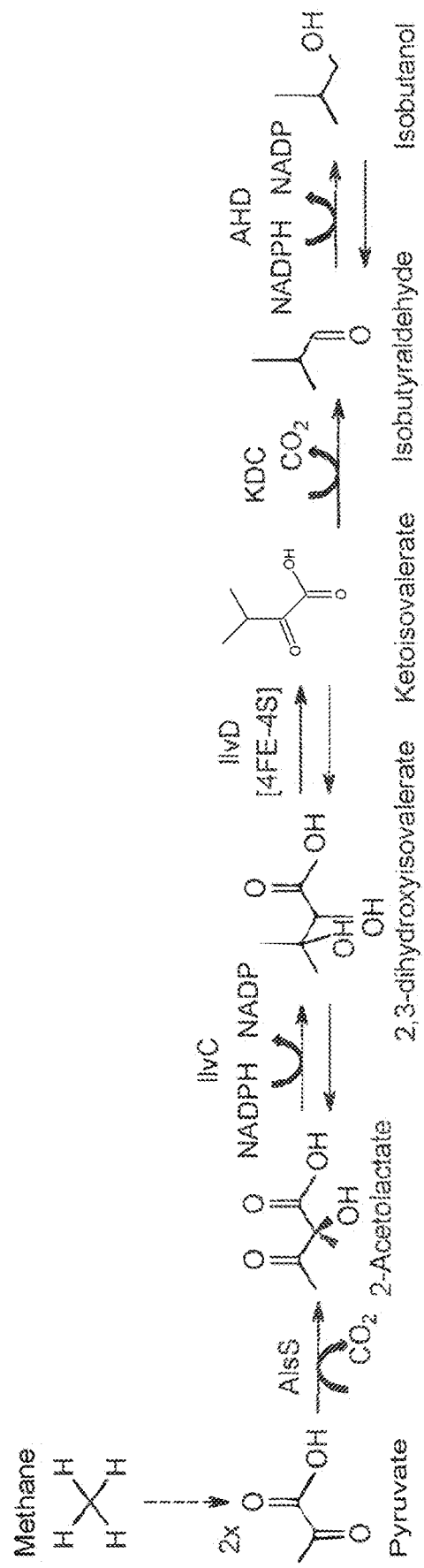
FIG. 3 shows a metabolic pathway from methane ($CH_4$) to isobutanol. Methane is converted to pyruvate by the pathway shown in FIG. 2, and pyruvate is converted into isobutanol through the action of at least five enzymes which include acetolactate synthase (gene name: AlsS); ketol-acid reductoisomerase (enzyme abbreviation: KARI; gene name: IlvC); dihydroxy-acid dehydratase (enzyme abbreviation: DHAD; gene name: IlvD); 2-keto acid decarboxylase (gene name: KDC); and alcohol dehydrogenase (gene name: ADH).

The genetically modified microorganisms above can be made by a variety of ways. A microorganism can be modified (e.g., genetically engineered) by any method to comprise and/or express one or more polynucleotides encoding for enzymes in a pathway that catalyze a conversion of a fermentable carbon source to one or more intermediates in a pathway for the production of a desired product, such as isobutanol. For example, the genetically modified microorganism can comprise one or more nucleic acids encoding for an enzyme capable of catalyzing one or more of the reactions: i) methane to methanol; ii) methanol to formaldehyde; and/or iii) formaldehyde to pyruvate. For example, the genetically modified microorganism can comprise one or more genes including but not limited to pMMO; sMMO; and/or methanol dehydrogenase (MDH). Such enzymes can include any of those enzymes as set forth in FIG. 2 or 3. For example, one or more of any of the genes above can be inserted into a microorganism. The genes can be inserted by an expression vector. The one or more genes can also be stably integrated into the genome of the microorganism.

The microorganism used in this method can be any described above, including but not limited to a prokaryote. Other microorganisms such as bacteria, yeast, or algae can be used. One microorganism of particular interest is a methanotroph, such as a methanotroph from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloferula, Methylomarinum*, or *Methyloacidoiphilum*. One desired species can include a *Methylococcus capsulatus*.

An exemplary method of making a genetically modified microorganism disclosed herein is contacting (or transforming) a microorganism with a nucleic acid that expresses at least one heterologous gene from: (i) acetolactate synthase; (ii) ketol-acid reductoisomerase; (iii) dihydroxy-acid dehydratase; (iv) 2-keto acid decarboxylase; (v) alcohol dehydrogenase; or (vi) any combination thereof. For example, in order to make a microorganism that produces an aldehyde, e.g., isobutyraldehyde, (i) acetolactate synthase; (ii) ketol-acid reductoisomerase; (iii) dihydroxy-acid dehydratase; and/or (iv) 2-keto acid decarboxylase can be transformed into a microorganism. Additionally, should a microorganism that produces an alcohol be desired, an additional gene encoding for an (v) alcohol dehydrogenase can be transformed into the microorganism. One or more of these enzymes can be heterologous to the microorganism. Additionally, one or more of these enzymes can be endogenous to the microorganism. Further, one or more of these enzymes can be overexpressed in the microorganism. The microorganism can be any microorganism that is capable of converting a carbon source into a desired product. In some cases, the product is isobutanol. In some cases, the product is isobutyraldehyde.

The acetolactate synthase; ketol-acid reductoisomerase; dihydroxy-acid dehydratase; 2-keto acid decarboxylase; and/or alcohol dehydrogenase, used in the method can be any of the variations described throughout. For example, the alcohol dehydrogenase can be from yeast such as from the genus *Saccharomyces* or a bacterium (e.g., a gram negative or gram positive bacterium) such as from the genus *Escherichia*. Other bacterial genera that can be used include *Clostridium, Escherichia, Geobacillus, Lactococcus, Oenococcus, Pectobacterium*, and/or *Psychrobacter*. More specifically, the alcohol dehydrogenase can be from the species *Saccharomyces cerevisiae, Escherichia coli, Clostridium acetobutylicum, Escherichia coli, Geobacillus stearothermophilus, Geobacillus thermoglucosidas, Lactococcus lactis, Oenococcus oeni, Pectobacterium atrosepticum*, and/or *Psychrobacter cryohalolentis*. Further, multiple alcohol dehydrogenases can be used. For example, one or more bacterial alcohol dehydrogenases and one or more yeast alcohol dehydrogenases can be expressed within a microorganism.

The one or more genes that are inserted into a microorganism can be heterologous to the microorganism itself. For example, if the microorganism is a methanotroph, the one or more genes that are inserted can be from yeast, a bacterium, or a different species of methanotroph. Further, the one or more genes can be endogenously part of the genome of the microorganism. When endogenous genes are used, they can be overexpressed or they can be modified so that expression is altered compared to the unmodified endogenous gene. For example, the endogenous gene can be made to be under the control of a different promoter, such as an inducible promoter.

Techniques for Genetic Modification

The microorganisms disclosed herein can be genetically engineered by using classic microbiological techniques. Some of such techniques are generally disclosed, for example, in Sambrook et al., 1989, Molecular Cloning: A Laboratory Manual, Cold Spring Harbor Labs Press.

The genetically modified microorganisms disclosed herein can include a polynucleotide that has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase gene expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements.

Where desired, the expression of one or more of the enzymes provided herein is under the control of a regulatory sequence that controls directly or indirectly the enzyme expression in a time-dependent fashion during the fermentation. Inducible promoters can be used to achieve this.

In some cases, a microorganism is transformed or transfected with a genetic vehicle, such as an expression vector comprising a heterologous polynucleotide sequence coding for the enzymes are provided herein.

To facilitate insertion and expression of different genes coding for the enzymes as disclosed herein from the constructs and expression vectors, the constructs can be designed with at least one cloning site for insertion of any gene coding for any enzyme disclosed herein. The cloning site can be a multiple cloning site, e.g., containing multiple restriction sites.

Transfection

Standard transfection techniques can be used to insert genes into a microorganism. As used herein, the term "transfection" or "transformation" can refer to the insertion of an exogenous nucleic acid or polynucleotide into a host cell. The exogenous nucleic acid or polynucleotide can be maintained as a non-integrated vector, for example, a plasmid, or alternatively, can be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextranmediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the transfection is a stable transfection.

Transformation

Expression vectors or other nucleic acids can be introduced to selected microorganisms by any of a number of suitable methods. For example, vector constructs can be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation can also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods can be used (e.g., Rose et al, 1990, Methods in Yeast Genetics, Cold Spring Harbor Laboratory Press, Cold Spring Harbor, N.Y.). Transformed cells can be isolated on selective media appropriate to the selectable marker used. Alternatively, or in addition, plates or filters lifted from plates can be scanned for GFP fluorescence to identify transformed clones.

For the introduction of vectors comprising differentially expressed sequences to certain types of cells, the method used can depend upon the form of the vector. Plasmid vectors can be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., N.Y., N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell can be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression or vectors for production of one or more enzymes as disclosed herein or with polynucleotides coding for one or more enzymes as disclosed herein and cultured in nutrient media modified as appropriate for the specific microorganism, inducing promoters, selecting transformants, or amplifying the genes encoding the desired sequences.

For example, within the context of a methanotroph, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR/Cas System

Methods that require any of the genes described herein can take advantage of pinpoint insertion of genes or the deletion of genes (or parts of genes). Methods described herein can take advantage of a CRISPR/Cas system. For example, double-strand breaks (DSBs) can be generated using a CRISPR/Cas system, e.g., a type II CRISPR/Cas system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of the target sequence.

A vector can be operably linked to an enzyme-coding sequence encoding a CRISPR enzyme, such as a Cas protein. Cas proteins that can be used include class 1 and class 2. Non-limiting examples of Cas proteins include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within 1, 2, 3, 4, 5, 6, 7, 8, 9, 10, 15, 20, 25, 50, 100, 200, 500, or more base pairs from the first or last nucleotide of a target sequence. A vector that encodes a CRISPR enzyme that is mutated with respect to a corresponding wild-type enzyme such that the mutated CRISPR enzyme lacks the ability to cleave one or both strands of a target polynucleotide containing a target sequence can be used.

A vector that encodes a CRISPR enzyme comprising one or more nuclear localization sequences (NLSs) can be used. For example, there can be 1, 2, 3, 4, 5, 6, 7, 8, 9, or 10 NLSs used. A CRISPR enzyme can comprise the NLSs at or near the amino-terminus, e.g., 1, 2, 3, 4, 5, 6, 7, 8, 9, or 10 NLSs at or near the carboxy-terminus, or any combination of these (e.g., one or more NLS at the amino-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise at most 6 NLSs. An NLS is considered near the N- or C-terminus when the nearest amino acid to the NLS is within 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a cell or embryo at least one guide RNA or nucleic acid, e.g., DNA encoding at least one guide RNA. A guide RNA can interact with an RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a cell or microorganism by transfecting the cell or microorganism with an isolated guide RNA or plasmid DNA comprising a sequence coding for the guide RNA and a promoter. A guide RNA can also be transferred into a cell or microorganism in other way, such as using virus-mediated gene delivery.

A guide RNA can be isolated. For example, a guide RNA can be transfected in the form of an isolated RNA into a cell or microorganism. A guide RNA can be prepared by in vitro transcription using any in vitro transcription system known in the art. A guide RNA can be transferred to a cell in the form of isolated RNA rather than in the form of plasmid comprising encoding sequence for a guide RNA.

A guide RNA can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from 10 nucleotides to 25 nucleotides (e.g., from 10 nts to 25 nts; or from 15 nts to 25 nts; or from 10 nts to 20 nts; or from 15 nts to 20 nts) or more. For example, a region of base pairing between a first region of a guide RNA and a target site in a chromosomal sequence can be 10, 11, 12, 13, 14, 15, 16, 17, 18, 19, 20, 22, 23, 24, 25, or more nucleotides in length. Sometimes, a first region of a guide RNA can be 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from 3 to 10 nucleotides in length, and a stem can range from 6 to 20 base pairs in length. A stem can comprise one or more bulges of 1 to 10 nucleotides. The overall length of a second region can range from 16 to 60 nucleotides in length. For example, a loop can be 4 nucleotides in length and a stem can be 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than 4 nucleotides in length. For example, the length of a third region can range from 5 to 60 nucleotides in length.

A guide RNA can be introduced into a cell or embryo as an RNA molecule. For example, an RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. An RNA coding sequence can be operably linked to a promoter sequence that is recognized by RNA polymerase III (Pol III). Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Site Specific Insertion

Inserting one or more genes in any microorganisms used in the of the methods disclosed throughout can be site-specific. For example, one or more genes can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, Φ31 integrase (a serine recombinase derived from *Streptomyces* phage Φ31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/Cas to facilitate the insertion of a transgene at the insertion site.

The techniques which can be used to allow a DNA or RNA construct entry into a host cell in the methods described herein include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods herein. Vectors that can be used include, but are not limited to eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, pMCIneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene or a portion of a gene can be inserted by using known methods, such as restriction enzyme-based techniques.

III. Other Methods

Making Useful Chemicals

The genetically modified microorganisms described herein can be used to make chemicals that are useful, including but not limited to 2-acetolactate; 2,3-dihydroxy-isovalerate; ketoisovalerate; isobutyraldehyde; and isobutanol. Other useful products or chemicals that can be made with the methods and microorganisms described throughout can include amino acids such as lysine and isoleucine, sugar/glycogen, acetate, pyruvate, lactate, citrate, isovaleraldehyde, isopentanol, acetylated isobutanol or acetylated isopentanol (isobutrylacetate and isoamylacetate), and pentadecanoic acid (rare odd chain fatty acid over produced by the genetically modified microorganisms disclosed throughout but not produced at high level in wild-type strains).

Further, some of these chemicals can be used to produce other useful products including but not limited to, isobutyl acetate, isobutyl esters such as diisobutyl phthalate (DIBP), methyl methacrylate (MMA), isobutene, para-xylene, paint solvents, varnish remover, ink ingredients, paint additives, gasoline additives, gasoline alternatives, automotive polish additives, automotive paint cleaner additives, and chemical extractants in the production of organic compounds.

The microorganism can be any of the microorganisms discussed throughout including but not limited to a prokaryote, such as a methanotroph.

The carbon substrate can be any carbon substrate discussed throughout including but not limited to methane.

2-acetolactate

With regards to 2-acetolactate, one method disclosed herein is a method of making 2-acetolactate comprising: (a) contacting a genetically modified microorganism with a carbon substrate, where the microorganism comprises a heterologous gene encoding for acetolactate synthase; and (b) growing the microorganism to produce 2-acteolactate. In some cases, the acetolactate synthase gene can be from the genus *Bacillus*, such as the species *Bacillus subtilis* and/or *Bacillus licheniformis*. For example, an acetolactate synthase that can be used can be encoded by a nucleic acid having substantial similarity to SEQ ID NO: 1 or 100. The microorganisms that can be used in this method are described throughout (such as a methanotroph). Additionally, the microorganism can be transformed with or made to express one or more of the genes to make other products such as 2,3-butanediol ("2,3-BDO") and/or isobutanol and/or isobutyraldehyde (such as the genes that are described throughout). Further, the carbon sources can be any carbon source described throughout, such as a $C_1$ carbon source. The 2-acetolactate produced can be substantially pure. The 2-acetolactate produced can be recovered.

The 2-acetolactate can be further processed through the use of one or more enzymatic reactions. For example, 2-acetolactate can be processed into 2,3-BDO by contacting it with alpha-acetolactate (budA) or acetoin reductase (butA). In some cases, the 2-acetolactate can be contacted with a 2,3-butanediol dehydrogenase.

2,3-Butanediol ("2,3-BDO")

With regards to 2,3-BDO, one method disclosed herein is a method of making 2,3-BDO comprising: (a) contacting a genetically modified microorganism with a carbon substrate, where the microorganism comprises a heterologous gene encoding for acetolactate synthase; and (b) growing the microorganism to produce 2,3-BDO. The microorganisms that can be used in this method are described throughout (such as a methanotroph). Additionally, the microorganism can be transformed with or made to express one or more of the genes (such as a gene encoding for an alpha-acetolactate (budA) or acetoin reductase (butA)) or other genes as disclosed throughout. Further, the carbon sources can be any carbon source described throughout, such as a $C_1$ carbon source. The 2,3-BDO produced can be substantially pure. The 2,3-BDO produced can be recovered.

The 2,3-BDO can be further processed through the use of one or more catalysts. For example, 2,3-BDO can be processed into methyl ethyl ketone (MEK) by contacting the 2,3-BDO with a dehydrating catalyst (such as alumina, direct reaction with sulfuric acid, Cu, $AlO_3$, and/or zeolite (or other solid acid catalysts)). 2,3-BDO can also be processed into 1,3-butadiene by contacting the 2,3-BDO with a catalyst capable of producing a hydride shift, such as alumina or sulfuric acid. 2,3-BDO can also be processed into butene by contacting the 2,3-BDO with a HBr following by Zn. MEK, 1,3-butadiene and butene can be converted into a variety of different products such as synthetic rubbers or solvents.

The 2,3-BDO can also be further processed by a diol dehydratase (B12). This enzymatic reaction can produce butan-2-one (also known as methyl ethyl ketone or MEK). Thus, disclosed is a method of making butan-2-one comprising: (a) contacting a genetically modified microorganism with a carbon substrate, where the microorganism comprises a heterologous gene encoding for diol dehydratase; and (b) growing the microorganism to produce butan-2-one. The microorganism can also comprise an acetolactate synthase (AlsS), alpha-acetolactate (budA), and/or acetoin reductase (butA).

In some cases, the butan-2-one can be further processed by an alcohol dehydrogenase. This enzymatic reaction can produce butan-2-ol (also known as 2-butanol). Thus, disclosed is a method of making butan-2-ol comprising: (a) contacting a genetically modified microorganism with a carbon substrate, where the microorganism comprises a heterologous gene encoding for an alcohol dehydrogenase; and (b) growing the microorganism to produce butan-2-ol. The microorganism can also comprise an acetolactate synthase (AlsS), alpha-acetolactate (budA), acetoin reductase (butA), and/or diol dehydratase (B12).

Diacetyl

Diacetyl (also known as butanedione) can also be produced from 2-acetolactate. Disclosed herein is a method of making 2-acetolactate comprising: (a) contacting a genetically modified microorganism with a carbon substrate, where the microorganism comprises a heterologous gene encoding for acetolactate synthase; (b) growing the microorganism to produce 2-acetolactate; and (c) further processing 2-acetolactate into diacetyl. In general, diacetyl can be made by the spontaneous oxidative decarboxylation of acetolactate. Milne, N., et al., "Excessive by-product formation: A key contributor to low isobutanol yields of engineered *Saccharomyces cerevisiae* strains," *Metabolic Engineering Communications* 3:39-51 (2016). Diacetyl can be produced during fermentation as a byproduct of valine synthesis, when 2-acetolactate escapes the cell and is spontaneously decarboxylated into diacetyl.

The microorganisms that can be used in this method are described throughout (such as a methanotroph). Additionally, the microorganism can be transformed with or made to express one or more of the genes as disclosed throughout. Further the carbon sources can be any carbon source described throughout, such as a $C_1$ carbon source. The diacetyl produced can be substantially pure. The diacetyl that is produced can be recovered.

Diacetyl can be used in food products as it has buttery characteristics. Therefore, diacetyl can be used in the manufacture of foods in which a buttery taste is desired, such as artificial butter flavoring, margarines or similar oil-based products (along with acetoin and beta-carotene) to make the final product butter-flavored. Diacetyl can also be used in electronic cigarette liquids for flavoring.

Diacetyl can also be used in alcoholic beverages. At low levels, diacetyl provides a slipperiness to the feel of the alcoholic beverage in the mouth. As diacetyl levels increase, it imparts a buttery or butterscotch flavor. For example, diacetyl can be contained in beer and wines. For example, concentrations from 0.005 mg/L to 1.7 mg/L were measured in chardonnay wines, and the amount needed for the flavor to be noticed is at least 0.2 mg/L.

2,3-dihydroxy-2-methylbutanoic acid 2,3-dihydroxy-2-methylbutanoic acid can be produced from the methods and microorganisms discussed herein. For example, disclosed is a method of making 2,3-dihydroxy-2-methylbutanoic acid comprising: (a) contacting a genetically modified microorganism with a carbon substrate, where the microorganism comprises a heterologous gene encoding for acetolactate synthase; (b) growing the microorganism to produce 2-acetolactate; and (c) contacting the 2-acetolactate with an enzyme that is capable of converting 2-acetolactate to 2,3-dihydroxy-2-methylbutanoic acid. In some cases the enzyme has an EC number 1.1.1.86. In some cases, the enzyme is a ketol-acid reductoisomerase.

The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The 2,3-dihydroxy-2-methylbutanoic acid produced can be substantially pure. The 2,3-dihydroxy-2-methylbutanoic acid that is produced can be recovered.

2,3-dihydroxy-2-methylbutanoic acid can also be used in alcoholic beverages. 2,3-dihydroxy-2-methylbutanoic acid can be contained in alcoholic beverages such as beer and wines. For example, concentrations from 0.26 ppm were measured in some German beers.

2,3-dihydroxyisovalerate

With regards to 2,3-dihydroxyisovalerate, one method disclosed herein is a method of making 2,3-dihydroxyisovalerate comprising (a) contacting a genetically modified microorganism with a carbon substrate, where the microorganism comprises at least one heterologous gene encoding for: (i) acetolactate synthase and/or (ii) ketol-acid reductoisomerase; and (b) growing the microorganism to produce 2,3-dihydroxyisovalerate. The microorganisms that can be used in this method are described throughout (such as a methanotroph). Additionally, the microorganisms can be transformed with or made to express one or more of the genes as disclosed throughout. Further the carbon sources can be any carbon source described throughout, such as a $C_1$ carbon source. The 2,3-dihydroxyisovalerate produced can be substantially pure. The 2,3-dihydroxyisovalerate that is produced can be recovered.

The 2,3-dihydroxyisovalerate can be further processed by the same microorganism, a different microorganism, or outside a microorganism (i.e., in vitro) through the use of additional enzymes such as a dihydroxy-acid dehydratase. The same microorganism can comprise a dihydroxy-acid dehydratase. In other instances, a different microorganism can comprise a dihydroxy-acid dehydratase or a dihydroxy-acid dehydratase is isolated from a cell and used in vitro. If the dihydroxy-acid dehydratase is in a different microorganism or is isolated from a cell, the microorganism/isolated enzyme can convert 2,3-dihydroxyisovalerate that is in the culture media (either by supplemental addition or by secretion by 2,3-dihydroxyisovalerate producing microorganism). The conversion of 2,3-dihydroxyisovalerate by dihydroxy-acid dehydratase can produce some desired products such as ketoisovalerate or isobutanol.

Amino Acids

Amino acids can be made using the methods and microorganisms disclosed throughout. For example, disclosed herein is a method of making amino acids comprising (a) contacting a genetically modified microorganism with a carbon substrate, where the microorganism comprises at least one heterologous gene encoding for: (i) acetolactate synthase and/or (ii) ketol-acid reductoisomerase; (b) growing the microorganism to produce 2,3-dihydroxyisovalerate; and (c) contacting the 2,3-dihydroxyisovalerate with one or more enzymes that are capable of converting 2,3-dihydroxyisovalerate into an amino acid. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The amino acids produced can be substantially pure. The amino acids that are produced can be recovered. The amino acids can be any one of valine, leucine, isoleucine, or any combination thereof.

The one or more enzymes that are capable of converting 2,3-dihydroxyisovalerate into an amino acid can be one or more of the following: dihydroxy-acid dehydratase; branched-chain amino acid transaminase (BAT2); branched-chain amino acid aminotransferase (BAT1); alpha-isopropylmalate synthase (LEU9, LEU4), isopropylmalate isomerase (LEU1), and/or beta-IPM dehydrogenase (LEU2).

For example, biosynthesis of valine includes steps of converting 2,3-dihydroxyisovalerate to 2-keto-isovalerate by dihydroxy-acid dehydratase, and conversion of 2-keto-isovalerate to valine by branched-chain amino acid transaminase (BAT2) and branched-chain amino acid aminotransferase (BAT1). Further, biosynthesis of leucine includes the same steps to 2-keto-isovalerate, followed by conversion of 2-keto-isovalerate to alpha-isopropylmalate by alpha-isopropylmalate synthase (LEU9, LEU4), conversion of alpha-isopropylmalate to beta-isopropylmalate by isopropylmalate isomerase (LEU1), conversion of beta-isopropylmalate to alpha-ketoisocaproate by beta-IPM dehydrogenase (LEU2), and finally conversion of alpha-ketoisocaproate to leucine by branched-chain amino acid transaminase (BAT2) and branched-chain amino acid aminotransferase (BAT1).

Ketoisovalerate

With regards to ketoisovalerate, one method disclosed herein is a method of making ketoisovalerate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, or (iv) any combination thereof; and (b) growing the microorganism to produce ketoisovalerate. The microorganisms that can be used in this method are described throughout (such as a methanotroph). Additionally, the microorganisms can be transformed with or made to express one or more of the genes as disclosed throughout. Further the carbon sources can be any carbon source described throughout, such as a $C_1$ carbon source. The ketoisovalerate produced can be substantially pure. The ketoisovalerate that is produced can be recovered.

The ketoisovalerate can be further processed by the same microorganism, a different microorganism, or outside a microorganism (i.e., in vitro) through the use of additional enzymes such as a 2-keto acid decarboxylase. The same microorganism can comprise a 2-keto acid decarboxylase. In other instances, a different microorganism can comprise a 2-keto acid decarboxylase or a 2-keto acid decarboxylase is isolated from a cell and used in vitro. If the 2-keto acid decarboxylase is in a different microorganism or is isolated from a cell, the microorganism/isolated enzyme can convert ketoisovalerate that is in the culture media (either by supplemental addition or by secretion by ketoisovalerate producing microorganism). The conversion of ketoisovalerate by 2-keto acid decarboxylase can produce some desired products such as isobutyraldehyde or isobutanol.

Isobutyraldehyde

With regards to isobutyraldehyde, one method disclosed herein is a method of making isobutyraldehyde comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isobutyraldehyde. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a C1 carbon source. The isobutyraldehyde produced can be substantially pure. The isobutyraldehyde that is produced can be recovered.

The isobutyraldehyde can be further processed by the same microorganism, a different microorganism, or outside a microorganism (i.e., in vitro) through the use of additional enzymes such as an alcohol dehydrogenase. The same microorganism can comprise an alcohol dehydrogenase. In other instances, a different microorganism can comprise an alcohol dehydrogenase or an alcohol dehydrogenase is isolated from a cell and used in vitro. If the alcohol dehydrogenase is in a different microorganism or is isolated from a cell, the microorganism/isolated enzyme can convert isobutyraldehyde that is in the culture media (either by supplemental addition or by secretion by isobutyraldehyde producing microorganism). The conversion of isobutyraldehyde by alcohol dehydrogenase can produce some desired products such as isobutanol or other products such as methyl methacrylate.

Isobutyrate

With regards to isobutyrate, one method disclosed herein is a method of making isobutyrate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isobutyrate. In some cases, isobutyraldehyde produced by the microorganism can be oxidized. This oxidization can produce isobutyrate. The oxidization can be performed by catalysts or an enzyme. In some cases, when enzymatic oxidization is required, a promiscuous phenylacetaldehyde dehydrogenase (PadA) can be used (e.g., an enzyme having an EC number of 1.2.1.39). The PadA can be from a microorganism such as E. coli. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isobutyrate produced can be substantially pure. The isobutyrate that is produced can be recovered.

The isobutyrate produced can be made into other products such as methyl methacrylate (MMA). Isobutyrate can also be combined with many other chemicals, which can in turn be used for a variety of purposes. For example, phenoxy ethyl isobutyrate or styralyl isobutyrate have pleasant scents and can be used in a variety of perfumes.

Methyl Methacrylate (MMA)

With regards to methyl methacrylate (MMA), disclosed herein is a method of making MMA comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; (b) growing the microorganism to produce isobutyraldehyde; and (c) contacting the isobutyraldehyde with one or more catalysts capable of converting isobutyraldehyde to MMA. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The MMA from this method can be substantially pure. The MMA produced can be recovered. The MMA can be converted into polymethyl methacrylate acrylic plastics.

Isobutyraldehyde can be oxidized (sometimes in liquid phase) to form isobutyric acid. The isobutyric acid can be dehydrogenated (e.g., in a gas phase) into methacrylic acid. The catalyst that can be used for dehydrogenation can be a heteropoly acid catalyst (e.g., 12-tungstosilicate and 12-molybdophosphate). The methacrylic acid can be then esterified to form methacrylates. Otake, M., and Onoda, T., "A New Route to Methacrylates from Isobutyraldehyde," *Studies in Surface Science and Catalysis*, Vol. 7, Part B: 780-791 (1981).

MMA is used primarily for the manufacture of polymethyl methacrylate acrylic plastics (PMMA). Methyl methacrylate can also be used for the production of the co-polymer methyl methacrylate-butadiene-styrene (MBS), which is used as a modifier for PVC. Another application of MMA is as cement used in total hip replacements as well as total knee replacements. MMA is also a raw material for the manufacture of other methacrylates. These derivatives include ethyl methacrylate (EMA), butyl methacrylate (BMA) and 2-ethyl hexyl methacrylate (2-EHMA). Methacrylic acid (MAA) is used as a chemical intermediate as well as in the manufacture of coating polymers, construction chemicals and textile applications.

Isovaleraldehyde

With regards to isovaleraldehyde, disclosed herein is a method of making isovaleraldehyde comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isovaleraldehyde. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isovaleraldehyde from this method can be substantially pure. The isovaleraldehyde produce can be recovered. Isovaleraldehyde can be produced as a significant product during the fermentation of pyruvate to isobutyraldehyde.

The amino acids produced by the methods and microorganisms described throughout can be converted into isovaleraldehyde. Isovaleraldehyde can be made when leucine is broken down. However, isovaleraldehyde can also be made by the hydroformylation of isobutene.

The isovaleraldehyde made by the methods and microorganisms described herein can be converted into different products. Isovaleraldehyde can be used as a flavoring in many different types of foods, such as beer, cheese, coffee, chicken, fish, chocolate, olive oil, and tea.

Isovaleraldehyde can also be used as a reactant in the synthesis of a number of compounds. For example, isovaleraldehyde can be used to synthesize 2,3-dimethyl-2-butene. 2,3-dimethyl-2-butene can then be converted to 2,3-dimethylbutane-2,3-diol and methyltert-butylketone, better known as pinacolone. Pinacolone can then be used in the synthesis of pesticides. Additionally, a range of pharmaceuticals, such as butizide, are synthesized from isovaleraldehyde and its corresponding acid.

Isovalerate

With regards to isovalerate, disclosed herein is a method of making isovalerate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, or (v) any combination thereof; and (b) growing the microorganism to produce isovalerate. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isovalerate from this method can be substantially pure. The isovalerate produced can be recovered. Isovalerate can be produced as a significant product during the fermentation of pyruvate to isobutyraldehyde. The amino acids produced by the methods and microorganisms described throughout can be converted into isovalerate. Isovalerate can be made when leucine is broken down.

The isovalerate made by the methods and microorganisms described herein can be converted into different products. Isovalerate esters can be used in perfumes as it has a pleasing scent. Isovaleric acid has also been used to synthesize β-hydroxyisovaleric acid.

Isopentanol With regards to isopentanol (also known as isoamyl alcohol or isopentyl alcohol), one method disclosed herein is a method of making isopentanol comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, or (iv) any combination thereof; and (b) growing the microorganism to produce isopentanol. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isopentanol produced can be substantially pure. The isopentanol that is produced can be recovered. The isopentanol can also be acetylated. Therefore, the microorganism can produce acetylated isopentanol.

Isopentanol is a main ingredient in the production of banana oil, an ester found in nature. Isopentanol is also produced as a flavoring for the food industry. Isopentanol is also one of the components of the aroma produced by black truffles. Isopentanol is also the main ingredient of Kovac's reagent, used for the bacterial diagnostic indole test. Isopentanol can also be used as an antifoaming agent in a Chloroform:Isomyl Alcohol reagent. Isopentanol is used in a phenol-chloroform extraction mixed with the chloroform to further inhibit RNase activity and prevent solubility of RNAs with long tracts of poly-adenine.

Isoamyl Acetate

With regards to isoamyl acetate, one method disclosed herein is a method of making isoamyl acetate comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, or (iv) any combination thereof; and (b) growing the microorganism to produce isoamyl acetate. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isoamyl acetate produced can be substantially pure. The isoamyl acetate that is produced can be recovered.

Isoamyl acetate can be formed by contact of isoamyl alcohol (e.g., isopentanol) and an acid catalyst (e.g., a lacial acetic acid or sulfuric acid). Sulfuric acid or an acidic ion exchange resin can be used as a catalyst.

Isoamyl acetate is used to confer banana flavor in foods. Pear oil commonly refers to a solution of isoamyl acetate in ethanol that is used as an artificial flavor. Isoamyl acetate can be used as a solvent for some varnishes and nitrocellulose lacquers. Isoamyl acetate can also be used in thermometers.

Pentadecanoic Acid

With regards to pentadecanoic acid, one method disclosed herein is a method of making pentadecanoic acid comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; and (b) growing the microorganism to produce pentadecanoic acid. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source.

The starter unit (propionyl-CoA) for pentadecanoic acid biosynthesis can be produced through amino acid degradation, such as isoleucine. The pentadecanoic acid that is produced can be recovered. The pentadecanoic acid produced can be substantially pure.

Pentadecanoic acid is rare in nature. It is a fatty acid of exogenous (primarily ruminant) origin. Many "odd" length long chain amino acids are derived from the consumption of dairy fats (milk and meat). The butterfat in cow's milk is its major dietary source and it is used as a marker for butterfat consumption. Pentadecanoic acid can decrease mother-to-child transmission of HIV through breastfeeding.

Isobutanol

With regards to isobutanol, one method disclosed herein is a method of making isobutanol comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; and (b) growing the microorganism to produce isobutanol. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isobutanol produced can be substantially pure. The isobutanol that is produced can be recovered.

The isobutanol can be further processed by the same microorganism, a different microorganism, or outside a microorganism (i.e., in vitro) through the use of additional enzymes or catalysts. The isobutanol can be made into different products such as isobutene.

Isobutene (aka Isobutylene)

With regards to isobutene, one method disclosed herein is a method of making isobutene comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; (b) growing the microorganism to produce isobutanol; and (c) dehydrating the isobutanol to form isobutene. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The isobutene produced can be substantially pure. The isobutene that is produced can be recovered.

In some instances, the dehydration of isobutanol can occur enzymatically. For example, an oleate hydratase can be used to convert the isobutanol produced herein to make isobutene. Should an enzymatic dehydration be desired, the genetically modified can comprises one or more oleate hydratases.

Isobutene can be further converted into different products. For example, isobutene can be used as an intermediate in the production of a variety of products. It is reacted with methanol and ethanol in the manufacture of the gasoline oxygenates methyl tert-butyl ether (MTBE) and ethyl tert-butyl ether (ETBE), respectively. Alkylation with butane produces isooctane, another fuel additive. Isobutene is also used in the production of methacrolein. Polymerization of isobutene produces butyl rubber (polyisobutylene). Antioxidants such as butylated hydroxytoluene (BHT) and butylated hydroxyanisole (BHA) are produced by Friedel-Crafts alkylation of phenols using isobutene.

Para-Xylene (p-Xylene)

With regards to para-xylene (p-xylene), one method disclosed herein is a method of making p-xylene comprising (a) contacting a genetically modified microorganism with a carbon substrate, where the microorganism comprises at least one heterologous gene encoding for: (i) acetolactate synthase, (ii) ketol-acid reductoisomerase, (iii) dihydroxy-acid dehydratase, (iv) 2-keto acid decarboxylase, (v) alcohol dehydrogenase, or (vi) any combination thereof; (b) growing the microorganism to produce isobutanol; and (c) contacting the isobutanol with a catalyst capable of converting isobutanol into p-xylene. The microorganisms that can be used in this method are described throughout (such as a methanotroph). Additionally, the microorganisms can be transformed with or made to express one or more of the genes as disclosed throughout. Further, the carbon sources can be any carbon source described throughout, such as a $C_1$ carbon source. The catalyst of (c) can be a catalyst that is capable of dehydrating isobutanol. The dehydration of isobutanol can form a $C_4$ alkene, such as isobutene. The $C_4$ alkene can subsequently be dimerized by an oligomerization catalyst to form a $C_8$ alkene, such as 2,4,4-trimethylpentenes or 2,5-dimethylhexene. The $C_8$ alkene can be dehydrocyclized by a dehydrocyclization catalyst to form p-xylene. The p-xylene that is produced can be recovered. The p-xylene produced can be substantially pure.

In some cases, the dehydration catalyst can be an organic or inorganic acid, or a metal salt, for example, an acidic γ-alumina catalyst. In some cases, the oligomerization catalyst can be a heterogeneous acidic catalyst. For example, the oligomerization catalyst can be an acidic zeolite, solid phosphoric acid, or a sulfonic acid resin. In some cases, the dehydrocyclization catalyst is a heterogeneous metal-containing dehydrogenation catalyst. In some cases, the dehydrocyclization catalyst is a supported chromium-containing compound. The dehydrocyclization catalyst can also be a chromium-oxide treated alumina; platinum- and tin-containing zeolites; or alumina, cobalt- or molybdenum-containing alumina.

p-xylene is an important chemical feedstock. Among other industrial applications, it is a raw material in the large scale synthesis of various polymers, such as for the production of terephthalic acid to make polyesters such as polyethylene terephthalate. It also can be polymerized directly to produce parylene. p-xylene is converted into either TPA or TPA esters by oxidation over a transition metal-containing catalyst. For example, p-xylene can be oxidized in air or oxygen (or air or oxygen diluted with other gases) over a catalyst containing nickel, manganese, and cobalt. p-xylene produced can be made into a renewable polyester by contacting TPA with ethylene glycol, propylene glycol, or butylene glycol in the presence of an acidic polymerization catalyst, such as antimony (III) oxide.

IV. Fermentation

In general, the microorganisms disclosed herein should be used in fermentation conditions that are appropriate to convert a carbon (such as methane) to isobutanol (or other desired product). Reaction conditions that should be considered include, but are not limited to, temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, it is preferred that the fermentation be performed at a pressure higher than ambient pressure. Operating at increased pressures allows a significant increase in the rate of carbon transfer (e.g., methane) from the gas phase to the liquid phase where it can be taken up by the microorganism as a carbon source for the production of isobutanol (or other desired products). This in turn means that the retention time (defined as the liquid volume in the bioreactor divided by the input gas flow rate) can be reduced when bioreactors are maintained at elevated pressure rather than atmospheric pressure.

The use of pressurized systems can greatly reduce the volume of the bioreactor required, and consequently the capital cost of the fermentation equipment. In some cases, reactor volume can be reduced in linear proportion to increases in reactor operating pressure, i.e., bioreactors operated at 10 atmospheres of pressure need only be one tenth the volume of those operated at 1 atmosphere of pressure.

It is also desirable that the rate of introduction of the gaseous carbon substrate (such as methane) is such as to ensure that the concentration of gaseous carbon substrate (such as methane) in the liquid phase does not become limiting. This is because a consequence of carbon substrate (e.g., methane) limited conditions can be that the isobutanol (or other desired product) is consumed by the culture (or other microorganism present).

Fermentation Conditions pH can be optimized based on the microorganism used. For example, the pH used during the methanotroph fermentation of methane to a desired product can be from 4 to 10. In other instances, the pH can be from 5 to 9; 6 to 8; 6.1 to 7.9; 6.2 to 7.8; 6.3 to 7.7; 6.4 to 7.6; or 6.5 to 7.5. For example, the pH can be from 6.6 to 7.4. In some cases, the pH can be from 5 to 9. In some cases, the pH can be from 6 to 8. In some cases, the pH can be from 6.1 to 7.9. In some cases, the pH can be from 6.2 to 7.8. In some cases, the pH can be from 6.3 to 7.7. In some cases, the pH can be from 6.4 to 7.6. In some cases, the pH can be from 6.5 to 7.5. In some cases, the pH used for the fermentation of methanotrophs can be greater than 6.

Temperature can also be adjusted based on the microorganism used. For example, the temperature used during the methanotroph fermentation of methane to a desired product can be from 30° C. to 45° C. In other instances, the temperature of the fermentation can be from 30° C. to 45° C.; 31° C. to 44° C.; 32° C. to 43° C.; 33° C. to 42° C.; 34° C. to 41° C.; 35° C. to 40° C. For example, the temperature can be from 36° C. to 39° C. (e.g., 36° C., 37° C., 38° C., or 39° C. In some cases, the temperature can be from 30° C. to 45° C. (e.g., 30° C., 31° C., 32° C., 33° C., 34° C., 35° C., 36° C., 37° C., 38° C., 39° C., 40° C., 41° C., 42° C., 43° C., 44° C., or 45° C. In some cases, the temperature can be from 31° C. to 44° C. (e.g., 31° C., 32° C., 33° C., 34° C., 35° C., 36° C., 37° C., 38° C., 39° C., 40° C., 41° C., 42° C., 43° C., or 44° C. In some cases, the temperature can be from 32° C. to 43° C. In some cases, the temperature can be from 33° C. to 42° C. (e.g., 33° C., 34° C., 35° C., 36° C., 37° C., 38° C., 39° C., 40° C., 41° C., or 42° C.). In some cases, the temperature can be from 34° C. to 41° C. (e.g., 34° C., 35° C., 36° C., 37° C., 38° C., 39° C., 40° C., or 41° C.). In some cases, the temperature can be from 35° C. to 40° C. (e.g., 35° C., 36° C., 37° C., 38° C., 39° C., or 40° C.).

In some cases, the temperatures can be within one tenth of a degree. For example, in some cases, the temperature of fermentation can be 37.0° C., 37.1° C., 37.2° C., 37.3° C., 37.4° C., 37.5° C., 37.6° C., 37.7° C., 37.8° C., 37.9° C., 38.0° C., 38.1° C., 38.2° C., 38.3° C., 38.4° C., 38.5° C., 38.6° C., 38.7° C., 38.8° C., 38.9° C., 39.0° C., 39.1° C., 39.2° C., 39.3° C., 39.4° C., 39.5° C., 39.6° C., 39.7° C., 39.8° C., 39.9° C., 40.0° C., 40.1° C., 40.2° C., 40.3° C., 40.4° C., 40.5° C., 40.6° C., 40.7° C., 40.8° C., 40.9° C., 41.0° C., 41.1° C., 41.2° C., 41.3° C., 41.4° C., 41.5° C., 41.6° C., 41.7° C., 41.8° C., 41.9° C., 42.0° C., 42.1° C., 42.2° C., 42.3° C., 42.4° C., 42.5° C., 42.6° C., 42.7° C., 42.8° C., 42.9° C., 43.0° C., 43.1° C., 43.2° C., 43.3° C., 43.4° C., 43.5° C., 43.6° C., 43.7° C., 43.8° C., 43.9° C., 44.0° C., 44.1° C., 44.2° C., 44.3° C., 44.4° C., 44.5° C., 44.6° C., 44.7° C., 44.8° C., 44.9° C., 45.0° C., 45.1° C., 45.2° C., 45.3° C., 45.4° C., 45.5° C., 45.6° C., 45.7° C., 45.8° C., 45.9° C., 46.0° C., 46.1° C., 46.2° C., 46.3° C., 46.4° C., 46.5° C., 46.6° C., 46.7° C., 46.8° C., 46.9° C., 47.0° C., 47.1° C., 47.2° C., 47.3° C., 47.4° C., 47.5° C., 47.6° C., 47.7° C., 47.8° C., or 47.9° C.

In some cases, the temperature of fermentation can be from 37.0° C. to 47.9° C. In some cases, the temperature of fermentation can be from 37.1° C. to 47.8° C. In some cases, the temperature of fermentation can be from 37.2° C. to 47.7° C. In some cases, the temperature of fermentation can be from 37.3° C. to 47.6° C. In some cases, the temperature of fermentation can be from 37.4° C. to 47.5° C. In some cases, the temperature of fermentation can be from 37.5° C. to 47.4° C. In some cases, the temperature of fermentation can be from 37.6° C. to 47.3° C. In some cases, the temperature of fermentation can be from 37.7° C. to 47.2° C. In some cases, the temperature of fermentation can be from 37.8° C. to 47.1° C. In some cases, the temperature of fermentation can be from 37.9° C. to 47.0° C. In some cases, the temperature of fermentation can be from 38.0° C. to 46.9° C. In some cases, the temperature of fermentation can be from 38.1° C. to 46.8° C. In some cases, the temperature of fermentation can be from 38.2° C. to 46.7° C. In some cases, the temperature of fermentation can be from 38.3° C. to 46.6° C. In some cases, the temperature of fermentation can be from 38.4° C. to 46.5° C. In some cases, the temperature of fermentation can be from 38.5° C. to 46.4° C. In some cases, the temperature of fermentation can be from 38.6° C. to 46.3° C. In some cases, the temperature of fermentation can be from 38.7° C. to 46.2° C. In some cases, the temperature of fermentation can be from 38.8° C. to 46.1° C. In some cases, the temperature of fermentation can be from 38.9° C. to 46.0° C. In some cases, the temperature of fermentation can be from 39.0° C. to 45.9° C. In some cases, the temperature of fermentation can be from 39.1° C. to 45.8° C. In some cases, the temperature of fermentation can be from 39.2° C. to 45.7° C. In some cases, the temperature of fermentation can be from 39.3° C. to 45.6° C. In some cases, the temperature of fermentation can be from 39.4° C. to 45.5° C. In some cases, the temperature of fermentation can be from 39.5° C. to 45.4° C. In some cases, the temperature of fermentation can be from 39.6° C. to 45.3° C. In some cases, the temperature of fermentation can be from 39.7° C. to 45.2° C. In some cases, the temperature of fermentation can be from 39.8° C. to 45.1° C. In some cases, the temperature of fermentation can be from 39.9° C. to 45.0° C. In some cases, the temperature of fermentation can be from 40.0° C. to 44.9° C. In some cases, the temperature of fermentation can be from 40.1° C. to 44.8° C. In some cases, the temperature of fermentation can be from 40.2° C. to 44.7° C. In some cases, the temperature of fermentation can be from 40.3° C. to 44.6° C. In some cases, the temperature of fermentation can be from 40.4° C. to 44.5° C. In some cases, the temperature of fermentation can be from 40.5° C. to 44.4° C. In some cases, the temperature of fermentation can be from 40.6° C. to 44.3° C. In some cases, the temperature of fermentation can be from 40.7° C. to 44.2° C. In some cases, the temperature of fermentation can be from 40.8° C. to 44.1° C. In some cases, the temperature of fermentation can be from 40.9° C. to 44.0° C. In some cases, the temperature of fermentation can be from 41.0° C. to 43.9° C. In some cases, the temperature of fermentation can be from 41.1° C. to 43.8° C. In some cases, the temperature of fermentation can be from 41.2° C. to 43.7° C. In some cases, the temperature of fermentation can be from 41.3° C. to 43.6° C. In some cases, the temperature of fermentation can be from 41.4° C. to 43.5° C. In some cases, the temperature of fermentation can be from 41.5° C. to 43.4° C. In some cases, the temperature of fermentation can be from 41.6° C. to 43.3° C. In some cases, the temperature of fermentation can be from 41.7° C. to 43.2° C. In some cases, the temperature of fermentation can be from 41.8° C. to 43.1° C. In some cases, the temperature of fermentation can be from 41.9° C. to 43.0° C. In some cases, the temperature of fermentation can be from 42.0° C. to 42.9° C. In some cases, the temperature of fermentation can be from 42.1° C. to 42.8° C. In some cases, the temperature of fermentation can be from 42.2° C. to 42.7° C. In some cases, the temperature of fermentation can be from 42.3° C. to 42.6° C. In some cases, the temperature of fermentation can be from 42.4° C. to 42.5° C.

Availability of oxygen and other gases such as gaseous $C_1$ carbon substrates (such as methane) can affect overall microorganism biomass accumulation. For example, when considering oxygen availability, the percent of dissolved oxygen (DO) within the media can be from 10% to 40%. In certain instances, the DO concentration can be from 10% to 20%; 15% to 25%; 17% to 30%; 20% to 35%; 25% to 40%. For example, in some cases the DO concentration can be from 10% to 20%. In other cases, the DO can be from 15% to 25%. In some instances, the DO can be from 17% to 30%. In some cases, the DO can be from 20% to 35%. In some cases, the DO can be from 25% to 40%. In some cases, the DO can be 15%. In some cases, the DO can be 20%. In some cases, the DO can be 25%. In some cases, these DO concentrations can be used to grow the number of methanotrophs, e.g., increase overall biomass.

When using a methanotroph, the type of methane substances can have an effect on yield and fermentation rates. For example, natural gas can be used, which typically has a methane content of above 85% (e.g., above 90%) methane. Other components within natural gas can include but are not limited to, ethane, propane, iso-butane, normal-butane, iso-pentane, normal pentane, hexanes plus, nitrogen, carbon dioxide, oxygen, hydrogen, and hydrogen sulfides.

"Pure" methane can be used as well. In these cases, the methane typically comes from a tank. The methane contained within these tanks can range from 90% or greater methane content and the remaining gas are other gases (such as carbon dioxide). For example, gas having a methane content, of greater than 90% can be used during the fermentation process. In certain instances, the methane concentration can be greater than 90%; 91%; 92%; 93%; 94%; 95%; 96%; 97%; 98%; 99%; or 99.9%. In some instances, the methane concentration can be 90% methane and 10% are other gases (such as carbon dioxide). In other instances, the methane concentration can be 91% methane and 9% are other gases (such as carbon dioxide). In some instances, the methane concentration can be 92% methane and 8% are other gases (such as carbon dioxide). In some instances, the methane concentration can be 93% methane and 7% are other gases (such as carbon dioxide). In some instances, the methane concentration can be 94% methane and 6% are other gases (such as carbon dioxide). In some instances, the methane concentration can be 95% methane and 5% are other gases (such as carbon dioxide). In other instances, the methane concentration can be 96% methane and 4% are other gases (such as carbon dioxide). In some instances, the methane concentration can be 97% methane and 3% are other gases (such as carbon dioxide). In some instances, the methane concentration can be 98% methane and 2% are other gases (such as carbon dioxide). In some instances, the methane concentration can be 99% methane and 1% is other gases (such as carbon dioxide). In some instances, the methane concentration can be 99.9% methane and 0.1% is other gases (such as carbon dioxide).

In cases where a switch is used, the media can comprise the molecule that induces or represses the switch. For example, when a lanthanum switch is used to repress the expression of one or more of the genes described herein, the media can comprise lanthanum, which will repress expression of the one or more genes under the control of the switch.

In the case of lanthanum any one of the following concentrations can effectively repress expression of the one or more genes: 0.1 µM; 0.5 µM; 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 50 µM; 100 µM or more. In one case, 0.1 µM lanthanum can be used to repression expression of the one or more genes under the control of a lanthanum switch. In other cases, at least 0.5 µM lanthanum can be used. In other cases, at least 1 µM lanthanum can be used. In other cases, at least 2 µM lanthanum can be used. In other cases, at least 3 µM lanthanum can be used. In other cases, at least 4 µM lanthanum can be used. In other cases, at least 5 µM lanthanum can be used. In other cases, at least 6 µM lanthanum can be used. In other cases, at least 7 µM lanthanum can be used. In other cases, at least 8 µM lanthanum can be used. In other cases, at least 9 µM lanthanum can be used. In other cases, at least 10 µM lanthanum can be used. In other cases, at least 12.5 µM lanthanum can be used. In other cases, at least 15 µM lanthanum can be used. In other cases, at least 17.5 µM lanthanum can be used. In other cases, at least 20 µM lanthanum can be used. In other cases, at least 25 µM lanthanum can be used. In other cases, at least 50 µM lanthanum can be used. In other cases, at least 100 µM lanthanum can be used. In some cases, a range of 0.5 µM lanthanum to 100 µM lanthanum will effectively repress gene expression. In some cases, a range of 0.5 µM lanthanum to 50 µM lanthanum will repress gene expression. In other cases, a range of 1 µM lanthanum to 20 µM lanthanum will repress gene expression. In some cases, a range of 2 µM lanthanum to 15 µM lanthanum will repress gene expression. In some cases, a range of 3 µM lanthanum to 12.5 µM lanthanum will repress gene expression. In some cases, a range of 4 µM lanthanum to 12 µM lanthanum will repress gene expression. In some cases, a range of 5 µM lanthanum to 11.5 µM lanthanum will repress gene expression. In some cases, a range of 6 µM lanthanum to 11 µM lanthanum will repress gene expression. In some cases, a range of 7 µM lanthanum to 10.5 µM lanthanum will repress gene expression. In some cases, a range of 8 µM lanthanum to 10 µM lanthanum will repress gene expression.

In some cases, the lanthanum in the media can be diluted to turn on expression of the one or more lanthanum repressed genes. For example, in some cases, the dilution of lanthanum containing media can be 1:1 (1 part lanthanum containing media to 1 part non-lanthanum containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising lanthanum. The media can then be diluted to effectively turn on the expression of the lanthanum repressed genes. The microorganism can be then grown in conditions to promote the production of desired products, such as 2,3-BDO and acetoin (or others disclosed throughout).

In some cases, other rare earth metals can be used. For example, other rare earth metals such as cerium (Ce), dysprosium (Dy), erbium (Er), europium (Eu), gadolinium (Gd), holmium (Ho), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof, can be used to repress or activate a molecular switch.

Bioreactor

Fermentation reactions can be carried out in any suitable bioreactor. In some embodiments of the invention, the bioreactor can comprise a first, growth reactor in which the microorganisms are cultured, and a second, fermentation reactor, to which broth from the growth reactor is fed and in which most of the fermentation product (isobutyraldehyde and/or isobutanol, for example) is produced.

Product Recovery

The fermentation of the microorganisms disclosed herein can produce a fermentation broth comprising a desired product (e.g., isobutyraldehyde and/or isobutanol) and/or one or more by-products as well as the microorganisms (e.g., a genetically modified methanotroph), in the growth/fermentation medium.

The microorganisms and the methods herein can produce isobutyraldehyde and/or isobutanol at surprisingly high efficiency, more so than other known fermentation processes. For example, the microorganisms and the methods disclosed herein can convert a carbon substrate (such as methane) at a rate of greater than 40% of the theoretical maximum. This means that at least 40% of the available carbon within the system is converted into product, such as isobutyraldehyde and/or isobutanol. In some cases, the conversion of a carbon substrate into isobutyraldehyde and/or isobutanol can be at least 41%, 42%, 43%, 44%, 45%, 46%, 47%, 48%, 49%, 50%, 51%, 52%, 53%, 54%, 55%, 56%, 57%, 58%, 59%, or 60%. In some cases, the conversion of a $C_1$ carbon substrate into isobutyraldehyde and/or isobutanol can be at least 40% of the theoretical maximum. In some cases, the conversion of a $C_1$ carbon substrate into isobutyraldehyde and/or isobutanol can be at least 41% of the theoretical maximum. In some cases, the conversion of a $C_1$ carbon substrate into isobutyraldehyde and/or isobutanol can be at least 42% of the theoretical maximum. In some cases, the conversion of a $C_1$ carbon substrate into isobutyraldehyde and/or isobutanol can be at least 43% of the theoretical maximum. In some cases, the conversion of a $C_1$ carbon substrate into isobutyraldehyde and/or isobutanol can be at least 43% of the theoretical maximum. In some cases, the conversion of a $C_1$ carbon substrate into isobutyraldehyde and/or isobutanol can be at least 44% of the theoretical maximum. In some cases, the conversion of a $C_1$ carbon substrate into isobutyraldehyde and/or isobutanol can be at least 45% of the theoretical maximum. In some cases, the conversion of a $C_1$ carbon substrate into isobutyraldehyde and/or isobutanol can be at least 46% of the theoretical maximum. In some cases, the conversion of a $C_1$ carbon substrate into isobutyraldehyde and/or isobutanol can be at least 47% of the theoretical maximum. In some cases, the conversion of a $C_1$ carbon substrate into isobutyraldehyde and/or isobutanol can be at least 48% of the theoretical maximum. In some cases, the conversion of a $C_1$ carbon substrate into isobutyraldehyde and/or isobutanol can be at least 49% of the theoretical maximum. In some cases, the conversion of a $C_1$ carbon substrate into isobutyraldehyde and/or isobutanol can be at least 50% of the theoretical maximum. In some cases, the conversion of a $C_1$ carbon substrate into isobutyraldehyde and/or isobutanol can be at least 51% of the theoretical maximum. In some cases, the conversion of a $C_1$ carbon substrate into isobutyraldehyde and/or isobutanol can be at least 52% of the theoretical maximum. In some cases, the conversion of a $C_1$ carbon substrate into isobutyraldehyde and/or isobutanol can be at least 53% of the theoretical maximum. In some cases, the conversion of a $C_1$ carbon substrate into isobutyraldehyde and/or isobutanol can be at least 54% of the theoretical maximum. In some cases, the conversion of a $C_1$ carbon substrate into isobutyraldehyde and/or isobutanol can be at least 55% of the theoretical maximum. In some cases, the conversion of a $C_1$ carbon substrate into isobutyraldehyde and/or isobutanol can be at least 56% of the theoretical maximum. In some cases, the conversion of a $C_1$ carbon substrate into isobutyraldehyde and/or isobutanol can be at least 57% of the theoretical maximum. In some cases, the conversion of a $C_1$ carbon substrate into isobutyraldehyde and/or isobutanol can be at least 58% of the theoretical maximum. In some cases, the conversion of a $C_1$ carbon substrate into isobutyraldehyde and/or isobutanol can be at least 59% of the theoretical maximum. In some cases, the conversion of a $C_1$ carbon substrate into isobutyraldehyde and/or isobutanol can be at least 60% of the theoretical maximum.

In certain methods when producing isobutyraldehyde, the overall amount isobutyraldehyde produced can be at least 1 g/L after 72 hours (or other time frame such as 48, 60, 84, 96, 108, or 120 hours). For example, the overall amount of isobutyraldehyde after 72 hours (or other time frame) produced can be at least 3 g/L to 7 g/L, 4 g/L to 8 g/L, 5 g/L to 9 g/L, 6 g/L to 10 g/L, 7 g/L to 11 g/L, 8 g/L to 12 g/L, 9 g/L to 13 g/L, 10 g/L to 14 g/L, 11 g/L to 15 g/L, 12 g/L to 16 g/L, 13 g/L to 17 g/L, 14 g/L to 18 g/L, 15 g/L to 19 g/L, 16 g/L to 20 g/L, 17 g/L to 21 g/L, or 18 g/L to 22 g/L. In some cases, the overall amount of isobutyraldehyde produced can be at least 7 g/L after 72 hours (or other time frame). In some cases, the overall amount of isobutyraldehyde produced can be at least 9 g/L after 72 hours (or other time frame). In some cases, the overall amount of isobutyraldehyde produced can be at least 12 g/L after 72 hours (or other time frame). In some cases, the overall amount of isobutyraldehyde produced can be at least 15 g/L after 72 hours (or other time frame). In some cases, the overall amount of isobutyraldehyde produced can be at least 18 g/L after 72 hours (or other time frame). In some cases, the overall amount of isobutyraldehyde produced can be at least 20 g/L after 72 hours (or other time frame).

In certain methods when producing isobutanol, the amount of isobutanol produced can be at least 1 g/L after 72 hours (or other time frame). For example, the amount of isobutanol produced can be at least 1 g/L to 5 g/L, 2 g/L to 6 g/L, 3 g/L to 7 g/L, or 4 g/L to 8 g/L, 5 g/L to 9 g/L, 6 g/L to 10 g/L, 7 g/L to 11 g/L, 8 g/L to 12 g/L, 9 g/L to 13 g/L, 10 g/L to 14 g/L, 11 g/L to 15 g/L, 12 g/L to 16 g/L, 13 g/L to 17 g/L, 14 g/L to 18 g/L, 15 g/L to 19 g/L, 16 g/L to 20 g/L, 17 g/L to 21 g/L, or 18 g/L to 22 g/L after 72 hours (or other time frame). In some cases, the amount of isobutanol produced can be at least 8 g/L after 72 hours (or other time frame). In some cases, the amount of isobutanol produced can be at least 7 g/L after 72 hours (or other time frame). In some cases, the amount of isobutanol produced can be at least 6 g/L after 72 hours (or other time frame). In some cases, the amount of isobutanol produced can be from 1 g/L to 5 g/L after 72 hours (or other time frame). In some cases, the amount of isobutanol produced can be from 2 g/L to 6 g/L after 72 hours (or other time frame). In some cases, the amount of isobutanol produced can be from 3 g/L to 7 g/L after 72 hours (or other time frame). In some cases, the amount of isobutanol produced can be from 4 g/L to 8 g/L after 72 hours (or other time frame). In some cases, the amount of isobutanol produced can be from 5 g/L to 9 g/L after 72 hours (or other time frame). In some cases, the amount of isobutanol produced can be from 6 g/L to 10 g/L after 72 hours (or other time frame). In some cases, the amount of isobutanol produced can be from 7 g/L to 11 g/L after 72 hours (or other time frame). In some cases, the amount of isobutanol produced can be from 8 g/L to 12 g/L after 72 hours (or other time frame). In some cases, the amount of isobutanol produced can be from 9 g/L to 13 g/L after 72 hours (or other time frame). In some cases, the amount of isobutanol produced can be from 10 g/L to 14 g/L after 72 hours (or other time frame). In some cases, the amount of isobutanol produced can be from 11 g/L to 15 g/L after 72 hours (or other time frame). In some cases, the amount of isobutanol produced can be from 12 g/L to 16 g/L after 72 hours (or other time frame). In some cases, the amount of isobutanol produced can be from 13 g/L to 17 g/L after 72 hours (or other time frame). In some cases, the amount of isobutanol produced can be from 14 g/L to 18 g/L after 72 hours (or other time frame). In some cases, the amount of isobutanol produced can be from 15 g/L to 19 g/L after 72 hours (or other time frame). In some cases, the amount of isobutanol produced can be from 16 g/L to 20 g/L after 72 hours (or other time frame). In some cases, the amount of isobutanol produced can be from 17 g/L to 21 g/L after 72 hours (or other time frame). In some cases, the amount of isobutanol produced can be from 18 g/L to 22 g/L after 72 hours (or other time frame).

In some cases, when methods such as "stripping" are used to isolate isobutanol (or isobutyraldehyde) continuously during fermentation, the amount of isobutanol (or isobutyraldehyde) present in the fermentation broth can be less than 10 g/L. For example, in some cases, the fermentation broth can comprise less than 9 g/L, 8 g/L, 7 g/L, 6 g/L, 5, g/L, 4 g/L, 3 g/L, 2 g/L, or 1 g/L of isobutanol (or isobutyraldehyde) during continuous fermentation. In some cases the fermentation broth titer can be less than 1 g/L of isobutanol (or isobutyraldehyde) during continuous fermentation.

In other cases, when microorganisms are used that normally produce at least some isobutyraldehyde and/or isobutanol, after genetic modification and fermentation, the genetically modified microorganism can produce isobutyraldehyde and/or isobutanol in concentrations that are at least 1.1× the amount that is normally produced. In some cases, the genetically modified microorganism can produce at least 2×, 3×, 4×, 5×, 10×, 25×, 50×, and or 100× the amount that is normally produced. In some cases, the genetically modified microorganism can produce at least 2× the amount that is normally produced. In some cases, the genetically modified microorganism can produce at least 3× the amount that is normally produced. In some cases, the genetically modified microorganism can produce at least 4× the amount that is normally produced. In some cases, the genetically modified microorganism can produce at least 5× the amount that is normally produced. In some cases, the genetically modified microorganism can produce at least 10× the amount that is normally produced. In some cases, the genetically modified microorganism can produce at least 25× the amount that is normally produced. In some cases, the genetically modified microorganism can produce at least 50× the amount that is normally produced. In some cases, the genetically modified microorganism can produce at least 100× the amount that is normally produced.

As discussed above, in certain embodiments the isobutyraldehyde and/or isobutanol produced in the fermentation reaction is converted to other desired products directly from the fermentation broth. In other embodiments, the isobutyraldehyde and/or isobutanol is first recovered from the fermentation broth before conversion to other desired products.

In some cases, isobutyraldehyde and/or isobutanol can be continuously removed from a portion of broth and recovered as purified isobutyraldehyde and/or isobutanol. In particular embodiments, the recovery of isobutyraldehyde and/or isobutanol includes passing the removed portion of the broth containing isobutyraldehyde and/or isobutanol through a separation unit to separate the microorganisms (e.g., genetically modified methanotroph) from the broth, to produce a cell-free isobutyraldehyde and/or isobutanol containing permeate, and returning the microorganisms to the bioreactor. The cell-free isobutyraldehyde and/or isobutanol-containing permeate can then can be stored or be used for subsequent conversion to other desired products.

The recovering of isobutyraldehyde and/or isobutanol and/or one or more other products or by-products produced in the fermentation reaction can comprise continuously removing a portion of the broth and recovering separately isobutyraldehyde and/or isobutanol and one or more other products from the removed portion of the broth. In some embodiments the recovery of isobutyraldehyde and/or isobutanol and/or one or more other products includes passing the removed portion of the broth containing isobutyraldehyde and/or isobutanol and/or one or more other products through a separation unit to separate microorganisms from the isobutyraldehyde and/or isobutanol and/or one or more other products, to produce cell-free isobutyraldehyde and/or isobutanol and one or more other product-containing permeate, and returning the microorganisms to the bioreactor.

In the above embodiments, the recovery of isobutyraldehyde and/or isobutanol and one or more other products can include first removing isobutyraldehyde and/or isobutanol from the cell-free permeate followed by removing the one or more other products from the cell-free permeate. The cell-free permeate can then be returned to the bioreactor.

Isobutyraldehyde and/or isobutanol, or a mixed product stream containing isobutyraldehyde and/or isobutanol, can be recovered from the fermentation broth. For example, methods that can be used can include but are not limited to, fractional distillation or evaporation, pervaporation, and extractive fermentation. For example, stripping, adsorption, pervaporation, membrane solvent extraction, and liquid liquid extraction can be used.

In liquid-liquid extraction, an extractant is contacted with the fermentation broth to partition the isobutyraldehyde and/or isobutanol between the fermentation broth and the extractant phase. The isobutyraldehyde and/or isobutanol and the extractant are recovered by a separation process, for example by distillation. In the recovery process, the isobutyraldehyde and/or isobutanol can also be separated from any water, non-condensable gas, and/or fermentation by-products which can have been removed from the fermentation broth through use of the extractant.

Pervaporation or vacuum membrane distillation can be used to concentrate isobutyraldehyde and/or isobutanol (Qureshi, N., el al., "Recovery of 2,3-Butanediol by Vacuum Membrane Distillation," *Separation Science and Technology* 29:13 (1994)) in water as an extract from the fermentation broth. A microporous polytetrafluoroethylene (PTFE) membrane is used in the integrated process, while a silicone membrane is usually used in pervaporative ethanol or butanol fermentations.

In certain cases, isobutyraldehyde and/or isobutanol and by-products are recovered from the fermentation broth by continuously removing a portion of the broth from the bioreactor, separating microbial cells from the broth (conveniently by filtration, for example), and recovering isobutyraldehyde and/or isobutanol and optionally other alcohols and acids from the broth. Alcohols can conveniently be recovered for example by distillation, and acids can be recovered for example by adsorption on activated charcoal. The separated microbial cells can be returned to the fermentation bioreactor. The cell free permeate remaining after the isobutyraldehyde and/or isobutanol have been removed is returned to the fermentation bioreactor. Additional nutrients can be added to the cell free permeate to replenish the nutrient medium before it is returned to the bioreactor.

Also, if the pH of the broth was adjusted during recovery of isobutyraldehyde and/or isobutanol and/or by-products, the pH should be re-adjusted to a similar pH to that of the broth in the fermentation bioreactor, before being returned to the bioreactor.

In certain embodiments, the isobutyraldehyde and/or isobutanol is continuously recovered from the fermentation broth or bioreactor and fed directly for chemical conversion to one or more desired products, such as gasoline additive or polymers. For example, the isobutyraldehyde and/or isobutanol can be fed directly through a conduit to one or more vessel suitable for chemical synthesis of one or more of the desired products.

Biomass

After the product is recovered from fermentation media, the remaining material can be spun down and harvested as biomass. This biomass can be cleaned in some cases, and then can be dried. The biomass can then be used as feed for fish, pigs, cows, and other animals. In some instances, the biomass is not dried, and can be used as a wetcake. The wetcake can also be used as animal feed.

In some cases, the biomass can comprises one or more of the microorganisms that are disclosed throughout. In some cases, the biomass can comprise homogeneous microorganisms. In some cases, the biomass can comprise a heterogeneous mix of microorganisms.

In some cases, the microorganism used in the biomass can comprise a methanotroph. In some cases, the methanotroph can be a *Methylococcus*. In some cases, the *Methylococcus* can be a *Methylococcus capsulatus*.

While some embodiments have been shown and described herein, such embodiments are provided by way of example only. Numerous variations, changes, and substitutions will now occur to those skilled in the art without departing from the invention. It should be understood that various alternatives to the embodiments of the invention described herein will be employed in practicing the invention.

EXAMPLES

Example 1: Genetic Engineering of Methanotrophs

To engineer a methanotroph to produce isobutyraldehyde or isobutanol, *M. capsulatus* was used as a starting point several isobutanol biosynthetic genes from a variety of sources. The various plasmids used are disclosed throughout. Generally however, the genes of the isobutanol pathway were expressed or overexpressed within a methanotroph. For example, various different combinations of α-acetolactate synthase (AlsS); ketol-acid reductoisomerase (IlvC); dihydroxy-acid dehydratase (IlvD); 2-keto acid decarboxylase (KDC); and alcohol dehydrogenase (ADH) were transformed into a methanotroph.

In order to produce methanotroph strains that can make isobutyraldehyde from methane, various different combinations of AlsS, ilvCs, ilvDs, and KDCs were transformed into a methanotroph and tested under conditions that promote isobutyraldehyde fermentation. In order to produce methanotroph strains that can produce isobutanol, the isobutyraldehyde strains were additionally transformed with various combinations of ADHs.

Example 2: Isobutanol Productivity

The various plasmids were transformed into transformation competent methanotroph strains, and the resulting strains (including biological replicate strains) were evaluated for isobutanol production in small scale microtiter plate fermentation or 1 L or 2 L fermentations, using methane as the carbon source. The various strains that were tested are found below.

Example 3: 2-keto acid decarboxylase (KDCs)

Figure 7:
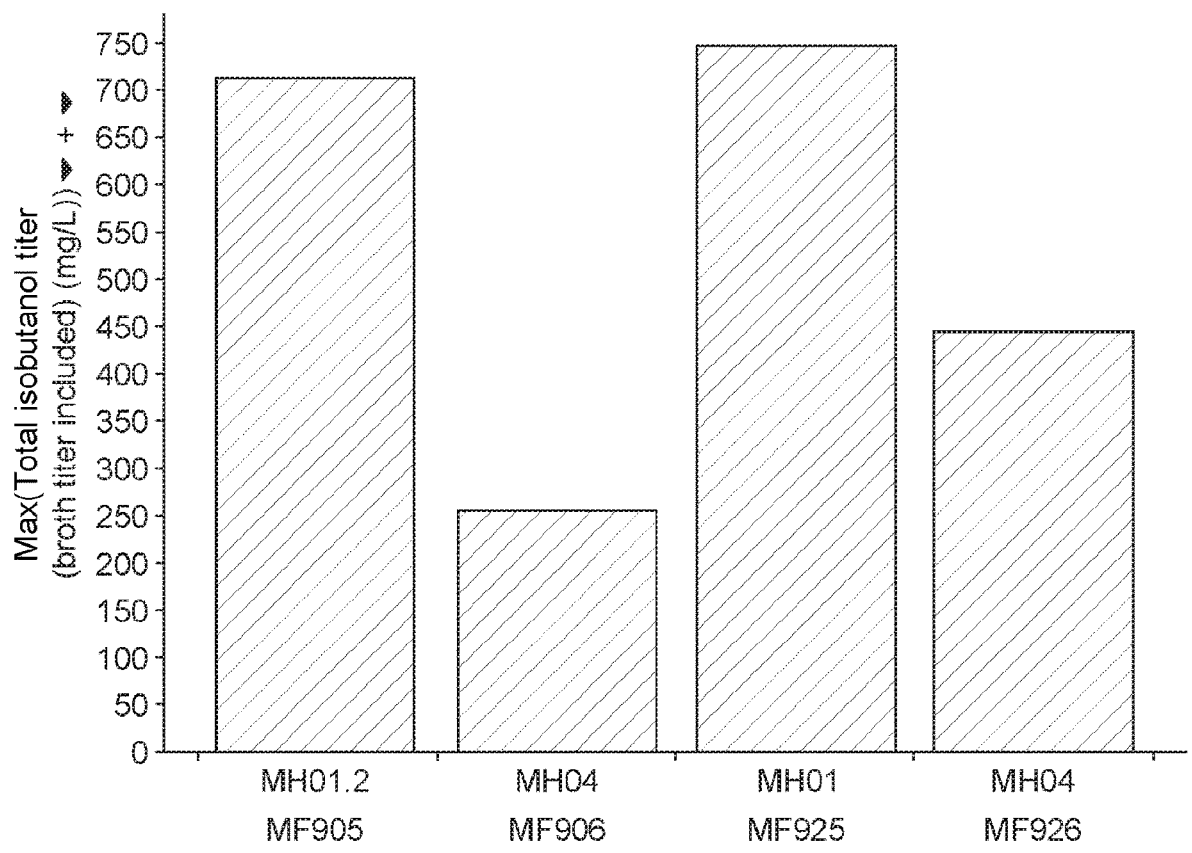
FIG. 7 shows a comparison of the isobutanol pathway in *E. coli* (see e.g., Atsumi, S., et al., "Non-fermentative pathways for synthesis of branch-chain higher alcohol as biofuels," *Nature*, 451(7174); 86-9 (2008) and Atsumi, S., et al., "Engineering the isobutanol biosynthetic pathway in *Escherichia coli* by comparison of three aldehyde reductase/alcohol dehydrogenase genes," *Appl. Microbiol. Biotechnol.*, 85(3): 651-7 (2010)) versus the isobutanol pathway designed herein using an *M. capsulatus* KDC. The data shows that KivD (used in the *E. coli* pathway by Atsumi et al.) does not produce nearly as much isobutanol compared to the *M. capsulatus* KDC when expressed in a methanotroph. *M. capsulatus* KDC is better in the context of the full pathway from pyruvate to isobutanol. MH04 comprises KivD, and MH01 comprises *M. capsulatus* KDC.

In order to improve isobutanol production, the effects of different KDCs on isobutanol production were compared using the methanotroph system disclosed herein. The isobutanol pathway in E. coli (see e.g., Atsumi et al. 2008 and Atsumi et al. 2010) was compared with the isobutanol pathway designed herein using an M. capsulatus KDC. The data in FIG. 7 shows that KivD (used in the E. coli pathway by Atsumi et al.) does not produce nearly as much isobutanol compared to the M. capsulatus KDC when expressed in a methanotroph. M. capsulatus KDC was found to be better in the context of the full pathway from pyruvate to isobutanol. For reference, MH04 comprises KivD, and MH01 comprises M. capsulatus KDC.

In order to test the effect different KDCs (e.g., Carnobacterium divergens v. Methylococcus capsulatus) have on the production of isobutanol in our strains, several different plasmids (Table 1, below) were transformed into a competent methanotroph strain and the resulting isobutanol production levels were evaluated.

Figure 8:
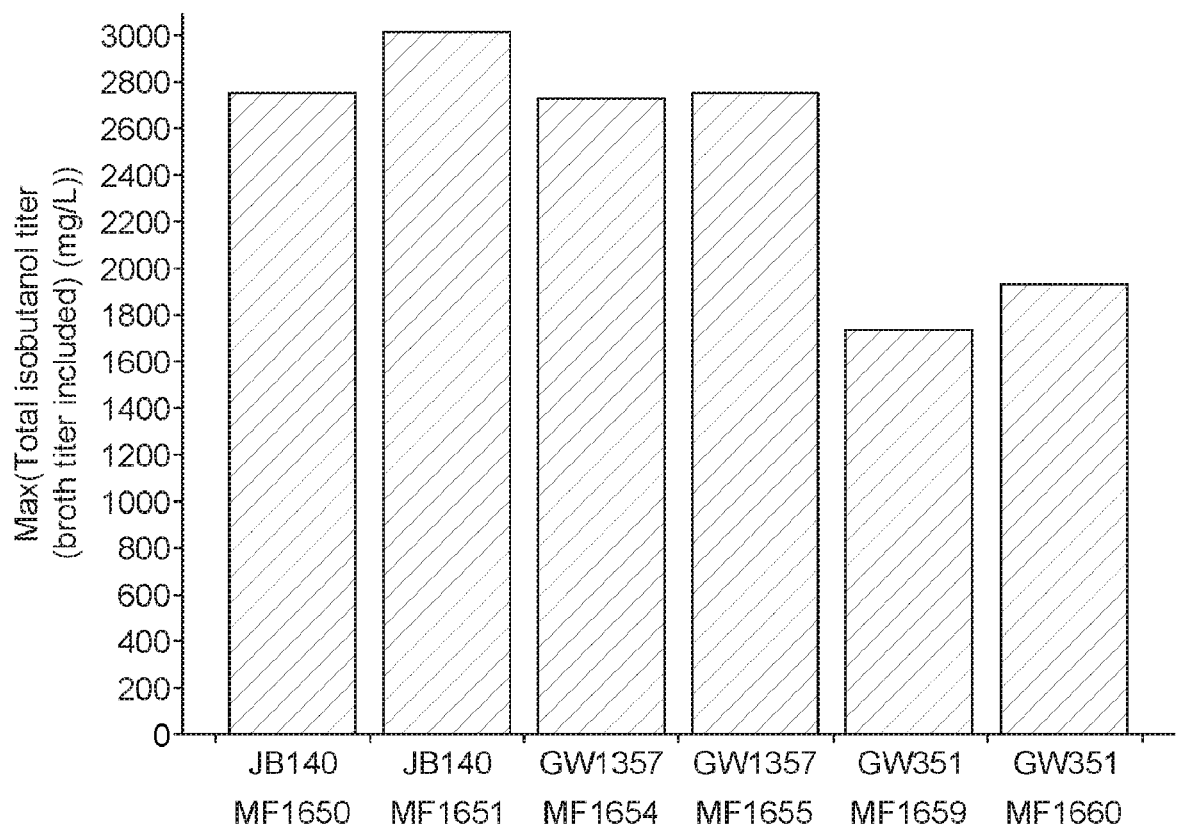
FIG. 8 shows isobutanol titers when methanotrophs are transformed with plasmids expressing a KDC from *Carnobacterium divergens* (CDI) (MF1650, MF1651; MF 1654; MI1655). Methanotrophs that were not transformed (MF1659, MF1660) with plasmids expressing *Carnobacterium divergens* (CDI) showed an approximate 40% decrease of isobutanol production.

As shown in FIG. 8, methanotrophs transformed with plasmids expressing a KDC from Carnobacterium divergens resulted in an approximate 40% increase over methanotrophs that expressed an endogenous Methylococcus capsulatus KDC.

The difference of overexpression of KDC from Methylococcus capsulatus and Lactococcus lactis was tested. Plasmids comprising isobutanol pathway genes, and KDCs from Methylococcus capsulatus or Lactococcus lactis were constructed and expressed. See Table 2. Methylococcus capsulatus transformants were produced with these plasmids and tested for the ability of the transformants to produce isobutanol.

TABLE 2

| | |
|---|---|
| MH01 | p.BAD > g.Mca.kdc_g.Sce.adh6_g.Bsu.alsS_g.Eco.ilvC_g.Eco.ilvD |
| MH04 | p.BAD > g.Lla.kivD_g.Sce.adh6_g.Bsu.alsS_g.Eco.ilvC_g.Eco.ilvD |

Figure 9:
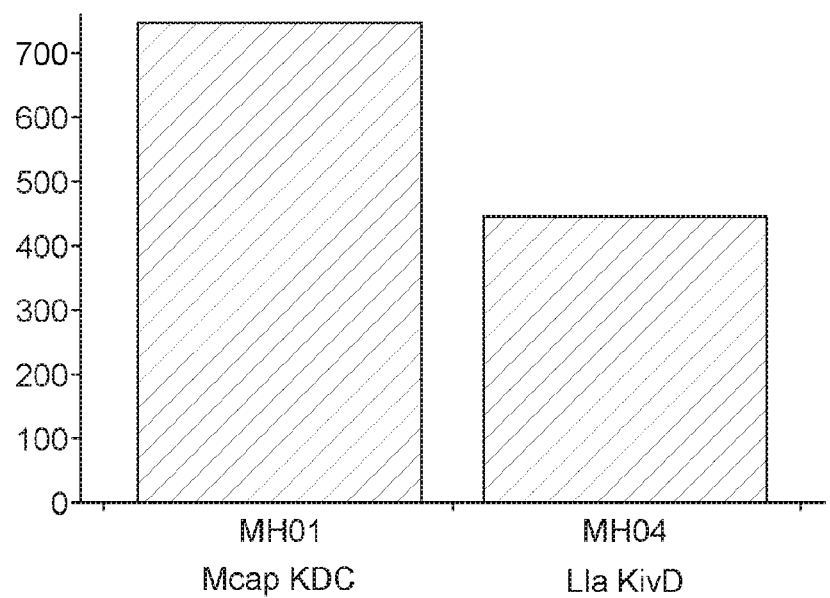
FIG. 9 shows the isobutanol production titer of methanotrophs that are transformed with *Methylococcus capsulatus* KDC or *Lactococcus lactis* KDC. KDC from *Methylococcus capsulatus* showed a vast improvement of isobutanol production (approximately 40%) compared to *Lactococcus lactis* KDC.

As seen in FIG. 9, KDC from Methylococcus capsulatus showed a vast improvement of isobutanol production compared to Lactococcus lactis KDC. The improvement was approximately a 40% increase.

Example 4: Alcohol Dehydrogenases (ADHs)

It was determined that not all the aldehydes produced by the genetically modified methanotrophs were converted into alcohols. In order to efficiently produce more alcohols such as isobutanol, different alcohol dehydrogenases were tested in the methanotroph model disclosed herein.

In order to test the effect alcohol dehydrogenases had on the production of isobutanol, several different plasmids were transformed into competent methanotroph strains and the resulting isobutanol production levels were evaluated.

Figure 10:
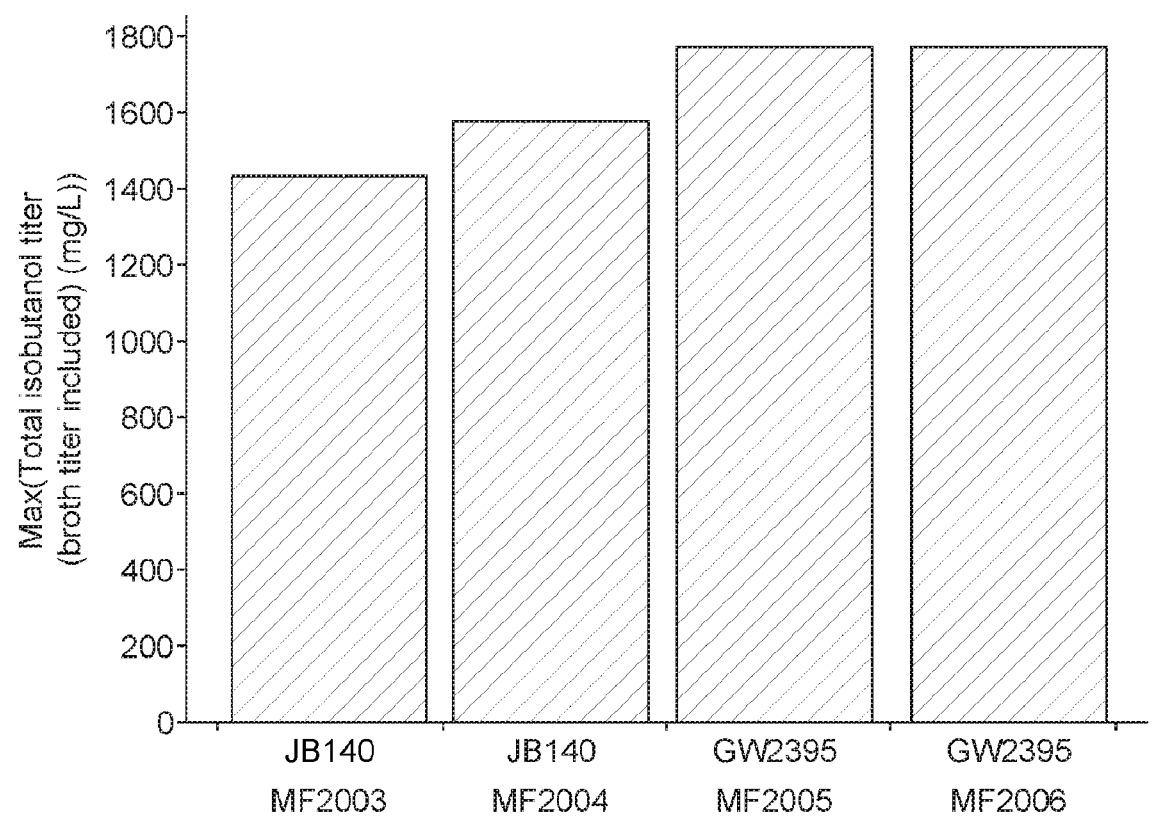
FIG. 10 shows isobutanol titers when methanotrophs are transformed with plasmids expressing either an Eco.fucO (MR2005; MF2006) or an Ec.YqdD (MF2003; MF2004) alcohol dehydrogenase. The methanotrophs expressing the Eco.fucO ADH showed increased isobutanol titers.

FIG. 10 shows isobutanol titers when methanotrophs are transformed with plasmids expressing either an Ec.fucO (MR2005; MF2006) or an Ec.YqdD (MF2003; MF2004) alcohol dehydrogenase. The methanotrophs expressing the Ec.fucO ADH showed increased isobutanol titers.

Another set of experiments testing different ADHs was performed. Constructs expressing different types of ADHs were created (Table 3, below). All methanotrophs expressed p.BAD>g.Mca.kdc variable ADH_g.Bsu.alsS_g.Eco.ilvC_g.Eco.ilvD. The ADH genes listed in Table 3 below were substituted into the plasmid listed as "variable ADH." The methanotrophs were then grown up in fermenters (2 L) and isobutanol production was tested.

TABLE 1

| | |
|---|---|
| JB140 | p.BAD > g.Cdi.kdc-g.Sce.adh6-Bsu.alsS-g.Eco.ilvC-g.Mca.ilvD-g.Eco.yqhD |
| SW1357 | p.BAD > Cdi.kdc_Sc.Adh6_Bs.AlsS-Mc.ilvC_Mc_ilvD |
| SW351 | p.BAD > g.Mca.kdc-g.Sce.adh6_g.Bsu.alsS_Ec.ilvC_Ec.ilvD |

TABLE 3

| Ref. # | SEQ ID NO: (Amino Acid) | SEQ ID NO: (Nucleotide) | ADH gene | Species |
|---|---|---|---|---|
| 1 | 23 | 24 | Ca_BdhA | C. acetobutylicum |
| 2 | 25 | 26 | Ca_BdhB | C. acetobutylicum |
| 3 | 27 | 28 | Ec_AdhP | E. coli |
| 4 | 29 | 30 | Ec_ahr | E. coli |
| 5 | 31 | 32 | Ec_FucO | E. coli |
| 6 | 33 | 34 | Ec_YjgB | E. coli |
| 7 | 35 | 36 | Ec_YqhD | E. coli |
| 8 | 37 | 38 | Gs_adh | G. stearothermophilus |
| 9 | 39 | 40 | Gs_adh2 | G. stearothermophilus |
| 10 | 41 | 42 | Gt_3237 | G. thermoglucosidas |
| 11 | 43 | 44 | Gt_3823 | G. thermoglucosidas |
| 12 | 45 | 46 | Ll_AdhA.29CB | L. lactis |
| 13 | 47 | 48 | Ll_AdhA | L. lactis |
| 14 | 49 | 50 | Oo_Adh3 | O. oeni |
| 15 | 51 | 52 | Pa_YqhD | P. atrosepticum |
| 16 | 53 | 54 | Psy_MadH | P. cryohalolentis |

Four of the top isobutanol producing plasmids were used that comprised: SL324 (p.BAD>g.Mca.kdc_g. Sce.adh6_g.Bsu.alsS_g.Eco.ilvC g.Eco.ilvD); JB03 (p.BAD> g.Mca.kdc_g.Cac.BdhB_g.Bsu.alsS_g.Eco.ilvC_g.Eco.ilvD); JB07 (p.BAD>g.Mca.kdc_g.Eco.FucO_g.Bsu.alsS_ g.Eco.ilvC_g.Eco.ilvD); and JB09 (p.BAD>g.Mca.kdc_g.Eco.YqhD_g.Bsu.alsS_g.Eco.ilvC_g.Eco.ilvD).

Figure 11:
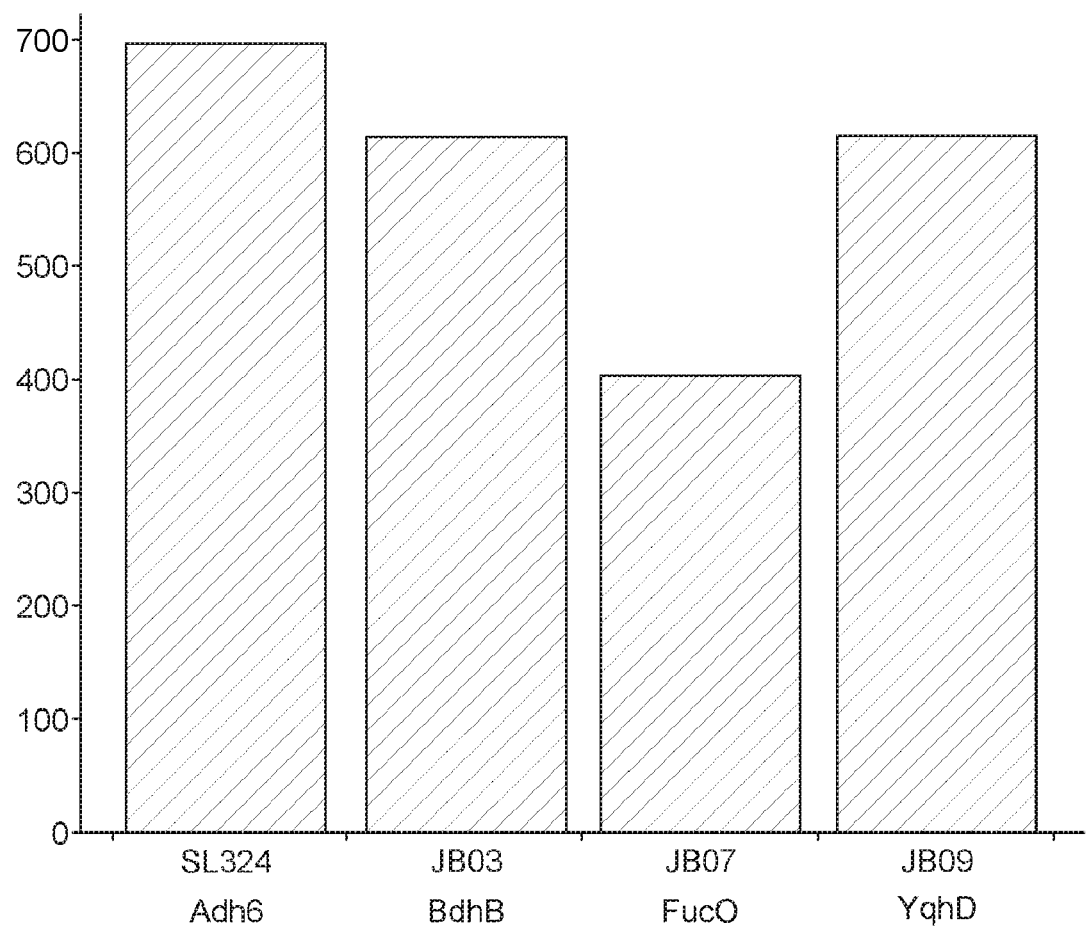
FIG. 11 shows isobutanol titers when methanotrophs are transformed with plasmids expressing different alcohol dehydrogenases and tested in a fermenter. Plasmids expressing Adh6, BdhB, FucO, and YqhD are represented. Methanotrophs expressing Adh6 produced the most isobutanol. BdhB and YqhD produced similar amounts of isobutanol.

As shown in FIG. 11, Adh6 produced the most isobutanol when testing in a fermenter (2 L). BdhB and YqhD produced similar amounts of isobutanol.

Example 5: Additional KDCs

Even with the optimization of ADHs, side products from the branch chain amino acid pathway were observed. Therefore, 21 additional KDCs listed in Table 4 were tested.

The following constructs in Table 5 were made and tested in 2 L fermenters:

TABLE 5

| Name | Genes |
|---|---|
| GW1035 | pBAD > Ach.KDC-Sc_Adh6-Bs_AlsS-Mc_IlvC-Mc_IlvD |
| GW1049 | pBAD > Cdi.KDC-Sc_Adh6-Bs_AlsS-Mc_IlvC-Mc_IlvD |
| GW1137 | pBAD > Mc.KDC-Adh6-Bs_AlsS-Mc_IlvC-Mc_IlvD |
| GW1145 | pBAD > Mde.KDC-Sc_Adh6-Bs_AlsS-Mc_IlvC-Mc_IlvD |
| GW1151 | pBAD > Mma-KDC-Sc_Adh6-Bs_AlsS-Mc_IlvC-Mc_IlvD |

Figure 12:
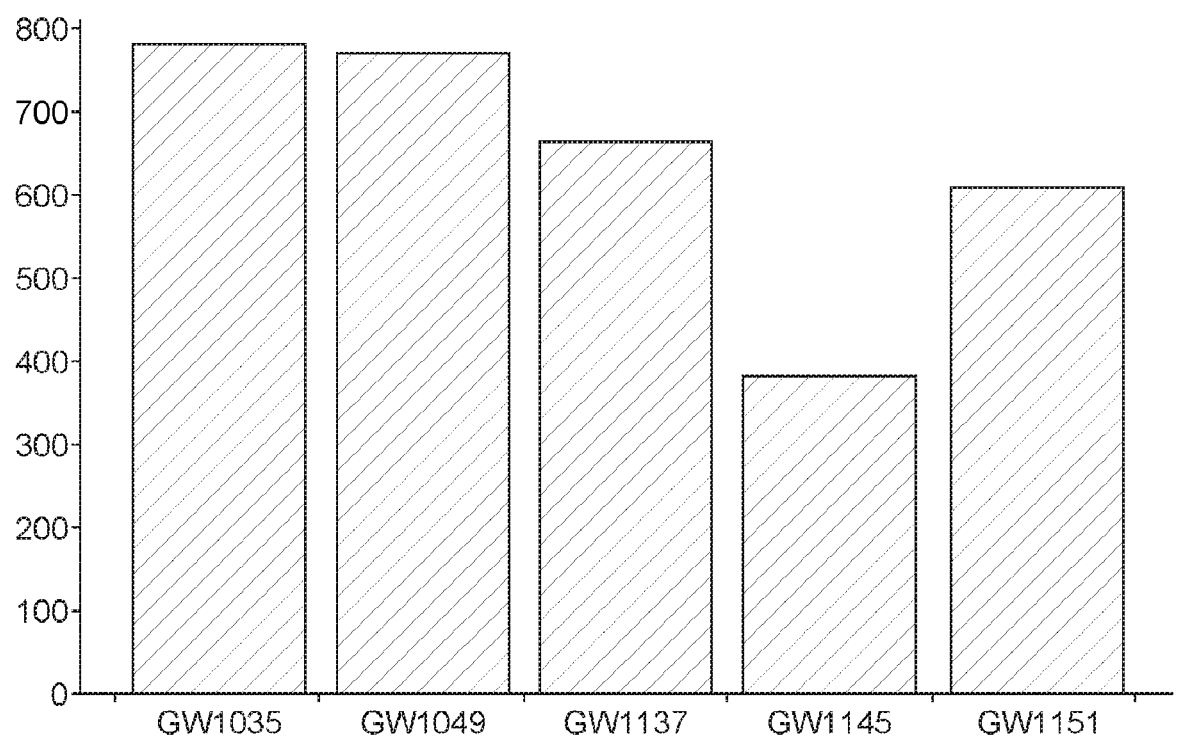
FIG. 12 shows isobutanol production levels using KDCs from *Andreprevotia chitinilytica* (GW1035), *Carnobacterium divergens* (GW1049), *Methylococcus capsulatus* (GW1137), *Methylomonas denitrificans* (GW1145), and *Methylobacter marinus* (GW1151). KDCs from *Andreprevotia chitinilytica* or *Carnobacterium divergens* showed increased ability to produce isobutanol titers at high titers, approximately 0.8 g/L of isobutanol. *Andreprevotia chitinilytica* or *Carnobacterium divergens* KDCs produced approximately double that of *Methylomonas denitrificans* KDC.

As shown in FIG. 12 KDCs from *Andreprevotia chitinilytica* or *Carnobacterium divergens* showed increased ability to produce isobutanol titers at high titers, approximately 0.8 g/L of isobutanol. *Andreprevotia chitinilytica* or *Carnobacterium divergens* KDCs produced approximately double that of *Methylomonas denitrificans* KDC.

TABLE 4

| Ref. No | SEQ ID NO: (Amino Acid) | SEQ ID NO: (Nucleotide) | KDC gene | Species |
|---|---|---|---|---|
| 1 | 55 | 56 | Msz.KDC | Methylocaldum szegediense |
| 2 | 57 | 58 | Mla.KDC | Methylosarcina lacus |
| 3 | 59 | 60 | Mde.KDC | Methylomonas denitrificans |
| 4 | 61 | 62 | Mme.KDC | Methylomonas methanica |
| 5 | 63 | 64 | Mcr.KDC | Methylohalobius crimeensis |
| 6 | 65 | 66 | Mma.KDC | Methylobacter marinus |
| 7 | 67 | 68 | Mlu.KDC | Methylobacter luteus |
| 8 | 69 | 70 | Lpu.KDC | Lamprocystis purpurea |
| 9 | 71 | 72 | Ach.KDC | Andreprevotia chitinilytica |
| 10 | 73 | 74 | Lla.KDC2 | Lactococcus lactis |
| 11 | 75 | 76 | Lla2.KDC2 | Lactococcus lactis |
| 12 | 77 | 78 | Sdi.KDC | Streptococcus didelphis |
| 13 | 79 | 80 | Eca.KDC | Enterococcus caccae |
| 14 | 81 | 82 | Eha.KDC | Enterococcus haemoperoxidus |
| 15 | 83 | 84 | Emo.KDC | Enterococcus moraviensis |
| 16 | 85 | 86 | Cma.KDC | Carnobacterium maltaromaticum |
| 17 | 87 | 88 | Bth.KDC | Brochothrix thermosphacta |
| 18 | 89 | 90 | Cga.KDC | Carnobacterium gallinarum |
| 19 | 91 | 92 | Cdi.KDC | Carnobacterium divergens |
| 20 | 93 | 94 | Hbi.KDC | Helicobacter bizzozeronii |
| 21 | 95 | 96 | Sau.KDC | Staphylococcus aureus subsp. aureus CIG290 |
| 22 | 97 | 98 | Fma.KDC | Fictibacillus macauensis |

Example 6: Isobutyraldehyde Productivity

In order to increase isobutyraldehyde, strains that did not have any heterologous alcohol dehydrogenases were designed. The same combinations of acetolactate synthase; ketol-acid reductoisomerase; dihydroxy-acid dehydratase; and 2-keto acid decarboxylase were generated and tested for isobutyraldehyde production. Data from two of the following strains are shown: GW692 (pBAD>Mc.KDC_ Bs.AlsS_ Ec.ILVC_Ec.ILVD); and SL691 (pBAD>Bsu.alsS-g. Cdi.kdc; p.mxaF>g.Mca.kdc-g.Eco.ilvC-g.Mca.ilvD).

Figure 13:
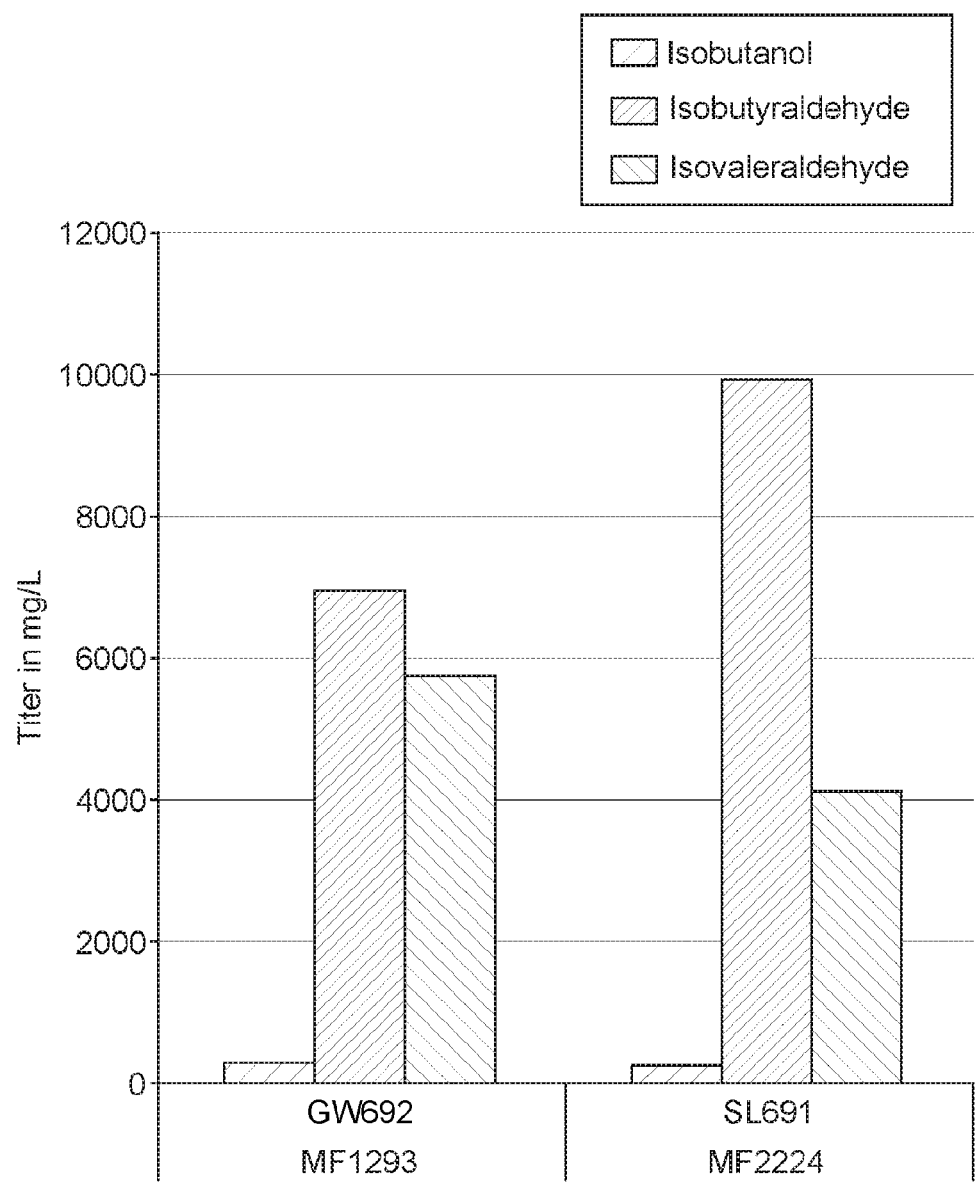
FIG. 13 shows production titers of isobutyraldehyde, isovaleraldehyde, and isobutanol of two strains that do not express heterologous alcohol dehydrogenase. The strains expressed acetolactate synthase; ketol-acid reductoisomerase; dihydroxy-acid dehydratase; and 2-keto acid decarboxylase; and are designated GW692 (pBAD>Mc.KDC_Bs.AlsS_Ec.ILVC_Ec.ILVD) and SL691 (p-BAD>Bsu.alsS-g.Cdi.kdc; p.mxaF>g.Mca.kdc-g.Eco.ilvC-g.Mca.ilvD). Strain GW692 produced approximately 7 g/L of isobutyraldehyde, whereas strain SL691 produced close to 10 g/L. Strain GW692 also produced approximately 5.8 g/L of isovaleraldehyde, whereas strain SL691 produced approximately 4.1 g/L.

As shown in FIG. 13, the production titers of isobutyraldehyde from the two strains were increased significantly. For example, strain GW692 produced approximately 7 g/L of isobutyraldehyde, whereas strain SL691 produced close to 10 g/L. Strain GW692 also produced approximately 5.8 g/L of isovaleraldehyde, whereas strain SL691 produced approximately 4.1 g/L. Negligible amounts of isobutanol were produced by both strains.

Example 7: Acetolactate Synthase

In order to increase the levels of 2-acteolactate, several strains were generated in which the acetolactate synthase were optimized. The plasmids described in Table 6 (below), were transformed into a methanotroph. The resulting strains were tested for the ability to utilize any increases of 2-acteolactate. Since 2,3-butanediol titers directly correlate to increases in 2-acetolactate in these strains, 2,3-BDO titers were measured as an indicator of increased 2-acteolactate production. Thus, if additional 2-acetolactate were produced by the differences in acetolactate synthase, there would be a correlating difference in 2,3-BDO titers.

Example 8: Regulating Gene Expression by Using Rare Earth Metals

Figure 15:
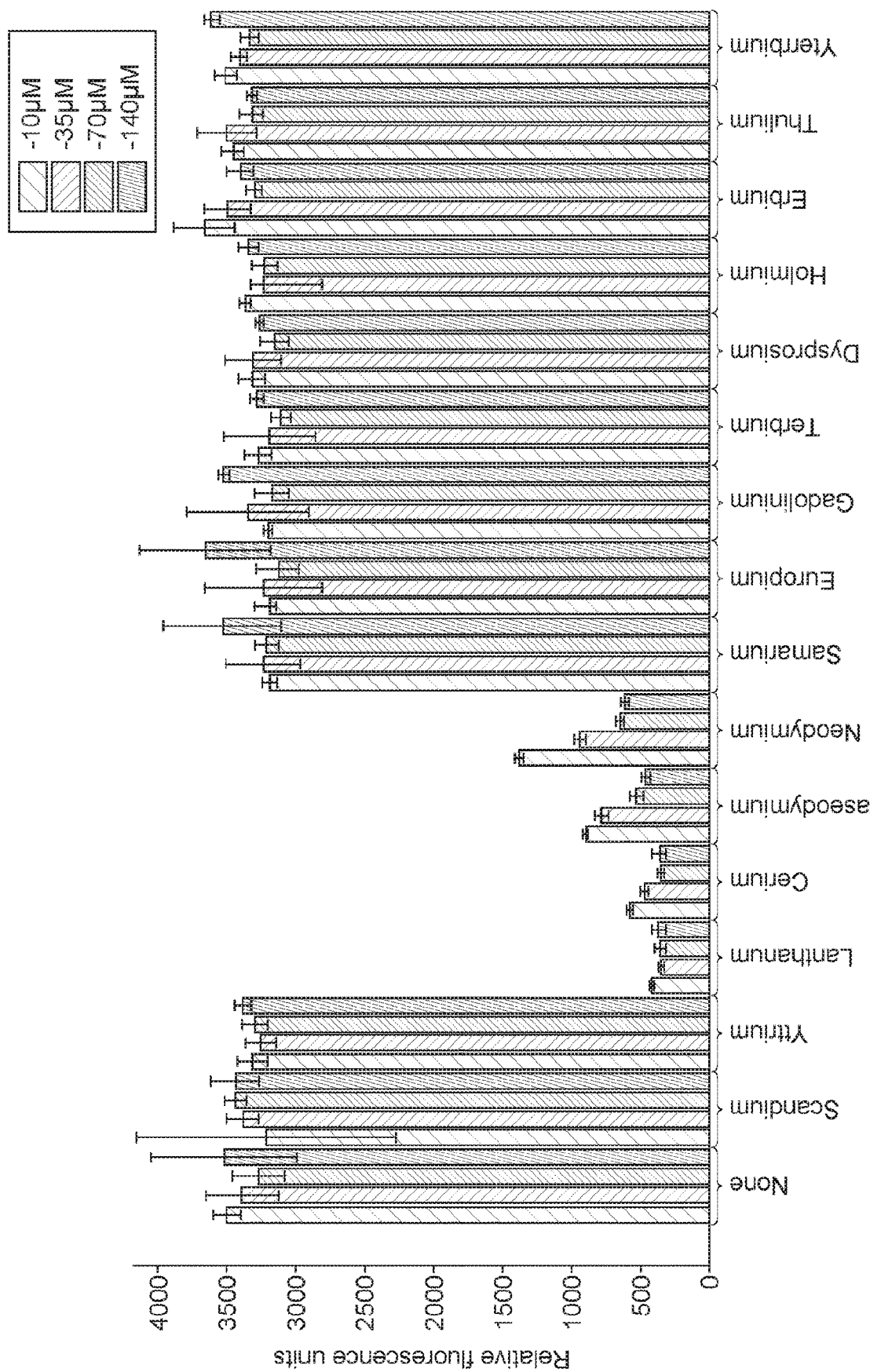
FIG. 15 shows the ability of various rare earth metals at a concentration of 10 µM, 35 µM, 70 µM, or 140 µM to activate or repress the pMxaF promoter as measured by mCherry. Scandium (Sc), yttrium (Y), samarium (Sm), europium (Eu), gadolinium (Gd), terbium (Tb), dysprosium (Dy), holmium (Ho), erbium (Er), thulium (Tm), and ytterbium (Yb) minimally activated or repressed the pMxaF promoter at 10 µM, 35 µM, 70 µM, or 140 µM. However, lanthanum (La), cerium (Ce), praseodymium (Pr), and neodymium (Nd) significantly repressed the expression of the pMxaF promoter at all concentrations. Maximal repression was observed starting at 35 µM for lanthanum, 70 µM for cerium, and 140 µM for praseodymium and neodymium.

In order to determine whether rare earth metals can be used to modify the expression of genes of the isobutyraldehyde and/or isobutanol pathways, different rare earth metals (at four different concentrations: 10, 35, 70, and 140 µM) were placed into the media in the presence of a *Methylococcus capsulatus* having a pMxaF promoter driving mCherry expression. The cultures were treated with for 24 hours with the respective rare earth metal. As seen in FIG. 15, lanthanum (La), cerium (Ce), praseodymium (Pr), and neodymium (Nd), repressed the pMxaF promoter. The other rare earth metals did not have an observable repressive effect on the pMxaF promoter.

Figure 16:
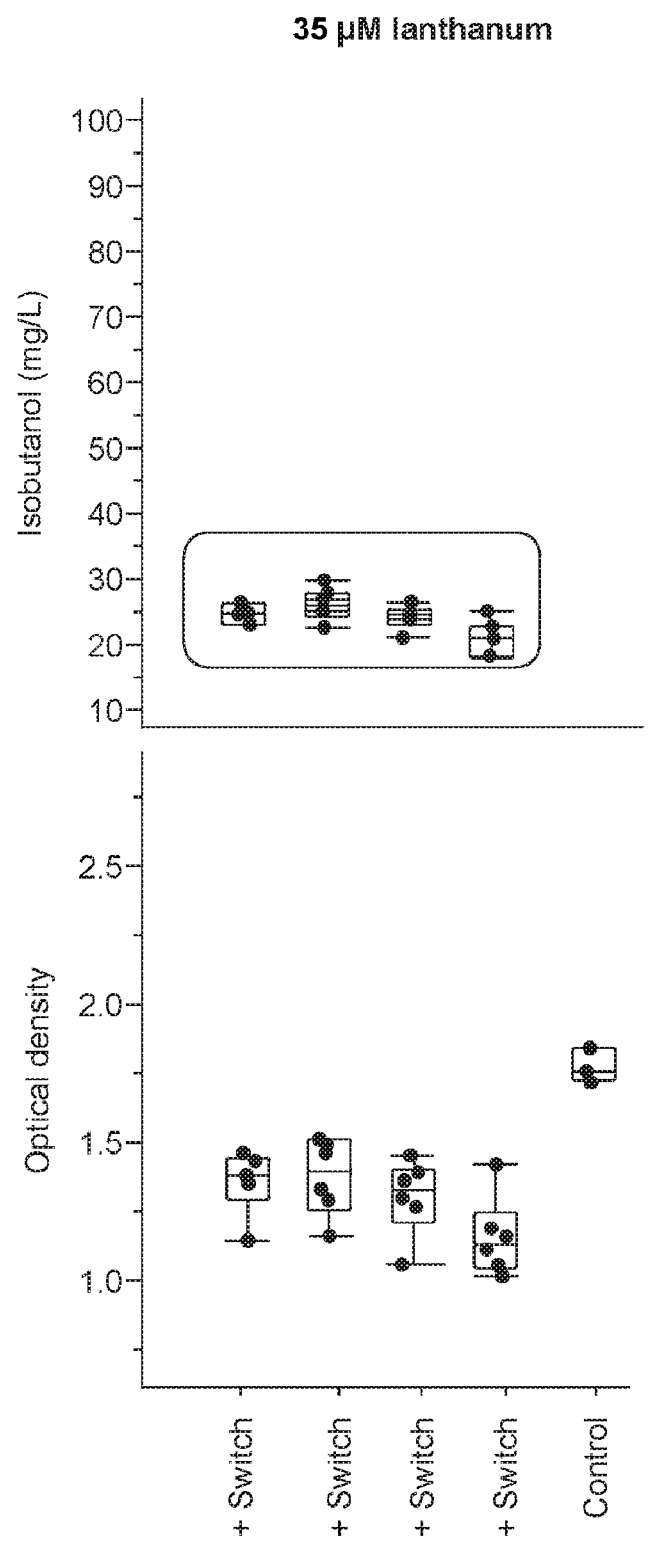
FIG. 16 shows the ability of a *M. capsulatus* strain expressing isobutanol pathway genes under the control of a rare earth metal switch to produce isobutanol. The strains were grown up in the presence of 35 µM lanthanum in shake bottles. After 24 hours, lanthanum was diluted out and the strain was allowed to produce isobutanol. Strains expressing isobutanol pathway genes under the control of a rare earth metal switch were able to produce isobutanol while the control strain did not. Optical density was highest in control strains.

*Methylococcus capsulatus* expressing isobutanol pathway genes under the control of a rare earth metal switch were grown up in the presence of 35 µM lanthanum in shake bottles. After 24 hours, lanthanum was diluted out and the strain was allowed to ferment isobutanol. As shown in FIG. 16, the strains expressing isobutanol pathway genes under the control of a rare earth metal switch were able to produce isobutanol. The control strain without isobutanol gene did not produce any isobutanol.

TABLE 6

| Strain | Strain Genotype | Average Titer (mg/L) | % diff. vs. XZ58 |
|---|---|---|---|
| XZ58 | p.BAD > g.Bsu.alsS > (rbs.GTW0001)g.Kpn.BudA > p.mxaF > g.Cau.ButA | 372 | 0.0% |
| XZ557 | p.BAD > g.Blic.alsS –> (rbs.GTW0001)g.Kpn.BudA-p.mxaF > g.Cau.ButA | 421 | 16.1% |
| XZ546 | p.BAD > g.Bsu.alsS-(rbs.Mca.MxaF)g.Kpn.BudA-p.mxaF > g.Cau.ButA | 373 | 0.3% |
| XZ562 | p.BAD > g.Blic.alsS-(rbs.Mca.MxaF)g.Kpn.BudA-p.mxaF > g.Cau.ButA | 538 | 44.6% |

Figure 14:
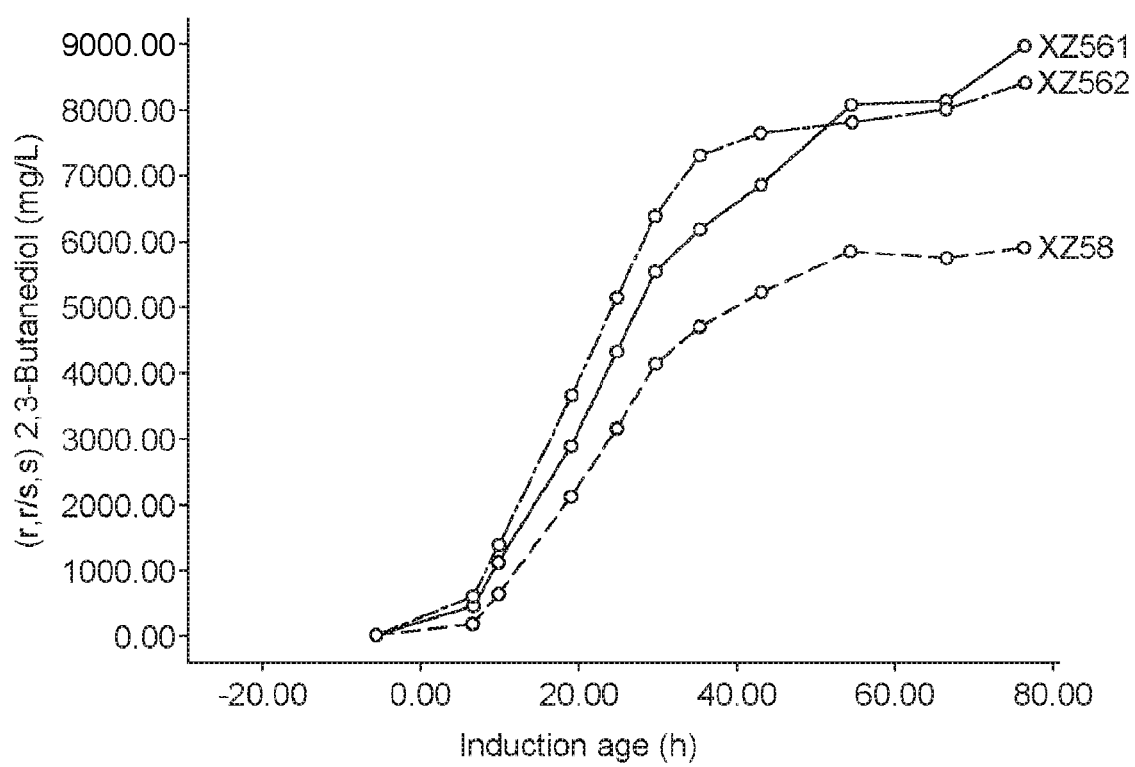
FIG. 14 shows that strains expressing a *Bacillus licheniformis* AlsS exhibited significantly improved 2-acetolate production, as indicated by measuring 2,3-BDO titers. In one strain expressing *Bacillus licheniformis* AlsS (XZ562), the 2,3-BDO titers increased an average of 44.6% over the XZ58 strain over the course of the fermentation run. Another biological replicate (XZ561), produced also significantly higher average 2,3-BDO titers compared to the XZ58 strain. This data indicates that methanotrophs expressing *Bacillus licheniformis* AlsS produce significantly higher levels of 2-acetolactate compared to methanotrophs expressing other AlsS, including the *Bacillus subtilis* AlsS.

The resulting strains from Table 6 were grown in a small scale microtiter plate fermentation using methane as the carbon source. As shown in Table 6 and in FIG. 14, the strains that expressed *Bacillus licheniformis* AlsS gene, showed better 2,3-BDO production titers than the strains that expressed *Bacillus subtilis* AlsS. In one example, a strain that has a substitution of only the AlsS gene (e.g., strains XZ557) exhibited an increase of 2,3-BDO production titer of up to 16.1% compared to strain XZ58. Strain XZ546, a strain having a substitution of only the ribosome binding site for the Kpn.BudA gene, showed virtually no increase of 2,3-BDO titers compared with strain XZ58. However, remarkably, a strain that contained rbs.Mca.MxaF for the Kpn.BudA, instead of a rbs.GTW0001 and expressed a *Bacillus licheniformis* AlsS gene (e.g., strain XZ562), exhibited a significant increase in 2,3-BDO titers, up to 44.6% compared to strain XZ58. This data indicates that methanotroph strains expressing *Bacillus licheniformis* AlsS, produce greatly increased levels of 2-acetolactate compared to those expressing *Bacillus subtilis* AlsS.

Example 9: Integration of Alcohol Dehydrogenase

In order to examine whether an integrated alcohol dehydrogenase gene could be used to produce isobutanol, a single copy of ADH6 was integrated into a *Methylococcus capsulatus* strain. Further, a strain expressing an ADH on a plasmid as well as having an integrated ADH was made. The strains were tested for their ability to form isobutanol.

Figure 17:
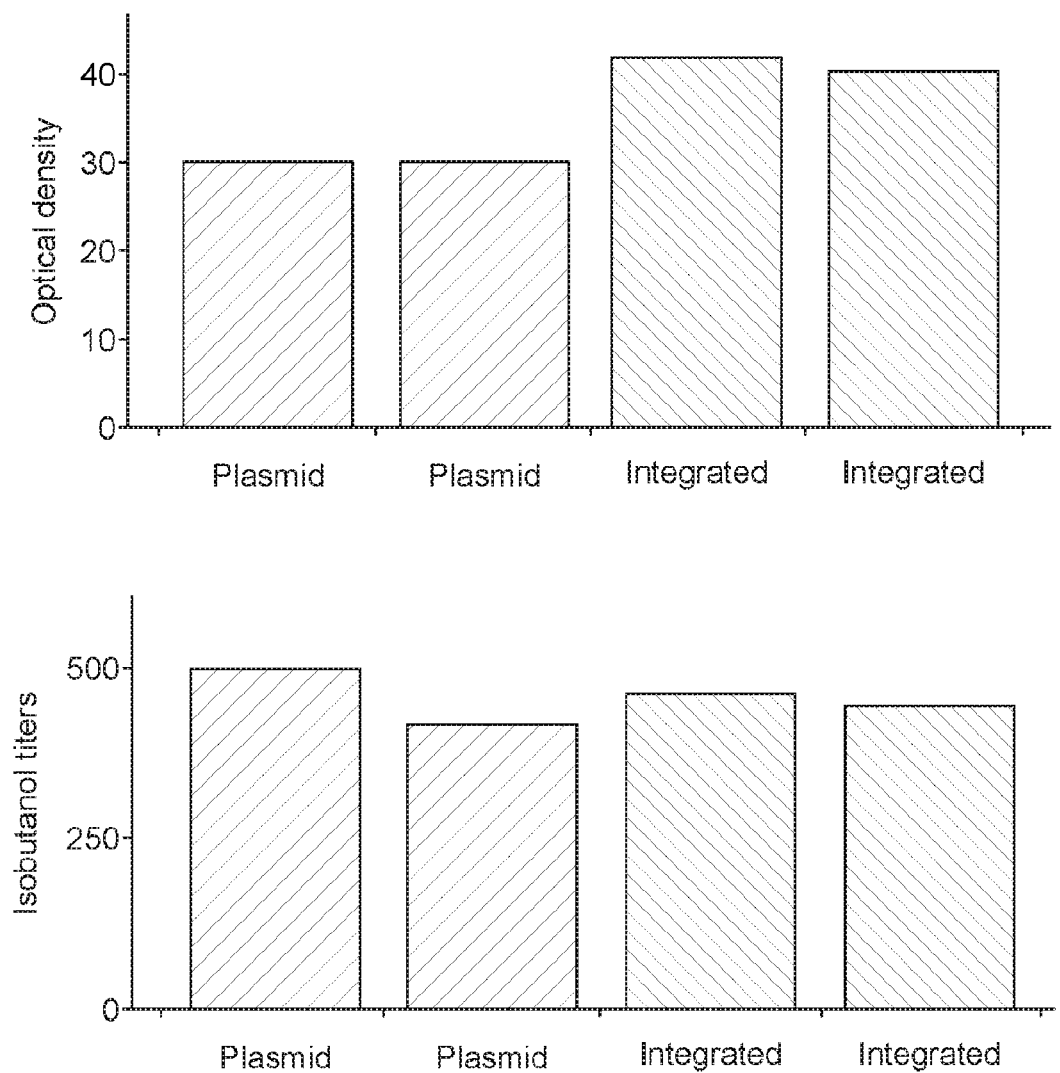
FIG. 17 shows the ability of *M. capsulatus* strain with an integrated copy of ADH6 to produce isobutanol. A significant amount of alcohol dehydrogenase activity from the integrated ADH was observed. Compared with the non-integrated ADH strains, there was no observable difference in total carbon, alcohol and aldehyde. Optimal density fared better with in strains with integrated copies of ADH6.

We observed a significant amount of alcohol dehydrogenase activity from the integrated ADH. The integrated ADH functioned as well as non-integrated ADH, as there was no difference in total carbon, alcohol and aldehyde in these strains. (See FIG. 17) Strains expressing both integrated ADH and a plasmid expressing ADH resulted in a better conversion of aldehydes to alcohols.

What is claimed is:

1. A genetically modified microorganism capable of converting a $C_1$ carbon to a multicarbon product, the microorganism comprising: (a) a gene encoding an acetolactate synthase comprising an amino acid sequence that is at least 90% identical to SEQ ID NO: 2; (b) a gene encoding a ketol-acid reductoisomerase comprising an amino acid sequence that is at least 90% identical to SEQ ID NO: 4; (c) a gene encoding a dihydroxy-acid dehydratase comprising an amino acid sequence that is at least 90% identical to SEQ ID NO: 8; and (d) a gene encoding a 2-keto acid decarboxylase comprising an amino acid sequence that is at least 90% identical to SEQ ID NO: 12; wherein at least one of the gene(s) is under the control of a rare earth metal switch.

2. The genetically modified microorganism of claim 1, further comprising a gene encoding an alcohol dehydrogenase comprising an amino acid sequence that is at least 90% identical to any one of SEQ ID NOs: 14, 16, 18, 23, 25, 27, 29, 31, 33, 35, 37, 39, 41, 43, 45, 47, 49, 51, and 53.

3. The genetically modified microorganism of claim 1, wherein the genetically modified microorganism is a methanotroph.

4. The genetically modified microorganism of claim 3, wherein the methanotroph is a *Methylococcus*.

5. The genetically modified microorganism of claim 1, wherein one or more of the gene(s) is heterologous to the microorganism.

6. The genetically modified microorganism of claim 1, wherein at least one of the gene(s) is overexpressed.

7. The genetically modified microorganism of claim 1, comprising multiple copies of at least one of the gene(s).

8. The genetically modified microorganism of claim 1, wherein the rare earth metal switch is a lanthanum switch.

9. The genetically modified microorganism of claim 1, further comprising a sugar permease gene.

10. A method of making the genetically modified microorganism of claim 1, comprising contacting a microorganism with: a polynucleotide encoding the acetolactate synthase; a polynucleotide encoding the ketol-acid reductoisomerase; a polynucleotide encoding the dihydroxy-acid dehydratase; and/or a polynucleotide encoding the 2-keto acid decarboxylase.

11. A method of making the genetically modified microorganism of claim 9, comprising contacting a microorganism with a polynucleotide encoding a sugar permease.

12. A method of making an aldehyde from a $C_1$ carbon comprising:
(a) contacting a $C_1$ carbon with the genetically modified microorganism of claim 1 comprising a gene encoding a 2-keto acid decarboxylase comprising an amino acid sequence that is at least 90% identical to SEQ ID NO:12; and
(b) growing the genetically modified microorganism to produce the aldehyde.

13. A method of making a useful product comprising:
(a) contacting the genetically modified microorganism of claim 1 with a C1 carbon substrate; and
(b) growing the genetically modified microorganism to produce the useful product, wherein the useful product comprises 2-acetolactate; 2,3-butanediol (2,3-BDO); diacetyl; 2,3-dihydroxy-2-methylbutanoic acid; 2,3-dihydroxyisovalerate; amino acids; ketoisovalerate; isobutyraldehyde; isobutyrate; methyl methacrylate (MMA); isovaleraldehyde; isovalerate; isopentanol; isoamyl acetate; pentadecanoic acid; isobutene; and/or p-xylene.

14. The genetically modified microorganism of claim 1, the microorganism comprising genes encoding: an acetolactate synthase comprising an amino acid sequence that is at least 90% identical to SEQ ID NO: 2; a ketol-acid reductoisomerase comprising an amino acid sequence that is at least 90% identical to SEQ ID NO: 4; a dihydroxy-acid dehydratase comprising an amino acid sequence that is at least 90% identical to SEQ ID NO: 8; a first 2-keto acid decarboxylase comprising an amino acid sequence that is at least 90% identical to SEQ ID NO: 10; and a second 2-keto acid decarboxylase comprising an amino acid sequence that is at least 90% identical to SEQ ID NO: 12.

15. The genetically modified microorganism of claim 14, wherein: the acetolactate synthase comprises an amino acid sequence that is at least 95% identical to SEQ ID NO: 2; the ketol-acid reductoisomerase comprises an amino acid sequence that is at least 95% identical to SEQ ID NO: 4; the dihydroxy-acid dehydratase comprises an amino acid sequence that is at least 95% identical to SEQ ID NO: 8; the first 2-keto acid decarboxylase comprises an amino acid sequence that is at least 95% identical to SEQ ID NO: 10; and the second 2-keto acid decarboxylase comprises an amino acid sequence that is at least 95% identical to SEQ ID NO: 12.

16. The genetically modified microorganism of claim 14, wherein: the acetolactate synthase comprises the amino acid sequence of SEQ ID NO: 2 or one that differs therefrom by up to 25 conservative substitutions; the ketol-acid reductoisomerase comprises the amino acid sequence of SEQ ID NO: 4 or one that differs therefrom by up to 25 conservative substitutions; the dihydroxy-acid dehydratase comprises the amino acid sequence of SEQ ID NO: 8 or one that differs therefrom by up to 25 conservative substitutions; the first 2-keto acid decarboxylase comprises the amino acid sequence of SEQ ID NO: 10 or one that differs therefrom by up to 25 conservative substitutions; and the second 2-keto acid decarboxylase comprises the amino acid sequence of SEQ ID NO: 12 or one that differs therefrom by up to 25 conservative substitutions.

17. The genetically modified microorganism of claim 14, wherein: the acetolactate synthase comprises the amino acid sequence of SEQ ID NO: 2 or one that differs therefrom by up to 10 conservative substitutions; the ketol-acid reductoisomerase comprises the amino acid sequence of SEQ ID NO: 4 or one that differs therefrom by up to 10 conservative substitutions; the dihydroxy-acid dehydratase comprises the amino acid sequence of SEQ ID NO: 8 or one that differs therefrom by up to 10 conservative substitutions; the first 2-keto acid decarboxylase comprises the amino acid sequence of SEQ ID NO: 10 or one that differs therefrom by up to 10 conservative substitutions; and the second 2-keto acid decarboxylase comprises the amino acid sequence of SEQ ID NO: 12 or one that differs therefrom by up to 10 conservative substitutions.

18. The genetically modified microorganism of claim 14, wherein: the acetolactate synthase comprises the amino acid sequence of SEQ ID NO: 2; the ketol-acid reductoisomerase comprises the amino acid sequence of SEQ ID NO: 4; the dihydroxy-acid dehydratase comprises the amino acid sequence of SEQ ID NO: 8; the first 2-keto acid decarboxylase comprises the amino acid sequence of SEQ ID NO: 10; and the second 2-keto acid decarboxylase comprises the amino acid sequence of SEQ ID NO: 12.

* * * * *